(12) United States Patent
Karin et al.

(10) Patent No.: US 8,227,193 B2
(45) Date of Patent: Jul. 24, 2012

(54) COMPOSITIONS AND METHODS FOR GENE EXPRESSION

(75) Inventors: Michael Karin, La Jolla, CA (US); Giussepina Bonizzi, Cremona (IT); Magali Bebien, San Diego, CA (US)

(73) Assignee: The Regents of The University of California, Oakland, CA (US)

( * ) Notice: Subject to any disclaimer, the term of this patent is extended or adjusted under 35 U.S.C. 154(b) by 1138 days.

(21) Appl. No.: 10/574,333

(22) PCT Filed: Sep. 29, 2004

(86) PCT No.: PCT/US2004/032246
§ 371 (c)(1),
(2), (4) Date: Jul. 21, 2008

(87) PCT Pub. No.: WO2005/033284
PCT Pub. Date: Apr. 14, 2005

(65) Prior Publication Data
US 2008/0280286 A1    Nov. 13, 2008

Related U.S. Application Data

(60) Provisional application No. 60/508,349, filed on Oct. 1, 2003.

(51) Int. Cl.
*C12Q 1/68* (2006.01)
*C07H 21/04* (2006.01)
(52) U.S. Cl. ........................ 435/6.19; 536/24.1
(58) Field of Classification Search ................ None
See application file for complete search history.

(56) References Cited

U.S. PATENT DOCUMENTS
5,851,760 A * 12/1998 Evans et al. .................. 435/6

OTHER PUBLICATIONS

Saccani et al (Molecular Cell, 2003. vol. 11, pp. 1563-1574).*
Toledano et al (PNAS, 1991. vol. 88, pp. 4328-4332).*

* cited by examiner

*Primary Examiner* — Celine Qian
(74) *Attorney, Agent, or Firm* — Medlen & Carroll, LLP

(57) ABSTRACT

The invention provides nucleotide sequences that mediate one or more functions of IKKα, kits and methods for using these sequences to identify therapeutic compounds that alter IKKα related pathology.

8 Claims, 36 Drawing Sheets

TTCGTACCATCCACCCACCCCCAGTCGAGAGAATAGGGGTACAGAGGGGAGGTGGCAAAGAAAATTCACGATAC
TGAGTATCTCTGGGAGACCTGTTTGGTCTCTTTGCTCGGTAGCGCAGCCCTACGTTAGAATGCATCTTCCCGGG
AATGACTGTAGTGAGACTTTGGCTGGGAATCCAAGTTATTCTAACTGTAGATTGGTCCACGTTGCCCTAAGCCT
AGCAGTCCACTGCGGCACAGACACCCTGGACATGAGGTGGGTCAGCTTAAGTTCCTGGCACGAAAGAAAGGGTA
CTCTGGCAACTTTTGGATGCGGCGAAACAGACTGTTTCGTCTCTCAGGTTCTTATTTCACGGCTTGTGCCTTTG
ACAGCCCCTTAGTTTCTCTATCTGCAGGATGGGAGCATTAAGCTCTACGACCCAGCCTCTTTACAATTCAGGTC
CAAAGAGCCCGCCCAAGTTGGGGACTGGGAAGATCAAAGGTCTCAGCACCCAGCGGAGCCGCGGACACTGAGGG
CGCCAAGAAGGGGGTGGGTAGGTAGGGAACTGGAAGGGCGGCTGCTCCGCAGGGGATGCGCGTCAGAGACCCCA
GCCACACTCCAGGCCCGCCCCTTGATGAGCCCCGCCCCGCCCCGCCTGGTTTTCGCCTCTAAAGCGCCCAGCGC
TCGCCTCCCGCTGCCGCACTTTCACTCTCGGTCC

Figure 8

MESCYNPGLDGIIEYDDFKLNSSIVEPKEPAPETADGPYLVIVE
QPKQRGFRFRYGCEGPSHGGLPGASSEKGRKTYPTVKICNYEGPAKIEVDLVTHSDPP
RAHAHSLVGKQCSELGICAVSVGPKDMTAQFNNLGVLHVTKKNMMGTMIQKLQRQRLR
SRPQGLTEAEQRELEQEAKELKKVMDLSIVRLRFSAFLRASDGSFSLPLKPVTSQPIH
DSKSPGASNLKISRMDKTAGSVRGGDEVYLLCDKVQKDDIEVRFYEDDENGWQAFGDF
SPTDVHKQYAIVFRTPPYHKMKIERPVTVFLQLKRKRGGDVSDSKQFTYYPLVEDKEE
VQRKRRKALPTFSQPFGGGSHMGGGSGGAAGGYGGAGGGGSLGFFPSSLAYSPYQSGA
GPMRCYPGGGGGAQMAATVPSRDSGEEAAEPSAPSRTPQCEPQAPEMLQRAREYNARL
FGLAHAAPSPTRLLRHRGRRALLAGQRHLLTAQDENGDTPLHLAIIHGQTSVIEQIVY
VIHHAQDLGVVNLTNHLHQTPLHLAVITGQTSVVSFLLRVGADPALLDRHGDSAMHLA
LRAGAGAPELLRALLQSGAPAVPQLLHMPDFEGLYPVHLAVRARSPECLDLLVDSGAE
VEATERQGGRTALHLATEMEELGLVTHLVTKLRANVNARTFAGNTPLHLAAGLGYPTL
TRLLLKAGADIHAENEEPLCPLPSPPTSDSDSDSEGPEKDTRSSFRGHTPLDLTCSTL
VKTLLLNAAQNTMEPPLTPPSPAGPGLSLGDTALQNLEQLLDGPEAQGSWAELAERLG
LRSLVDTYRQTTSPSGSLLRSYELAGGDLAGLLEALSDMGLEEGVRLLRGPETRDKLP
STEVKEDSAYGSQSVEQEAEKLGPPPEPPGGLSHGHPQPQVTDLLPAPSPLPGPPVQR
PHLFQILFNTPHPPLSWDK

Figure 9

```
   1 actttcctgc cccttccccg gccaagccca actccggatc tcgctctcca ccggatctca
  61 cccgccacac ccggacaggc ggctggagga ggcgggcgtc taaaattctg ggaagcagaa
 121 cctggccgga gccactagac agagccggc ctagcccaga gacatggaga gttgctacaa
 181 cccaggtctg gatggtatta ttgaatatga tgatttcaaa ttgaactcct ccattgtgga
 241 acccaaggag ccagccccag aaacagctga tggcccctac ctggtgatcg tggaacagcc
 301 taagcagaga ggcttccgat ttcgatatgg ctgtgaaggc ccctcccatg gaggactgcc
 361 cggtgcctcc agtgagaagg gccgaaagac ctatcccact gtcaagatct gtaactacga
 421 gggaccagcc aagatcgagg tggacctggt aacacacagt gacccacctc gtgctcatgc
 481 ccacagtctg gtgggcaagc aatgctcgga gctggggatc tgcgccgttt ctgtggggcc
 541 caaggacatg actgcccaat ttaacaacct gggtgtcctg catgtgacta agaagaacat
 601 gatggggact atgatacaaa aacttcagag gcagcggcctc cgctctaggc cccagggcct
 661 tacggaggcc gagcagcggg agctggagca agaggccaaa gaactgaaga aggtgatgga
 721 tctgagtata gtgcggctgc gcttctctgc cttccttaga gccagtgatg gctccttctc
 781 cctgcccctg aagccagtca cctcccagcc catccatgat agcaaatctc cggggggcatc
 841 aaacctgaag atttctcgaa tggacaagac agcaggctct gtgcggggtg gagatgaagt
 901 ttatctgctt tgtgacaagg tgcagaaaga tgacattgag gttcggttct atgaggatga
 961 tgagaatgga tggcaggcct tggggactt ctctcccaca gatgtgcata acagtatgc
1021 cattgtgttc cggacacccc cctatcacaa gatgaagatt gagcggcctg taacagtgtt
1081 tctgcaactg aaacgcaagc gaggagggga cgtgtctgat tccaaacagt tcacctatta
1141 ccctctggtg gaagacaagg aagaggtgca gcggaagcgg aggaaggcct tgcccaccctt
1201 ctcccagccc ttcggggggg gctcccacat gggtggaggc tctggggggtg cagccggggg
1261 ctacggagga gctggaggag gtggcagcct cggtttcttc ccctcctccc tggcctacag
1321 cccctaccag tccggcgcgg gccccatgcg gtgctacccg ggaggcgggg gcggggcgca
1381 gatggccgcc acggtgccca gcagggactc cggggaggaa gccgcggagc cgagcgcccc
1441 ctccaggacc ccccagtgcg agccgcaggc cccggagatg ctgcagcgag ctcgagagta
1501 caacgcgcgc ctgttcggcc tggcgcacgc agccccgagc cctactcgac tactgcgtca
1561 ccgcggacgc cgcgcgctgc tggcgggaca gcgccacctg ctgacggcgc aggacgagaa
1621 cggagacaca ccactgcacc tagccatcat ccacgggcag accagtgtca ttgagcagat
1681 agtctatgtc atccaccacg cccaggacct cggcgttgtc aaccctcacca accacctgca
1741 ccagacgccc ctgcaccgcg cggtgatcac gggggcagacg agtgtggtga gctttctgct
1801 gcgggtaggt gcagacccag ctctgctgga tcggcatgga gactcagcca tgcatctggc
1861 gctgcgggca ggcgctggtg ctcctgagct gctgcgtgca ctgcttcaga gtggagctcc
1921 tgctgtgccc cagctgttgc atatgcctga ctttgaggga ctgtatccag tacacctggc
1981 ggtccgagcc cgaagccctg agtgcctgga tctgctggtg gacagtgggg ctgaagtgga
2041 ggccacagag cggcagggg gacgaacagc cttgcatcta gccacagaga tggaggagct
2101 ggggttggtc acccatctgg tcaccaagct ccgggccaac gtgaacgctc gcacctttgc
2161 gggaaacaca cccctgcacc tggcagctgg actggggtac ccgaccctca cccgcctcct
2221 tctgaaggct ggtgctgaca tccatgctga aaacgaggag ccctgtgcc cactgccttc
2281 accccctacc tctgatagcg actctagctc tgaaggcct gagaaggaca cccgaagcag
2341 cttccggggc cacacgcctc ttgaccctcac ttgcagcacc tggtgaaga ccttgctgct
2401 aaatgctgct cagaacacca tggagccacc cctgaccccg cccagcccag cagggccggg
2461 actgtcactt ggtgatacag ctctgcagaa cctggagcag ctgctagacg ggccagaagc
2521 ccagggcagc tgggcagagc tggcagagcg tctgggctg cgcagcctgg tagacacgta
2581 ccgacagaca acctcaccca gtggcagcct cctgcgcagc tacgagctgg ctggcgggga
2641 cctggcaggt ctactggagg ccctgtctga catgggccta gaggagggag tgaggctgct
2701 gaggggtcca gaaacccgag acaagctgcc cagcacagag gtgaaggaag acagtgcgta
2761 cgggagccag tcagtggagc aggaggcaga gaagctgggc ccacccctg agccaccagg
2821 agggctctcg cacggcacc cccagcctca ggtgactgac ctgctgcctg ccccagccc
2881 ccttcccgga ccccctgtac agcgtcccca cctatttcaa atcttattta acaccccaca
2941 cccaccccctc agttgggaca aataaaggat tctcatggga agggaggac cccgaattcc
3001 t
```

Figure 10

MDNCYDPGLDGIPEYDDFEFSPSIVEPKDPAPETADGPYLVIVE

QPKQRGFRFRYGCEGPSHGGLPGASSEKGRKTYPTVKICNYEGPAKIEVDLVTHSDPP

RAHAHSLVGKQCSELGVCAVSVGPKDMTAQFNNLGVLHVTKKNMMEIMIQKLQRQRLR

SKPQGLTEAERRELEQEAKELKKVMDLSIVRLRFSAFLRASDGSFSLPLKPVISQPIH

DSKSPGASNLKISRMDKTAGSVRGGDEVYLLCDKVQKDDIEVRFYEDDENGWQAFGDF

SPTDVHKQYAIVFRTPPYHKMKIERPVTVFLQLKRKRGGDVSDSKQFTYYPLVEDKEE

VQRKRRKALPTFSQPFGGGSHMGGGSGGSAGGYGGAGGGGSLGFFSSSLAYNPYQSGA

APMGCYPGGGGGAQMAGSRRDTDAGEGAEEPRTPPEAPQGEPQALDTLQRAREYNARL

FGLAQRSARALLDYGVTADARALLAGQRHLLMAQDENGDTPLHLAIIHGQTGVIEQIA

HVIYHAQYLGVINLTNHLHQTPLHLAVITGQTRVVSFLLQVGADPTLLDRHGDSALHL

ALRAGAAAPELLQALLRSGAHAVPQILHMPDFEGLYPVHLAVHARSPECLDLLVDCGA

EVEAPERQGGRTALHLATEMEELGLVTHLVTKLHANVNARTFAGNTPLHLAAGLGSPT

LTRLLLKAGADIHAENEEPLCPLPSPSTSGSDSDSEGPERDTQRNFRGHTPLDLTCST

KVKTLLLNAAQNTTEPPLAPPSPAGPGLSLGDAALQNLEQLLDGPEAQGSWAELAERL

GLRSLVDTYRKTPSPSGSLLRSYKLAGGDLVGLLEALSDMGLHEGVRLLKGPETRDKL

PSTEVKEDSAYGSQSVEQEAEKLCPPPEPPGGLCHGHPQPQVH

Figure 11

```
   1 ggcgggcgtc cgaaactctg gaaagctgaa ccggggcccg aagccgcaag acacagcagg
  61 gcctagccca gagatatgga caattgctac gatccaggcc tggatggcat ccccgaatat
 121 gatgattttg aattcagccc ctccatcgtg gagcctaagg atccagcccc tgagacagct
 181 gatggcccct atctggtgat tgtggaacag cccaaacagc gaggcttcag atttcgatat
 241 ggctgtgaag gccctccca tggaggtttg ccaggtgcct ccagtgagaa gggccggaag
 301 acctatccta ctgtcaagat ctgtaactat gagggaccgg ccaagattga ggtggacctg
 361 gtgacacaca gtgacccacc tcgtgcgcat gcccacagtc tggtgggcaa gcagtgttca
 421 gagttgggag tgtgcgctgt gtctgtagga cccaaggaca tgactgctca atttaataat
 481 ctgggtgtcc tgcatgtaac caagaagaac atgatggaga ttatgatcca gaaacttcag
 541 aggcagcgtc tccgctccaa gcctcagggc cttacagagg ctgagcggcg ggagctagag
 601 caggaggcca aggagctgaa gaaagtcatg gatctgagca ttgtacggct gcgcttctca
 661 gctttccttc gagctagcga tggctccttc tccttgcccc tgaagcctgt gatctcccag
 721 cccatccatg acagcaagtc tccaggggcc tcgaacctga agatctcccg aatggacaag
 781 acagcgggtt ccgtgcgcgg tggagacgaa gtttatttgc tctgtgataa ggtgcaaaaa
 841 gacgacattg aggttcggtt ctatgaggat gatgagaatg gatggcaagc ctttggggac
 901 ttctctccca cagacgttca taaacagtat gccattgtgt tccggacacc gccctatcac
 961 aagatgaaga tcgagaggcc tgtaacagtg ttcctgcagc tgaaacgcaa gcgtggggggc
1021 gatgtctcgg actccaaaca gttcacatat taccctctgg tggaagacaa ggaggaagtg
1081 cagaggaagc ggagaaaggc cttgccaccc ttctcccagc ccttcggggg cggatcccac
1141 atgggtggag gttctggagg ctccgctggg ggttatggag gcgctggagg aggtggcagc
1201 ctcggctttt tctcctcctc cttggcctac aaccctacc aatccggtgc agccccaatg
1261 ggctgttatc cgggtggggg aggtggagcg cagatggccg gttctagacg ggacaccgat
1321 gctggcgagg gggcagagga gcccaggacg ccccggagg ctccccaggg cgaaccacag
1381 gcccttgaca cactgcagcg agctcgcgag tacaacgcgc gcctgttcgg tctggcgcag
1441 cgcagcgccc gagcgttgct ggactacgc gtcaccgcag acgcgcgtgc tctgctagcg
1501 ggacagcgcc acctgctgat ggcacaggac gagaacggag acacgccact gcacctggcc
1561 atcatccatg ggcagactgg tgtcattgag cagatagccc acgtcattta tcacgctcag
1621 tacctcggcg tcatcaacct caccaaccac ctgcaccaga cgcctctgca cctggcggta
1681 atcactggc agacaagggt ggtgagcttc ctgctgcaga tgggtgcaga ccccacgctg
1741 ctggatcggc acggagctc cgccctccac ttggctctcc gggcaggtgc tgcagcccca
1801 gagctgttgc aggcactgtt gcgcagcgga gcccatgctg tgccccaaat attgcacatg
1861 cctgattttg agggactata ccctgtacac ctggcagtcc atgcccgaag ccctgagtgc
1921 ctggatctgt tagttgactg tggagctgaa gtggaggccc cagagaggca aggggccga
1981 actgccctgc atctagccac agagatggag gagttgggc tggtcaccca tctagtcacc
2041 aagctccatg ctaatgtgaa tgcccggacc tttgctggaa acacacccct ccacctggca
2101 gctggactcg ggtccccaac tcttactcgc ctccttctaa aggctggtgc tgacatccat
2161 gcagagaatg aggagcctct gtgccgctg ccctcaccct cgacctctgg gagcgactcc
2221 gactctgaag ggcctgagag ggatacccaa agaaacttctc gaggccatac ccctcttgac
2281 ctcacttgca gtaccaaggt gaagactctg ctgctaaatg ctgctcagaa caccacggag
2341 ccaccccgg ccccaccag ccctgcaggg caggctgt ccctggggga tgcagccctg
2401 cagaacctgg agcaactgct ggatggtccc gaagcccagg gcagctgggc agagctggca
2461 gagcgactgg ggttgagaag cctggtggac acatacagga agacccgtc tcccagcggc
2521 agtctccttc gtagttacaa gctggctggt ggggacttgg tgggtctatt ggaggccttg
2581 tctgacatgg gtctccatga gggagtcagg ctgctgaaag gtcctgagac ccgcgacaag
2641 ctgccagca cagaggtgaa agaagacagt gcctatggga ccagtcagt ggagcaggag
2701 gcagagaagc tgtgtccacc ccctgagcct ccaggagggc tctgccacgg cacccccag
2761 cctcaggtgc actgaatggc cccggtcaac ttccacccag atccctctgt acagcatccc
2821 tgtctaatcg aaatcttatt taaacctcaa gcccacatct cggtgggtca aataaagggg
2881 aagacccctc cccaacttac ggtaaaaaaa aaaaaaaa
```

Figure 12

```
  1 atattacaac tttttctact cttgatggac atttatattt tcaacttttg cctgttataa
 61 ataatgctgc tatgaatatt attctacatg tcttttgaca gaactatgca ctaattttc
121 agagaatata cttaggaata gcattgctat catagggcag gcgaatattt aattttggca
181 gatattg
```

Figure 13

```
  1 mpsrraares apelgalgss dlsslsltvs rttdeleiid eyikengfgl vgtqlsempr
 61 lvprgpasls svtlgpaapp ppatpswsct lgrlvspgpc prpylviteq pkqrgmrfry
121 ecegrsagsi lgessteask tqpaielrdc gglrevevta clvwkdwphr vhphslvgkd
181 ctdgvcrvrl rphvsprhsf nnlgiqcvrk keieaaierk iqlgidpyna gslknhqevd
241 mnvvricfqa syrdqqghlh rmdpilsepv ydkkstntse lricrinkes gpctggeely
301 llcdkvqked isvvfstasw egradfsqad vhrqiaivfk tppyedleis epvtvnvflq
361 rltdgvcsep lpftylprdh dsygvdkkrk rglpdvlgel sssdphgies krrkkkpvfl
421 dhflpghssg lflppsalqp adsdffpasi slpgleppgg pdllddgfay dpsaptlftm
481 ldllppappl asavvgsgga gatvvessgp eplsldsfaa pgpgdvgtas lvgsnmfpnq
541 yreaafgggl lspgpeat
```

Figure 14

MPSRRAARESAPELGALGSSDLSSLSLTVSRTTDELEIIDEYIK

ENGFGLVGTQLSEMPRLVPRGPASLSSVTLGPAAPPPPATPSWSCTLGRLVSPGPCPR

PYLVITEQPKQRGMRFRYECEGRSAGSILGESSTEASKTQPAIELRDCGGLREVEVTA

CLVWKDWPHRVHPHSLVGKDCTDGVCRVRLRPHVSPRHSFNNLGIQCVRKKEIEAAIE

RKIQLGIDPYNAGSLKNHQEVDMNVVRICFQASYRDQQGHLHRMDPILSEPVYDKKST

NTSELRICRINKESGPCTGGEELYLLCDKVQKEDISVVFSTASWEGRADFSQADVHRQ

IAIVFKTPPYEDLEISEPVTVNVFLQRLTDGVCSEPLPFTYLPRDHDSYGVDKKRKRG

LPDVLGELSSSDPHGIESKRRKKKPVFLDHFLPGHSSGLFLPPSALQPADSDFFPASI

SLPGLEPPGGPDLLDDGFAYDPSAPTLFTMLDLLPPAPPLASAVVGSGGAGATVVESS

GPEPLSLDSFAAPGPGDVGTASLVGSNMFPNQYREAAFGGGLLSPGPEAT

Figure 15

```
   1 ggccttcggg ctgtcggtcc ctacggccgg gccatgccga gtcgccgcgc tgccagagag
  61 tccgcgcccg agctaggggc cttgggttcc agtgacctct cttccctgtc actaacggtc
 121 tccaggacca cagatgaatt ggaaatcatc gacgaataca ttaaggagaa cggctttggc
 181 ctggtcggga cacagctgag tgagatgccg cgcctggtgc ccgcggggcc cgcctcactg
 241 agcagcgtca cgctgggccc tgctgcacca ccgcctccgg ccacgccgtc ctggagctgc
 301 acactgggca ggctggtgtc acccggcccg tgcccacggc cgtacctggt catcacagag
 361 cagccaaagc agcgtggcat gcgcttccgc tacgagtgcg agggccgctc ggccggcagc
 421 atcctcgggg agagcagcac cgaagccagc aagacccagc ccgccatcga gcttcgagac
 481 tgtggcgggc tgcgggaggt ggaggtgacg gcgtgcctgg tgtggaagga ctggccacac
 541 cgggtacacc cacatagcct cgtggggaaa gactgcacgg acggcgtctg cagggtgcgg
 601 ctgcggcctc acgtcagccc ccggcacagc tttaacaacc tgggcatcca gtgtgttagg
 661 aagaaggaaa ttgaagctgc cattgagcgg aagatccagc tgggaattga ccctacaat
 721 gctggctccc tgaagaacca tcaggaggtc gacatgaatg tcgtcaggat ctgcttccag
 781 gcctcctatc gggaccagca gggacatctg caccgcatgg accccatcct ctctgagcct
 841 gtctacgaca agaagtccac caacacatcg gagctgcgga tttgccgaat caacaaggag
 901 agcgggccgt gcacaggtgg tgaggagctg tacttgctct gtgacaaggt gcaaaaagag
 961 gacatatccg tggtgttcag cacagcttcc tgggaaggcc gtgccgactt ctctcaagct
1021 gatgtgcacc ggcagatcgc cattgtgttc aaaacgccac cctacgagga cctggagatc
1081 tcagagcccg tgactgtcaa tgtgttcttg cagcggctca cggatgggggt gtgcagcgag
1141 ccgctgccct tcacgtacct gcctcgggat catgacagct acggtgtgga caagaagcga
1201 aagcggggac tgcctgatgt ccttggagag ttgagcagct ctgatccaca tggaatcgag
1261 agcaaacgaa ggaaaaagaa accagtgttc ttggaccact tcctgcctgg ccacagctca
1321 ggcctgttcc tcccaccatc ggctctgcag ccggcagact ctgatttctt ccctgcttcc
1381 atatcccttc ctgggctgga gcctcctggt ggacccgatc tcctggacga tggctttgcc
1441 tatgatcctt ctgccccac gctcttcact atgttggacc tgctgccccc agcaccacca
1501 cttgccagtg ctgtggtggg tagcgggggt gcaggggcca ccgttgtgga gtcttctggc
1561 ccagagcccc tatcactgga ctcttttgca gcgccgggcc ccggggatgt tggtactgct
1621 agccttgtgg gcagcaacat gtttcccaac cagtaccgag aggcagcttt cggggggtggc
1681 ctcctatctc cagggcctga agccacgtag cctctgaggt aacagaggag gcactgggtg
1741 aggtatgtgg tatagcactc cattccgaag ccaaccttga tcagtcttcc agcttcctca
1801 tcctgaatcg gacatctgca gcgctggtgg aagatgggg agcactccgg ttctctttga
1861 gcccatttta cagaatgctg agtccgaaga ggaaaagggg ctcctgcaga tggacccctt
1921 ctcaggacag attctcagag attgtacata ggggaggagg gagcaggtcc ccagccttct
1981 cccctaatcc tgaagaaggc agtggattgt tcagttttcc caataaaaat tagtttttta
2041 aaaaaagga attcc
```

Figure 16

MREQGREGSSFLSQQLGPTIEDVMDLINSDRDVISSPSVFVCED

APSSILSTVTVAHYVPHEQCPSTSWAPQREGPNPELNITEQPKQRGMRFRYQCEGRST

GSILGEKSTEHNKTLPEIEIINCDGLEEIHVIVCLVWRDPPHRVHPHGLVGKDCHNGI

CEVTLNPQNGVAKHSFSNLGIQCVRKREIDSAVNERLKLNIDPYKAGKWRLHEEVDLN

VVRLCFQASCTGPGFKYDIPPVLSDPIYDKKSTNTSELKISRMNKEYGRCEGGEEVYI

LCDKVQKEDILVIFGEDKWEARADFSQADVHRQIAIVLKTPPYHDLHITEPACVRVFL

QRITDGIRSEGMPFVYMPRVKDPNGVHSKRKHRDCSQLGDIGDPDPHGIEMKRRKVRP

SYADHLIPPYPDINLPLMDSFNHNEGYHDLPLMNPDEDAFHFLTEDPHFSDLLTHDPY

FLDGYSNQFLPDQVNGVTAHLVGSSLALTDEEQPLPDCAFNDSGCRR

Figure 17

```
   1 ggttcgtccg tggttagggg ggtgtgtata agcgctgcca agccactcgc atgataaggg
  61 ttcacttaca aatgtaatat ttctcagctt ttaattacgc ctttggataa aagaaacaca
 121 atgagagaac aggggaggga agggtcttct tttttgtctc agcaacttgg accaacaatt
 181 gaagatgtca tggatcttat taattctgac cgggatgtaa tttcttcgcc ttccgtgttt
 241 gtttgcgagg acgccccttc tagtatcctc agtactgtaa ctgtcgcaca ttatgtgccc
 301 catgagcaat gcccatccac atcctgggct cctcagcgag aaggtccaaa tccagaatta
 361 aacatcactg agcaaccaaa acagagaggg atgcgcttcc gttaccagtg tgaggggaga
 421 tcgactggaa gtatacttgg ggagaaaagc acagagcata ataagaccct tccagagatt
 481 gagatcatca actgtgatgg gcttgaagaa attcatgtca ttgtgtgtct cgtctggaga
 541 gatcctcccc atcgcgtgca cccccatggc cttgtaggta aagactgcca taatggcatc
 601 tgtgaggtca ccctgaatcc tcagaatgga gtagcaaagc acagtttcag taatcttggc
 661 attcagtgtg tgcggaaaag ggaaatcgac tcggcggtaa atgaacggct gaaattaaat
 721 atcgatcctt ataaagctgg gaaatgcgt ctccatgaag aagtagattt gaacgtggtc
 781 agactctgct tccaggcctc ctgtactggg ccggggttta aatatgacat tccccctgtg
 841 ctttctgacc cgatctatga caagaaatct acaaatacat cagaactgaa gatttctcgc
 901 atgaacaaag aatatggacg atgtgaaggg ggcgaggagg tctatatcct ctgtgataag
 961 gttcagaaag aggatatcct ggtaatattt ggagaagata gtgggaggc tcgtgctgat
1021 ttctcacagg cagatgtgca cagacagata gcgattgtgc taaagacacc accatatcat
1081 gatctgcata tcacagaacc agcttgtgtg cgtgtgtttc tgcagaggat tacagatggc
1141 atacgcagtg aagggatgcc atttgtctac atgccacgag ttaaagatcc caatggtgtg
1201 cactctaaga ggaaacatcg ggactgttca caactcggtg atataggaga tcctgatcca
1261 catgggattg aaatgaagag aagaaaagta agacctagtt atgcagatca tttaatccct
1321 ccttacccag atataaattt accctcatg gattccttca accataatga aggttaccac
1381 gaccttcctc tgatgaaccc tgatgaagat gcatttcact ttctcactga ggacccacat
1441 ttttcagatc tcctgacaca cgacccttac tttctggatg ttattcgaa tcaatttctg
1501 ccagaccagg tgaatggagt cacagctcat cttgtgggtt ccagccttgc tttaaccgac
1561 gaagaacaac ctttaccaga ctgtgctttt aatgacagtg ttgccggag ataaccgtat
1621 attcagagat tccaatattt gactctgttt tcagcacttg aactacaaag cccacttcag
1681 ttacagtttg tatatacata gatacatgta tatatatgtg taagagagct tatagttctg
1741 ggaaatataa ggaatttctg ttgttagagg gaggataaaa cacagtgatc taaagatttc
1801 taccatgaag tcttaatatt ccatagctga caaaatggtc cctactgaag aggtccatgc
1861 ctccgcaata tggaataaag ttcacaaaca gaaagacact gaagaaacca ctatatattt
1921 ctaattctaa aaaatagata ccactttttg tatgaacttg taagctcaat aatggaccaa
1981 catttattct aggctgtaga aaagaataaa gaggaccttt aatggggag aggaatttag
2041 gaagcagtac cattggcttg tcagtaacta ggatcacaat tgcatcctcc agtaaagaca
2101 gaactctgga cttcagtggc acttgctctg tatgtacaga gatatgtatt taataaaggt
2161 agtttggtct gtttatgtga aaatatggta taggacagag gggacatagt ttttgcacta
2221 gtatatgatg acagaataga agattggtgg ttaaaaggat ttattactta atatacattt
2281 gaaacact
```

Figure 18

MADDDPYGTGQMFHLNTALTHSIFNAELYSPEIPLSTDGPYLQI
LEQPKQRGFRFRYVCEGPSHGGLPGASSEKNKKSYPQVKICNYVGPAKVIVQLVTNGK
NIHLHAHSLVGKHCEDGVCTVTAGPKDMVVGFANLGILHVTKKKVFETLEARMTEACI
RGYNPGLLVHSDLAYLQAEGGGDRQLTDREKEIIRQAAVQQTKEMDLSVVRLMFTAFL
PDSTGSFTRRLEPVVSDAIYDSKAPNASNLKIVRMDRTAGCVTGGEEIYLLCDKVQKD
DIQIRFYEEEENGGVWEGFGDFSPTDVHRQFAIVFKTPKYKDVNITKPASVFVQLRRK
SDLETSEPKPFLYYPEIKDKEEVQRKRQKLMPNFSDSFGGGSGAGAGGGGMFGSGGGG
GSTGSPGPGYGYSNYGFPPYGGITFHPGVTKSNAGVTHGTINTKFKNGPKDCAKSDDE
ESLTLPEKETEGEGPSLPMACTKTEPIALASTMEDKEQDMGFQDNLFLEKALQLARRH
ANALFDYAVTGDVKMLLAVQRHLTAVQDENGDSVLHLAIIHLHAQLVRDLLEVTSGLI
SDDIINMRNDLYQTPLHLAVITKQEDVVEDLLRVGADLSLLDRWGNSVLHLAAKEGHD
RILSILLKSRKAAPLIDHPNGEGLNAIHIAVMSNSLPCLLLLVAAGAEVNAQEQKSGR
TPLHLAVEYDNISLAGCLLLEGDAHVDSTTYDGTTPLHIAAGRGSTRLAALLKAAGAD
PLVENFEPLYDLDDSWEKAGEDEGVVPGTTPLDMAANWQVFDILNGKPYEPVFTSDDI
LPQGDMKQLTEDTRLQLCKLLEIPDPDKNWATLAQKLGLGILNNAFRLSPAPSKTLMD
NYEVSGGTIKELMEALQQMGYTEAIEVIQAAFRTPATTASSPVTTAQVHCLPLSSSST
RQHIDELRDSDSVCDSGVETSFRKLSFTESLTGDSPLLSLNKMPHGYGQEGPIEGKI

Figure 19A

```
   1 agcggccgcc gcgggcgcgc tctagcagcg caggccggag ctcagggccc cgcgcgcccg
  61 gcccgccccg cgcttctccg cccgcgccgc agccatggcg cgccgctgag ccgccgccc
 121 gcccgcccgc gccccgaccc ggctcggctc ccgccggtcc gcgccgctcc gcagcggagc
 181 ccgcaggcga ggagaggccg cgcgcatctc cagggtaccc tcagaggcca gaagagggtg
 241 tcagagccct tgtaactgga gtttgacggt cgtgagctgc gcatcttcac catggcagac
 301 gatgatccct acggaactgg gcaaatgttt catttgaaca ctgctttgac tcactcaata
 361 tttaatgcag aattatattc accagaaata ccactgtcaa cagatggccc ataccttcaa
 421 atattagagc aaccaaaaca gaggggattt cgattccgct atgtgtgtga aggcccatca
 481 cacggagggc ttccgggagc tctagtgag aagaacaaga atcctaccc acaggtcaaa
 541 atttgcaact atgtggggcc tgcaaaggtt atcgttcagt tggtcacaaa tggaaaaaac
 601 atccacctgc acgcccacag cctggtgggc aagcactgtg aggacggggt atgcaccgta
 661 acagcaggac ccaaggacat ggtggttggc tttgcaaacc tgggaatact tcatgtgact
 721 aagaaaaagg tatttgaaac actggaagca cggatgacag aggcgtgtat tagggctat
 781 aatcctggac ttctggtgca ttctgacctt gcctatctac aagcagaagg cggaggagac
 841 cggcaactca cagacagaga gaaggagatc atccgccagg cagccgtgca gcagaccaag
 901 gagatggacc tgagcgtggt gcgcctcatg ttcacagcct tcctccctga cagcactggc
 961 agcttcactc ggagactgga gcctgtggtg tcagacgcca tctatgatag caaagccccg
1021 aatgcatcca acctgaaaat cgtgagaatg gacagaacag caggatgtgt gacgggaggg
1081 gaggagattt accttctctg tgacaaggtt cagaaagatg acatccagat tcggttttat
1141 gaagaggaag aaaatggcgg agtttgggaa ggatttgggg acttttcccc cacggatgtt
1201 catagacagt ttgccattgt cttcaaaacg ccaaagtata aggatgtcaa cattacaaag
1261 ccagcttccg tgtttgttca gcttcggagg aaatcagacc tggaaactag tgaaccgaaa
1321 ccctttctct actaccctga aatcaaagac aaagaggaag tgcaaaggaa acgccagaag
1381 cttatgccga acttctcgga cagcttcggc ggcggcagtg gagcgggagc cggtggtgga
1441 ggcatgttcg gtagtggcgg tggcggaggg agtaccggaa gccctggccc agggtatggc
1501 tactcgaact acggatttcc tccctacggt gggattacat tccatcccgg agtcacgaaa
1561 tccaacgcag gggtcaccca tggcaccata aacaccaaat ttaaaatgg ccctaaagat
1621 tgtgccaaga gtgatgacga ggagagtctg actctccctg agaaggaaac tgaaggtgaa
1681 gggcccagcc tgcccatggc ctgcaccaag acggaaccca tcgccttggc atccaccatg
1741 gaagacaagg agcaggacat gggatttcag gataacctct ttctcgagaa ggctctgcag
1801 ctcgccaggc gacacgccaa cgccccttttc gactacgcag tgaccgggga tgtgaagatg
1861 ttgctggccg tgcaacgcca tctcaccgcc gtgcaggatg agaatgggga cagtgtctta
1921 cacttagcca tcatccacct ccacgctcag ctcgtgaggg atctgctgga agtacatctt
1981 ggtttgatct ctgatgacat catcaacatg agaaatgacc tgtatcagac acctctgcac
2041 ttggccgtga tcaccaagca ggaagatgta gtagaggatt tgctgagggt tggggctgac
2101 ctgagccttc tggaccgctg gggcaactct gtcctgcacc tagctgccaa agaaggacac
2161 gacagaatcc tcagcatcct gctcaagagc agaaaagcag cgcccttat cgaccacccc
2221 aatggggaag gtctaaatgc catccacata gctgtgatga gcaatagcct gccatgtctg
2281 ctgctgctgg tggctgccgg ggcagaagtc aatgctcagg agcagaagtc tgggcgcacg
2341 ccgctgcacc tggccgtgga gtacgacaac atctccttgg ctggctgcct gcttctggag
2401 ggtgatgccc acgtggacag taccacctat gatgggacta cacctctgca tatagcggcc
2461 ggaagagggt ccaccagact ggcagctctt ctcaaagcag caggagcaga ccccctggtg
2521 gagaactttg agcctctcta tgacctggac gactcttggg agaaggctgg agaagatgag
2581 ggagtggtgc aggtaccac accctggac atggctgcca actggcaggt atttgacata
2641 ctaaatggga aaccgtatga gcctgtgttc acatctgatg atatactacc acaagggac
2701 atgaagcagc tgacagaaga cacgaggcta caactctgca aactgctgga aattcctgat
2761 ccagacaaaa actgggccac tctggcacag aagttgggtc tggggatatt gaacaatgcc
2821 ttccggctga gtcctgctcc ttctaaaact ctcatggaca actatgaggt ctctgggggt
2881 accatcaaag agctgatgga ggccctgcaa cagatgggct acacagaggc cattgaagtg
2941 atccaggcag ccttccgcac cccggcaacc acagcctcca gccccgtgac cactgctcag
```

Figure 19B

```
3001 gtccactgtc tgcctctctc gtcttcctcc acgaggcagc acatagatga actccgggat
3061 agtgacagcg tctgtgacag tggtgtggag acatccttcc gcaaactcag ctttacagag
3121 tctcttactg gagacagccc actgctatct ctgaacaaaa tgccccacgg ttatgggcag
3181 gaaggaccta ttgaaggcaa aatttagcct gctggccgtt cccccacact gtgtaaacca
3241 aagccctgac agtccattgc atcgtcccaa aggaggaagg caaagcgaat ccaaaggtgc
3301 tggagaatcg ccggcctgca gggtcactcg atttcattca aggccttccg aatttggcgt
3361 ccttcttggt tctgaaatga aatgtagttg ccacgcacag acggtgtcta gcaatcatgg
3421 cgctcgctcg ctcagctgca ctctatggct caggtgcagt gtcttgagct ttctctgctg
3481 ctactggatc acatttgctt tgtgttgtta ctgctgtccc tccgctgggt tcctgctgtc
3541 attaaaaggt gtcgctgtcc ccacccggtg tcctttctag ccatctactg taagttgtgc
3601 attcaaatta agattaagga aaaacatatt tttaaatgag taccttgatg cgcaataaaa
3661 aaaaagacat ttcttttttt aatgtggttt atctgtgatt taaaaataaa aaacacatga
3721 acttatcaat atttaaaaca tgctacaatc agtgntgaaa atagtatttt ccccgtttta
3781 tgcattttac atttgtaaat atgttttcta atcaatactt taaaagaaga atgttgaatt
3841 tataaaatgc tatttacttt tttatttata ataaagtaca gcacatgtga ct
```

Figure 20

MDDLFPLIFPSEPAQASGPYVEIIEQPKQRGMRFRYKCEGRSAG

SIPGERSTDTTKTHPTIKINGYTGPGTVRISLVTKDPPHRPHPHELVGKDCRDGYYEA

DLCPDRSIHSFQNLGIQCVKKRDLEQAISQRIQTNNNPFHVPIEEQRGDYDLNAVRLC

FQVTVRDPAGRPLLLTPVLSHPIFDNRAPNTAELKICRVNRNSGSCLGGDEIFLLCDK

VQKEDIEVYFTGPGWEARGSFSQADVHRQVAIVFRTPPYADPSLQAPVRVSMQLRRPS

DRELSEPMEFQYLPDTDDRHRIEEKRKRTYETFKSIMKKSPFNGPTEPRPPTRRIAVP

TRNSTSVPKPAPQPYTFPASLSTINFDEFSPMLLPSGQISNQALALAPSSAPVLAQTM

VPSSAMVPLAQPPAPAPVLTPGPPQSLSAPVPKSTQAGEGTLSEALLHLQFDADEDLG

ALLGNSTDPGVFTDLASVDNSEFQQLLNQGVSMSHSTAEPMLMEYPEAITRLVTGSQR

PPDPAPTPLGTSGLPNGLSGDEDFSSIADMDFSALLSQISS

Figure 21

```
   1 tttactttag cgcgccgtgg gctcagctgc gaccccggcc ccgccccgg gaccctgacc
  61 atggacgatc tgtttcccct catctttccc tcagagccag cccaggcttc tgggccttat
 121 gtggagatca tcgaacagcc gaagcaacgg ggcatgcgat tccgctataa atgcgagggg
 181 cgctcagcgg gcagtattcc tggcgagaga agcacagata ccaccaagac acacccccacc
 241 atcaagatca atggctacac aggaccagga acagttcgaa tctccctggt caccaaggat
 301 ccacctcacc ggcctcatcc acatgaactt gtggggaagg actgccggga tggctactat
 361 gaggctgacc tctgcccaga ccgcagtatc catagcttcc agaacctggg gatccagtgt
 421 gtgaagaagc gagacctgga gcaagccatt agccagcgaa tccagaccaa caataacccc
 481 tttcacgttc ctatagagga gcagcgcggg gactatgact tgaatgcagt gcgcctctgc
 541 ttccaggtga cagtgcggga cccagcaggc aggcccctcc tcctgacccc tgtcctctca
 601 catccgattt tgataaccg ggcccccaac actgccgagc tcaagatctg ccgagtaaac
 661 cggaactctg ggagctgcct cggtggggat gagatcttct tgctgtgcga caaggtgcag
 721 aaagaagaca ttgaggtgta tttcacggga ccaggctggg aggcacgagg ctccttttct
 781 caagctgatg tgcatcggca agtggccatt gtgttccgga ctcctccgta cgccgacccc
 841 agcctccagg ctcctgttcg agtctccatg cagctacggc ggccttctga tcgcgagctc
 901 agtgagccca tggagttcca gtacttgcca gacacagatg atcgccaccg gattgaagag
 961 aagcgcaaaa ggacctatga gaccttcaag agtatcatga agaagagtcc tttcaatgga
1021 ccaactgaac cccggcctcc aacccggcgt attgctgtgc ctacccgaaa ctcaacttct
1081 gtccccaagc cagccccgca gccctacacc ttcccagcat ccctcagcac catcaacttt
1141 gatgagtttt cccccatgct gttaccatca gggcagatct caaaccaggc cctggcctta
1201 gcaccgtcct ctgccccagt ccttgcccag accatggtcc cttcctcagc catggtacct
1261 ctggctcagc ccccagctcc tgcccagtt ctaacccgg gtcctcccca gtccctgtct
1321 gcacctgttc caaagagcac ccaggctggg aaggcacgc tgtcggaagc cctgctgcac
1381 ctgcagtttg atgctgatga agacttgggg gccttgcttg gcaacagcac agacccagga
1441 gtgttcacag acctggcatc tgtggacaac tcagagtttc agcagctcct gaaccagggt
1501 gtgtccatgt ctcactccac agctgagccc atgctgatgg agtaccctga agctataact
1561 cgcctggtga cagggtccca gaggcccct gacccagctc ccacacccct ggggacctcg
1621 gggcttccca atggtctctc cggagatgaa gacttctcct ccattgcgga catggacttc
1681 tctgctcttt tgagtcagat cagctcctaa ggtgctgaca gcgaccctgc tcagagcacc
1741 aggtttcagg gcactgaagc cttcccgaag tgcgtacaca ttctggggag tgtgctccag
1801 ctgccccga cttgtttggg tgatctctct ggggcggcac gttttactct ttatctcgct
1861 ttcggaggtg ctttcgcagg agcattaacc tcctggagac ggagctggga ggactcggtg
1921 catccctgtg ttgatagctc ctgcttcggt agggaactct gagatcctgc ttccatctcc
1981 agcttctagc actctcctag agagggacag actggagcca tgccttaggc catatagcct
2041 tactatcaag tgtcttcctc cacgcggatt cctgtacacc ttgatccaaa gcagtgctcc
2101 caagagcagc tcctacgtgg tgctgcccga caccagcaca tgaggggccg ctcttctgtc
2161 ctgtggagct cctgccctgc cagctctcca tgctgagctg tggccaaggg gaacaggtgg
2221 gatgttgctg gccgccttca gaatcagggg gagtttagtc tgagacatcc ctgctccccc
2281 tttttttcaa gtgccttaat agcagggcaa actgtagagt caggagggca ggctagatgc
2341 tcagccacaa gacagccttt actgaaaaag ctattggact cttgctcttt ctagctctga
2401 actaataaat gtcttatcac gctg
```

Figure 22

MERPPGLRPGAGGPWEMRERLGTGGFGNVCLYQHRELDLKIAIK

SCRLELSTKNRERWCHEIQIMKKLNHANVVKACDVPEELNILIHDVPLLAMEYCSGGD

LRKLLNKPENCCGLKESQILSLLSDIGSGIRYLHENKIIHRDLKPENIVLQDVGGKII

HKIIDLGYAKDVDQGSLCTSFVGTLQYLAPELFENKPYTATVDYWSFGTMVFECIAGY

RPFLHHLQPFTWHEKIKKKDPKCIFACEEMSGEVRFSSHLPQPNSLCSLIVEPMENWL

QLMLNWDPQQRGGPVDLTLKQPRCFVLMDHILNLKIVHILNMTSAKIISFLLPPDESL

HSLQSRIERETGINTGSQELLSETGISLDPRKPASQCVLDGVRGCDSYMVYLFDKSKT

VYEGPFASRSLSDCVNYIVQDSKIQLPIIQLRKVWAEAVHYVSGLKEDYSRLFQGQRA

AMLSLLRYNANLTKMKNTLISASQQLKAKLEFFHKSIQLDLERYSEQMTYGISSEKML

KAWKEMEEKAIHYAEVGVIGYLEDQIMSLHAEIMGLQKSPYGRRQGDLMESLEQRAID

LYKQLKHRPSDHSYSDSTEMVKIIVHTVQSQDRVLKELFGHLSKLLGCKQKIIDLLPK

VEVALSNIKEADNTVMFMQGKRQKEIWHLLKIACTQSSARSLVGSSLEGAVTPQTSAW

LPPTSAEHDHSLSCVVTPQDGETSAQMIEENLNCLGHLSTIIHEANEEQGNSMMNLDW

SWLTE

Figure 23

```
   1 tcgacggaac ctgaggccgc ttgccctccc gccccatgga gcggcccccg gggctgcggc
  61 cgggcgcggg cgggccctgg gagatgcggg agcggctggg caccggcggc ttcgggaacg
 121 tctgtctgta ccagcatcgg gaacttgatc tcaaaatagc aattaagtct tgtcgcctag
 181 agctaagtac caaaaacaga gaacgatggt gccatgaaat ccagattatg aagaagttga
 241 accatgccaa tgttgtaaag gcctgtgatg ttcctgaaga attgaatatt ttgattcatg
 301 atgtgcctct tctagcaatg gaatactgtt ctggaggaga tctccgaaag ctgctcaaca
 361 aaccagaaaa ttgttgtgga cttaaagaaa gccagatact ttctttacta agtgatatag
 421 ggtctgggat tcgatatttg catgaaaaca aaattataca tcgagatcta aaacctgaaa
 481 acatagttct tcaggatgtt ggtggaaaga taatacataa aataattgat ctgggatatg
 541 ccaaagatgt tgatcaagga agtctgtgta catcttttgt gggaacactg cagtatctgg
 601 ccccagagct ctttgagaat aagccttaca cagccactgt tgattattgg agctttggga
 661 ccatggtatt tgaatgtatt gctggatata ggcttttttt gcatcatctg cagccattta
 721 cctggcatga gaagattaag aagaaggatc caaagtgtat atttgcatgt gaagagatgt
 781 caggagaagt tcggtttagt agccatttac ctcaaccaaa tagcctttgt agtttaatag
 841 tagaacccat ggaaaactgg ctacagttga tgttgaattg ggaccctcag cagagaggag
 901 gacctgttga ccttactttg aagcagccaa gatgttttgt attaatggat cacattttga
 961 atttgaagat agtacacatc ctaaatatga cttctgcaaa gataatttct tttctgttac
1021 cacctgatga aagtcttcat tcactacagt ctcgtattga gcgtgaaact ggaataaata
1081 ctggttctca agaacttctt tcagagacag gaatttctct ggatcctcgg aaaccagcct
1141 ctcaatgtgt tctagatgga gttagaggct gtgatagcta tatggtttat ttgtttgata
1201 aaagtaaaac tgtatatgaa gggccatttg cttccagaag tttatctgat tgtgtaaatt
1261 atattgtaca ggacagcaaa atacagcttc caattataca gctgcgtaaa gtgtgggctg
1321 aagcagtgca ctatgtgtct ggactaaaag aagactatag caggctcttt cagggacaaa
1381 gggcagcaat gttaagtctt cttagatata atgctaactt aacaaaaatg aagaacactt
1441 tgatctcagc atcacaacaa ctgaaagcta aattggagtt ttttcacaaa agcattcagc
1501 ttgacttgga gagatacagc gagcagatga cgtatgggat atcttcagaa aaaatgctaa
1561 aagcatggaa agaaatggaa gaaaaggcca tccactatgc tgaggttggt gtcattggat
1621 acctggagga tcagattatg tctttgcatg ctgaaatcat ggggctacag aagagcccct
1681 atggaagacg tcagggagac ttgatggaat ctctggaaca gcgtgccatt gatctatata
1741 agcagttaaa acacagacct tcagatcact cctacagtga cagcacagag atggtgaaaa
1801 tcattgtgca cactgtgcag agtcaggacc gtgtgctcaa ggagctgttt ggtcatttga
1861 gcaagttgtt gggctgtaag cagaagatta ttgatctact ccctaaggtg gaagtggccc
1921 tcagtaatat caaagaagct gacaatactg tcatgttcat gcagggaaaa aggcagaaag
1981 aaatatggca tctccttaaa attgcctgta cacagagttc tgcccgctct cttgtaggat
2041 ccagtctaga aggtgcagta accctcaga catcagcatg ctgcccccg acttcagcag
2101 aacatgatca ttctctgtca tgtgtggtaa ctcctcaaga tggggagact tcagcacaaa
2161 tgatagaaga aaatttgaac tgccttggcc atttaagcac tattattcat gaggcaaatg
2221 aggaacaggg caatagtatg atgaatcttg attggagttg gttaacagaa tga
```

Figure 24

MERPPGLRPGAGGPWEMRERLGTGGFGNVSLYQHRELDLKIAIK

SCRLELSSKNRERWCHEIQIMKKLDHANVVKACDVPEELNFLINDVPLLAMEYCSGGD

LRKLLNKPENCCGLKESQILSLLSDIGSGIRYLHENKIIHRDLKPENIVLQDVGGKTI

HKIIDLGYAKDVDQGSLCTSFVGTLQYLAPELFENKPYTATVDYWSFGTMVFECIAGY

RPFLHHLQPFTWHEKIKKKDPKCIFACEEMTGEVRFSSHLPQPNSLCSLIVEPMESWL

QLMLNWDPQQRGGPIDLTLKQPRCFALMDHILNLKIVHILNMTSAKIISFLLPCDESL

HSLQSRIERETGINTGSQELLSETGISLDPRKPASQCVLDGVRGCDSYMVYLFDKSKT

VYEGPFASRSLSDCVNYIVQDSKIQLPIIQLRKVWAEAVHYVSGLKEDYSRLFQGQRA

AMLSLLRYNANLTKMKNTLISASQQLKAKLEFFRKSIQLDLERYSEQMTYGISSEKML

KAWKEMEEKAIHYSEVGVIGYLEDQIMSLHTEIMELQKSPYGRRQGDLMESLEQRAID

LYKQLKHRPPDHLYSDSTEMVKIIVHTVQSQDRVLKELFGHLSKLLGCKQKIIDLLPK

VEVALSNIKEADNTVMFMQGKRQKEIWHLLKIACTQSSARSLVGSSLEGTVTPPVSAW

LPPTLADREHPLTCVVTPQDGETLAQMIEENLNCLGHLSTIIREANEDQSSSLMSLDW

SWLAE

Figure 25 (A)

```
   1 gggaccggcc ttagaccggc ggcgttgcct gaggcggctg gcgctcccgc cccatggagc
  61 ggcccccggg gctgcggccg ggcgcgggcg gcccctggga gatgcgggaa cggcttggca
 121 ccggcggttt cgggaacgtc agtctgtacc agcaccggga acttgatctc aaaatagcaa
 181 ttaagtcttg tcgtttagag ctaagttcca aaaacagaga gcgatggtgc catgaaatcc
 241 agatcatgaa aaagttggac catgcgaatg ttgtaaaggc ctgtgatgtc cctgaggaat
 301 tgaactttt aattaacgat gtgcctcttc tggcaatgga gtactgttct ggaggggacc
 361 tccggaagct actcaacaaa ccagaaaatt gttgtggact taaagaaagc cagatacttt
 421 ctttactgag tgacatagga tctgggatcc gatatctgca tgaaaacaaa attatacatc
 481 gagatctaaa acctgaaaat atagttcttc aagatgttgg tgggaagaca atacataaaa
 541 taattgattt gggttatgcc aaagatgttg atcaaggaag tctctgtaca tcttttgtgg
 601 gaacattgca gtatttggcc ccagagctct ttgaaaataa gccgtacaca gccactgtgg
 661 attattggag ctttgggacc atggtgtttg aatgtattgc tggatatagg ccttttttgc
 721 atcatctgca gccatttacc tggcatgaga agattaagaa gaaagatcca aagtgtatat
 781 ttgcatgtga agagatgact ggagaagttc ggtttagtag ccatttacct cagccaaaca
 841 gcctttgtag tttaatagta gagccaatgg aaagctggct ccaattgatg ctgaattggg
 901 acccacagca gagaggggga cctattgatc ttactttgaa gcagccaaga tgttttgcat
 961 taatggatca cattctcaat ttaaagatag tgcacatcct aaatatgact tctgcaaaaa
1021 tcatttctt tctgttacca tgtgatgaaa gtcttcattc actacagtct cgaattgagc
1081 gtgaaacagg aataaataca ggttctcagg agcttctgtc agagacaggg atttctctgg
1141 atcctcggaa accagcctct cagtgtgttc tagatggagt tagaggctgt gatagctaca
1201 tggtttattt gtttgataaa agtaagactg tatatgaagg accatttgca tccagaagtt
1261 tatctgattg tgtaaattat attgtacaag acagcaaaat acaactgcca attatacagc
1321 tgcggaaagt atgggctgaa gcagtgcact acgtatctgg gctaaaggaa gactacagca
1381 ggctcttcca gggacaaaga gcagcaatgt taagtcttct tagatataat gctaacttga
1441 caaaaatgaa gaatactttg atctcagcat cacagcaact caaagctaaa ttggagtttt
1501 ttcgaaaaag cattcagctt gacttggaga gatatagtga gcagatgact tatgggatat
1561 cttcagaaaa aatgttaaaa gcatggaaag aaatggaaga aaaggccatt cactattctg
1621 aggttggtgt cattggttat cttgaggatc aaattatgtc tttgcacact gaaatcatgg
1681 agctgcagaa gagcccctac ggacgacgcc agggagactt gatggagtct ctggagcagc
1741 gtgccattga tctctataag cagctaaagc acagacctcc tgatcacttg tacagcgaca
1801 gcacagagat ggtgaagatc atcgtgcaca ccgtgcagag tcaggaccgt gttctcaagg
1861 agctgttgg tcacctgagc aagttgttgg gctgcaagca gaagattatt gatctactcc
1921 ccaaggtgga agtggccctc agtaacatca agaagctgaa caatactgtc atgtttatgc
1981 agggaaagag gcagaaagaa atttggcacc tccttaaaat tgcctgtaca cagagttctg
2041 cccgctctct tgtaggatcc agtctagaag gcacagtaac ccctccagta tcagcatggc
2101 tgcccctac attagcagac cgtgaacatc ctctgacatg tgtggtaact cctcaagatg
2161 gagagacgtt agcacaaatg atagaagaaa atctgaactg tcttggccat ttaagtacta
2221 ttattcgtga agcaaatgag gaccagagca gtagtttgat gagtcttgat tggagttggt
2281 tagcagaatg actcgacact cgttcactgt cctggagcct acgaagctgt tttgtcattt
2341 actccaaagt catctttact tgctgaagcc attcctcact taccagtccg tgaggagatg
2401 gctgtgatcg gaaactacga gtgactttac aagcacagta gcttggtgtt ttgtttgttt
2461 ctaataatta tgatctctga acagatagaa ttttatagca aattagtgaa attaattatt
```

Figure 25 (B)

```
2521 cttttttaaca ccgcaactaa tgagggagat cattagtgac ctgcttatct tataaaattg
2581 gaaaaatact actactagtt tagctgatga aaaagataat cttctaaagg cctaaatttt
2641 cggcataagg cccaacatgg tattagtata caggaatgaa aaattcaccc agtgttcatt
2701 tgaagtaaag ttttatctat gggttttctg tggaagagac tgctgacaag taaaattgct
2761 cttcctgaag actaagccca gcctccttgt gttgctctca gcaagtgttc ttcatggcat
2821 cacatggagt cagatgaatc ccatctttaa tcacacattt aatagagtcc ttttcctgtg
2881 taagggttg gacttttgtg cctttgatat cagctgacca taatgaattg tgttgtgtgc
2941 tatatgtata tgtatttaag gtgtacattt aataatatca aagagaagat gcctgttaat
3001 ttataatgta tttgaaagtt gtattgtttt tgcatttgta aaaatgggtt acttgtttaa
3061 acaatctttt atgtcttgtc atacaaattc caaagggtct gcattccttt atctgtaatt
3121 acagtctcag aatccaagtt ctgaaaacaa ggtatctatt ctgatctgac actggatctg
3181 cttatcccat ttagtgtgaa tattcattga tttatgtgtt tgattattgg gatgtgctgc
3241 cacaggctct cttgaaggtt gatgtagtgt ggcgtatgca ctgaattacc tttctaaaat
3301 ctgaacagtt ctcattctga aacatctaga cttaagggtt tcagataaaa gactgcggtt
3361 ctctgcctta tgttaaataa cttagaagat gttattttgt ttgaaaaaat gtgaaatgct
3421 tttatattct agtttttcac tttgcatatt aaatgatttt aaaatt
```

Fig. 28
A.
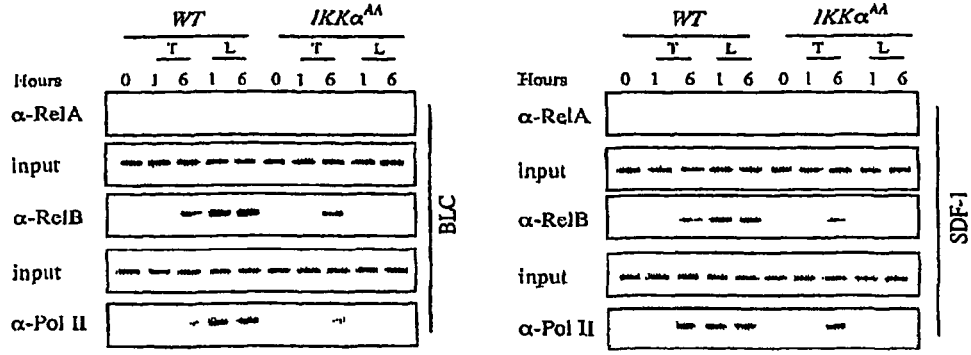
B.
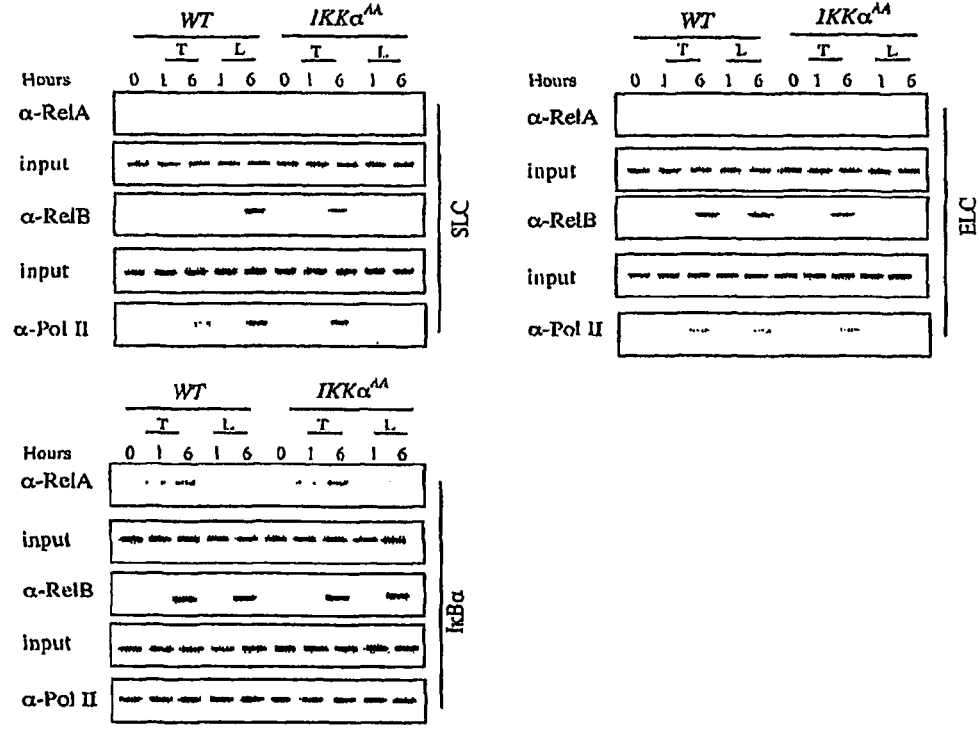

SEQ ID NO:124

5' ChIP primer
↓
GACAAATCTATAAATATTACTGAGCACCCAGCCTTAGCCTTCCCTTGCAAGGTGCC
AGGGACATAATGAAATGATGATGCTGTCGTCCTGTGTTCATAAAGCTATATTGAAACATAT
CGAAGAACTTGGCAGTCTTTTCACTATGAAAGTCATCAAAGCCACCATCACTTGTGGC
TTAACGTAAGCCATTTTTGCATCAATGCAAGCAAGGAAGAATGCCCTACATCCCTATA
CAGTTGGCATGCCATTGGTTCTTGGTTAAAAGGAACATAGGTGGGTTGAATGGCCATGACCA
AAACACTTCCTAAAGGTACCTTAGTGTGCGTCGCAGGGTTCAAGAGGGACTGCTCTGC
CTAGCCTATTCAGAACCTGGGTTCATCCTAGCACTAAAACACAGTCCTTGAGAGG
TTCTCCTCTTTTATTCACCCTGAGCATCCACGATCCTGACATTTTAATCTGAT
TTTAAGAAGTCTTTGTTATTACT AACACTGCCTCCAGGAAGATTCTAAATTTTGAA
GGGAATTTCTCTTCTGTAAGGCAGCCTCAGCCAATATTTTGGAGANTTGAAAAC
TAACATTGCACCTACAGTAAGAAGAGACAGGCCTAG TCGGAGGGCCCTGCTGGTAT ↓ 3' ChIP primer
GAGCTAAAGGTTGA

SEQ ID NO:125

AAATAAATACGACTCTGGACTCTGGAAATGCACCCACGAACTCC
ACTCCACCTCCAGGCAGAATG

B.

C.

| | | |
|---|---|---|
| Consensus-κB | 5' GGGACTTTCC 3' | SEQ ID NO:58 |
| BLC-κB | 5' GGGAGATTTG 3' | SEQ ID NO:59 |
| ELC-κB | 5' AGGAGATTTG 3' | SEQ ID NO:60 |
| VCAM-1-κB | 5' GGGATTTCCC 3' | SEQ ID NO:61 |

Figure 31

MSRDRFRSRGGGGGGFHRRGGGGGRGGLHDFRSPPPGMGLNQNR
GPMGPGPGQSGPKPPIPPPPPHQQQQQPPPQQPPPQQPPPHQPPPHPQPHQQQQPPPP
PQDSSKPVVAQGPGPAPGVGSTPPASSSAPPATPPTSGAPPGSGPGPTPTPPPAVTSA
PPGAPPPTPPSSGVPTTPPQAGGPPPPPAAVPGPGPGPKQGPGPGGPKGGKMPGGPKP
GGGPGLSTPGGHPKPPRRGGGEPRGGRQHHPPYHQQHHQGPPPGGPGGRSEEKISDSE
GFKANLSLLRRPGEKTYTQRCRLFVGNLPADITEDEFKRLFAKYGEPGEVFINKGKGF
GFIKLESRALAEIAKAELDDTPMRGRQLRVRFATHAAALSVRNLSPYVSNELLEEAFS
QFGPIERAVVIVDDRGRSTGKGIVEFASKPAARKAFERCSEGVFLLTTTPRPVIVEPL
EQLDDEDGLPEKLAQKNPMYQKERETPTRFAQHGTFEYEYSQRWKSLDEMEKQQREQV
EKNMKDAKDKLESEMEDAYHEHQANLLRQDLMRRQEELRRMEELHNQEMQKRKEMQLR
QEEERRREEEMMIRQREMEDQMRRQREESYSRMGYMDPRERDMRMGGGGAMNMGDPY
GSGGQKFPPLGGGGGIGYEANPGVPPATMSGSMMGSDMRTERFGQGGAGPVGGQGPRG
MGPGTPAGYGRGREEYEGPNKKPRF

Figure 32

```
   1 tctgtgtcat ccgccatttt gtgagaagca aggtggcctc cacgtttcct gagcgtcttc
  61 ttcgcttttg cctcgaccgc cccttgacca cagacatgtc tcgggatcgg ttccggagtc
 121 gtggcggtgg cggtggtggc ttccacaggc gtggaggagg cggcggccgc ggcggcctcc
 181 acgacttccg ttctccgccg cccggcatgg gcctcaatca gaatcgcggc cccatgggtc
 241 ctggcccggg ccagagcggc cctaagcctc cgatcccgcc accgcctcca caccaacagc
 301 agcaacagcc accaccgcag cagccaccgc cgcagcagcc gccaccgcat cagccgccgc
 361 cgcatccaca gccgcatcag cagcagcagc cgccgccacc gccgcaggac tcttccaagc
 421 ccgtcgttgc tcagggaccc ggccccgctc ccggagtagg cagcacacca ccagcctcca
 481 gctcggcccc gcccgccact ccaccaacct cggggccccc gccagggtcc gggccaggcc
 541 cgactccgac cccgccgcct gcagtcacct cggcccctcc cggggcgccg ccacccaccc
 601 cgccaagcag cggggtccct accacacctc ctcaggccgg aggcccgccg cctccgcccg
 661 cggcagtccc gggcccgggt ccagggccta agcagggccc aggtccgggt ggtcccaaag
 721 gcggcaaaat gcctggcggg ccgaagccag gtggcggccc gggcctaagt acgcctggcg
 781 gccaccccaa gccgccgcgt cgaggcggcg gggagccccg cggggccgc cagcaccacc
 841 cgccctacca ccagcagcat caccaggggc ccccgcccgg cgggcccggc ggccgcagcg
 901 aggagaagat ctcggactcg gaggggttta aagccaattt gtctctcttg aggaggcctg
 961 gagagaaaac ttacacacag cgatgtcggt tgtttgttgg aatctacct gctgatatca
1021 cggaggatga attcaaaaga ctatttgcta aatatggaga accaggagaa gtttttatca
1081 acaaaggcaa aggattcgga tttattaagc ttgaatctag agctttggct gaaattgcca
1141 aagccgaact ggatgataca cccatgagag gtagacagct tcgagttcgc tttgccacac
1201 atgctgctgc cctttctgtt cgtaatcttt caccttatgt ttccaatgaa ctgttggaag
1261 aagcctttag ccaatttggt cctattgaaa gggctgttgt aatagtggat gatcgtggaa
1321 gatctacagg gaaaggcatt gttgaatttg cttctaagcc agcagcaaga aaggcatttg
1381 aacgatgcag tgaaggtgtt ttcttactga cgacaactcc tcgtccagtc attgtggaac
1441 cacttgaaca actagatgat gaagatggtc ttcctgaaaa acttgcccag aagaatccaa
1501 tgtatcaaaa ggagagagaa accctactc gttttgccca gcatggcacg tttgagtacg
1561 aatattctca gcgatggaag tctttggatg aaatggaaaa acagcaaagg gaacaagttg
1621 aaaaaaacat gaaagatgca aaagacaaat tggaaagtga atggaagat gcctatcatg
1681 aacatcaggc aaatcttttg cgccaagatc tgatgagacg acaggaagaa ttaagacgca
1741 tggaagaact tcacaatcaa gaaatgcaga aacgtaaaga aatgcaattg aggcaagagg
1801 aggaacgacg tagaagagag gaagagatga tgattcgtca acgtgagatg gaagaccaaa
1861 tgaggcgcca aagagaggaa agttacagcc gaatgggcta catggatcca cgggaaagag
1921 acatgcgaat gggtggcgga ggagcaatga acatgggaga tccctatggt tcaggaggcc
1981 agaaattcc acctctagga ggtggtggtg gcataggtta tgaagctaat cctggcgttc
2041 caccagcaac catgagtggt tccatgatgg gaagtgacat gcgtactgag cgctttgggc
2101 agggaggtgc ggggcctgtg ggtggacagg tcctagagg aatgggcct ggaactccag
2161 caggatatgg tagagggaga gaagagtacg aagcccaaa caaaaaaccc cgattttaga
2221 tgtgatattt aggctttcat tccagtttgt tttgttttt tgtttagata ccaatctttt
2281 aaattcttgc attttagtaa gaaagctatc ttttatgga tgttagcagt ttattgacct
2341 aatatttgta aatggtctgt ttgggcaggt aaaattatgt aatgcagtgt ttggaacagg
2401 agaatttttt tttccttttt atttctttat tttttctttt ttactgtata atgtccctca
2461 agtttatggc agtgtacctt gtgccactga atttccaaag tgtaccaatt ttttttttt
2521 tactgtgctt caaataaata gaaaatagt tataaaaaa aaaaaaaaa aaaaaaaaa
2581 aaaaaaaaa aaaaaaaaa aaaaaaaaa aaaaaaaaa aa
```

Figure 33

```
  1 MSRDRFRSRG GGGGGFHRRG GGGGRGGLHD FRSPPPGMGL NQNRGPMGPG PGGPKPPLPP
 61 PPPHQQQQQP PPQQPPPQQP PPHQQPPPHQ PPHQQPPPPP QESKPVVPQG PGSAPGVSSA
121 PPPAVSAPPA NPPTTGAPPG PGPTPTPPPA VPSTAPGPPP PSTPSSGVST TPPQTGGPPP
181 PPAGGAGPGP KPGPGPGGPK GGKMPGGPKP GGGPGMGAPG GHPKPPHRGG GEPRGGRQHH
241 APYHQQHHQG PPPGGPGPRT EEKISDSEGP KANLSLLRRP GEKTYTQRCR LFVGNLPADI
301 TEDEFKRLFA KYGEPGEVFI NKGKGFGFIK LESRALAEIA KAELDDTPMR GRQLRVRFAT
361 HAAALSVRNL SPYVSNELLE EAFSQFGPIE RAVVIVDDRG RSTGKGIVEF ASKPAARKAF
421 ERCSEGVFLL TTTPRPVIVE PLEQLDDEDG LPEKLAQKNP MYQKERETPP RFAQHGTFEY
481 EYSQRWKSLD EMEKQQREQV EKNMKDAKDK LESEMEDAYH EHQANLLRQD LMRRQEELRR
541 MEELHSQEMQ KRKEMQLRQE EERRRREEEM MIRQREMEEQ MRRQREESYS RMGYMDPRER
601 DMRMGGGGTM NMGDPYGSGG QKFPPLGGGG GIGYEANPGV PPATMSGSMM GSDMRTERFG
661 QGGAGPVGGQ GPRGMGPGTP AGYGRGREEY EGPNKKPRF
```

Figure 34

```
   1 cttctgcctc gaccgccect tgactacagc tatgtctcgg gatcggttcc ggagtcgcgg
  61 tggcggcggt ggaggctttc accggcgtgg aggaggtggc ggccgcggcg gccttcacga
 121 cttccgctct ccgccgccgg gcatgggcct caaccagaac cgcggcccca tgggcccggg
 181 ccctggcggc ccgaagccgc cgctcccgcc tccacctcct caccagcagc agcagcagcc
 241 gccgccgcag cagcctccgc cgcagcagcc gccgccgcac cagcagccgc cgccgcacca
 301 gccgccccat caacagcccc cgcctccgcc gcaggaatcc aagcccgtcg tcccccaagg
 361 ccccggctcg gcgccggggg tgagcagtgc gcctccgccg gcggtctcgg ctccgcccgc
 421 caacccccg accaccggcg ccctccggg cctggtcca accccgactc cgccgcccgc
 481 cgtcccctcc accgccccg gaccgcctcc cccatcgacg ccgagcagcg gagtctcgac
 541 cacccctcca cagaccggcg gccctccgcc accgcccgcc ggggcgccg ggccggggcc
 601 taagccgggg ccaggccctg gcggtccaaa aggcggcaag atgcccggtg ggcctaagcc
 661 tggaggtggc ccgggcatgg gcgctcctgg tggccacccg aagccaccac accgaggtgg
 721 cggcgagccc cgtgggggcc ggcagcatca tgcgccctac caccagcagc accaccaggg
 781 gccccctccc ggcggaccgg gaccgcgcac ggaggagaag atctccgact cggagggatt
 841 taagccaac ttgtctctct tgcggaggcc tggagaaaaa acttacacac agcgctgtcg
 901 gttgtttgtg gggaatctac ctgctgatat cacagaggat gaattcaaaa gactgtttgc
 961 taaatacgga gaacccggag aagtttttat caacaaaggc aaagggttcg ggttcattaa
1021 gcttgaatct agagccttgg ctgaaatcgc caaagctgag cttgatgata ctcccatgag
1081 aggtagacag cttcgggttc gatttgccac acacgctgca gccctgtctg ttcgaaatct
1141 ctctccttat gtttccaacg aacttttgga agaggccttt agccagtttg gtcctattga
1201 aagggctgtt gtaattgtgg atgatcgcgg aagatctaca gggaaaggca ttgttgagtt
1261 tgcttccaag ccagcagcaa gaaaagcatt tgaaagatgc agtgaaggtg ttttcctact
1321 gacaacgact cctcgcccag tcattgtgga accacttgaa cagttagatg acgaagatgg
1381 tcttcctgaa aagctggccc agaagaatcc aatgtatcaa aaggagagag aaacaccacc
1441 tcgttttgct cagcatggca catttgagta tgaatattct caacgatgga agtccttgga
1501 tgaaatggaa aaacagcaaa gggaacaagt tgaaaaaaac atgaaggatg ctaaagacaa
1561 attggaaagt gaaatggaag atgcttacca tgaacaccaa gcaaatcttt tgcgccaaga
1621 tctgatgaga cgccaggaag aattaaggcg catggaggaa cttcacagtc aagaaatgca
1681 gaaacgtaaa gaaatgcagt tgaggcaaga ggaggaacgg cgtagacgag aggaagagat
1741 gatgattcgc caacgtgaga tggaagaaca aatgagacgc caacgagaag aaagttacag
1801 caggatgggc tacatggatc caagagaaag agacatgaga atgggtggtg gtggaacaat
1861 gaacatggga gatccctatg gttcaggagg ccagaaattt ccaccactag gtggtggtgg
1921 tggcataggt tatgaagcta atcctggagt tccaccagca accatgagtg gttccatgat
1981 gggaagcgac atgcgtactg agcgctttgg gcagggaggt gcgggtcctg tgggtggaca
2041 gggtcctaga ggaatgggc ctggaactcc agcaggatat ggtagaggga gagaagagta
2101 tgaagggcca aataaaaac cccgatttta gatatttagg ctttcattct agtttggttt
2161 tgtcttttct tgtttagata ccacttaaat tcttggcatt ttagtaagca agctaccttt
2221 ttatggatgt tagcagttta ttgacctgat atttgtaaat ggcctgtttg ggcaggtaaa
2281 attatgtaac gcagtgttca aaacaggaga aaaattttt tcatttactt tttttttaa
2341 ctgtataatg tttctcaagt taatggcagt gtaccttgtg ccaccgaatt tccaaagtgt
2401 accattttt ttttactgtg cttcaaataa atagaaaaaa tagttataaa aaaaaaaaaa
2461 aaaa
```

COMPOSITIONS AND METHODS FOR GENE EXPRESSION

This application is the U.S. National stage filing of PCT Application No. PCT/US2004/032246, filed Sep. 29, 2004, which claims priority to U.S. provisional Patent Application Ser. No. 60/508,349, filed on Oct. 1, 2003, now abandoned, each of which is herein incorporated by reference in its entirety.

This invention was made, in part, with government support under grant numbers AI43477, ES04151, ES06376, and ACA71871 awarded by the National Institutes of Health. The U.S. government has certain rights in the invention.

FIELD OF THE INVENTION

The invention relates to the field of nucleotide sequences that mediate one or more functions of IKKα.

A Sequence Listing has been submitted in an ASCII text file entitled "ucsd10835gtk09242010", created Sep. 24, 2010, consisting of 151,383 bytes, the entire content of which is herein incorporated by reference.

BACKGROUND

Proinflammatory cytokines and pathogen associated molecular patterns (PAMPs) activate a classical NF-κB signaling pathway. Upon activation there is inducible degradation of specific inhibitors, IκBs, that retain various NF-κB dimers in the cytoplasm (Ghosh et al. (2002) Cell, 109, S81-96). Alternatively, there is an NF-κB signaling pathway induced by IκB Kinase (IKK)α activation of RelB:p52 dimers that induce several chemokine genes (for example lymphotoxin β) needed for organization of secondary lymphoid organs. While the mechanisms of NF-κB activation are well understood (Ghosh et al. (2002) Cell, 109, S81-96), the generation of biological specificity by this complex system is more enigmatic (Pomerantz et al. (2002) Mol Cell, 10, 693-695).

In vivo analysis revealed that IKKα activates an alternative NF-κB pathway based on processing of NF-κB2/p100 and release of RelB:p52 dimers in response to LTα/β trimers (Dejardin et al. (2002) Immunity, 17, 525-535) and other TNF family members (Claudio et al. (2002) Nat Immunol, 3, 958-965; Kayagaki et al. (2002) Immunity, 17, 515-524). This pathway is required for secondary lymphoid organogenesis and induction of genes involved in this process, but has no apparent role in TNFα-induced functions (Dejardin et al. (2002) Immunity, 17, 525-535; Senftleben et al. (2001) Science, 293, 1495-1499). However, the mechanisms by which IKKα regulates cytokine-induced gene expression are obscure and controversial (Israel et al. (2003) Nature, 423, 596-597).

Therefore, it is important to know more about how RelB:p52 dimers are involved in induction of organogenic chemokines and other important regulatory molecules to activation of the alternative pathway for diseases associated with alterations in IKKα activity.

SUMMARY OF THE INVENTION

The invention provides nucleotide sequences that mediate one or more functions of IKKα, kits and methods for using these sequences to identify therapeutic compounds that alter IKKα related pathology.

The invention provides an isolated nucleotide sequence comprising 5'-NGGAGANNTG-3' (SEQ ID NO:57); wherein N at position 1 is chosen from G and A, N at position 7 is chosen from T and C, and N at position 8 is chosen from T and C, and wherein the isolated sequence specifically binds with a polypeptide sequence comprising SEQ ID NO:62. In one embodiment, binding with the polypeptide sequence increases transcription of a nucleic acid sequence of interest that is operably linked to 5'-NGGAGANNTG-3' (SEQ ID NO:57); wherein N at position 1 is chosen from G and A, N at position 7 is chosen from T and C, and N at position 8 is chosen from T and C. In another embodiment, the isolated nucleotide sequence does not bind a protein comprising one or more of RelB, RelA, p50, RelB:p50, RelA:p50, and RelA:p52. In another embodiment, the isolated nucleotide sequence does not bind one or more of RelB:Rel, RelA:RelA, p50:p50, RelB:p50, RelA:p50, and RelA:p52 dimers. In a further embodiment, the isolated nucleotide sequence comprises 5'-GGGAGATTTG-3' (SEQ ID NO:59). In yet another embodiment, the isolated nucleotide sequence comprises 5'-GGGAGACCTG-3' (SEQ ID NO:2). In an alternative embodiment, the isolated nucleotide sequence comprises 5'-AGGAGATTTG-3' (SEQ ID NO:60). In yet another embodiment, the isolated nucleotide sequence is a probe, enhancer, and/or promoter. In preferred embodiment, the promoter is chosen from one or more of Sdf-1 promoter, Blc promoter, Elc promoter, and Slc promoter. In another embodiment, the isolated nucleotide sequence is chosen from one or more of nonsense sequence, intron, and exon. In yet a further embodiment the polypeptide sequence comprises RelB. Preferably, the polypeptide sequence comprises RelB:p52.

Also provided is a method for identifying one or more test compounds that alters binding of RelB Rel homology domain RelB RHD) and/or RelB:p52 dimers with a RelBκB sequence, comprising: a) contacting i) the isolated nucleotide sequence of the invention with ii) a polypeptide comprising RelB RHD listed as SEQ ID NO:62 in the presence and absence of the one or more test compounds; and b) detecting altered specific binding of the nucleotide sequence with SEQ ID NO:62 in the presence of the one or more test compounds compared to in the absence of the one or more test compounds, and c) identifying the one or more test compounds as altering binding of RelB RHD and/or RelB:p52 dimers with a RelBκB sequence. In one embodiment, the method further comprises d) contacting the nucleotide sequence, in the presence of the one or more test compounds, with one or more compositions comprising a polypeptide that comprises RelB RHD listed as SEQ ID NO:62, wherein the composition is chosen from cell extract, cytoplasmic extract, and nuclear extract, wherein the composition is isolated from a mammalian cell comprising IKKα having reduced kinase activity compared to wild type IKKα, and wherein the mammalian cell is treated with one or more IKKα activators chosen from lymphotoxin B (LTβ), B cell activating factor belonging to the TNF family (BAFF), anti-LTβR antibody, and CD40 ligand (CD40L); and e) detecting unaltered specific binding of the isolated nucleotide sequence with the SEQ ID NO:62 in the presence and absence of the one or more test compounds. In one embodiment, the polypeptide comprising RelB RHD is recombinant. In another embodiment, the polypeptide comprising SEQ ID NO:62 is RelB and/or RelB:p52. In a further embodiment, the polypeptide comprising SEQ ID NO:62 is chosen from one or more of RelB and RelB:p52, and is isolated from a mammalian cell treated with one or more IKKα activators chosen from lymphotoxin B (LTβ), B cell activating factor belonging to the TNF family (BAFF), anti-LTβR antibody, and CD40 ligand (CD40L).

While not limiting the invention to any type or source of cell, in one embodiment, the mammalian cell is from a mammal chosen from human, and mouse. In one embodiment, the mammalian cell is in vivo and/or in vitro. The mammalian cell may be a primary cell and/or from a cell line.

In one embodiment, the method further comprises detecting unaltered binding of the isolated nucleotide sequence to a protein comprising one or more of RelA Rel homology domain (RelA RHD) listed as SEQ ID NO:65, RelA, p50, and RelA:p50, in the presence and absence of the one or more test compounds. Preferably, the polypeptide comprising one or more of RelA Rel homology domain (RelA RHD) comprising SEQ ID NO:65, RelA, p50, and RelA:p50 is recombinant. Alternatively, the polypeptide is chosen from one or more of RelA, p50 and RelA:p50, and is isolated from a cell treated with one or more IKKβ activators chosen from tumor necrosis factor α (TNFα), interleukin 1β (IL1β), and lipopolysaccharide (LPS).

In one embodiment, the method further comprises detecting unaltered binding of the isolated nucleotide sequence to one or more proteins chosen from a polypeptide comprising one or more of RelA RHD, RelA, p52, and RelA:p52, in the presence and absence of the one or more test compounds. Alternatively, the method further comprises detecting unaltered binding of the isolated nucleotide sequence to one or more proteins chosen from a polypeptide comprising one or more of RelB RHD, RelB, p50, and RelB:p50, in the presence and absence of the one or more test compounds. In yet another alternative, the method further comprises detecting unaltered binding of an isolated nucleotide sequence comprising the consensus-κB sequence 5'-GGGACTTTCC-3' (SEQ ID NO:58) to a polypeptide comprising one or more of RelB RHD listed as SEQ ID NO:62, and RelB in the presence of the one or more test compounds. In preferred embodiment, the method further comprises identifying the one or more test compounds as altering IKKα cellular activity and/or identifying the one or more test compounds as altering symptoms associated with IKKα related pathology.

While not limiting the invention to any method for detection, in one embodiment, the detecting comprises using an array, using electrophoretic mobility shift assay (EMSA), immunoprecipitation, ELISA, footprinting assay, reporter gene assay, and/or optical affinity biosensor system assay and the like. In one embodiment the detecting comprises using a plurality of reaction compartments. Preferably, each of the reaction compartments comprises one test compound. More preferably, the test compound in each of the reaction compartments is different from the test compound in other reaction compartments. In one embodiment, the plurality of reaction compartments comprises a micro-well titre plate. Alternatively, the plurality of reaction compartments comprises at least 48 or at least 96 of the reaction compartments.

Also provided by the invention is a method for identifying one or more test compounds that alters binding of RelB Rel homology domain (RelB RHD) with a RelBκB sequence, comprising: a) contacting i) the isolated nucleotide sequence of the invention, wherein SEQ ID NO:57 is operably linked to a nucleic acid sequence encoding a reporter molecule with ii) a polypeptide comprising RelB Rel homology domain (RelB RHD) listed as SEQ ID NO:62 such that the SEQ ID NO:62 specifically binds with SEQ ID NO:57, wherein the contacting is in the presence and absence of the one or more test compounds; b) detecting an altered level of expression of the reporter molecule in the presence of the one or more test compounds compared to in the absence of the one or more test compounds, thereby identifying the one or more test compounds as altering binding of RelB Rel homology domain (RelB RHD) with a RelBκB sequence. In one embodiment, the method further comprises: c) contacting the isolated nucleotide sequence, in the presence of the one or more test compounds, with one or more compositions comprising a polypeptide that comprises RelB RHD listed as SEQ ID NO:62, wherein the composition is chosen from cell extract, cytoplasmic extract, and nuclear extract, wherein the composition is isolated from a mammalian cell comprising non-activatable IKKα, and wherein the mammalian cell is treated with one or more IKKα activators chosen from lymphotoxin B (LTβ), B cell activating factor belonging to the TNF family (BAFF), anti-LTβR antibody, and CD40 ligand (CD40L); and d) detecting unaltered binding of the isolated nucleotide sequence with SEQ ID NO:62 in the presence and absence of the one or more test compounds.

In one embodiment, the method further comprises detecting unaltered binding of the isolated nucleotide sequence to one or more proteins chosen from a polypeptide comprising one or more of RelA RHD, RelA, p50, and RelA:p50, in the presence and absence of the one or more test compounds. In another embodiment, the method further comprises detecting unaltered binding of the isolated nucleotide sequence to one or more proteins chosen from a polypeptide comprising one or more of RelA RHD, RelA, p52, and RelA:p52, in the presence and absence of the one or more test compounds. In yet another embodiment, the method further comprises detecting unaltered binding of the isolated nucleotide sequence to one or more proteins chosen from a polypeptide comprising one or more of RelB RHD listed as SEQ ID NO:62, RelB, p50, and RelB:p50, in the presence and absence of the one or more test compounds. In a further comprising detecting unaltered binding of an isolated nucleotide sequence comprising the consensus-κB sequence 5'-GGGACTTTCC-3' (SEQ ID NO:58) to a polypeptide comprising one or more of RelB RHD listed as SEQ ID NO:62, and RelB in the presence of the one or more test compounds. In one embodiment, the method further comprises identifying the one or more test compounds as altering IKKα cellular activity and/or as altering symptoms associated with IKKα related pathology. In a further embodiment, the nucleic acid sequence of interest encodes a reporter molecule. Preferably, the reporter molecule is chosen from one or more of RNA and polypeptide. In one embodiment, the reporter molecule is chosen from one or more of luciferase, green fluorescent protein, β-galactosidase, human placental alkaline phosphatase, horseradish peroxidase, and chloramphenicol acetyltransferase.

The invention also provides a method for expression of a nucleic acid sequence of interest, comprising: a) providing: i) a cell comprising the isolated nucleotide sequence of the invention, wherein the SEQ ID NO:57 is operably linked to the nucleic acid sequence of interest; and ii) a polypeptide comprising RelB Rel homology domain (RelB RHD) listed as SEQ ID NO:62; b) contacting the cell with the polypeptide such that the SEQ ID NO:62 specifically binds with SEQ ID NO:57, and the nucleic acid sequence of interest is expressed.

Also provided herein is a test compound identified according to any of the invention's methods, such as using an array, using electrophoretic mobility shift assay (EMSA), immunoprecipitation, ELISA, footprinting assay, reporter gene assay, optical affinity biosensor system assay, and/or reporter gene assay and the like.

The invention additionally provides a method for altering symptoms of an IKKα related pathology comprising administering to a mammalian subject one or more compounds that alters binding of RelB Rel homology domain (RelB RHD) with a RelBκB sequence. In one embodiment, the method further comprises observing altered symptoms of the IKKα related pathology. In a preferred embodiment, the symptoms are reduced or increased. The method may comprise observing altered symptoms of the IKKα related pathology.

The invention provides a kit comprising the isolated nucleotide sequences of the invention. In one embodiment, the kit further comprising instructions for binding the isolated nucleotide sequence with a polypeptide comprising RelB RHD listed as SEQ ID NO:62.

BRIEF DESCRIPTION OF THE DRAWINGS

FIG. 1 shows that stromal cell-derived chemokine production requires IKKα. Panel (A) shows Impaired FDC maturation is inherent to the stroma of Ikkα$^{AA/AA}$ mice. Top panel: Cryosections of spleen from WT (n=6) and Ikkα$^{AA/AA}$ (n=6) mice, isolated 7 days post-immunization with SRBC, were stained for FDCs (arrows) with FDC-M2 (orange) and anti-B220 (green). Bottom panel: Lethally irradiated WT (n=6) or Ikkα$^{AA/AA}$ (n=6) mice were reconstituted with Ikkα$^{AA/AA}$ or WT bone marrow, respectively. Spleens were isolated and analyzed as above. An FDC network is present in WT mice reconstituted with Ikkα$^{AA/AA}$ bone marrow, while primarily peri-follicular rings of CD35$^+$ immature FDCs are present in Ikkα$^{AA/AA}$ reconstituted with WT bone marrow. Panel (B) shows impaired B/T cell segregation in Ikkα$^{AA/AA}$ spleens. Lethally irradiated WT (n=3) or Ikkα$^{AA/AA}$ (n=3) mice reconstituted with Ikkα$^{AA/AA}$ or WT bone marrow cells were immunized and analyzed as described herein. Impaired B/T cell segregation is intrinsic to the Ikkα$^{AA/AA}$ stroma. Panel (C) shows defective chemokine gene expression by Ikkα$^{AA/AA}$ spleens. Total splenocytes from naïve and SRBC-immunized (day 2) WT (n=3) and Ikkα$^{AA/AA}$ (n=3) mice were isolated. RNA was extracted and analyzed by real-time PCR for expression of mRNAs encoding BLC, SLC, ELC and SDF-1 and two of their receptors (CXCR5, CCR7). The results are averages±SD of three independent experiments normalized to the level of cyclophilin mRNA.

FIG. 7 shows the nucleotide sequence (SEQ ID NO:1) of the sdf-1 gene promoter. The sequence 5'-GGGAGACCTG-3' (SEQ ID NO:2) which binds to NFκ-B2/p52 is highlighted in bold.

FIG. 8 shows an exemplary amino acid sequence (SEQ ID NO:3) of human NFκ-B2 (p49/p100) (GenBank accession number NM 002502).

FIG. 9 shows an exemplary nucleotide sequence (SEQ ID NO:4) encoding human NFκ-B2 (p49/p100) (GenBank accession number NM 002502).

FIG. 10 shows an exemplary amino acid sequence (SEQ ID NO:5) of mouse NFκ-B2 (p49/p100) (GenBank accession number BC027423).

FIG. 11 shows an exemplary nucleotide sequence (SEQ ID NO:6) encoding mouse NFκ-B2 (p49/p100) (GenBank accession number BC027423).

FIG. 12 shows the 3' untranslated terminal repeat of an exemplary Rhesus monkey NFκ-B2 gene (SEQ ID NO:7) (GenBank accession number AY186590).

FIG. 13 shows an exemplary amino acid sequence (SEQ ID NO:8) of mouse RelB (GenBank accession number A42023).

FIG. 14 shows an exemplary amino acid sequence (SEQ ID NO:9) of mouse RelB (GenBank accession number M83380).

FIG. 15 shows an exemplary nucleotide sequence (SEQ ID NO:10) encoding mouse RelB (GenBank accession number M83380).

FIG. 16 shows an exemplary amino acid sequence (SEQ ID NO:11) of *Xenopus Laevis* RelB (GenBank accession number D63332).

FIG. 17 shows an exemplary nucleotide sequence (SEQ ID NO:12) encoding *Xenopus Laevis* RelB (GenBank accession number D63332).

FIG. 18 shows an exemplary amino acid sequence (SEQ ID NO:13) of mouse NFκ-B1, also known as p105 (GenBank accession number NM 008689), which is processed to p50 (SEQ ID NO: 123) (GenBank accession number NP_032715).

FIG. 19 shows an exemplary nucleotide sequence (SEQ ID NO:14) encoding mouse NFκ-B1, also known as p105, (GenBank accession number NM 008689), which is processed to p50 (SEQ ID NO:123) (GenBank accession number NP_032715).

FIG. 20 shows an exemplary amino acid sequence (SEQ ID NO:15) of mouse RelA (GenBank accession number M61909).

FIG. 21 shows an exemplary nucleotide sequence (SEQ ID NO:16) encoding mouse RelA (GenBank accession number M61909).

FIG. 22 shows an exemplary amino acid sequence (SEQ ID NO:17) (GenBank # AAC51671 and GenBank # AAC51671) of human IKKα.

FIG. 23 shows an exemplary nucleotide sequence (SEQ ID NO:18) (GenBank # AF009225) encoding human IKKα.

FIG. 24 shows an exemplary amino acid sequence (SEQ ID NO:19) (NIH # NP-031726) of mouse IKKα.

FIG. 25 shows an exemplary nucleotide sequence (SEQ ID NO:20) (NIH # NM-007700) of mouse IKKα.

FIG. 28 shows that IKKα is required for recruitment of RelB to the Blc, Sdf-1, Elc and Slc promoters. Primary cultures of stromal cells Panel (A) and bone marrow-derived dendritic cells (BMDC) (B) from WT and Ikkα$_{AA/AA}$ mice show that when left unstimulated or stimulated with TNFα (T) or anti-LTβR (L). At the indicated time points (hrs) the cells were collected and recruitment of RelA, RelB and the large subunit of RNA polymerase (Pol II) to the indicated promoter regions were examined by ChIP experiments.

FIG. 29 shows that The Blc and Elc promoters contain a unique κB site that is selectively recognized by RelB:p52 dimers.

Panel (A) shows an exemplary sequence of the 700 bp region covering the proximal Blc promoter, contained within the ChIP primer set. A RelB-selective κB site and the TATA box are highlighted. The sequence contained within Probe 1 is indicated by the brackets and is underlined. Panel (B) shows an exemplary DNA binding analysis. The different probes were incubated with two different amounts (250 and 500 ng) of the indicated NF-κB dimers and DNA binding was analyzed by EMSA. Note that the NP-κB subunits are not the full-length proteins, thus giving rise to complexes with different electrophoretic mobilities. Panel (C) shows exemplary sequences of the different κB sites used in these experiments.

Figure 30:
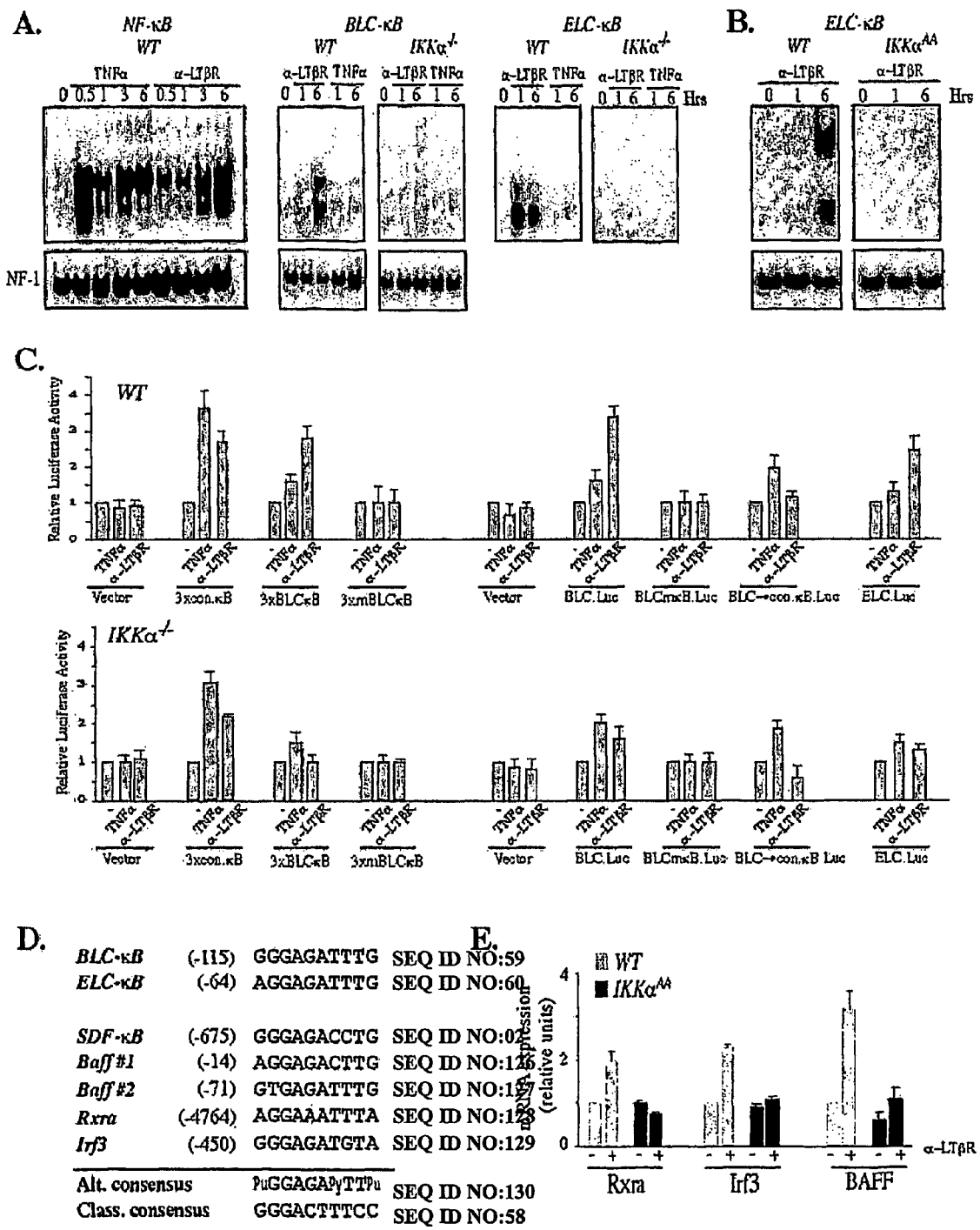

FIG. 30 shows that selective, IKKα-dependent, activation of the Blc and Elc promoters by LTβR engagement and IKKα-dependent induction of Rxra, Irf3 and Baff mRNAs. Panels (A-B) shows an exemplary engagement of LTβR selectively induces Blc-κB and Elc-κB binding activities. WT and IKKα-defective MEFs (A) and bone marrow-derived dendritic cells (BMDC) (B) were left unstimulated or stimulated with either TNFα or anti-LTβR for the indicated times. Nuclear extracts were prepared and incubated with $^{32}$P-labeled probes corresponding to the consensus κB site (NF-κB) or the Blc-κB and Elc-κB sites. DNA binding activity was analyzed by EMSA. NF-1 DNA binding activity was measured as an internal control. Panel (C) shows an exemplary functional analysis of the different κB sites in the Blc and Elc promoters. Triple repeats of the consensus κB (conκB), Blc-κB and a mutant Blc-κB (mBlc-κB) site were cloned upstream to a minimal SV40 promoter (pGL3-Promoter vector, Promega). In addition, the Blc (+12 to −688) and Elc (+530 to −320) promoter regions were cloned upstream to a luciferase reporter (pGL3-Basic vector, Promega). To determine the importance of the Blc-κB site, it was converted by site directed mutagenesis either to an inactive mutant version (mκB) or the consensus κB (conκB) site. The different plasmids were transfected into WT and Ikkα$^{-/-}$ MEFs. After 6 hrs with TNFα or anti-LTβR, luciferase activity was determined. The results are averages±SD of three independent experiments normalized to β-galactosidase activity produced by a cotransfected β-galactosidase expression vector. Panel (D) shows an exemplary alignment of novel κB sites from the control regions of IKKα-dependent genes. The novel κB sites from the Blc, Elc and Sdf-1 5' regulatory region were aligned with those identified by computer analysis in the regulatory regions of three other IKKα-dependent genes. These sites form a consensus sequence (Alt. consensus) that although similar is distinct from the one associated with the classical NF-κB pathway (Class. consensus). Panel (E) shows an exemplary IKKα-dependent induction of Baff, Rxra and Irf3. Expression of the indicated mRNAs was analyzed by Real Time-PCR as described above using RNA isolated from non-stimulated and anti-LTβR-stimulated stromal cells (Rxra and Irf3) and BMDCs (Baff) of the indicated genotypes.

FIG. 31 shows an exemplary amino acid sequence (SEQ ID NO:130) of human NFκ-B2 (p52/p100) (GenBank accession number P23246).

FIG. 32 shows an exemplary nucleotide sequence (SEQ ID NO:131) encoding human NFκ-B2 (p52/p100) (GenBank accession number BC051192).

FIG. 33 shows an exemplary amino acid sequence (SEQ ID NO:132) of mouse NFκ-B2 (p52/p100) (GenBank accession number NP_076092).

FIG. 34 shows an exemplary nucleotide sequence (SEQ ID NO:133) encoding mouse NFκ-B2 (p52/p100) (GenBank accession number NM_023603).

DEFINITIONS

To facilitate understanding of the invention, a number of terms are defined below.

The terms "purified," "to purify," "purification," "isolated," "to isolate," "isolation," and grammatical equivalents thereof as used herein, refer to the reduction in the amount of at least one contaminant from a sample. For example, a nucleotide sequence is purified by at least a 10%, preferably by at least 30%, more preferably by at least 50%, yet more preferably by at least 75%, and most preferably by at least 90%, reduction in the amount of undesirable proteins and/or undesirable nucleic acids, such as those present in a nuclear and/or cytoplasmic cell extract. Thus purification of a nucleotide sequence results in an "enrichment," i.e., an increase in the amount, of the nucleotide sequence in the sample.

As used in this specification and the appended claims, the singular forms "a," "an" and "the" includes both singular and plural references unless the content clearly dictates otherwise.

As used herein, the term "or" when used in the expression "A or B," where A and B refer to a composition, disease, product, etc., means one, or the other, or both.

The term "on" when in reference to the location of a first article with respect to a second article means that the first article is on top and/or into the second article, including, for example, where the first article permeates into the second article after initially being placed on it.

As used herein, the term "comprising" when placed before the recitation of steps in a method means that the method encompasses one or more steps that are additional to those expressly recited, and that the additional one or more steps may be performed before, between, and/or after the recited steps. For example, a method comprising steps a, b, and c encompasses a method of steps a, b, x, and c, a method of steps a, b, c, and x, as well as a method of steps x, a, b, and c. Furthermore, the term "comprising" when placed before the recitation of steps in a method does not (although it may) require sequential performance of the listed steps, unless the content clearly dictates otherwise. For example, a method comprising steps a, b, and c encompasses, for example, a method of performing steps in the order of steps a, c, and b, the order of steps c, b, and a, and the order of steps c, a, and b, etc.

Unless otherwise indicated, all numbers expressing quantities of ingredients, properties such as molecular weight, reaction conditions, and so forth as used in the specification and claims are to be understood as being modified in all instances by the term "about." Accordingly, unless indicated to the contrary, the numerical parameters in the specification and claims are approximations that may vary depending upon the desired properties sought to be obtained by the present invention. At the very least, and without limiting the application of the doctrine of equivalents to the scope of the claims, each numerical parameter should at least be construed in light of the number of reported significant digits and by applying ordinary rounding techniques. Notwithstanding that the numerical ranges and parameters describing the broad scope of the invention are approximation, the numerical values in the specific examples are reported as precisely as possible. Any numerical value, however, inherently contains standard deviations that necessarily result from the errors found in the numerical value's testing measurements.

The term "not" when preceding, and made in reference to, any particularly named molecule (such as RelA, RelB, mRNA, etc.) or phenomenon (such as biological activity, biochemical activity, etc.) means that the particularly named molecule or phenomenon is excluded, unless this term is defined differently. In particular, the term "does not bind to a protein" when made in reference to the binding of nucleotide sequence comprising the invention's RelBκB sequences (e.g., SEQ ID NO:57) is a relative term that means that the level of binding of the nucleotide sequence comprising the invention's RelBκB sequences (e.g., SEQ ID NO:57) to the protein is reduced by at least 5%, preferably at least 10%, more preferably at least 25%, yet more preferably at least 50%, further more preferably at least 75%, and most preferably at least 90%, relative to the level of binding of the nucleotide sequence comprising the invention's RelBκB sequences (e.g., SEQ ID NO:57) to a polypeptide sequence comprising SEQ ID NO:62. The term "does not bind to a protein" need not, although it may, mean an absolute absence of binding of the nucleotide sequence comprising the invention's RelBκB sequences (e.g., SEQ ID NO:57) with the protein. The invention does not require, and is not limited to nucleotides sequences that 100% do not bind with the protein.

The term "altering" and grammatical equivalents as used herein in reference to the level of any a substance (e.g., "RelB," "RelA," "p50," "RelB:50," "RelA:p50," "RelA:p52," "RelB RHD," "RelB DD," "Rel A RHD," and "Rel A DD," etc.) and/or phenomenon (e.g., binding, expression, transcription, enzyme activity, pain, etc.) refers to an increase and/or decrease in the quantity of the substance and/or phenomenon, regardless of whether the quantity is determined objectively, and/or subjectively.

The term "increase," "elevate," "raise," and grammatical equivalents when in reference to the level of a substance (e.g., "RelB," "RelA," "p50," "RelB:50," "RelA:p50," "RelA:p52," "RelB RHD," "RelB DD," "Rel A RHD," and "Rel A DD," etc.) and/or phenomenon (e.g., binding, expression, transcription, enzyme activity, pain, etc.) in a first sample relative to a second sample, mean that the quantity of the substance and/or phenomenon in the first sample is higher than in the second sample by any amount that is statistically significant using any art-accepted statistical method of analysis. In one embodiment, the increase may be determined subjectively, for example when a patient refers to their subjective perception of disease symptoms, such as pain, clarity of vision, etc. In another embodiment, the quantity of the substance and/or phenomenon in the first sample is at least 10% greater than the quantity of the same substance and/or phenomenon in a second sample. In another embodiment, the quantity of the substance and/or phenomenon in the first sample is at least 25% greater than the quantity of the same substance and/or phenomenon in a second sample. In yet another embodiment, the quantity of the substance and/or phenomenon in the first sample is at least 50% greater than the quantity of the same substance and/or phenomenon in a second sample. In a flier embodiment, the quantity of the substance and/or phenomenon in the first sample is at least 75% greater than the quantity of the same substance and/or phenomenon in a second sample. In yet another embodiment, the quantity of the substance and/or phenomenon in the first sample is at least 90% greater than the quantity of the same substance and/or phenomenon in a second sample.

The terms "reduce," "inhibit," "diminish," "suppress," "decrease," and grammatical equivalents when in reference to the level of a substance (e.g., "RelB," "RelA," "p50," "RelB:p50," "RelA:p50," "RelA:p52," "RelB RHD," "RelB DD," "Rel A RHD," and "Rel A DD," etc.) and/or phenomenon (e.g., binding, expression, transcription, enzyme activity, pain, etc.) in a first sample relative to a second sample, mean that the quantity of substance and/or phenomenon in the first sample is lower than in the second sample by any amount that is statistically significant using any art-accepted statistical method of analysis. In one embodiment, the reduction may be determined subjectively, for example when a patient refers to their subjective perception of disease symptoms, such as pain, clarity of vision, etc. In another embodiment, the quantity of substance and/or phenomenon in the first sample is at least 10% lower than the quantity of the same substance and/or phenomenon in a second sample. In another embodiment, the quantity of the substance and/or phenomenon in the first sample is at least 25% lower than the quantity of the same substance and/or phenomenon in a second sample. In yet another embodiment, the quantity of the substance and/or phenomenon in the first sample is at least 50% lower than the quantity of the same substance and/or phenomenon in a second sample. In a further embodiment, the quantity of the substance and/or phenomenon in the first sample is at least 75% lower than the quantity of the same substance and/or phenomenon in a second sample. In yet another embodiment, the quantity of the substance and/or phenomenon in the first sample is at least 90% lower than the quantity of the same substance and/or phenomenon in a second sample.

Reference herein to any specifically named protein (such as "RelB," "RelA," "p50," "RelB:p50," "RelA:p50," "RelA:p52," "RelB RHD," "RelB DD," "Rel A RHD," and "Rel A DD," etc.) refers to any and all equivalent fragments, fusion proteins, and variants of the specifically named protein having at least one of the biological activities (such as those disclosed herein and/or known in the art) of the specifically named protein, wherein the biological activity is detectably by any method. The term "fragment" when in reference to a protein refers to a portion of that protein that may range in size from four (4) contiguous amino acid residues to the entire amino acid sequence minus one amino acid residue. Thus, a polypeptide sequence comprising "at least a portion of an amino acid sequence" comprises from four (4) contiguous amino acid residues of the amino acid sequence to the entire amino acid sequence.

The term A "variant" of a protein as used herein is defined as an amino acid sequence which differs by insertion, deletion, and/or conservative substitution of one or more amino acids from the protein. The term "conservative substitution" of an amino acid refers to the replacement of that amino acid with another amino acid which has a similar hydrophobicity, polarity, and/or structure. For example, the following aliphatic amino acids with neutral side chains may be conservatively substituted one for the other: glycine, alanine, valise, leucine, isoleucine, serine, and threonine. Aromatic amino acids with neutral side chains which may be conservatively substituted one for the other include phenylalanine, tyrosine, and tryptophan. Cysteine and methionine are sulphur-containing amino acids which may be conservatively substituted one for the other. Also, asparagine may be conservatively substituted for glutamine, and vice versa, since both amino acids are amides of dicarboxylic amino acids. In addition, aspartic acid (aspartate) my be conservatively substituted for glutamic acid (glutamate) as both are acidic, charged (hydrophilic) amino acids. Also, lysine, arginine, and histidine may be conservatively substituted one for the other since each is a basic, charged (hydrophilic) amino acid. Guidance in determining which and how many amino acid residues may be substituted, inserted or deleted without abolishing biological and/or immunological activity may be found using computer programs well known in the art, for example, DNAStar™ software. In one embodiment, the sequence of the variant has at least 95% identity with the sequence of the protein in issue. In another embodiment, the sequence of the variant has at least 90% identity with the sequence of the protein in issue. In yet another embodiment, the sequence of the variant has at least 85% identity with the sequence of the protein in issue. In a further embodiment, the sequence of the variant has at least 80% identity with the sequence of the protein in issue. In yet another embodiment, the sequence of the variant has at least 75% identity with the sequence of the protein in issue. In another embodiment, the sequence of the variant has at least 70% identity with the sequence of the protein in issue. In another embodiment, the sequence of the variant has at least 65% identity with the sequence of the protein in issue.

Reference herein to any specifically named nucleotide sequence (such as 5'-NGGAGANNTG-3' (SEQ ID NO:57), etc.) includes within its scope any and all equivalent fragments, homologs, and sequences that hybridize under high and/or medium stringent conditions to the specifically named nucleotide sequence, and that have at least one of the biological activities (such as those disclosed herein and/or known in the art) of the specifically named nucleotide sequence, wherein the biological activity is detectably by any method. The "fragment" may range in size from an exemplary 6, 7, 8, and 9, contiguous nucleotide residues to the entire nucleic acid sequence minus one nucleic acid residue. Thus, a nucleic acid sequence comprising "at least a portion of" a nucleotide sequence comprises from six (6) contiguous nucleotide residues of the nucleotide sequence to the entire nucleotide sequence.

The term "homolog" of a specifically named nucleotide sequence refers to an oligonucleotide sequence which exhibits greater than or equal to 50% identity to the specifically named nucleotide sequence when sequences having a length of 8 bp or larger are compared. Alternatively, a homolog of a specifically named nucleotide sequence is defined as an oligonucleotide sequence which has at least 95%, at least 90%, at least 85%, at least 75%, at least 70%, or at least 65%, identity with the specifically named nucleotide sequence in issue.

With respect to sequences that hybridize under stringent condition to the specifically named nucleotide sequence, high stringency conditions comprise conditions equivalent to binding or hybridization at 68° C. in a solution containing 5×SSPE, 1% SDS, 5×Denhardt's reagent and 100 µg/ml denatured salmon sperm DNA followed by washing in a solution containing 0.1×SSPE, and 0.1% SDS at 68° C. when a probe of about 100 to about 1000 nucleotides in length is employed. "Medium stringency conditions" when used in reference to nucleic acid hybridization comprise conditions equivalent to binding or hybridization at 42° C. in a solution of 5×SSPE (43.8 g/l NaCl, 6.9 g/l NaH2PO4-H2O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 85% to 95% homology to the first nucleic acid sequence, then another hybridization condition is said to be equivalent to the hybridization condition of interest if this other hybridization condition also results in hybridization of the first nucleic acid sequence with the other nucleic acid sequences that have from 85% to 95% homology to the first nucleic acid sequence.

As will be understood by those of skill in the art, it may be advantageous to produce a nucleotide sequence encoding a protein of interest, wherein the nucleotide sequence possesses non-naturally occurring codons. Therefore, in some preferred embodiments, codons preferred by a particular prokaryotic or eukaryotic host (Murray et al., Nucl. Acids Res., 17 (1989)) are selected, for example, to increase the rate of expression or to produce recombinant RNA transcripts having desirable properties, such as a longer half-life, than transcripts produced from naturally occurring sequence.

The term "naturally occurring" as used herein when applied to an object (such as cell, etc.) and/or chemical (such as amino acid, amino acid sequence, nucleic acid, nucleic acid sequence, codon, etc.) means that the object and/or compound can be found in nature. For example, a naturally occurring polypeptide sequence refers to a polypeptide sequence that is present in an organism (including viruses) that can be isolated from a source in nature, wherein the polypeptide sequence has not been intentionally modified by man in the laboratory.

The term "chosen from A, B and C" means selecting one or more of A, B, and C.

A "composition comprising a particular nucleotide sequence" as used herein refers broadly to any composition containing the recited nucleotide sequence. The composition may comprise an aqueous solution containing, for example, salts (e.g., NaCl), detergents (e.g., SDS), and other components (e.g., Denhardt's solution, dry milk, salmon sperm DNA, etc.).

DESCRIPTION OF THE INVENTION

The invention provides nucleotide sequences that mediate one or more functions of IKKα, kits and methods for using these sequences to identify therapeutic compounds that alter IKKα related pathology. The present invention relates to compositions and methods of altering signal transduction of extracellular signals that is mediated by IKKα into specific patterns of gene expression and, thus, of altering IKKα-mediated gene expression in the cells in which it occurs.

IκB Kinase (IKK)α is required for activation of an alternative NF-κB signaling pathway based on processing of the NF-κB2/p100 precursor protein, which associates with RelB in the cytoplasm. This pathway, which leads to activation of RelB:p52 dimers, is required for induction of several chemokine genes needed for organization of secondary lymphoid organs. We investigated why induction of these genes in response to engagement of the lymphotoxin β receptor (LTβR) is selectively dependent on the alternative NF-κB signaling pathway. Using chromatin immunoprecipitation, data herein shows that the promoters of these exemplary genes are recognized by RelB:p52 dimers and not RelA:p50 dimers, the ubiquitous target for the classical NF-κB signaling pathway. Furthermore, data herein demonstrates the identification in these exemplary promoters of a novel type of NF-κB binding site that is preferentially recognized by RelB:p52 dimers. This site links induction of organogenic chemokines to activation of the alternative pathway.

Figure 6:
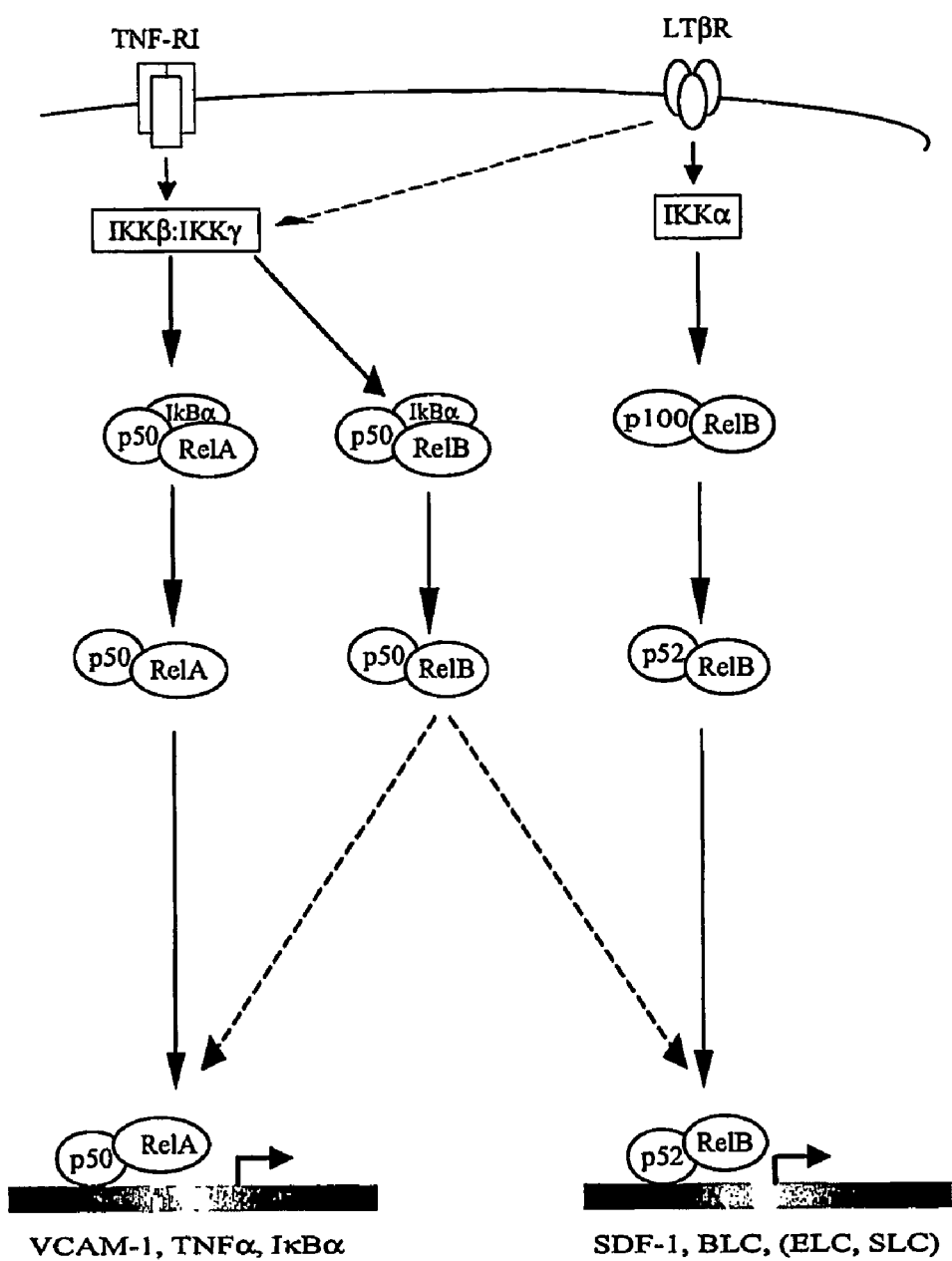
FIG. 6 shows an exemplary model explaining selective gene activation by the two NF-κB signaling pathways. Engagement of TNF-R1 results in activation of the canonical NF-κB signaling pathway which depends on IKKβ and IKKγ. This pathway leads to degradation of IκB and presence of RelA:p50 and RelB:p50 dimers in the nucleus. RelA:p50, and to a lesser extent RelB:p50, are recruited and lead to activation of the Vcam-1, Tnfα and IκBα genes. The RelA:p50 dimer is essentially not recruited to the Sdf-1, Blc, Slc and Elc promoters. By contrast, engagement of LTβR results in robust activation of the alternative pathway which depends on IKKα. This pathway leads to processing of p100 and the nuclear translocation of RelB:p52 dimers. These dimers are recruited to the Sdf-1, Blc, Slc and Elc promoters leading to their activation. LTβR engagement can also lead to modest activation of the canonical pathway with all of its sequalae. RelB:p50 dimers may make a small contribution to activation of both classes of genes.

Two distinct pathways leading to selective activation of RelA:p50 and RelB:p52 dimers, dependent on IKKβ or IKKα, respectively, were identified (S. Ghosh, M. Karin, Cell 109, S81-96 (2002)). Each pathway has distinct biological functions (Q. Li, D. Van Antwerp, F. Mercurio, K.-F. Lee, I. M. Verma, Science 284, 321-325 (1999); L.-W. Chen et al., Nat Med 9, 575-581 (2003); U. Senftleben et al., Science 293, 1495-1499 (2001)), that could be mediated in part through selective gene activation (E. Dejardin et al., Immunity 17, 525-535 (2002)). How this occurs was previously unknown. Data herein shows in two different cell types, splenic stromal cells and BMDC, that IKKα is required for induction of four genes encoding chemokines critical for organogenesis of the spleen and maintenance of its microarchitecture because these genes are selectively recognized by RelB-containing dimers, most likely RelB:p52 (FIG. 6). These genes are preferentially activated by engagement of LTβR and are weakly responsive to TNFα. Whereas the induction by TNFα of these and other genes is IKKα-independent, the response to LTβR engagement is strictly IKKα-dependent, because of two events. First, RelB:p52 dimers have to enter the nucleus, a process dependent on IKKα-mediated p100 processing (E. Dejardin et al., Immunity 17, 525-535 (2002); Z. B. Yilmaz, D. S. Weih, V. Sivakumnar, F. Weih, Embo J 22, 121-130 (2003)). Second, RelB:p52 dimers are selectively recruited to the IKKα-dependent gene promoter. The selective recruitment of RelB to the Blc and the Elc promoters is likely to depend on a novel κB site that is much more effectively recognized by RelB:p52 in comparison to RelA:p50 or even RelB:p50. It is the inventors' consideration that this unique specificity of RelB:p52 dimers is entirely consistent with sequence differences between the DNA binding loops of RelA and RelB, but was previously unknown (G. Ghosh, G. Vanduyne, S. Ghosh, P. B. Sigler, Nature 373, 303-310 (1995)). The inventors also consider that additional factors may contribute to selective IKKα-dependent gene activation and that IKKα may also be responsible in certain cell types for activation of the canonical NF-κB pathway (Y. Cao et al., Cell 107, 763-775 (2001)) or for potentiating its ability to activate transcription (A. Israel, Nature 423, 596-597 (2003); Y. Yamamoto et al., Nature 423, 655-659 (2003); V. Anest et al., Nature 423, 659-63 (Jun. 5, 2003)). Nonetheless, the major mechanism responsible for selective gene activation through the IKKα-dependent alternative NF-κB signaling pathway is based on specific recruitment of RelB:p52 dimers to target gene promoters.

Without intending to limit the invention to any particular mechanism, and while an understanding of mechanism is not required, it is the inventors' consideration that the functional separation between the two NF-κB signaling pathways optimizes adaptive immunity through proper organization of secondary lymphoid organs. By contrast, IKKβ is mostly involved in inflammatory and innate immune responses. Thus IKKβ-mediated NF-κB signaling is responsible for rapid responses to infection and injury, that require recruitment of immune cells out of lymphoid organs to sites of infection. This response depends on pro-inflammatory chemokines, such as MIP-1, MCP-1 and RANTES, which are induced by the canonical NF-κB signaling pathway (E. Alcamo et al., J Immunol 167, 1592-1600 (2001)) (Hoffman, A. et al., personal communication). The arrival of antigens to secondary lymphoid tissues from distal sites of infection and its processing, presentation and recognition require coordinated activity of DC, macrophages, T cells and B cells, whose recruitment to secondary lymphoid organs depends on IKKα-regulated organogenic chemokines. Premature expression of such chemokines would compromise the immediate anti-microbial response as it may abort the emigration of immune cells to the periphery. It is, therefore, the inventors' view that the genes for organogenic chemokines are not activated by the canonical NF-κB signaling pathway. Consistent with its delayed function in adaptive immunity, activation of the alternative, IKKα-dependent, NF-κB signaling pathway is slower than activation of the canonical NF-κB signaling pathway and may depend on prior activation of the latter (E. Dejardin et al., Immunity 17, 525-535 (2002)). The dependence of the two pathways on distinct but related protein kinases and transcription factors allows for both functional integration and kinetic separation.

To facilitate understanding of the invention, the invention is further described under (A) The NFκB signalling pathways, (B) IKKα and the generation of biological specificity, (C) The biological functions of IKKα and RelB:p52, (D) Target DNA sequences for NFκ-B2/p52, (ED) Methods for identifying test compounds that alter RelB DNA-binding activity, (F) Detection of specific binding, and screening test compounds, using arrays, (G) Detection of specific binding, and screening test compounds, using electrophoretic mobility shift (EMS) assays, (H). Detection of specific binding, and screening test compounds, using footprinting Assays, (I) Detection of specific binding, and screening test compounds, using reporter gene assays, (J) Detection of specific binding, and screening test compounds, using optical affinity biosensor system assays, (K) Methods for expressing a nucleic acid sequence of interest, (L) Methods of altering symptoms of diseases associated with IKKα pathology, (M) Kits, and (O) Additional considerations.

A. The NFκB Signalling Pathways

The mechanisms responsible for selective gene activation by closely related transcription factors, which lie downstream to different members of the same cell surface receptor family, remain largely unsolved and represent a major problem in the molecular biology of signal transduction. The NF-κB family of transcription factors represents one such case. This family consists of five subunits: RelA, c-Rel, RelB, NF-κB1/p50 and NF-κB2/p52, that form more than a dozen dimers (Ghosh et al. (1998) Ann Rev Immunol 16, 225-260). In vitro these dimers appear to recognize DNA binding sites, including a KB site (Huxford et al. (1999) Cold Spring Harb Symp Quant Biol 64, 533-540; Attar et al. (1997) Semin Cancer Biol 8, 93-101; Gerondakis et al. (1999) Oncogene 18, 6888-6895; Sanjabi et al. (2000) Proc Natl Acad Sci USA 97, 12705-12710). How each NF-κB dimer selectively activates distinct set of genes is not clear and it seems to be a general problem applicable to other families of closely related transcription factors that serve as nuclear targets for signals emanating at cell surface receptors (Massague et al. (2000) Cell 103, 295-309).

One step towards explanation of biological specificity in the NF-κB response entailed the description of two distinct NF-κB signaling pathways. The canonical NF-κB signaling pathway, which is activated by proinflammatory cytokines and pathogen associated molecular patterns (PAMPs), depends on inducible degradation of specific inhibitors, IκBs, which retain most NF-κB dimers in the cytoplasm (reviewed by Ghosh and Karin, 2002; Ghosh et al. (2002) Cell, 109, S81-96). This pathway is largely dependent on IKKβ, a catalytic subunit of a complex that also contains the IKKα catalytic subunit and the IKKγ/NEMO regulatory subunit (reviewed by Rothwarf and Karin, 1999; Ghosh et al. (1998) Ann Rev Immunol, 16, 225-260). In this pathway, IKKβ phosphorylates IκBs at N-terminal sites to trigger their ubiquitin-dependent degradation and subsequent nuclear entry of NF-κB dimers, which mostly contain RelA and c-Rel, as the transcription activating subunits (reviewed by Ghosh and Karin, 2002; Karin et al. (2000) Annu Rev Immunol, 18, 621-663).

A second, alternative NF-κB activation pathway based on regulated processing of the NF-κB2/p100 precursor protein was also described (Senftleben et al. (2001a) Science 293, 1495-1499; Xiao et al. (2001) Mol Cell 7, 401-409). NF-κB2/p100 contains an N-terminal Rel homology domain (RHD), common to all NF-κB proteins, and an inhibitory IκB-like C-terminal domain (Ghosh et al. (1998) Ann Rev Immunol 16, 225-260). The presence of the latter prevents nuclear translocation of p100 and its partners. The preferred cytoplasmic partner for p100 is RelB (Solan et al. (2002) J Biol Chem 277, 1405-1418). Overexpression of the protein kinase NIK causes ubiquitin-dependent degradation of the p100 C-terminal domain and release of mature NF-κB2/p52, which contains the N-terminal RHD (Xiao et al. (2001) Mol Cell 7, 401-409). This process depends on IKKα, which directly phosphorylates p100 in vitro at sites required for its processing, but does not require IKKβ (Senftleben et al. (2001a) Science 293, 1495-1499) or IKKγ (Claudio et al. (2002) Nat Immunol 3, 958-965; Yilmaz et al. (2003) EMBO J 22, 121-130) Dejardin et al. (2002) Immunity 17, 525-535). NF-κB2/p100 processing promotes the nuclear translocation of RelB (Dejardin et al. (2002) Immunity 17, 525-535; Solan et al.

(2002) J Biol Chem 277, 1405-1418). Recently, this pathway was found to be selectively activated by certain members of the TNF cytokine family, including lymphotoxin (LT) $\alpha_1:\beta_2$ trimers acting through LTβ receptor (LTβR), B cell activating factor (BAFF; also known as Blys/TALL-1/THANK and B cell activating factor belonging to the TNF family) acting through BAFF-R and CD40 ligand (CD40L) whose receptor is CD40 (Claudio et al. (2002) Nat Immunol 3, 958-965; Cooper et al. (2002) EMBO J 21, 5375-5385; Dejardin et al. (2002) Immunity 17, 525-535; Kayagaki et al. (2002) Immunity 17, 515-524; Yilmaz et al. (2003) EMBO J 22, 121-130).

IKKα and IKKβ, activate at least a dozen NF-κB dimers, composed of five subunits (S. Ghosh, M. Karin, (2002) Cell, 109, S81-96). While the mechanisms of NF-κB activation are well understood (S. Ghosh, M. Karin, (2002) Cell, 109, S81-96), the generation of biological specificity by this complex system is more enigmatic (J. L. Pomerantz, D. Baltimore, *Mol Cell* 10, 693-695 (2002)). Mouse mutagenesis experiments indicate that IKKβ activates the classical NF-κB pathway, represented by RelA:p50 dimers, in response to stimuli such as tumor necrosis factor (TNF)α (Li et al. (1999) Science, 284, 321-325 and Chen et al. (2003) Nat Med, 9, 575-581). The mechanisms by which IKKα regulates cytokine-induced gene expression are more obscure and controversial (Israel et al. (2003) Nature, 423, 596-597). In vivo analysis revealed that IKKα activates an alternative NF-κB pathway based on processing of NF-κB2/p100 and release of RelB:p52 dimers (U. Senftleben et al., *Science* 293, 1495-1499 (2001)) in response to LT α/β trimers (Dejardin et al. (2002) Immunity, 17, 525-535) and other TNF family members (Claudio et al. (2002) Nat Immunol, 3, 958-965; Kayagaki et al. (2002) Immunity, 17, 515-524). This pathway is involved in secondary lymphoid organogenesis and induction of genes involved in this process, but has no apparent role in TNFα-induced functions (Dejardin et al. (2002) Immunity, 17, 525-535; Senftleben et al. (2001) Science, 293, 1495-1499). We used mice in which IKKα was rendered inactivateable (Cao et al. (2001) Cell, 107, 763-775) to study the mechanism responsible for selective gene induction by the alternative NF-κB signaling pathway. Using primary cultures of splenic stromal cells, myeloid dendritic cells, and bone marrow-derived myeloid dendritic cells (BMDCs) we found that generation of gene induction specificity by IKKα depends on selective activation of RelB:p52 dimers, which recognize a unique type of NF-κB binding sites. This novel cis element is responsible for rendering the induction of chemokines involved in secondary lymphoid organogenesis IKKα-dependent.

IKKα plays a role in proper compartmentalization of the spleen, germinal center (GC) formation and development of other secondary lymphoid organs (Kaisho et al. (2001) J Exp Med 193, 417-426; Senftleben et al. (2001a) Science 293, 1495-1499). Lethally irradiated mice reconstituted with IKKα-deficient hematopoietic stem cells lack GCs and marginal zone macrophages and exhibit reduced B cell maturation, suggesting that IKKα acts within hematopoietic derivatives (Kaisho et al. (2001) J Exp Med 193, 417-426; Senftleben et al. (2001a) Science 293, 1495-1499). Indeed, loss of IKKα activity interferes with p100 processing in B cells, without affecting activation of the canonical NF-κB pathway (Senftleben et al. (2001a) Science 293, 1495-1499). As B cells play a role in inducing mature follicular dendritic cell (FDC) networks and the latter in turn play a role in GC formation (Cyster et al. (2000) Immunol Rev 176, 181-193; Fu et al. (1999) Annu Rev Immunol 17, 399-433), it is not clear whether the defects in spleen development and organization are secondary to the B cell autonomous function of IKKα or reflect a role for IKKα in other compartments. Similar defects are also displayed by Nfkb2$^{-/-}$ and RelB$^{-/-}$ mice. Furthermore, whereas two of the receptors whose activation leads to p100 processing, BAFF-R and CD40, are expressed on B cells, the third receptor, LTβR, is expressed on stromal cells of secondary lymphoid organs (Fu et al. (1999) Annu Rev Immunol 17, 399-433). LTβR signaling is involved in stromal cell function and Ltbr$^{-/-}$ mice exhibit defective development of secondary lymphoid organs (Fu et al. (1999) Annu Rev Immunol 17, 399-433).

Injection of agonistic anti-LTβR antibody into wild type (WT) and Ikkα$^{AA/AA}$ mice, which express a non-activatable form of IKKα (Cao et al. (2001) Cell 107, 763-775), revealed interesting changes in gene expression within the spleen. Certain genes, such as those encoding chemokines SLC/CCL21, ELC/CCL19, BLC/CXCL13 and SDF-1/CXCL12, were induced in WT but not the Ikkα$^{AA/AA}$ spleen, whereas other genes, such as Vcam-1, Mip-1β and Mip-2, were more efficiently induced in the Ikkα$^{AA/AA}$ spleen (Dejardin et al. (2002) Immunity 17, 525-535). Although these differences in gene expression were correlated with defective LTβR-induced p100 processing, the molecular basis for this gene induction pattern was not determined. Moreover the target cell type(s) in which these genes are differentially expressed have not been identified. This is of importance since the chemokines whose induction is IKKα-dependent control many of the critical cell-cell interactions and cell migration patterns involved in morphogenesis of the spleen and other secondary lymphoid organs (Ansel et al. (2001) Curr Opin Immunol 13, 172-179; Kim et al. (1999) J Leukoc Biol 65, 6-15).

The inventors further investigated the mechanisms responsible for the IKKα-dependent induction of the Slc, Elc, Blc, and Sdf-1 genes, as they offer an excellent model system for understanding the basis for the different biological functions and target gene specificity of the two NF-κB activation pathways (Pomerantz et al. (2002) Mol Cell 10, 693-695). The inventors first identified the exemplary cells in which IKKα activity plays a role in induction of these genes as the stromal cells of the spleen, where they are directly induced in response to LTβR engagement. Next, the inventors found that at least two of the four chemokine gene promoters are directly recognized by RelB-containing, but not by RelA-containing, NF-κB dimers. Recruitment of RelB to these promoters correlates with their transcriptional activation. Furthermore, at least one of these promoters contains a novel κB site that is selectively recognized by RelB:p52 dimers. While an understanding of the mechanism of the invention is not necessary, and without limiting the invention to any particular mechanism, data herein shows that the IKKα provides receptor selectivity for the RelB-dependent response; in this case it allows its activation by LTβR but not by the related type 1 TNFα receptor (TNFR1). Further, data herein shows that IKKα provides RelB with the proper heterodimeric partner, which is p52 rather than p50. Nuclear translocation of RelB in the absence of p52, brought about by TNFα is not sufficient for rapid activation of the IKKα-dependent chemokine genes in stromal cells. Thus, in cells where its amounts are limiting, RelB activates specific target genes when complexed with p52.

B. IKKα and the Generation of Biological Specificity

The NF-κB family consists of five subunits, forming more than a dozen different dimers. Each family member may activate distinct target genes in addition to a common gene set. How this specificity and diversity is established has not, heretofore, been clear. While an understanding of the mechanism of the invention is not necessary, and without intending to limit the invention to any mechanism, it is the inventors view that IκB kinase α (IKKα) activates an alternative NF-κB pathway by inducing processing of NF-κB2/p100 and release of RelB:p52 dimers. This pathway is selectively activated in splenic stromal cells after lymphotoxin β receptor engagement causing activation of specific genes, required for maintenance of splenic microarchitecture. At least two of these genes are selectively recognized in vivo by RelB-containing dimers but not by RelA-containing dimers. Data herein shows that IKKα provides the specificity for this response both by allowing its selective activation by certain cell surface receptors and not others, and by providing RelB with the proper heterodimeric partner, p52, leading to recognition of unique DNA sites.

It is the inventors' view that two distinct pathways lead to activation of NF-κB transcription factors. The canonical pathway depends on the IKKβ catalytic subunit of the IKK complex which targets IκB proteins to degradation. This pathway activates classical NF-κB dimers, the most common of which is the RelA:p50 heterodimer (Ghosh et al. (2002) Cell 109, S81-96). The second pathway, termed the alternative pathway, depends on the IKKα catalytic subunit, acting in isolation from IKKβ or IKKγ/NEMO, IKKα targets the NF-κB2/p100 precursor protein to proteolytic processing, leading to activation of RelB:p52 dimers (Ghosh et al. (2002) Cell 109, S81-96). Mutational analysis in mice indicated that the two pathways have distinct biological functions (Li et al. (1999a) Science 284, 321-325; Li et al. (1999b) J Exp Med 189, 1839-1845; Senftleben et al. (2001a) Science 293, 1495-1499; Senftleben et al. (2001b) Immunity 14, 217-230) and even provided preliminary evidence that they may activate distinct target genes (Dejardin et al. (2002) Immunity 17, 525-535). The ability of both pathways to be activated within the same cell in response to engagement of a single receptor, for instance the LTβR, each leading to induction of a distinct gene set has raised questions regarding the mechanism responsible for target gene specificity (Pomerantz et al. (2002) Mol Cell 10, 693-695). In fact, how activation of structurally related transcription factors within the same cell results in activation of distinct target genes leading to different biological responses, is a general question that applies to many signal transduction pathways involved in gene regulation. Data herein shows the ability of the alternative NF-κB signaling pathway to selectively activate a set of target genes that are not responsive to the canonical pathway.

Data herein shows that IKKα provides target gene specificity at two levels. First, it allows RelB:p52 dimers to be activated in response to engagement of certain members of the TNFR family. As shown here, RelB and p52 are simultaneously present in nuclei of fibroblasts or stromal cells after engagement of LTβR but not after occupancy of TNFR1. Second, IKKα provides RelB with the proper heterodimeric partner: p52 instead of p50. As shown above, RelB:p52 dimers interact more effectively with the Blc κB site than RelB:p50 dimers. Nevertheless, this selectivity, as discussed below, is not absolute. The second function was surprising as it was thought that RelB nuclear translocation is tightly linked to processing of p100, with which RelB associates in the cytoplasm (Dejardin et al. (2002) Immunity 17, 525-535; Solan et al. (2002) J Biol Chem 277, 1405-1418). Furthermore, it was believed that RelB:p52 dimers are not different in their sequence selectivity from RelA:p50 or RelB:p50 dimers. Thus the sole role of IKKα was thought to be induction of RelB nuclear entry via processing of p100 dimers. We found, however, that stimulation of either MEFs or splenic stromal cells with TNFα results in effective nuclear translocation of RelB in the absence of p100 processing. Nevertheless, TNFα does not lead to as efficient recruitment of RelB-containing dimers to the IKKα-dependent target genes as anti-LTβR does. The delayed and weak recruitment of RelB to the Blc and Sdf-1 promoters (exemplary sequence in FIG. 7) after TNFα stimulation is likely to be due to the formation of RelB:p50 dimers, whose concentration may be sufficiently high several hrs after TNFR1 engagement. By contrast, the more rapid and robust recruitment of RelB to the same promoters seen after stimulation of LTβR is likely to be due to formation of RelB:p52 dimers. As RelB:p52 dimers bind more effectively to the type of κB site present in the Blc promoter, their effective concentration does not need to be as high as that of concentration of RelB:p50 dimers.

These conclusions are derived from several different experiments. First, NF-κB:DNA complexes formed by incubation of a canonical κB site with nuclear extracts can be supershifted by anti-RelB antibodies when the nuclear extracts are from LTβR-stimulated and not from TNFα-stimulated cells. Second, ChIP experiments reveal that RelB is recruited to target gene promoters more rapidly and efficiently in anti-LTβR-stimulated than in TNFα-stimulated cells. Third, RelB:p52 dimers bind much more efficiently to the Blc κB site than RelB:p50 and especially RelA:p50 dimers. In addition, the conclusion that selective activation of the Blc, Sdf-1, Elc and Slc genes is dependent on RelB:p52 dimers is strongly supported by the results of two other gene disruption experiments, as expression of these genes is defective in spleens of RelB$^{-/-}$ and Nfκb2$^{-/-}$ mice but not in Nfκb1$^{-/-}$ mice (Weih et al. (2001) J Immunol 167, 1909-1919). Like the Ikkα$^{AA/AA}$ mutation, the RelB and Nfκb2 gene disruptions have no effect on the expression of TNFα or chemokine receptors.

While an understanding of the mechanism of the invention is not necessary, and without intending to limit the invention to any particular mechanism, it is the inventors' view that RelB appears to differ in its DNA binding properties from the two other Rel proteins: RelA and c-Rel. Whereas RelA and c-Rel can bind DNA as homodimers, RelB homodimers have very poor DNA binding activity. The binding of RelB to DNA is therefore dependent on heterodimerization with p50 or p52. Whereas RelB:p52 and RelB:p50 dimers bind with similar efficiency to the consensus κB site, the Blc κB site is more efficiently recognized by RelB:p52 dimers. Furthermore, the Blc κB site is poorly recognized by RelA:p50 dimers. The basis for DNA target site selection by different NF-κB dimers is not well understood, as RelA and p50 homo- and heterodimers have been studied (Phelps et al., 2000; Chen et al. (1998) Nat Struct Biol 5, 67-73; Huang et al. (2001) Structure (Camb) 9, 669-678). While an understanding of the mechanism of the invention is not necessary, and without intending to limit the invention to any particular mechanism, it is the inventors' view that RelA and c-Rel discriminate against DNA sequences with a third G:C basepair. The inventor's view is that the classical RelA:p50 binding site is: 5'-GGGRNWTTCC-3' (SEQ ID NO:120) (where R, N and W denote purine, any nucleotide and A or T, respectively). In this site, the 5' half site (5'-GGGRN-3') (SEQ ID NO:121) is occupied by p50 and the 3' half site (5'-TTCC-3') (SEQ ID NO:122) is occupied by RelA.

While an understanding of the mechanism of the invention is not necessary, and without intending to limit the invention to any particular mechanism, it is the inventors' view that the 5' half site (5'-GGGAG-3') (SEQ ID NO:66) of the Blc κB site, whose sequence is: 5'-GGGAGATTTG-3' (SEQ ID NO:59), is recognized by p52, while the 3' half site (5'-TTTG-3') (SEQ ID NO:67) is recognized by RelB. Also without limiting the invention to any particular mechanism, it is the inventors' view that the last two basepairs of the 3' half site interfere with its recognition by RelA. The inventors noted that RelB differs from RelA in the sequence of its DNA binding loops 1 and 3 (Ghosh et al. (1995) Nature 373, 303-310). For instance, RelB has a glutamic acid in loop 1 instead of a conserved lysine in RelA and c-Rel, and lysine and threonine in loop 3 instead of asparagine and proline in RelA. While an understanding of the mechanism of the invention is not necessary, and without intending to limit the invention to any particular mechanism, it is the inventors' view that it may be possible that these differences may be sufficient to alter the sequence selectivity of RelB from that of RelA. Furthermore, the inventors noted the differential DNA binding of RelA:p50 and RelA:p52 dimers (Nijnik et al. (2003) Nucleic Acids Res 31, 1497-1501; Schmid et al. (1994) J Biol Chem 269, 32162-32167). It is also the inventors' view that certain NF-κB sites, such as the consensus κB site, may be effectively recognized by all or most dimers, whereas other sites, such as the invention's RelBκB site, may be preferentially recognized by one type of dimer. Intriguingly, a very similar sequence to the invention's RelBκB site in Blc is present in the Sdf-1 promoter.

C. The Biological Functions of IKKα and RelB:p52

The inventors observed that the RelB:p52-specific target genes whose activation depends on IKKα are functionally related, encoding major chemokines that play a role in the development and organization of the spleen and secondary lymphoid organs (Ansel et al. (2001) Curr Opin Immunol 13, 172-179; Kim et al. (1999) J Leukoc Biol 65, 6-15). Based on the functional analysis described above, IKKα also plays a role in for differentiation of FDCs, which most likely arise from stromal progenitors (Mackay et al. (1998) Nature 395, 26-27). Formation and maintenance of the mature FDC network is an active process that requires production of $LT\alpha_1\beta_2$ heterotrimers by B cells, which engage LTβR on stromal cells (Mackay et al. (1998) Nature 395, 26-27). Although TNFR1 may also be involved in this process, its contribution is minor relative to that of LTβR (Mackay et al. (1998) Nature 395, 26-27). Indeed, the inventors found that TNFα fails to induce effective NF-κB2/p100 processing or expression of the four IKKα-dependent chemokine genes. We also found that injection of agonistic anti-TNFR1 antibody into Ikkα$^{AA/AA}$ mice failed to promote FDC maturation.

The transplantation experiments described herein indicate that one of the major sites of IKKα action is the stromal cell, the cell type that expresses LTβR (Fu et al. (1999) Annu Rev Immunol 17, 399-433). Furthermore, the manifestations of disrupted LTβR signaling (Fu et al. (1999) Annu Rev Immunol 17, 399-433) are strikingly similar to those of the Ikkα$^{AA/AA}$ mutation. Thus, although IKKα is involved in NF-κB2/p100 processing in B cells and has a B cell autonomous function (Senftleben et al. (2001a) Science 293, 1495-1499), it is the inventors' view that most of the defects in spleen development and morphogenesis in Ikkα$^{AA/AA}$ mice are probably due to defective LTβR signaling. Despite the similarities between the LTβR and IKKα deficiencies, engagement of LTβR also results in activation of the canonical NF-κB signaling pathway, leading to induction of genes such as Vcam-1, Tnfα and Baff, which are not dependent on IKKα. Without limiting the invention to any mechanism, these findings suggest to the inventors that either the canonical NF-κB signaling pathway is not required for the developmental and morphogenetic functions of LTβR, or that in the absence of LTβR, functions that depend on the canonical pathway can be induced by other receptors, for instance TNFR1. Interestingly, mice deficient in NF-κB2 or RelB expression exhibit splenic phenotypes that are quite similar to the one exhibited by Ikkα$^{AA/AA}$ mice (Caamano et al. (1998) J Exp Med 187, 185-196; Franzoso et al. (1998) J Exp Med 187, 147-159; Poljak et al. (1999) J Immunol 163, 6581-6588; Weih et al. (2001) J Immunol 167, 1909-1919). Transplantation experiments revealed that the stromal cell is also a major site of NF-κB2 and RelB action (Franzoso et al. (1998) J Exp Med 187, 147-159; Weih et al. (2001) J Immunol 167, 1909-1919).

While an understanding of the mechanism of the invention is not necessary, and without limiting the invention to any particular mechanism, the inventors are of the view that IKKα is responsible for selective activation of RelB:p52 target genes whose major functions are in development and organization of secondary lymphoid organs as structures that optimize adaptive immunity, especially the T-cell dependent humoral response. IKKβ, on the other hand, is mostly involved in inflammatory and innate immune responses. Thus IKKβ-mediated NF-κB signaling is in charge of rapid responses to infection and injury. At the early stage of the response to bacterial or viral pathogens, it is important to attract inflammatory cells (macrophages, neutrophils), as well as mature lymphocytes with the proper specificity out of lymphoid organs to sites of infection and injury. This targeting is dependent on pro-inflammatory chemokines, such as MIP-1, MCP-1 and RANTES, whose induction is dependent on activation of the canonical NF-κB signaling pathway. On the other hand, antigen arrives in the secondary lymphoid tissues from distal sites of infection and is recognized, processed and presented by the combined activity of DC, macrophages, T cells and B cells. Orchestration of these key cell-cell interactions is controlled by chemokines induced by the alternative NF-κB signaling pathway. Premature expression of such chemokines would compromise the response to infectious agents as it will cause the recruitment of myeloid and lymphoid cells from sites of infection back to lymphoid organs. It is, therefore the inventors' view that expression of chemokines involved in innate immune responses appears to be highly dependent on RelA (Alcamo et al. (2001) J Immunol 167, 1592-1600). At late stages of the response to infection, it becomes important to engage the adaptive immune response. Consistent with its delayed function, activation of the alternative, IKKα-dependent, NF-κB signaling pathway is slower than activation of the canonical NF-κB signaling pathway. The dependence of the two pathways on distinct but related protein kinases allows for both functional integration and kinetic separation. For instance, activation of IKKβ and the canonical pathway by pathogen associated molecular patterns (PAMPs); such as lipopolysaccharides (LPS), can lead to increased expression of cytokines, such as LTα, that activate the alternative pathway, as well as NF-κB2/p100 (Dejardin et al. (2002) Immunity 17, 525-535), which serves as a substrate for the IKKα-dependent processing pathway. The processing of p100 provides RelB with its partner, p52, leading to activation of genes that are involved in, for example, mounting the humoral response.

D. Target DNA Sequences for NFκ-B2/p52

The invention provides a RelBκB nucleotide sequences that specifically bind to proteins, which are involved in the IKKα rather than in the IKKβ pathway. In particular, the invention provides an isolated nucleotide sequence comprising 5'-NGGAGANNTG-3' (SEQ ID NO:57); wherein N at position 1 is chosen from G and A, N at position 7 is chosen from T and C, and N at position 8 is chosen from T and C (see, FIG. 4C), and wherein the isolated sequence specifically binds with a polypeptide sequence comprising RelB Rel homology domain (RHD), which is exemplified by SEQ ID NO:62, i.e., amino acids 1-400 of the exemplary mouse RelB shown in FIG. 13, GenBank accession A42023. As used herein the terms "κB site," "κB sequence," "RelBκB site," "RelBκB sequence," and "RelBκB recognition sequence," "RelB-specific binding site," and "RelB-specific binding sequence" are used interchangeably.

The terms nucleotide sequence "comprising a particular nucleic acid sequence" and protein "comprising a particular amino acid sequence" and equivalents of these terms, refer to any nucleotide sequence of interest and to any protein of interest that contains the particularly named nucleic acid sequence and the particularly named amino acid sequence, respectively. The invention does not limit on the source (e.g., cell type, tissue, animal, etc.), nature (e.g., synthetic, recombinant, purified from cell extract, etc.), and/or sequence of the nucleotide sequence of interest and/or protein of interest. In one embodiment, the nucleotide sequence of interest and protein of interest include coding sequences of structural genes (e.g., probe genes, reporter genes, selection marker genes, oncogenes, drug resistance genes, growth factors, etc.).

In one embodiment, binding of the invention's RelBκB sequences with the polypeptide sequence increases transcription of a nucleic acid sequence of interest that is operably linked to the invention's RelBκB sequences.

The terms "protein of interest," "peptide of interest," "nucleotide sequence of interest," and "molecule of interest" refer to any peptide sequence, nucleotide sequence, and molecule, respectively, the manipulation of which may be deemed desirable for any reason, by one of ordinary skill in the art. In one embodiment, the protein of interest refers to a protein encoded by a nucleic acid sequence of interest. Nucleotide sequences of interest include, but are not limited to, coding sequences of structural genes (e.g., reporter genes, selection marker genes, oncogenes, drug resistance genes, growth factors, etc.), and non-coding regulatory sequences which do not encode an mRNA or protein product, (e.g., promoter sequence, polyadenylation sequence, termination sequence, enhancer sequence, etc.). Illustrative genomic sequences which may be modified using the invention's methods include, but are not limited to, sequences which encode enzymes; lymphokines (e.g., interleukins, interferons, TNF, etc.); growth factors (e.g., erythropoietin, G-CSF, M-CSF, GM-CSF, etc.); neurotransmitters or their precursors or enzymes responsible for synthesizing them; trophic factors (e.g., BDNF, CNTF, NGF, IGF, GMF, aFGF, bFGF, NT3, NT5, HARP/pleiotrophin, etc.); apolipoproteins (e.g., ApoAI, ApoAIV, ApoE. etc.); lipoprotein lipase (LPL); the tumor-suppressing genes (e.g. p53, Rb, Rap1A, DCC k-rev, S etc.); factors involved in blood coagulation (e.g., Factor VII, Factor VII, Factor Ix, etc.); suicide genes (thymidine kinase or cytosine deaminase); blood products; hormones; etc. In another preferred embodiment, the genomic sequences are those for which a mutant has been associated with a human disease. Such genomic sequences are exemplified, but not limited to, the adenosine deaminase (ADA) gene (GenBank Accession No. M13792) associated with adenosine deaminase deficiency with severe combined immune deficiency; alpha-1-antitrypsin gene (GenBank Accession No. M11465) associated with alpha1-antitrypsin deficiency; beta chain of hemoglobin gene (GenBank Accession No. NM_000518) associated with beta thalassemia and Sickle cell disease; receptor for low density lipoprotein gene (GenBank Accession No. D16494) associated with familial hypercholesterolemia; lysosomal glucocerebrosidase gene (GenBank Accession No. K02920) associated with Gaucher disease; hypoxanthine-guanine phosphoribosyltransferase (HPRT) gene (GenBank Accession No. M26434, J00205, M27558, M27559, M27560, M27561, M29753, M29754, M29755, M29756, M29757) associated with Lesch-Nyhan syndrome; lysosomal arylsulfatase A (ARSA) gene (GenBank Accession No. NM_000487) associated with metachromatic leukodystrophy; ornithine transcarbamylase (OTC) gene (GenBank Accession No. NM_000531) associated with ornithine transcarbamylase deficiency; phenylalanine hydroxylase (PAH) gene (GenBank Accession No. NM_000277) associated with phenylketonuria; purine nucleoside phosphorylase (NP) gene (GenBank Accession No. NM_000270) associated with purine nucleoside phosphorylase deficiency; the dystrophin gene (GenBank Accession Nos. M18533, M17154, and M18026) associated with muscular dystrophy; the utrophin (also called the dystrophin related protein) gene (GenBank Accession No. NM_007124) whose protein product has been reported to be capable of functionally substituting for the dystrophin gene; and the human cystic fibrosis transmembrane conductance regulator (CFTR) gene (GenBank Accession No. M28668) associated with cystic fibrosis.

Exemplary molecules of interest include, but are not limited to, a peptide, glycopeptide, polysaccharide, lipopeptide, glycolipid, lipid, steroid, nucleic acid, etc.

The term "operably linked" when in reference to the relationship between nucleic acid sequences and/or amino acid sequences refers to linking the sequences such that they perform their intended function. For example, operably linking a promoter sequence to a nucleotide sequence of interest refers to linking the promoter sequence and the nucleotide sequence of interest in a manner such that the promoter sequence is capable of directing the transcription of the nucleotide sequence of interest and/or the synthesis of a polypeptide encoded by the nucleotide sequence of interest. The term also refers to the linkage of amino acid sequences in such a manner so that a functional protein is produced.

In another embodiment, the isolated nucleotide sequence does not bind with a protein comprising one or more of RelB, RelA, p50, RelB:p50, RelA:p50, and RelA:p52.

In one embodiment, the isolated nucleotide sequence comprises one or more of 5'-GGGAGATTTG-3' (SEQ ID NO:59) as exemplified by the sequence in the blc-1 gene promoter (FIG. 4C), 5'-GGGAGACCTG-3' (SEQ ID NO:2) as exemplified by the sequence in the sdf-1 gene promoter, and 5'-AGGAGATTTG-3' (SEQ ID NO:60) as exemplified by the sequence in the elc gene promoter (FIG. 4C).

The isolated nucleotide sequence that contains the RelBκB sequences of the invention include, for example, introns, exons, as well as nonsense sequences.

In one embodiment, the isolated nucleotide sequence that contains the RelBκB sequences of the invention is a probe. The term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to fluorescent, radioactive, and luminescent systems. It is not intended that the present invention be limited to any particular detection system or label. Exemplary "probe" genes sequence (i.e., sequence useful in the detection, identification and isolation of particular polypeptide sequence) encode ligand-binding systems useful for the isolation of polypeptides such as the staphylococcal protein A and its derivative ZZ (which binds to human polyclonal IgG), histidine tails (which bind to $Ni^{2+}$), biotin (which binds to streptavidin), maltose-binding protein (MBP) (which binds to amylose), glutathione S-transferase (which binds to glutathione), etc. Exemplary "reporter" gene sequences (i.e. sequences that encodes a molecule such as RNA, polypeptide, etc., that is detectable in enzyme-based histochemical assays, fluorescent, radioactive, and luminescent systems, etc.) include luciferase gene, green fluorescent protein gene, E. coli β-galactosidase gene, human placental alkaline phosphatase gene, and chloramphenicol acetyltransferase gene. Probes are useful in the methods disclosed below.

In another embodiment, the isolated nucleotide sequence that contains the RelBκB sequences of the invention encodes a "fusion protein," i.e., two or more polypeptides that are "operably linked" i.e., wherein the linkage of nucleic acid sequences and/or amino acid sequences is such that the linked sequences perform their intended function. For example, operably linking a promoter sequence to a nucleotide sequence of interest refers to linking the promoter sequence and the nucleotide sequence of interest in a manner such that the promoter sequence is capable of directing the transcription of the nucleotide sequence of interest and/or the synthesis of a polypeptide encoded by the nucleotide sequence of interest. The term also refers to the linkage of amino acid sequences in such a manner so that a functional protein is produced. Exemplary sequences that may be linked to the invention's sequence include those for adenosine deaminase (ADA) gene (GenBank Accession No. M13792); alpha-1-antitrypsin gene (GenBank Accession No. M11465); beta chain of hemoglobin gene (GenBank Accession No. NM_000518); receptor for low density lipoprotein gene (GenBank Accession No. D16494); lysosomal glucocerebrosidase gene (GenBank Accession No. K02920); hypoxanthine-guanine phosphoribosyltransferase (HPRT) gene (GenBank Accession No. M26434, J00205, M27558, M27559, M27560, M27561, M29753, M29754, M29755, M29756, M29757); lysosomal arylsulfatase A (ARSA) gene (GenBank Accession No. NM_000487); ornithine transcarbamylase (OTC) gene (GenBank Accession No. NM_000531); phenylalanine hydroxylase (PAH) gene (GenBank Accession No. NM_000277); purine nucleoside phosphorylase (NP) gene (GenBank Accession No. NM_000270); the dystrophin gene (GenBank Accession Nos. M18533, M17154, and M18026); the utrophin (also called the dystrophin related protein) gene (GenBank Accession No. NM_007124); and the human cystic fibrosis transmembrane conductance regulator (CFTR) gene (GenBank Accession No. M28668).

In a further embodiment, the isolated nucleotide sequence that contains the RelBκB sequences of the invention is a non-coding regulatory sequence which does not encode an mRNA or protein product, (e.g., promoter sequence, polyadenylation sequence, termination sequence, enhancer sequence, etc.).

In a preferred embodiment, the isolated nucleotide sequence that contains the RelBκB sequences of the invention is an enhancer. The term "enhancer" refers to a cis-acting regulatory sequence which functions in transcription activation of genes. Activation of an enhancer results in an increase in the rate of transcription. Enhancers may be placed 5' and/or 3' to the transcription tart site, can function in either orientation, and can operate even when placed at a distance of more than 3 kb from the transcriptional start site. In one embodiment, enhancers contain the consensus sequence 5'-GTGAAG-3' (SEQ ID NO:68). Exemplary enhancers include the SV40 viral enhancer. In particular, NF-κB responsive sites have been characterized in the promoters and enhancer of numerous genes (Ghosh et al. (1998) Ann. Rev. Immunol. 16:225-60)

In a further preferred embodiment, the isolated nucleotide sequence that contains the RelBκB sequences of the invention is a promoter. The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription. The term "promoter" encompasses a single promoter sequence as well as to a plurality (i.e., one or more) of promoter sequences which are operably linked to each other and to at least one DNA sequence of interest. For example, one of skill in the art knows that it may be desirable to use a double promoter sequence (i.e., a DNA sequence containing two promoter sequences) or a triple promoter sequence (i.e., a DNA sequence containing three promoter sequences) to control expression of a DNA sequence of interest. Double promoters are exemplified, but not limited to, T7-T3 (such as SEQ ID NO:69 5'-TAATACGACTCACTAT-AGGGATTAACCCTCACTAAAGGGA-3'), T3-T7 (such as SEQ ID NO:70 5'-ATTAACCCTCACTAAAGG-GATAATACGACTCACTATAGGG-3'), T7-SP6 (such as SEQ ID NO:71 5'-TAATACGACTCACTATAGGGTATT-TAGGTGACACTATAG-3'), SP6-T7 (such as SEQ ID NO:72 5'-TATTTAGGTGACACTATAGTAATAC-GACTCACTATAGGG-3'), SP6-T3 (such as SEQ ID NO:73 5'-TATTTAGGTGACACTATAGATTAACCCT-CACTAAAGGGA-3'), T3-SP6 (such as SEQ ID NO:74 5'-ATTAACCCTCACTAAAGGGATATTTAG-GTGACACTATAG-3'), vaRNA I-tRNA, vaRNA I-CMV, vaRNA I-RSV, vaRNA I-SV40, vaRNA I-PEPCK, vaRNA I-MT, vaRNA I-SRα, vaRNA I-P450 family, vaRNA I-GAL7, $T_7$-vaRNA I, $T_3$-vaRNA, vaRNA I-SP6, vaRNA I-K11, and vaRNA I-heat shock protein double promoters, while triple promoters are exemplified, but not limited to, the CMV-T7-vaRNA I triple promoter. The term "promoter" also covers so-called "leaky" promoters, which regulate expression of a selected DNA primarily in one tissue, but cause expression in other tissues as well.

As used herein "promoter" refers to viral, phage, prokaryotic and/or eukarytoic transcriptional control sequences. Viral promoters are exemplified by CMV, RSV, SV40, herpes simplex thymidine kinase promoter, as well as any of the various retroviral LTR promoter elements (e.g. the MMTV LTR).

Figure 2:
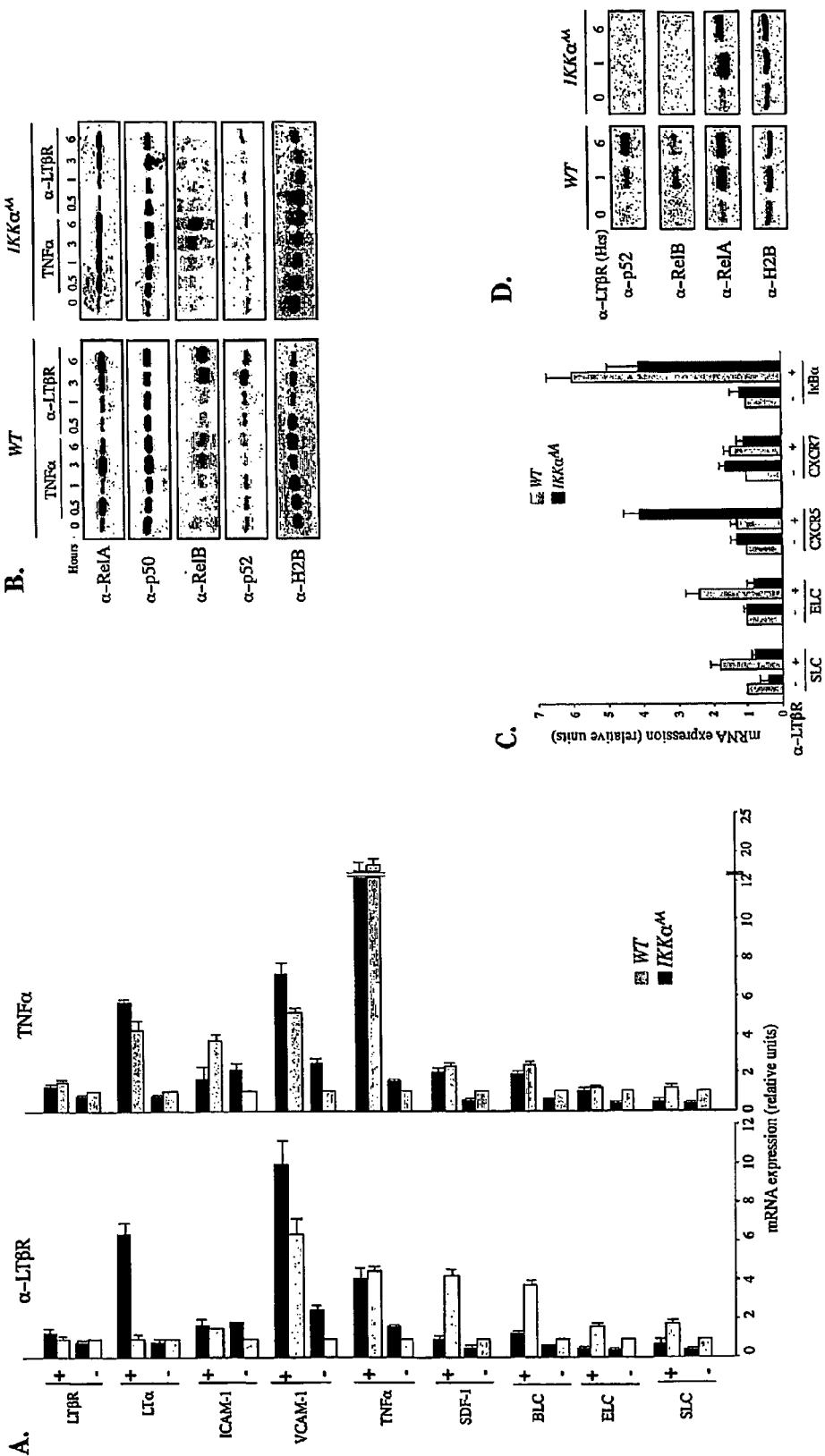
FIG. 2 shows IKKα is required for LTβR-induced RelB:p52 nuclear translocation and chemokine expression in splenic stromal cells and myeloid dendritic cells. Ikkα$^{AA/AA}$ stromal cells (A) and bone marrow-derived dendritic cells (BMDC) (C) exhibit specific defects in LTβR-induced gene expression. Total RNA was extracted from either WT or Ikkα$^{AA/AA}$ stromal cells or BMDC before and after stimulation with 2 μg/ml agonistic anti-LTβR antibody or 20 ng/ml TNFα. Gene expression was analyzed by real-time PCR. Results are averages±SD of three independent experiments normalized to the level of cyclophilin mRNA. Panels (13, D) show nuclear translocation of NF-κB proteins. Stromal cells (1) and bone marrow-derived dendritic cells (BMDC) (D) were stimulated with either anti-LTβR antibody or TNFα as indicated. At the indicated time points (hrs) after agonist addition, nuclear extracts were prepared and analyzed by immunoblotting for presence of the indicated NF-κB subunits. The levels of histone H2B were examined to control for loading and proper cell fractionation. Contamination with cytoplasmic proteins was monitored by blotting with anti-actin antibody.

Phage promoters are exemplified, but not limited to, promoters from T3 phage, SP6 phage, T7 phage, T5 phage, phage .phi.105, phage .phi.105MU331, lambda phage promoters (e.g. $P_{RM}$ and $P_R$). The term "promoter" includes portions of the "full length" promoter that may be extended (e.g., by PCR) to obtain a full length promoter. Thus, for example, a T7 promoter comprises 2 to 20, preferably 2 to 15, more preferably 2 to 10, yet more preferably 2 to 5 contiguous nucleotides of SEQ ID NO:75 (5'-TAATACGACTCACTAT-AGGG-3'). Exemplary T7 promoters may be 18 nucleotides long such as SEQ ID NO:76 (5'-TAATACGACTCACTATA-3') (see U.S. Patent Application No. 20020068290A1, to Yarovinsky, Timur, Jun. 6, 2002), 16 nucleotides long such as SEQ ID NO:77 (5'-TAATACGACTCACTAT-3'), SEQ ID NO:78 (5'-AATACGACTCACTATA-3'), and SEQ ID NO:79 (5'-ATACGACTCACTATAG-3'), 14 nucleotides long such as SEQ ID NO:80 (5'-ACGACTCACTATAG-3'), SEQ ID NO:81 (5'-ATACGACTCACTAT-3'), and SEQ ID NO:82 (5'-TACGACTCACTATA-3'), and 10 nucleotides long such as SEQ ID NO:83 (5'-CGACTCACTA-3'), SEQ ID NO:84 (5'-TACGACTCAC-3'), and SEQ ID NO:85 (5'-ATAC-GACTCA-3'). In a preferred embodiment, the T7 promoter is a hexanucleotide exemplified by SEQ ID NO:86 (5'-ATAGGG-3'), (FIG. 2), SEQ ID NO:87 (5'-TAATAC-3'), and SEQ BD NO:88 (5'-ACGACT-3').

In yet another example, a T3 promoter comprises 2 to 20, preferably 2 to 15, more preferably 2 to 10, yet more preferably 2 to 5 contiguous nucleotides of SEQ ID NO:89 (5'-ATTAACCCTCACTAAAGGGa-3'). Exemplary T3 promoters may be 18 nucleotides long such as SEQ ID NO:90 (5'-TTAACCCTCACTAAAGGG-3'), SEQ ID NO:91 (5'-TAACCCTCACTAAAGGGA-3), and SEQ ID NO:92 (5'-ATTAACCCTCACTAAAGG-3'), 16 nucleotides long such as SEQ ID NO:93 (5'-ACCCTCACTAAAGGGA-3'), SEQ ID NO:94 (5'-TAACCCTCACTAAAGG-3'), and SEQ ID NO:95 (5'-TTAACCCTCACTAAAG-3'), 14 nucleotides long such as SEQ ID NO:96 (5'-CCTCACTAAAGGGA-3'), SEQ ID NO:97 (5'-ATTAACCCTCACTA-3'), and SEQ ID NO:98 (5'-AACCCTCACTAAAG-3'), 10 nucleotides long such as SEQ ID NO:99 (5'-ACCCTCACTA-3'), SEQ ID NO:100 (5'-CCTCACTAAA-3'), and SEQ ID NO:101 (5'-ATTAACCCTC-3'), and 6 nucleotides long such as SEQ ID NO:102 (5'-ATTAAC-3'), SEQ ID NO:103 (5'-AAGGGA-3'), and SEQ ID NO:104 (5'-CACTAA-3').

In a further example, a SP6 promoter comprises 2 to 19, preferably 2 to 15, more preferably 2 to 10, yet more preferably 2 to 5 contiguous nucleotides of SEQ ID NO:105 (5'-TATTTAGGTGACACTATAG-3'). Exemplary SP6 promoters may be 16 nucleotides long such as SEQ ID NO:106 (5'-TTAGGTGACACTATAG-3'), SEQ ID NO:107 (5'-TTTAGGTGACACTATA-3'), and SEQ ID NO:108 (5'-TATTTAGGTGACACTA-3'), 14 nucleotides long such as SEQ ID NO:109 (5'-ATTTAGGTGACACT-3'), SEQ ID NO:110 (5'-TATTTAGGTGACAC-3'), and SEQ ID NO:111 (5'-TTTAGGTGACACTA-3'), 10 nucleotides long such as SEQ ID NO:112 (5'-TTAGGTGACA-3'), SEQ ID NO:113 (5'-TAG-GTGACAC-3'), and SEQ ID NO:114 (5'-ATTTAGGTGA-3'), and 6 nucleotides long such as SEQ ID NO:115 (5'-CTATAG-3), SEQ ED NO:116 (5'-TATTTA-3'), and SEQ ID NO:117 (5'-GACACT-3').

Prokaryotic promoters include those carrying optimal −35 and −10 (Pribnow box) sequences for transcription by a prokaryotic (e.g. *E. coli*) RNA polymerase. In addition, some prokaryotic promoters contain overlapping binding sites for regulatory repressors (e.g. the Lac promoter and the synthetic TAC promoter, which contain overlapping binding sites for lac repressor thereby conferring inducibility by the substrate homolog IPTG). Prokaryotic genes from which suitable promoters sequences may be obtained include the *E. coli* lac, ara and trp genes. Further exemplary promoters include, PEPCK, MT, SRα, P450 family, GAL7, K11, and heat shock protein promoters.

In particularly preferred embodiments, the promoter is chosen from one or more of Sdf-1 promoter, Blc promoter, Elc promoter, and Slc promoter.

It is expressly contemplated that the invention RelBκB sequences may be in any orientation. Thus, reference to 5'-NGGAGANNTG-3' (SEQ ID NO:57) includes within its scope sequences in the reverse orientation, i.e., 5'-GTNNA-GAGGN-3' (SEQ ID NO:118).

It is also contemplated that where the invention's RelBκB sequences are contained within a nucleotide sequence such as probe, enhancer, promoter, intron, exon, and nonsense sequence, the invention's RelBκB sequences may be in the middle, closer to the 5' end than to the 3' end, and/or closer to the 3' end than to the 5' end, of the nucleotide sequence. For example, data herein shows that the invention's RelBκB sequence is closer to the 5' end than the 3' end of the blc-1 gene promoter FIG. 4C), and is close to the 3' end than the 5' end of the sdf-1 gene promoter.

It is further contemplated that a nucleotide sequence contain one or more of the invention's RelBκB sequences, preferably from 1 to 20, more preferably from 1 to 15, yet more preferably from 1 to 10, and most preferably from 1 to 5, of the invention's RelB KB sequences. Further, it is contemplated that, where more than one of the inventions" RelBκB sequences is present, these sequences may be the same or different.

In one embodiment, the invention's RelBκB sequences specifically bind with a polypeptide sequence comprising binds with a polypeptide sequence comprising a RelB Rel homology domain (RHD). In one preferred embodiment, the RelB RHD is exemplified by SEQ ID NO:62, i.e., amino acids 1-400 of the exemplary mouse RelB shown in FIG. 13, GenBank accession A42023. In a more preferred embodiment, SEQ ID NO:62 is contained in one or more of RelB and RelB:p52.

The terms "specific binding," "binding specificity," and grammatical equivalents thereof when made in reference to the binding of a first molecule (such as a polypeptide, glycoprotein, nucleic acid sequence, etc.) to a second molecule (such as a polypeptide, glycoprotein, nucleic acid sequence, etc.) refer to the preferential interaction between the first molecule with the second molecule as compared to the interaction between the second molecule with a third molecule. Specific binding is a relative term that does not require absolute specificity of binding; in other words, the term "specific binding" does not require that the second molecule interact with the first molecule in the absence of an interaction between the second molecule and the third molecule. Rather, it is sufficient that the level of interaction between the first molecule and the second molecule is higher than the level of interaction between the second molecule with the third molecule. "Specific binding" of a first molecule with a second molecule also means that the interaction between the first molecule and the second molecule is dependent upon the presence of a particular structure on or within the first molecule; in other words the second molecule is recognizing and binding to a specific structure on or within the first molecule rather than to nucleic acids or to molecules in general. For example, if a second molecule is specific for structure "A" that is on or within a first molecule, the presence of a third nucleic acid sequence containing structure A will reduce the amount of the second molecule which is bound to the first molecule. The conditions for binding molecules may be determined using routine methods, commercially available methods, and methods disclosed herein.

E. Methods for Identifying Test Compounds that Alter RelB DNA-Binding Activity

The invention further provides methods for identifying one or more test compounds that alter binding of RelB Rel homology domain (RelB RHD) with a RelBκB sequence of the present invention. In one embodiment, the invention's methods comprise: a) contacting i) the isolated nucleotide sequence comprising RelBκB sequences described supra with ii) a polypeptide comprising RelB RHD, as exemplified by SEQ ID NO:62, in the presence and absence of the one or more test compounds; and detecting altered specific binding of the nucleotide sequence with RelB RHD, as exemplified by SEQ ID NO:62, in the presence of the one or more test compounds compared to in the absence of the one or more test compounds, and c) identifying the one or more test compounds as altering binding of RelB RHD with a RelBκB sequence. In one embodiment, it may be desirable to use a control such as non-activatable form of IKKα.

The terms "RelB DNA-binding activity" and "IKKα mediated cellular activity" are used interchangeably to refer to the binding of RelB Rel homology domain (RelB RHD) with the invention's RelBκB sequence.

The terms "NF-κB2," "NF-κB2," "NF-κB2/p100," "NF-κ B2/p100," "NFκB2/p100," "p100," "p52/p100," "p49/p100," "lyt," "lyt10, "lyt-10," are used herein interchangeably to refer to a polypeptide that is a precursor of a transcription factor, and that contains an N-terminal Rel homology domain (RHD) that is common to all NF-κB proteins as well as an inhibitory IκB-like C-terminal domain of ankyrin repeats (Ghosh et al. (1998) Ann Rev Immunol 16, 225-260). Exemplary NF-κB2 sequences include those from human (FIGS. 8, 9), mouse (FIGS. 10, 11), Rhesus monkey (see, FIG. 12)

The terms "NF-κB2/p52," "NF-κ B2/p52," "p49," "p52," "p508," are used herein interchangeably to refer to a transcription factor that contains a DNA-binding protein, and that is the cleavage product resulting from the ubiquitin-dependent proteolytic digestion of NF-κ B2, which remove the C-terminal domain of NF-κ B2, leaving the RHD. This degradation is caused by the protein kinase NIK and is mediated by phosphorylation of NF-κ B2 by IKKα.

The test compounds identified by the invention's methods refer to any type of molecule (for example, a peptide, nucleic acid, carbohydrate, lipid, organic, and inorganic molecule, etc.) obtained from any source (for example, plant, animal, and environmental source, etc.), or prepared by any method (for example, purification of naturally occurring molecules, chemical synthesis, and genetic engineering methods, etc.). The terms "agent," "test agent," "molecule," "test molecule," "compound," and "test compound" as used interchangeably herein. Test compounds are exemplified by, but not limited to, antibodies, nucleic acid sequences, and other agents as further described below.

In one preferred embodiment, the agent that alters binding of RelB RHD with a RelBκB sequence is an antibody, such as RelB RHD antibody, and/or RelBκB sequence antibody. The terms "antibody" and "immunoglobulin" are interchangeably used to refer to a glycoprotein or a portion thereof (including single chain antibodies), which is evoked in an animal by an immunogen and which demonstrates specificity to the immunogen, or, more specifically, to one or more epitopes contained in the immunogen. The term "antibody" includes polyclonal antibodies, monoclonal antibodies, naturally occurring antibodies as well as non-naturally occurring antibodies, including, for example, single chain antibodies, chimeric, bifunctional and humanized antibodies, as well as antigen-binding fragments thereof, including, for example, Fab, F(ab')$_2$, Fab fragments, Fd fragments, and Ev fragments of an antibody, as well as a Fab expression library. It is intended that the term "antibody" encompass any immunoglobulin (e.g., IgG, IgM, IgA, IgE, IgD, etc.) obtained from any source (e.g., humans, rodents, non-human primates, caprines, bovines, equines, ovines, etc.). The term "polyclonal antibody" refers to an immunoglobulin produced from more than a single clone of plasma cells; in contrast "monoclonal antibody" refers to an immunoglobulin produced from a single clone of plasma cells. Monoclonal and polyclonal antibodies may or may not be purified. For example, polyclonal antibodies contained in crude antiserum may be used in this unpurified state.

Naturally occurring antibodies may be generated in any species including murine, rat, rabbit, hamster, human, and simian species using methods known in the art. Non-naturally occurring antibodies can be constructed using solid phase peptide synthesis, can be produced recombinantly or can be obtained, for example, by screening combinatorial libraries consisting of variable heavy chains and variable light chains as previously described [Huse et al., Science 246:1275-1281 (1989)]. These and other methods of making, for example, chimeric, humanized, CDR-grafted, single chain, and bifunctional antibodies are well known to those skilled in the art (Winter and Harris, Immunol. Today 14:243-246 (1993); Ward et al., Nature 341:544-546 (1989); Hilyard et al., Protein Engineering: A practical approach (ML Press 1992); and Borrabeck, Antibody Engineering, 2d ed. (Oxford University Press 1995).

Those skilled in the art know how to make polyclonal and monoclonal antibodies which are specific to a desirable polypeptide. For the production of monoclonal and polyclonal antibodies, various host animals can be immunized by injection with the peptide corresponding to any molecule of interest in the present invention, including but not limited to rabbits, mice, rats, sheep, goats, etc. In one preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies directed toward molecules of interest in the present invention, any technique that provides for the production of antibody molecules by continuous cell-lines in culture may be used (See, e.g., Harlow and Lane, *Antibodies: A Laboratory Manual, Cold Spring Harbor Laboratory Press*, Cold Spring Harbor, N.Y.). These include but are not limited to the hybridoma technique originally developed by Köhler and Milstein (Köhler and Milstein, Nature 256:495-497 [1975]), as well as the trioma technique, the human B-cell hybridoma technique (See e.g., Kozbor et al. Immunol. Today 4:72 [1983]), and the EBV-hybridoma technique to produce human monoclonal antibodies (Cole et al., in *Monoclonal Antibodies and Cancer Therapy*, Alan R. Liss, Inc., pp. 77-96 [1985]). In some particularly preferred embodiments of the present invention, the present invention provides monoclonal antibodies of the IgG class.

In additional embodiments of the invention, monoclonal antibodies can be produced in germ-free animals utilizing technology such as that described in PCT/US90/02545. In addition, human antibodies may be used and can be obtained by using human hybridomas (Cote et al., Proc. Natl. Acad. Sci. U.S.A. 80:2026-2030 [1983]) or by transforming human B cells with EBV virus in vitro (Cole et al., in *Monoclonal Antibodies and Cancer Therapy*, Alan R. Liss, pp. 77-96 [1985]).

Furthermore, techniques described for the production of single chain antibodies (See e.g., U.S. Pat. No. 4,946,778; herein incorporated by reference) can be adapted to produce single chain antibodies that specifically recognize a molecule of interest (e.g., at least a portion of an AUBP or mammalian exosome, as described herein). An additional embodiment of the invention utilizes the techniques described for the construction of Fab expression libraries (Huse et al., Science 246:1275-1281 [1989]) to allow rapid and easy identification of monoclonal Fab fragments with the desired specificity for a particular protein or epitope of interest (e.g., at least a portion of an AUBP or mammalian exosome).

The invention also contemplates humanized antibodies. Humanized antibodies may be generated using methods known in the art, including those described in U.S. Pat. Nos. 5,545,806; 5,569,825 and 5,625,126, the entire contents of which are incorporated by reference. Such methods include, for example, generation of transgenic non-human animals which contain human immunoglobulin chain genes and which are capable of expressing these genes to produce a repertoire of antibodies of various isotypes encoded by the human immunoglobulin genes.

According to the invention, techniques described for the production of single chain antibodies (U.S. Pat. No. 4,946,778; herein incorporated by reference) can be adapted to produce specific single chain antibodies as desired. An additional embodiment of the invention utilizes the techniques known in the art for the construction of Fab expression libraries (Huse et al., Science, 246:1275-1281 [1989]) to allow rapid and easy identification of monoclonal Fab fragments with the desired specificity.

Antibody fragments that contain the idiotype (antigen binding region) of the antibody molecule can be generated by known techniques. For example, such fragments include but are not limited to: the F(ab')2 fragment that can be produced by pepsin digestion of an antibody molecule; the Fab' fragments that can be generated by reducing the disulfide bridges of an F(ab')2 fragment, and the Fab fragments that can be generated by treating an antibody molecule with papain and a reducing agent.

In the production of antibodies, screening for the desired antibody can be accomplished by techniques known in the art (e.g., radioimmunoassay, ELISA [enzyme-linked immunosorbent assay], "sandwich" immunoassays, immunoradiometric assays, gel diffusion precipitin reactions, immunodiffusion assays, in situ immunoassays [e.g., using colloidal gold, enzyme or radioisotope labels], Western blots, precipitation reactions, agglutination assays (e.g., gel agglutination assays, hemagglutination assays, etc.), complement fixation assays, immunofluorescence assays, protein A assays, and immunoelectrophoresis assays, etc.

In an alternative embodiment, the agent that alters the level of binding of RelB RHD with a RelBκB sequence is a nucleic acid sequence. The terms "nucleic acid sequence" and "nucleotide sequence" as used herein refer to two or more nucleotides which are covalently linked to each other. Included within this definition are oligonucleotides, polynucleotide, and fragments or portions thereof, DNA or RNA of genomic or synthetic origin which may be single- or double-stranded, and represent the sense or antisense strand. Nucleic acid sequences which are particularly useful in the instant invention include, without limitation, antisense sequences and ribozymes.

In one embodiment, the agent that alters the level of binding of RelB RHD with a RelBκB sequence is an antisense nucleic acid sequence. Antisense sequences have been successfully used to inhibit the expression of several genes [Markus-Sekura (1988) Anal. Biochem. 172:289-295; Hambor et al. (1988) J. Exp. Med. 168:1237-1245; and patent EP 140 308], including the gene encoding VCAM1, one of the integrin α4β1 ligands [U.S. Pat. No. 6,252,043, incorporated in its entirety by reference]. The terms "antisense DNA sequence" and "antisense sequence" as used herein interchangeably refer to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Sense mRNA generally is ultimately translated into a polypeptide. Thus, an "antisense DNA sequence" is a sequence which has the same sequence as the non-coding strand in a DNA duplex, and which encodes an "antisense RNA" (i.e., a ribonucleotide sequence whose sequence is complementary to a "sense mRNA" sequence). The designation (−) (i.e., "negative") is sometimes used in reference to the antisense strand, with the designation (+) sometimes used in reference to the sense (i.e., "positive") strand. Antisense RNA may be produced by any method, including synthesis by splicing an antisense DNA sequence to a promoter which permits the synthesis of antisense RNA. The transcribed antisense RNA strand combines with natural mRNA produced by the cell to form duplexes. These duplexes then block either the further transcription of the mRNA or its translation, or promote its degradation.

Antisense oligonucleotide sequences may be synthesized using any of a number of methods known in the art (such as solid support and commercially available DNA synthesizers, standard phosphoramidate chemistry techniques, and commercially available services, e.g., Genta, Inc.).

In some alternative embodiments, the agent that alters the level of binding of RelB RHD with a RelBκB sequence is a ribozyme nucleic acid sequence. Ribozyme sequences have been successfully used to inhibit the expression of several genes including the gene encoding VCAM1, which is one of the integrin α4β1 ligands [U.S. Pat. No. 6,252,043, incorporated in its entirety by reference]. The term "ribozyme" refers to an RNA sequence that hybridizes to a complementary sequence in a substrate RNA and cleaves the substrate RNA in a sequence specific manner at a substrate cleavage site. Typically, a ribozyme contains a "catalytic region" flanked by two "binding regions." The ribozyme binding regions hybridize to the substrate RNA, while the catalytic region cleaves the substrate RNA at a "substrate cleavage site" to yield a "cleaved RNA product."

Molecules which find use as agents for specifically altering the level of specific binding of RelB RHD with a RelBκB sequence include organic molecules, inorganic molecules, and libraries of any type of molecule, which can be screened using a method of the invention, and which may be prepared using methods known in the art. These agents are made by methods for preparing oligonucleotide libraries [Gold et al., U.S. Pat. No. 5,270,163, incorporated by reference]; peptide libraries [Koivunen et al. J. Cell Biol., 124: 373-380 (1994)]; peptidomimetic libraries [Blondelle et al., Trends Anal. Chem. 14:83-92 (1995)] oligosaccharide libraries [York et al., Carb. Res. 285:99-128 (1996); Liang et al., Science 274: 1520-1522 (1996); and Ding et al., Adv. Expt. Med. Biol. 376:261-269 (1995)]; lipoprotein libraries [de Kruif et al., FEBS Lett., 399:232-236 (1996)]; glycoprotein or glycolipid libraries [Karaoglu et al., J. Cell Biol. 130:567-577 (1995)]; or chemical libraries containing, for example, drugs or other pharmaceutical agents [Gordon et al., J. Med. Chem. 37:1385-1401 (1994); Ecker and Crook, Bio/Technology 13:351-360 (1995), U.S. Pat. No. 5,760,029, incorporated by reference]. Libraries of diverse molecules also can be obtained from commercial sources.

The invention's methods identify one or more test compounds that alter binding of RelB Rel homology domain (RelB RHD) to the invention's nucleotides sequences. The term "Rel" refers to a family of reticuloendotheliosis proteins (such as RelA, RelB, p50, p52, v-rel, c-rel, etc.). "RelB" is exemplified by mouse sequences shown in FIGS. 13-15, and *Xenopus Laevis* sequences shown in FIGS. 16-17. "RelA" is also known as "p65" and is exemplified by sequences shown in FIGS. 20 and 21. Exemplary "NFκ-B1" also referred to as "p105" that are processed into "p50" are isolated from mouse (FIGS. 18, and 19).

"Rel homology domain," "RHD," "DNA-binding domain," and "DBD," are used interchangeably herein to refer to a polypeptide sequence on a member of the Rel family of proteins (such as RelA, RelB, p50, p52, v-rel, c-rel, etc.) that is at the N-terminal end of the polypeptide sequence of the Rel family protein member, that binds to a target DNA sequence (such as the consensus sequence 5'-GGGGG-YNNCCY-3' (SEQ ID NO:119) and/or to one or more of the invention's RelBκB sequences), that is involved in binding to a member of the Rel family of proteins in forming homodimers (such as p52:p52, p50-p50, etc.) and/or heterodimers (such as RelB-p52, RelA:p50, etc.), and/or that is involved in binding to one or more IκB family members (such as IκB, IκBα, IκBβ, IκBε, IκBγ, and Bcl-3; Ghosh et al. (1998) Annu. Rev. Immunol. 16:225-60).

In one embodiment, the RHD is about 400 amino acids. In another embodiment, the RHD is about 350 amino acids. In yet another embodiment, the RHD is about 300 amino acids. Examples of the RHD include the RHD of human p52 (SEQ ID NO:64, i.e., residues 1-340 of GenBank accession NM 002502 in FIG. 8, RHD of murine RelB (SEQ ID NO:62, i.e., residues 1-400 of GenBank accession A42023 in FIG. 13, and RelB RHD disclosed in Ghosh et al. (1998) Ann. Rev. Immunol. 16:225-60.

The RHD contains the "dimerization domain," also known as "DD". The dimerization domain is exemplified by the RelB DD listed as SEQ ID NO:63.

In one embodiment, the invention's methods may further comprise d) contacting the nucleotide sequence, in the presence of the one or more test compounds, with one or more compositions comprising a polypeptide that comprises RelB RHD, as exemplified by SEQ ID NO:62. The term "control" as used herein when in reference to a sample, cell, tissue, animal, etc., refers to any type of sample, cell, tissue, animal, etc. that one of ordinary skill in the art may use for checking the results of another sample, cell, tissue, animal, etc., by maintaining the same conditions except in some one particular factor, and thus inferring the causal significance of this varied factor.

In one embodiment, In one embodiment, it may be desirable to use a control such as non-activatable form of IKKα. In such an embodiment, the invention's methods may further comprise d) contacting the nucleotide sequence, in the presence of the one or more test compounds, with one or more compositions comprising a polypeptide that comprises RelB RHD, as exemplified by SEQ ID NO:62, wherein the composition comprising a polypeptide that comprises RelB RHD, as exemplified by SEQ ID NO:62, is chosen from one or more of cell extract, cytoplasmic extract, and nuclear extract, and wherein the composition is isolated from a mammalian cell comprising IKKα having reduced kinase activity, and the mammalian cell is treated with one or more IKKα activators chosen from lymphotoxin B (LTβ), B cell activating factor belonging to the TNF family (BAFF), anti-LTβR antibody, and CD40 ligand (CD40L); and e) detecting unaltered specific binding of the isolated nucleotide sequence with RelB RHD, as exemplified by SEQ ID NO:62, in the presence and absence of the one or more test compounds.

The term "mammal" refers to the exemplary animals of rodent, primate (including simian and human) ovine, bovine, ruminant, lagomorph, porcine, caprine, equine, canine, feline, ave, etc. Preferred mammals are selected from the order Rodentia, such as mouse and rat.

The term "IKKα" refers to the exemplary human and mouse amino acids shown in FIGS. 22 and 24, respectively, which are encoded by the exemplary nucleic acid sequences of FIGS. 23 and 25, respectively. IKKα contains a "IKKα kinase domain," which is also referred to as "IKKα protein kinase domain," and "IKKα protein kinase catalytic domain," and which refers to amino acids 1 to 301 of the human IKKα kinase (FIG. 22), and/or to amino acids 1 to 301 of the mouse IKKα kinase (FIG. 24), and/or portions thereof that exhibit IKKα kinase activity.

Various methods are known in the art for generating transgenic animals that express reduced IKKα activity. For example, transgenic animals expressing non-activatable IKKα. Exemplary animals include knockout mice in which at least a portion of the ikkα gene is knocked out (Hu et al. (1999) Science 284:316-320; Takeda et al. (1999) Science 284:313-316); knockin mice such as Ikkα$^{AA/AA}$ mice, which express a non-activatable form of IKKα as a result of the introduction of a knockin Ikkα$^{AA}$ allele that inactivates the kinase activity of IKKα (Cao et al. (2001) Cell 107, 763-775); transgenic mice expressing an IKKα kinase domain in which Serine at one or more of amino acids 176 and 180 the of IKKα kinase polypeptide is replaced with Alanine; and/or in which Lysine at amino acid 44 of IKKα kinase polypeptide is replaced with Alanine or Methionine (Delhase et al. (1999) Science 284:309); other mutations are also known in the art to inactivate IKKα.

In one embodiment, the polypeptide comprising RelB RHD is recombinant. In a preferred embodiment, the polypeptide comprising the exemplary SEQ ID NO:62 is RelB and/or RelB:p52. In a yet more preferred embodiment, the polypeptide comprising the exemplary SEQ ID NO:62 is chosen from one or more of RelB and RelB:p52, and is isolated from a mammalian cell treated with one or more IKKα activators chosen from lymphotoxin B (LTβ), B cell activating factor belonging to the TNF family (BAFF), anti-LTβR antibody, and CD40 ligand (CD40L).

The term "IKKα activator" refers to a compound that allows phosphorylation of IKKα, and expression of IKKα kinase activity. In one embodiment, such a compound also allows expression of IKKβ kinase activity. However, in a preferred embodiment, the IKKα activator results in a greater statistically significant increase in IKKα kinase activity compared to an increase in IKKα kinase activity. Exemplary IKKα activators include, without limitation, lymphotoxin (LT) $\alpha_1$:$\beta_2$ trimers acting through LTβ receptor (LTβR), B cell activating factor (BAFF; also known as Blys/TALL-1/THANK and B cell activating factor belonging to the TNF family) acting through BAFF-R and CD40 ligand (CD40L) whose receptor is CD40 (Claudio et al. (2002) Nat Immunol 3, 958-965; Coope et al. (2002) EMBO J 21, 5375-5385; Dejardin et al. (2002) Immunity 17, 525-535; Kayagaki et al. (2002) Immunity 17, 515-524; Yilmaz et al. (2003) EMBO J 22, 121-130).

In one embodiment, the mammalian cell is in vivo (for example, in an animal that harbors a recombinant expression vector or that contains wild type homologous sequences). Alternatively, the mammalian cell is in vitro (for example, cells that harbors a recombinant expression vector or that contains wild type homologous sequences). The mammalian cell may be a primary cell or from a cell line. Furthermore, the mammalian cell may be chosen from one or more of B cell, stromal cell of lymph organ such as spleen, fibroblast cell such as embryo fibroblasts (EFs), including mouse embryo fibroblasts (MEFs), macrophage cell such as stromal macrophage cell, dendritic cell, neuron cell, plasma cell, lymphoid cell, lymphoblastoid cell, myeloid cell, Reed-Sternber (HRS) cell of Hodgkin's lymphomas, epithelial cell such as breast cell, gastric cell, lung cell, prostate cell, cervical cell, pancreatic cell, colon cell, rectal cell, ovarian cell, stomach cell, esophagus cell, mouth cell, tongue cell, gum cell, skin cell, muscle cell, heart cell, liver cell, bronchial cell, cartilage cell, bone cell, testis cell, kidney cell, endometrium cell, uterus cell, bladder cell, thyroid cell, brain cell, gall bladder cell, and ocular cell (such as cell of the cornea, cell of uvea, cell of the choroids, cell of the macula, vitreous humor cell, etc.).

In another alternative embodiment, it may be desirable to use RelA:p52 as control. Thus, the method further comprises detecting unaltered binding of the isolated nucleotide sequence to one or more proteins chosen from a polypeptide comprising one or more of RelA RHD, RelA, p52, and RelA:p52, in the presence and absence of the one or more test compounds.

In a further alternative, it may be desirable to use RelB:p50 as a control. Thus, the method further comprises detecting unaltered binding of the isolated nucleotide sequence to one or more proteins chosen from a polypeptide comprising one or more of RelB RHD, RelB, p50, and RelB:p50, in the presence and absence of the one or more test compounds.

Alternatively, the consensus-κB sequence may be used as a control. Thus, the method further comprises detecting unaltered binding of an isolated nucleotide sequence comprising the consensus-κB sequence 5'-GGGACTTTCC-3' (SEQ ID NO:58) to a polypeptide comprising one or more of RelB RHD, as exemplified by SEQ ID NO:62, and RelB in the presence of the one or more test compounds.

The methods may further comprise identifying the one or more test compounds as altering symptoms associated with IKKα related pathology.

The invention's methods involve detecting the level of specific binding of the isolated nucleotide sequence with RelB RHD, as exemplified by SEQ ID NO:62. Methods for "detecting" such binding are known in the art and disclosed herein. For example, binding of polypeptides (including dimerized polypeptides such as RelB:p52 and RelA:p50) to DNA molecules may be determined by methods including, but are not limited to, direct binding in solution, direct binding where one or more components is immobilized on a solid surface, electrophoretic mobility shift assays, nucleolytic cleavage protection assays such as DNAse I footprinting assay, reporter gene assay, optical affinity biosensor system assay, PCR-based target detection assay, chemical footprinting assay, filter binding assay, immunological assay, sedimentation centrifugation assay, spectroscopic assay, HPLC and other column and thin layer chromatographic assays, immunologic detection assays such as ELISA, tagged antibody, and precipitation assays. These exemplary methods are disclosed in the art such as in U.S. Pat. Nos. 5,783,384, 6,333,153.

In a preferred embodiment, detecting the level of specific binding of the isolated nucleotide sequence that contains the invention's RelBκB sequences (e.g., SEQ ID NO:57) with the protein RelB RHD, as exemplified by SEQ ID NO:62, employs arrays, electrophoretic mobility shift assay (EMSA), immunoprecipitation, ELISA, footprinting assay, reporter gene assay, optical affinity biosensor system assays and the like. One of skill in the art that these exemplary methods are also useful for detecting specific binding of the isolated nucleotide sequence that contains the invention's RelBκB sequences (e.g., SEQ ID NO:57) with the protein RelB RHD, as exemplified by SEQ ID NO:62, are also useful in screening test compounds that alter such binding.

F. Detection of Specific Binding, and Screening Test Compounds, Using Arrays

The level of specific binding of the isolated nucleotide sequence that contains the invention's RelBκB sequences (e.g., SEQ ID NO:57) with the protein RelB RHD, as exemplified by SEQ ID NO:62, may be determined using an "array", i.e., a plurality (i.e., more than one) of reaction compartments. In one embodiment, each of the reaction compartments comprises one test compound. More preferably, the test compound in each of the reaction compartments is different from the test compound in other reaction compartments. Alternatively, some of the reaction compartments may contain the same test compound, e.g., for duplicate/triplicate testing of the same test compound. In one embodiment, the plurality of reaction compartments comprises a micro-well titre plate, also called microplate, such as those used in binding assays, e.g., an ELISA assay, receptor, binding and nucleic acid probe hybridization techniques. Binding may be determined by mixing the components of the reaction mixture in solution, or binding of one or more components that are in solution to one or more surface bound (i.e., immobilized) molecules. In one embodiment, the plurality of reaction compartments comprises at least 48 or at least 96 of the reaction compartments.

Apparatus and methods for using arrays to facilitate screening of a large number of test compounds are known in the art. For example, Santini Jr. et al. U.S. Pat. No. 6,551,838 discloses microfabricated devices for the storage and selective exposure of chemicals and devices. U.S. Pat. No. 5,843,767 to Beattie discloses a microfabricated, flowthrough "genosensors" for the discrete detection of binding reactions. The apparatus includes a nanoporous glass wafer having tapered wells in which nucleic acid recognition elements are immobilized. U.S. Pat. No. 6,083,763 to Balch discloses an apparatus for analyzing molecular structures within a sample substance using an array having a plurality of test sites upon which the sample substance is applied. The test sites typically are in microplate arrays, such as microtitre plates. U.S. Pat. No. 5,797,898 and U.S. Pat. No. 6,123,861 to Santini, et al. describe microchip devices that release drug molecules from reservoirs having reservoir caps that actively or passively disintegrate. U.S. Pat. No. 5,252,294 to Kroy discloses micromechanical structures having closed cavities for use in storage and handling of substances, for example, in research and testing of the substances.

G. Detection of Specific Binding, and Screening Test Compounds, Using Electrophoretic Mobility Shift (EMS) Assays The level of specific binding of the isolated nucleotide sequence that contains the invention's RelBκB sequences (e.g., SEQ ID NO:57) with the protein RelB RHD, as exemplified by SEQ ID NO:62, may be determined using electrophoretic mobility shift assays, also known as gel retardation assays. In gel retardation assays, a double stranded synthetic oligonucleotide is constructed, having the specific nucleotide sequence to that the sequence-specific DNA-binding protein binds. The oligonucleotide is labeled, usually with radioactive phosphate, and incubated with the preparation containing the DNA-binding protein. The oligonucleotide is then electrophoresed on a suitable gel. The binding of a sequence-specific DNA-binding protein is detected as a retardation in the migration of the radioactive oligonucleotide.

Exemplary EMS assays are disclosed herein (FIG. 4B, 5A, 5B) and known in art such as in U.S. Pat. Nos. 6,333,153, 5,900,358, 6,548,540, and 6,150,090, incorporated by reference. Briefly, a nucleic acid binding protein is contacted with a target nucleic acid sequence under suitable conditions to promote specific binding between the protein and the target nucleic acid sequence, electrophoresing the mixture, and detecting the amount of and/or location of the protein and/or the labeled target nucleic acid sequence. The protein may be detected using antibodies, while the target nucleic acid sequence may be detected by detecting a label attached thereto. The "label" may be radioactive or non-radioactive (such as a fluorescent molecule, a chemiluminescent molecule, and biotin). Methods for non-radioactive gel shift assays are known in the art such as those in U.S. Pat. No. 5,900,358.

H. Detection of Specific Binding, and Screening Test Compounds, Using Footprinting Assays The level of specific binding of the isolated nucleotide sequence that contains the invention's RelBκB sequences (e.g., SEQ ID NO:57) with the protein RelB RHD, as exemplified by SEQ ID NO:62, may be determined using footprinting assays. Generally, "footprinting" assays involve binding of a DNA binding protein to a target nucleic acid sequence, which protects the bound portion of the nucleic acid sequence from subsequent nuclease digestion (e.g., using DNase I). More particularly, in foot printing assays, a radioactively-labeled DNA molecule containing the DNA sequence (such as SEQ ID NO:57) to which the sequence-specific DNA-binding molecule (e.g., RelB RHD as exemplified by SEQ ID NO:62) binds is incubated with the sequence-specific DNA-binding molecule and then digested with DNAaseI, an enzyme that cuts DNA molecules regardless of their sequence. This forms DNA fragments of all possible lengths that can be separated by sequencing gel electrophoresis. A "ladder" of these different length fragments is formed on the gel. Binding of the sequence-specific DNA-binding molecule to its cognate nucleotide recognition sequence protects the DNA in that region from digestion with DNAaseI. This protection is observed as a region of reduced intensity of radioactivity on a sequencing gel, i.e., the "ladder" is missing contiguous "rungs" where the protein was bound.

Methods for footprinting assays are known in the art such as those disclosed in U.S. Pat. Nos. 5,510,256, 6,548,734, 6,537,810, and 6,150,090.

I. Detection of Specific Binding, and Screening Test Compounds, Using Reporter Gene Assays The level of specific binding of the isolated nucleotide sequence that contains the invention's RelBκB sequences (e.g., SEQ ID NO:57) with the protein RelB RHD, as exemplified by SEQ ID NO:62, may be determined using reporter gene assays. Methods for reporter gene assays are known in art such as those disclosed in U.S. Pat. Nos. 6,537,973 and 6,150,090, incorporated by reference.

In one embodiment, the invention provides a method for identifying one or more test compounds that alters binding of RelB Rel homology domain (RelB RHD) with a RelBκB sequence, comprising: a) contacting i) an isolated nucleotide sequence containing the invention's RelBκB sequences (e.g., SEQ ID NO:57), that is operably linked to a nucleic acid sequence encoding a reporter molecule with ii) a polypeptide comprising RelB Rel homology domain-(RelB RHD, as exemplified by SEQ ID NO:62), such that RelB RHD specifically binds with the invention's RelB KB sequences (e.g., SEQ ID NO:57), wherein the contacting is in the presence and absence of the one or more test compounds; b) detecting an altered level of expression of the reporter molecule in the presence of the one or more test compounds compared to in the absence of the one or more test compounds, thereby identifying the one or more test compounds as altering binding of RelB Rel homology domain (RelB RHD) with a RelB κB sequence.

A "reporter molecule" as used herein refers to RNA and/or polypeptide, etc. which is detectable in any detection system, including, but not limited to enzyme (e.g., ELISA, as well as enzyme-based histochemical assays), fluorescent, radioactive, and luminescent systems. Exemplary reporter genes include, for example, luciferase, green fluorescent protein (GFP) gene, *E. coli* β-galactosidase gene, human placental alkaline phosphatase gene, horseradish peroxidase, and chloramphenicol acetyltransferase gene.

The term "level of expression" refers to the quantity of RNA and/or protein that is produced following transcription of a DNA sequence that encodes the RNA and/or protein. Methods for determining the level of expression of proteins are known in the art such as Enzyme Linked Immunosorbent Assay (ELISA) as described herein, immunofluorescence assays wherein the transfected cells are incubated with a first antibody that is specific for the expressed protein and flouresecently labeled second antibody that is specific for the immunoglobulin of the first antibody, followed by observation of immunofluorescence under the microscope, and detecting the activity of the protein (e.g., β-glucuronidase encoded by the uid A gene). Methods for determining the level of expression of RNA are known in the art such as Northern blots.

In one embodiment, the nucleotide sequence comprising the RelBκB sequences of the invention are operably linked to the nucleotide sequence encoding the reporter molecule in an expression vector. Expression vectors are exemplified by, but not limited to, plasmid, phagemid, shuttle vector, cosmid, and virus.

The expression vectors of the invention may be introduced into cells using techniques well known in the art. The term "introducing" a nucleic acid sequence into a cell refers to the introduction of the nucleic acid sequence into a target cell to produce a transformed cell. Methods of introducing nucleic acid sequences into cells are well known in the art. For example, where the nucleic acid sequence is a plasmid or naked piece of linear DNA, the sequence may be "transfected" into the cell using, for example, calcium phosphate-DNA co-precipitation, DEAE-dextran-mediated transfection, polybrene-mediated transfection, electroporation, microinjection, liposome fusion, lipofection, protoplast fusion, and biolistics. Alternatively, where the nucleic acid sequence is encapsidated into a viral particle, the sequence may be introduced into a cell by "infecting" the cell with the virus.

Transformation of a cell may be stable or transient. The terms "transient transformation" and "transiently transformed" refer to the introduction of one or more nucleotide sequences of interest into a cell in the absence of integration of the nucleotide sequence of interest into the host cell's genome. Transient transformation may be detected by, for example, enzyme-linked immunosorbent assay (ELISA) which detects the presence of a polypeptide encoded by one or more of the nucleotide sequences of interest. Alternatively, transient transformation may be detected by detecting the activity of the protein (e.g., β-glucuronidase) encoded by the nucleotide sequence of interest. The term "transient transformant" refer to a cell which has transiently incorporated one or more nucleotide sequences of interest. Transient transformation with the invention's vectors may be desirable in, for example, cell biology or cell cycle investigations which require efficient gene transfer.

In contrast, the terms "stable transformation" and "stably transformed" refer to the introduction and integration of one or more nucleotide sequence of interest into the genome of a cell. Thus, a "stable transformant" is distinguished from a transient transformant in that, whereas genomic DNA from the stable transformant contains one or more nucleotide sequences of interest, genomic DNA from the transient transformant does not contain the nucleotide sequence of interest. Stable transformation of a cell may be detected by Southern blot hybridization of genomic DNA of the cell with nucleic acid sequences which are capable of binding to one or more of the nucleotide sequences of interest. Alternatively, stable transformation of a cell may also be detected by the polymerase chain reaction of genomic DNA of the cell to amplify the nucleotide sequence of interest.

One of skill in the art appreciates that there are several cell type suitable for transformation with expression vectors containing the invention's sequences, such as eukaryotic cells (e.g., yeast, insect, and mammalian cells) and prokaryotic cells (e.g., bacterial cells such as E. coli, and viruses).

In one embodiment, it may be desirable to use a control sample containing IKKα having reduced kinase activity (including non-activatable IKKα) compared to wild-type IKKα. Thus, in one embodiment the method further comprises: c) contacting the isolated nucleotide sequence, in the presence of the one or more test compounds, with one or more compositions comprising a polypeptide that comprises RelB RHD, as exemplified by SEQ ID NO:62, wherein the composition is chosen from cell extract, cytoplasmic extract, and nuclear extract, wherein the composition is isolated from a mammalian cell comprising non-activatable IKKα, and wherein the mammalian cell is treated with one or more IKKα activators chosen from lymphotoxin B (LTβ), B cell activating factor belonging to the TNF family (BAFF), anti-LTβR antibody, and CD40 ligand (CD40L); and d) detecting unaltered binding of the isolated nucleotide sequence with RelB RHD, as exemplified by SEQ ID NO:62, in the presence and absence of the one or more test compounds.

In another embodiment, it may be desirable to use RelA:p50 as a control. Thus in one embodiment, the method further comprises detecting unaltered binding of the isolated nucleotide sequence to one or more proteins chosen from a polypeptide comprising one or more of RelA RHD, RelA, p50, and RelA:p50, in the presence and absence of the one or more test compounds.

In a further embodiment, RelA:p52 may be used as control. Thus, the method further comprises detecting unaltered binding of the isolated nucleotide sequence to one or more proteins chosen from a polypeptide comprising one or more of RelA RHD, RelA, p52, and RelA:p52, in the presence and absence of the one or more test compounds.

Where RelB:p50 is used a control, the method may further comprise detecting unaltered binding of the isolated nucleotide sequence to one or more proteins chosen from a polypeptide comprising one or more of RelB RHD, as exemplified by SEQ ID NO:62, RelB, p50, and RelB:p50, in the presence and absence of the one or more test compounds.

Alternatively, one control involves using the consensus-κB sequence by detecting unaltered binding of an isolated nucleotide sequence comprising the consensus-κB sequence 5'-GGGACTTTCC-3' (SEQ ID NO:58) to a polypeptide comprising one or more of RelB RHD, as exemplified by SEQ ID NO:62, and RelB in the presence of the one or more test compounds.

In one embodiment, the method further comprising identifying the one or more test compounds as altering IKKα cellular activity and/or as altering symptoms associated with IKKα related pathology.

J. Detection of Specific Binding, and Screening Test Compounds, Using Optical Affinity Biosensor System Assays The level of specific binding of the isolated nucleotide sequence that contains the invention's RelBκB sequences (e.g., SEQ ID NO:57) with the protein RelB RHD, as exemplified by SEQ ID NO:62, may be determined using optical affinity biosensor system (OABS) assays. The use of optical affinity biosensor systems is known in the art, for example U.S. Pat. No. 6,333,153. For example, in an OABS system such as the IAsys™ system (Affinity Sensors, Cambridge, United Kingdom), binding and dissociation events can be detected as one molecule in solution binds to or dissociates from another molecule immobilized on a detector surface of the system. Thus, an OABS may be used to detect specific binding between invention's RelBκB sequences and one or more proteins, such as RelB:p52, RelB, and RelB RHD, as exemplified by SEQ ID NO:62, by immobilizing either the protein or the target DNA on the detector surface of the OABS.

K. Methods for Expressing a Nucleic Acid Sequences of Interest

The invention also provides methods for inducing expression of a nucleotide sequence of interest by placing this sequence under the regulatory control of the invention RelBκB sequences (e.g., SEQ ID NO:57), and inducing expression by making available proteins that specifically bind to the invention's RelBκB sequences, such as RelB:p52. These methods are useful where it is desirable to have inducible gene expression in response to a stimulus, where constitutive gene expression is less desirable than inducible gene expression. Alternatively, these methods are useful to induce expression of genes which, in their wild type form, are under transcriptional control of the invention's sequences, such as genes whose expression is altered by IKKα activity.

In one embodiment, the invention provides a method for expression of a nucleic acid sequence of interest, comprising: a) providing: i) a cell comprising an isolated nucleotide sequence comprising invention RelBκB sequences (e.g., SEQ ID NO:57), wherein the invention RelBκB sequence is operably linked to the nucleic acid sequence of interest; and ii) a polypeptide comprising RelB Rel homology domain (RelB RED, as exemplified by SEQ ID NO:62); and b) contacting the cell with the polypeptide such that the RelB RHD, as exemplified by SEQ ID NO:62, specifically binds with invention RelBκB sequences (e.g., SEQ ID NO:57), and the nucleic acid sequence of interest is expressed.

Nucleotide sequences that may be employed in the invention's methods include, for example, genes whose expression may be altered (increased and/or decreased) by IKKα kinase activity, such as genes encoding cytokines such interferon-β (IFN-β), interleukin-1 (IL-1), interleukin-2 (IL-2), interleukin-6 (IL-6), interleukin-8 (IL-8), interleukin-12 (IL-12), LTα, and LTβ; chemokines such as IL-8, MIP-1α, MCP1, RANTES, and eotaxin; growth factors such as granulocyte-macrophage colony-stimulating factor (GM-CSF) and vascular endothelial growth factor (VEGF); adhesion molecules such as ICAM, VCAM, and E-selectin, acute phase proteins such as SAA; inducible effector enzymes such as iNOS and COX-2; IgK, CD40 ligand (CD40L), G1 cylcins, cell-cycle regulators such as cyclin D1 and cyclin D2; regulators of apoptosis and cell proliferation such as BCL-$X_L$, cIAP-1, c-IAP-2, A1/BFL1, Fas ligand, c-myc, and cyclin D1; caspase-8/FADD (FAS-associated death domain)-like IL-1β- converting enzyme (FLICE) inhibitory protein (c-FLIP); several metalloproteinases (MMPs), i.e., proteolytic enzymes that promote tumor invasion of surrounding tissue; HTLV-I trans-activator (tax); evolutionarily conserved antimicrobial peptides such as β defensins; molecules involved in the adaptive immune response such as MHC proteins, costimulatory molecules such as B7.1.

Additional nucleotide sequences that may be employed in the invention's methods include, for example, genes encoding a "protein of interest," as described supra.

L. Methods of Altering Symptoms of Diseases Associated with Ikkα Pathology

The invention also provides methods for altering symptoms of IKKα related pathology comprising administering to a mammalian subject one or more compounds that alters binding of RelB Rel homology domain (RelB RHD) with a RelBκB sequence, wherein the one or more compound is identified according to any of the invention's methods. In one embodiment, the invention methods further comprise observing altered symptoms of the IKKα related pathology, wherein the symptoms are reduced or increased. These methods are useful in, for example, identifying compounds (e.g. environmental, chemical, natural occurring, man-made, etc.) that may be implicated in causation and/or exacerbation of IKKα related pathology. Additionally, these methods are useful to identify therapeutic compound that reduce symptoms associated with IKKα related pathology.

The terms "pathology," "disease" and "pathological condition" are used interchangeably to refer to a state, signs, and/or symptoms that are associated with any impairment, interruption, cessation, or disorder of the normal state of a living animal or of any of its organs or tissues that interrupts or modifies the performance of normal functions, and may be a response to environmental factors (such as malnutrition, industrial hazards, or climate), to specific infective agents (such as worms, bacteria, or viruses), to inherent defect of the organism (such as various genetic anomalies, or to combinations of these and other factors. The term "disease" includes responses to injuries, especially if such responses are excessive, produce symptoms that excessively interfere with normal activities of an individual, and/or the tissue does not heal normally (where excessive is characterized as the degree of interference, or the length of the interference).

In particular, the term "IKKα related pathology" refers to pathologies that are associated with altered levels of expression of IKKα, altered levels of kinase activity of IKKα, and/or altered levels of binding of the RelB Rel homology domain (RHD) that is exemplified by SEQ ID NO:62, with a cell's RelBκB sequences (such as SEQ ID NO:57). In one embodiment, IKKα related pathologies may involve overproliferation and/or underproliferation of cells, such as B cells, mammary epithelial cells, cells involved in inflammatory disease, epithelial cells involved in disease such as cancer, and cells involved in infection by microorganisms.

For example, IKKα related pathologies involving overproliferation and/or underproliferation of B cells are exemplified, but not limited to, spleen disorganization, lymphomas (such as diffuse large B-cell lymphomas (DBCLs) which include germinal-center-like and B-cell-like, Hodgkin's B-cell lymphoma, non-Hodgkin's B-cell lymphomas, B-cell lymphomas, virus-induced lymphomas, Birkett's lymphoma, mucosa-associated lymphoid tissue (MALT) lymphomas), leukemia (such as chronic lymphocytic leukaemia (CLL), B-cell lymphocytic leukaemia (B-CLL), virus-induced leukaemias), lymphoid hyperplasia, splenomegaly.

IKKα related pathologies involving overproliferation and/or underproliferation of mammary epithelial cells are exemplified by defects in lactation, defects in alveolar development such as during pregnancy, lactation, and involution, and mammary cancer.

IKKα related pathologies may also involve overproliferation and/or underproliferation of cells involved in inflammatory disease such as, without limitation, sepsis, septic shock, endotoxic shock, inflammatory bowel disease (IBD) such as Crohn's disease and ulcerative colitis, multiple sclerosis, inflammatory diseases involving acute or chronic inflammation of bone and/or cartilage in a joint, anaphylactic reaction, nephritis, asthma, conjunctivitis, inflammatory gum disease, systemic lupus erythematosus, insulin dependent diabetes mellitus, pulmonary sarcoidosis, ocular inflammation, allergy, emphysema, ischemia-reperfusion injury, fibromyalagia, an inflammatory cutaneous disease selected from psoriasis and dermatitis, or an arthritis selected from rheumatoid arthritis, gouty arthritis, juvenile rheumatoid arthritis, and osteoarthritis.

IKKα related pathologies may also involve overproliferation and/or underproliferation of cells infected by a microorganism. The terms "infection by a microorganism" and "microbial infection" are used interchangeably to refer to the undesirable presence of a microorganism (such as bacteria, fingi, protozoa and/or viruses) in a subject. Bacterial and/protozoal infections and disorders related to such infections in humans include the following: pneumonia, otitis media, sinusitis, bronchitis, tonsillitis, and mastoiditis related to infection by *Streptococcus pneumoniae, Haemophilus influenzae, Moraxella catarrhalis, Staphylococcus aureus*, or *Peptostreptococcus* spp.; pharynigitis, rheumatic fever, and glomerulonephritis related to infection by *Streptococcus pyogenes*, Groups C and G streptococci, *Clostridium diptheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis, S. hemolyticus*, etc.), *Streptococcus pyogenes, Streptococcus agalactiae*, Streptococcal groups C-F (minute-colony streptococci), *Viridans streptococci, Corynebacterium minutissimum, Clostridium* spp., or *Bartonella henselae*; uncomplicated acute urinary tract infections related to infection by *Staphylococcus saprophyticus* or *Enterococcus* spp.; urethritis and cervicitis; and sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and Toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chiamydia trachomatis, Neisseria gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; gastroenteritis related to infection by *Campylobacter jejuni*; intestinal protozoa related to infection by *Cryptosporidium* spp.; odontogenic infection related to infection by *Viridans streptococci*; persistent cough related to infection by *Bordetella pertussis*; gas gangrene related to infection by *Clostridium perfringens* or *Bacteroides* spp.; and atherosclerosis related to infection by *Helicobacter pylori* or *Chlamydia pneumoniae*, and gastrointestinal infections related to the protozoa *Entameba histolytica, Cryptosporidium parvum, Giardia lamblia,* and *amoebae.*

Frequently seen parasitic protozoal diseases include malaria, caused by the four *Plasmodium* species: *P. falciparum, P. vivax, P. ovale* and *P. malariae,* toxoplasmosis, caused by *Toxoplasma gondii,* leishmaniasis, caused by *Leishmania* species such as *Leishmania donovani,* and Chagas' disease (American trypanosomiasis), caused by *Trypanosoma cruzi.*

Fungal infections of humans include candidiasis, aspergillosis, mucormycosis, cryptococcosis, ringworms (caused by *Tinea corpis* and *Tinia capitis*), athlete's foot (caused by *Tinea pedis*), nail infections (caused by onychomycosis), and "jock itch" (caused by *Tinea cruris*).

Viral infections of humans include infections with polyomavirus, papillomavirus, T-cell leukemia virus), herpes simplex virus, adenovirus, Rous sarcoma virus, cytomegalovirus, retroviruses such as enteroviruses, Epstein Barr virus (EBV) implicated in Burkitt's and Hodgkins lymphomas, as well as B-cell lymphomas in immunocompromised hosts, HIV virus, hepatitis B virus, pseudorabies virus, papilloma virus.

IKKα related pathologies may also involve overproliferation and/or underproliferation of epithelial cell, such as epithelial cell cancer. The terms "cancer" refers to a neoplasm which contains at least one cancer cell. A "cancer cell" refers to a cell undergoing early, intermediate or advanced stages of multi-step neoplastic progression as previously described (H. C. Pitot (1978) in "Fundamentals of Oncology," Marcel Dekker (Ed.), New York pp 15-28), including pre-neoplastic cell (i.e., hyperplastic cell and dysplastic cell) and neoplastic cell. The term "cancer" is used herein to refer to a neoplasm, which may or may not be metastatic. Exemplary cancers within the scope of the invention include carcinomas such as breast cancer, gastric cancer, lung cancer, prostate cancer, cervical cancer, pancreatic cancer, colon cancer, colorectal cancer, ovarian cancer; stomach cancer, esophagus cancer, mouth cancer, tongue cancer, gum cancer, skin cancer (e.g., melanoma, basal cell carcinoma, Kaposi's sarcoma, etc.), muscle cancer, heart cancer, liver cancer, bronchial cancer, cartilage cancer, bone cancer, testis cancer, kidney cancer, endometrium cancer, uterus cancer, bladder cancer, bone marrow cancer, lymphoma cancer, spleen cancer, thymus cancer, thyroid cancer, brain cancer, neuron cancer, mesothelioma, gall bladder cancer, ocular cancer (e.g., cancer of the cornea, cancer of uvea, cancer of the choroids, cancer of the macula, vitreous humor cancer, etc.), joint cancer (such as synovium cancer), glioblastoma, lymphoma, leukemia, and hereditary non-polyposis cancer (HNPC), colitis-associated cancer. Cancers are further exemplified by sarcomas (such as osteosarcoma and Kaposi's sarcoma).

Other IKKα related pathologies include, for example, multiple myeloma, T-cell lymphomas, sporadic adenomatous polyps, hereditary familial adenomatous polyposis (FAP).

The compounds identified in accordance with the invention's methods may be administered in a pharmaceutically effective amount. As used herein, the actual amount encompassed by the term "pharmaceutically effective amount" will depend on the route of administration, the type of subject being treated, and the physical characteristics of the specific subject under consideration. These factors and their relationship to determining this amount are well known to skilled practitioners in the medical, veterinary, and other related arts. This amount and the method of administration can be tailored to achieve optimal efficacy but will depend on such factors as weight, diet, concurrent medication and other factors which those skilled in the art will recognize.

The dosage amount and frequency are selected to create an effective level of the compound without substantially harmful effects. A pharmaceutically effective amount may be determined using in vitro and in vivo assays known in the art.

Methods of administering a pharmaceutically effective amount of the invention's compounds are well known in the art and include, without limitation, administration in parenteral, oral, intraperitoneal, intranasal, topical, sublingual, rectal, and vaginal forms. Parenteral routes of administration include, for example, subcutaneous, intravenous, intramuscular, intrasternal injection, and infusion routes.

The compounds may be administered before, concomitantly with, and/or after manifestation of one or more symptoms of a disease or condition. Also, the compounds may be administered before, concomitantly with, and/or after administration of another type of drug or therapeutic procedure (e.g., surgery).

Pharmaceutical compositions preferably comprise one or more compounds of identified in accordance with the present invention, that are associated with one or more pharmaceutically acceptable carrier, diluent or excipient. In preparing such compositions, the active ingredients are usually mixed with or diluted by an excipient or enclosed within such a carrier which can be in the form of a capsule or sachet in which the coating may be gelatin, sugar, shellac, and other enteric coating agents. When the excipient serves as a diluent, it may be a solid, semi-solid, or liquid material which acts as a vehicle, carrier, or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders. Examples of suitable excipients include lactose, dextrose, sucrose, sorbitol, mannitol, starch, gum acacia, calcium silicate, microcrystalline cellulose, polyvinylpyrrolidone, cellulose, water, syrup, and methyl cellulose.

Pharmaceutically acceptable carriers are known in the art such as those described in, for example, Remingtons Pharmaceutical Sciences, Mack Publishing Co. (A. R. Gennaro edit. 1985). Exemplary pharmaceutically acceptable carriers are sterile saline, phosphate-buffered saline at physiological pH, polyethylene glycols, polypropylene copolymers, and water soluble gels.

Other compounds that may be included with the invention's compositions include, for example, diluents, fillers, salts, buffers, preservatives (e.g., sodium benzoate, sorbic acid and esters of p-hydroxybenzoic acid), stabilizers, dyes, antioxidants, flavoring agents, lubricating agents (such as talc, magnesium stearate and mineral oil), wetting agents, emulsifying and suspending agents, preserving agents such as methyl- and propylhydroxybenzoates, sweetening agents and/or flavoring agents.

The pharmaceutically acceptable carriers may be liquid, with the compositions being, for example, an oral syrup or injectable liquid. Compositions in solid or liquid form may include an agent which binds to the active component(s) and thereby assists in the delivery of the active components. Suitable agents which may act in this capacity include a monoclonal or polyclonal antibody, a protein or a liposome.

Alternatively, the pharmaceutical composition of the present invention may consist of gaseous dosage units, e.g., it may be in the form of an aerosol useful in, for example, inhalatory administration. The term "aerosol" is used to denote a variety of systems ranging from those of colloidal nature to systems consisting of pressurized packages. Delivery may be by a liquefied or compressed gas or by a suitable pump system which dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, spacers and the like, which together may form a kit. Preferred aerosols may be determined by one skilled in the art, without undue experimentation.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, chewing gum, wafer or the like form. Such a solid composition will typically contain one or more inert diluents or edible carriers. In addition, one or more of the following adjuvants may be present: binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The composition may be intended for rectal administration, for example in the form of a suppository which will melt in the rectum and release the drug. The composition for rectal administration may contain an oleaginous base as a suitable nonirritating excipient. Such bases include, without limitation, lanolin, cocoa butter and polyethylene glycol.

When the composition is in the form of a capsule, e.g., a gelatin capsule, it may contain, in addition to materials of the above type, a liquid carrier such as polyethylene glycol, cyclodextrin or a fatty oil.

The composition may be in the form of a liquid, e.g., an elixir, syrup, solution, emulsion or suspension. The liquid may be for oral administration or for delivery by injection, as two examples. When intended for oral administration, preferred compositions contain, in addition to the invention's compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

The pharmaceutical compositions may be prepared by methodology well known in the pharmaceutical art. A composition intended to be administered by injection can be prepared by combining the compound of any one of Formulae A-E with water so as to form a solution. A surfactant may be added to facilitate the formation of a homogeneous solution or suspension. Surfactants are compounds that non-covalently interact with the compound of any one of Formulae A-E so as to facilitate dissolution or homogeneous suspension of the active compound in the aqueous delivery system.

M. Kits

The invention also provides kits comprising an isolated nucleotide sequence comprising one or more of the invention's RelBκB sequences. In one embodiment, the kit further comprises instructions for binding the isolated nucleotide sequence with a polypeptide comprising RelB RHD, as exemplified by SEQ ID NO:62. The kits are useful in any of the invention's methods.

As used herein, the term "kit" is used in reference to a combination of reagents and other materials. It is contemplated that the kit may include reagents such as buffering agents, nucleic acid stabilizing reagents, protein stabilizing reagents, signal producing systems (e.g., florescence generating systems as Fret systems), antibodies, control proteins, control nucleic acid sequences, as well as testing containers (e.g., microtiter plates, etc.). It is not intended that the term "kit" be limited to a particular combination of reagents and/or other materials. In one embodiment, the kit further comprises instructions for using the reagents. The test kit may be packaged in any suitable manner, typically with the elements in a single container or various containers as necessary along with a sheet of instructions for carrying out the test. In some embodiments, the kits also preferably include a positive control sample. Kits may be produced in a variety of ways known in the art.

O. Additional Considerations

Two distinct pathways leading to selective activation of RelA:p50 and RelB:p52 dimers, dependent on IKKβ or IKKα, respectively, were identified (Ghosh et al. (2002) Cell, 109, S81-96). Each pathway has distinct biological functions (Chen et al. (2003) Nat Med, 9, 575-581; Li et al. (1999) Science, 284, 321-325; Senftleben et al. (2001) Science, 293, 1495-1499), that could be mediated in part through selective gene activation (Dejardin et al. (2002) Immunity, 17, 525-535). How this occurs was previously unknown. We now show in two exemplary cell types, splenic stromal cells and BMDC, that IKKα is required for induction of four genes encoding chemokines critical for spleen organogenesis and maintenance of tissue microarchitecture, because these genes are selectively recognized by RelB-containing dimers, most likely RelB:p52. These genes are preferentially activated by engagement of LTβR and are weakly induced by TNFα. Whereas the TNFα response is IKKα-independent, the response to LTβR engagement is strictly IKKα-dependent. The latter requires two events. First, RelB:p52 dimers have to enter the nucleus, a process dependent on IKKα-mediated p100 processing (Dejardin et al. (2002) Immunity, 17, 525-535; Yilmaz et al. (2003) Embo J, 22, 121-130). Second, RelB:p52 dimers are selectively recruited to the IKKα-dependent gene promoter. The selective recruitment of RelB to the Blc and the Elc promoters is likely to depend on a novel κB site, whose consensus sequence (FIG. 30D) is distinct from that of the classical κB site. Unlike the classical site, the novel site is preferentially recognized by RelB:p52 dimers. This unique sequence specificity is entirely consistent with sequence differences between the DNA binding loops of RelA and RelB, but were previously unknown (Ghosh et al. (1995) Nature, 373, 303-310). It is entirely possible, however, that additional factors may contribute to selective IKKα-dependent gene activation and that IKKα may also be responsible in certain cell types for activation of the canonical NF-κB pathway (Cao et al. (2001) Cell, 107, 763-775) or for potentiating its ability to activate transcription (Anest et al. (2003) Nature, 423, 659-663; Israel et al. (2003) Nature, 423, 596-597; Yamamoto et al. (2003) Nature, 423, 655-659). Nonetheless, an important mechanism responsible for selective gene activation through the IKKα-dependent alternative NF-κB signaling pathway is based on specific recruitment of RelB:p52 dimers to target gene promoters. Sites similar to the RelB:p52 selective κB site were detected in the 5' regulatory region of three other genes, whose expression was found to be IKKα-dependent (FIG. 30D).

It is the inventor's view that IKKβ-mediated NF-κB signaling is responsible for rapid responses to infection and injury that require recruitment of immune cells out of lymphoid organs to sites of infection. This response depends on pro-inflammatory chemokines, such as MIP-1, MCP-1 and RANTES, which are induced by the canonical NF-κB signaling pathway (Alcamo et al. (2001) J Immunol, 167, 1592-1600). The arrival of antigens to secondary lymphoid tissues from distal sites of infection and their processing, presentation and recognition require coordinated activity of DC, macrophages, T cells and B cells, whose recruitment to secondary lymphoid organs depends on IKKα-regulated organogenic chemokines. Premature expression of such chemokines would compromise the immediate anti-microbial response as it may abort the emigration of immune cells to the periphery. It is, therefore, logical that expression of organogenic chemokines would not be induced through the canonical NF-κB signaling pathway. Consistent with its delayed function in adaptive immunity, activation of the alternative NF-κB signaling pathway is slower than the canonical NF-κB signaling pathway and seems to depend on prior activation of the latter (Dejardin et al. (2002) Immunity, 17, 525-535). The dependence of the two pathways on distinct but related protein kinases and transcription factors allows for both functional integration and kinetic separation.

EXPERIMENTAL

The following examples serve to illustrate certain preferred embodiments and aspects of the present invention and are not to be construed as limiting the scope thereof.

Example 1

Materials And Methods

The following is a brief description of exemplary materials and methods that may be used in the invention's methods.
A. Primary Cell Cultures
Primary stromal cell cultures were established from spleens of wild type (WT) and Ikkα$^{AA/AA}$ mice as described (Skibinski et al. (1998) Eur J Immunol 28, 3940-3948). Briefly, spleens were gently ground and released cells cultured in DMEM supplemented with heat-inactivated FCS (Invitrogen, Carlsbad, Calif.). After one week, non-adherent cells were removed, adherent cells were washed twice with PBS and cultured one more week in DMEM/FCS. Absence of contaminating myeloid and lymphoid cells was verified by flow cytometry (FACSCalibur, Becton Dickinson) using antibodies to B220, TCRβ and MAC-1 (all from BD Pharmingen, San Diego, Calif.). Stromal cells were uniformly positive for ICAM-1 (clone BBIG-I1 R&D Systems, Minneapolis, Mn).
B. Adoptive Transfers
Bone marrow cells (3-4×10$^6$ cells per mouse) were isolated from femurs of WT or Ikkα$^{AA/AA}$ mice and injected intravenously via the tail vein into sublethally or lethally irradiated recipients. Mice were H-2 matched and, in the case of Ikkα$^{AA/AA}$, were from the F3-F5 backcross to C57Bl/6. Generation of chimeric mice from Ikkα$^{-/-}$ fetal liver cells was as described (Senftleben et al. (2001a) Science 293, 1495-1499). Mice were provided antibiotics in drinking water and sacrificed 6-8 weeks post reconstitution. Splenocytes were prepared by gentle mincing of spleens between frosted glass slides; 10$^7$ cells were introduced into sublethally irradiated (750 rad) Rag2$^{-/-}$ mice (C57Bl/6 Taconic, Germantown, N.Y.) by tail vein injection and sacrificed 10 days post-transfer. B-cells were prepared by depletion with anti-CD43 magnetic beads (MACS, Auburn, Calif.) resulting in 92-95% purity. 10$^7$ purified B-cells were injected i.v into B-cell deficient muMT mice (Jackson Laboratory, Bar Harbor, Me.). Recipient mice were sacrificed 15-20 days post-transfer. Some mice were immunized intraperitoneally (i.p.) with SRBC (Colorado Serum Company, Denver, Co) 7 days prior to sacrifice (Poljak et al. (1999) J Immunol 163, 6581-6588).
C. Immunohistochemical Analysis
Cryosections (8-10 µM) of spleen were prepared, dried and fixed with acetone before immunohistochemical analysis (Poljak et al. (1999) J Immunol 163, 6581-6588; Weih et al. (2001) J Immunol 167, 1909-1919). Staining reagents were: ER-TR9 (RDI, Flanders N.J.), FDC-M2 (ImmunoKontact, UK), BM-8-bio (RDI), ICAM-1 (Santa-Cruz Biologicals, Calif.), MOMA-1 (FITC Calbiochem), MAdCAM (clone MECA-3670), CD11c-bio (clone HL-3), B220, and CD35-bio (clone 8C12) (all from BD Pharmingen). Primary antibodies were revealed using species-specific secondary reagents. Sections were viewed by immunofluorescence microscopy (HM505E Microm Inc, Walldorf, Germany) and images captured with a digital camera (Nikon E800 Scope with Spot Diagnostics Digital Camera, A.G. Heinze Inc., Lake Forest, Calif.).
D. Electrophoretic Mobility Shift Assay (EMSA) and Immunoblotting
Nuclear and cytoplasmic extracts were prepared and analyzed as previously described for the levels of NF-κB subunits and DNA binding activity (Bonizzi et al. (1999) Mol Cell Biol 19, 1950-1960; Mercurio et al. (1993) Genes Dev 7, 705-718; Senftleben et al. (2001a) Science 293, 1495-1499). Recombinant NF-κB subunits were produced in E. coli and purified as described (Chen et al., 1999).
E. Analysis of Gene Expression
RNA was extracted from WT and Ikkα$^{AA/AA}$ stromal cells after stimulation with an agonistic anti-LTβR antibody, or from total splenocytes of naïve and immunized WT and Ikkα$^{AA/AA}$ mice (Cao et al. (2001) Cell 107, 763-775). Real-time PCR™ was performed using a PE Biosystems 5700 thermocycler following the SyBr Green™ detection protocol as outlined by the manufacturer. Briefly, 12 ng of total cDNA, 50 nM of each primer and 1× SyBr Green™ mix were used in a total volume of 25 µl. All values were standardized to that of cyclophilin mRNA. Primer sequences used for real-time PCR™ were as follows:

```
IkB
(5'-CCAGAACAACCTGCAGCAGAC-3'      (SEQ ID NO: 21)
and

5'-GCTCAGGATCACAGCCAGCTT-3',      (SEQ ID NO: 22))

ELC
(5'-CATCTGAGCGATTCCAGTCA-3',      (SEQ ID NO: 23)
5'-ACTGTGTGCGCAAGAATCTG-3',       (SEQ ID NO: 24))

SLC
(5'-GAGTGTCTCCCAGGGAATGA-3',      (SEQ ID NO: 25)
5'-CTTGGGACCTGAGTGACCCT-3',       (SEQ ID NO: 26))

BLC
(5'-CCATTTGGCACGAGGATTCAC-3',     (SEQ ID NO: 27)
5'-ATGAGGCTCAGCACAGCAAC-3',       (SEQ ID NO: 28))

CXCR7
(5'-GAGAGACAAGAACCAAAAGCAC-3',    (SEQ ID NO: 29)
5'-GGGAAGAATTAGGAGGAAAAGG-3',     (SEQ ID NO: 30))

CXCR5
(5'-ACTACCCACTAACCCTGGAC-3',      (SEQ ID NO: 31)
5'-AGGTGATGTGGATGGAGAGGAG-3',     (SEQ ID NO: 32))

BAFF
(5'-AGCTCCAGGAGAAGGCAACTC-3',     (SEQ ID NO: 33)
5'-ACGGCACGCTTATTTCTGCT-3',       (SEQ ID NO: 34))

LTα
(5'-CAGCAAGCAGAACTCACTGC-3',      (SEQ ID NO: 35)
5'-AAGAGAAGCCATGTCGGAGA-3',       (SEQ ID NO: 36))

LTβ
(5'-TACACCAGATCGAGGGGTTC-3',      (SEQ ID NO: 37)
5'-GAGCTCAGGGTTGAGGTCAG-3',       (SEQ ID NO: 38))

LTβR
(5'-CGGGACACTTCCAGAACACT-3',      (SEQ ID NO: 39)
5'-CCCTGGATCTCACATCTGGT-3',       (SEQ ID NO: 40))

TNFα
(5'-ACAGAAAGCATGATCCGCG-3',       (SEQ ID NO: 41)
5'-GCCCCCCATCTTTTGGG-3',          (SEQ ID NO: 42))

VCAM
(5'-GACAGGCCACTAAACGCGAA-3',      (SEQ ID NO: 43)
5'-CAGAACGGACTTGGACCCCT-3',       (SEQ ID NO: 44))

ICAM-1
(5'-GATCACATTCACGGTGCTG-3',       (SEQ ID NO: 45)
5'-GAGAAATTGGCTCCGTGGTC-3'.       (SEQ ID NO: 46))
```

F. Chromatin Immunoprecipitation Assays (ChIP)

ChIP assays were carried out as described (Saccani and Natoli (2002) Dynamic changes in histone H3 Lys 9 methylation occurring at tightly regulated inducible inflammatory genes, Genes Dev 16, 2219-2224). Polyclonal antibodies to p65 (C-20), RelB (C-19) and Pol II (N-19) were from the supplier Santa Cruz. The following sequences of the promoter-specific primers were used: Blc +12 to −688 (5'-GACAAATGTATAAATATTTACTGA-3' (SEQ ID NO:47) and 5'-AACCTTTAGCTCGGAGTCTGCAT-3' (SEQ ID NO:48), Sdf-1 +22 to −678 (5'-TTCGTACCATCCAC-CCACCCCCAG-3' (SEQ ID NO:49), and 5'-ACCGAGAGT-GAAAGTGCGGCAGCG-3' (SEQ ID NO:50)), Vcam-1 +30 to −640 (5'-GGCATTTAAGACACTTAATTG-3' (SEQ ID NO:51) and 5'-ATAAATCTCTGGCCTCCTG-3' (SEQ ID NO:52)), Ikbα+20 to −340 (5'-CGCTAAGAGGAACAGC-CTAG-3' (SEQ ID NO:53) and 5'-CAGCTGGCTGAAA-CATGG-3' (SEQ ID NO:54)), and Tnfα+20 to −545 (5'-GCTGCTCTGCCTTCAGCAGC-3' (SEQ ID NO:55) and 5'-TCCACGCTGAGGGAGCTTCT-3' (SEQ ID NO:56)).

G. Construction, Expression and Purification of an Exemplary DNA-Binding Domain (DBD) of Human p52 (Residues 1-340 of SEQ ID NO:64) and of Murine RelB (Residues 1-400 of SEQ ID NO:62)

1. Construction of the p52 DBD E. coli E. coli Expression Vector:

cDNA corresponding to human p52 was amplified by polymerase chain reaction (PCR) using two primers. The 5' primer contained an Nde1 restriction endonuclease (RE) cleavage site and the 3' primer contained the BamH1 RE cleavage site. The PCR product was cleaned and restricted by Nde1 and BamH1 which is referred to as the insert. An E. coli E. coli T7-expression vector (pET11a, Novagen) was also restricted by the same endonuclease pair. The linearized vector and the insert were mixed and ligated together in the presence of DNA ligase, followed by identification of the correct recombinant plasmid.

2. Bacterial Expression of p52 DBD:

The recombinant plasmid was transformed into an E. coli E. coli strain, BL21(DE3). A 2 ml LB broth was inoculated with a fresh single colony and was grown for three hours. The small culture was transferred into a 2 L broth for large scale protein production. The culture was grown to optical density (O.D.) of approximately 0.4 at 37° C. followed by induction with 0.1 mM IPTG. Induction allows the expression of p52 DBD in large amounts. The culture was allowed to grow for an additional 10-12 hours at room temperature.

3. p52 DBD Purification:

Cells were pelleted by centrifugation and the pellet was suspended in buffer A (20 mM Tris 7.5, 50 mM NaCl, 10 mM bME, 0.1 mM EDTA and 0.1 mM PMSF). Suspended cells were sonicated followed by centrifugation to remove cell debris. Clear supernatant was then loaded onto an anion exchange column pre-equilibrated with buffer A. The flow through containing p52 DBD was collected and loaded onto a cation exchange column. The bound protein was eluted by a linear gradient of NaCl at a concentration from 50 mM to 500 mM. Fractions were analyzed by SDS-PAGE and the fractions containing p52 DBD were pooled, concentrated and subjected to size exclusion chromatography. The peak fractions containing the p52 DBD were pooled and concentrated for further use.

4. Construction of RelB DBD E. coli Expression Vector:

Construction of an exemplary recombinant murine RelB DBD expression vector was done essentially as described above for the p52 DBD expression vector with the exception of the use of pET15b (Novagen) instead of pET11a. This vector expresses RelB DBD as a poly histidine fusion protein.

5. Bacterial Expression of RelB DBD:

Expression of RelB DBD was done essentially as described above for p52 DBD expression.

6. RelB DBD Purification:

RelB DBD was purified using two chromatographic steps. In the first step, the supernatant of cell extract was loaded onto a Ni affinity column which specifically binds to poly-histidine peptide. In this case the poly histine tagged RelB DBD (His-RelB DBD) remained bound to the column. Bound protein was eluted with 250 mM imidazole which competes with histindine for binding to the $Ni^{2+}$ affinity matrix. Eluted His-RelB DBD was concentrated and loaded onto a size exclusion column, Superdex 200 column (Pharmacia). Fractions containing His-RelB DBD were pooled and concentrated.

H. Preparation of an Exemplary Rel DBD/p52 DBD Heteordimer:

His-RelB DBD and p52 DBD that had been purified as described above were mixed together in 1:1.2 molar ratio (i.e., with excess p52 DBD) and diluted to ~0.4 mg/ml concentration in a denaturing buffer B (7 M urea, 0.5 M NaCl, 20 mM Tris pH 7.5, 5 mM DTT, 10% glycerol). The denatured protein mixture (100 ml total volume that contained 40 mg total protein) was refolded by slowly removing urea by dialysis. The sample was subjected to dialysis against 2 L buffer C (buffer C was the same as buffer B except it lacked urea) for 6 hours. The dialysis step was repeated two more times. After dialysis, the refolded heterodimer was loaded onto the Ni-affinity column. Excess, uncomplexed p52 DBD flows through the column because it has no poly-His tag to bind Ni-affinity matrix. The heterodimer was eluted with imidazole. The eluate was concentrated and further purified using size exclusion chromatography (Superdex 200, Pharmacia). Fractions containing the heterodimer were pooled and concentrated. The presence of both proteins was confirmed by standard western blotting.

Example 2

Stromal Cell-Derived Chemokine Production Requires IKKα

Figure 1:
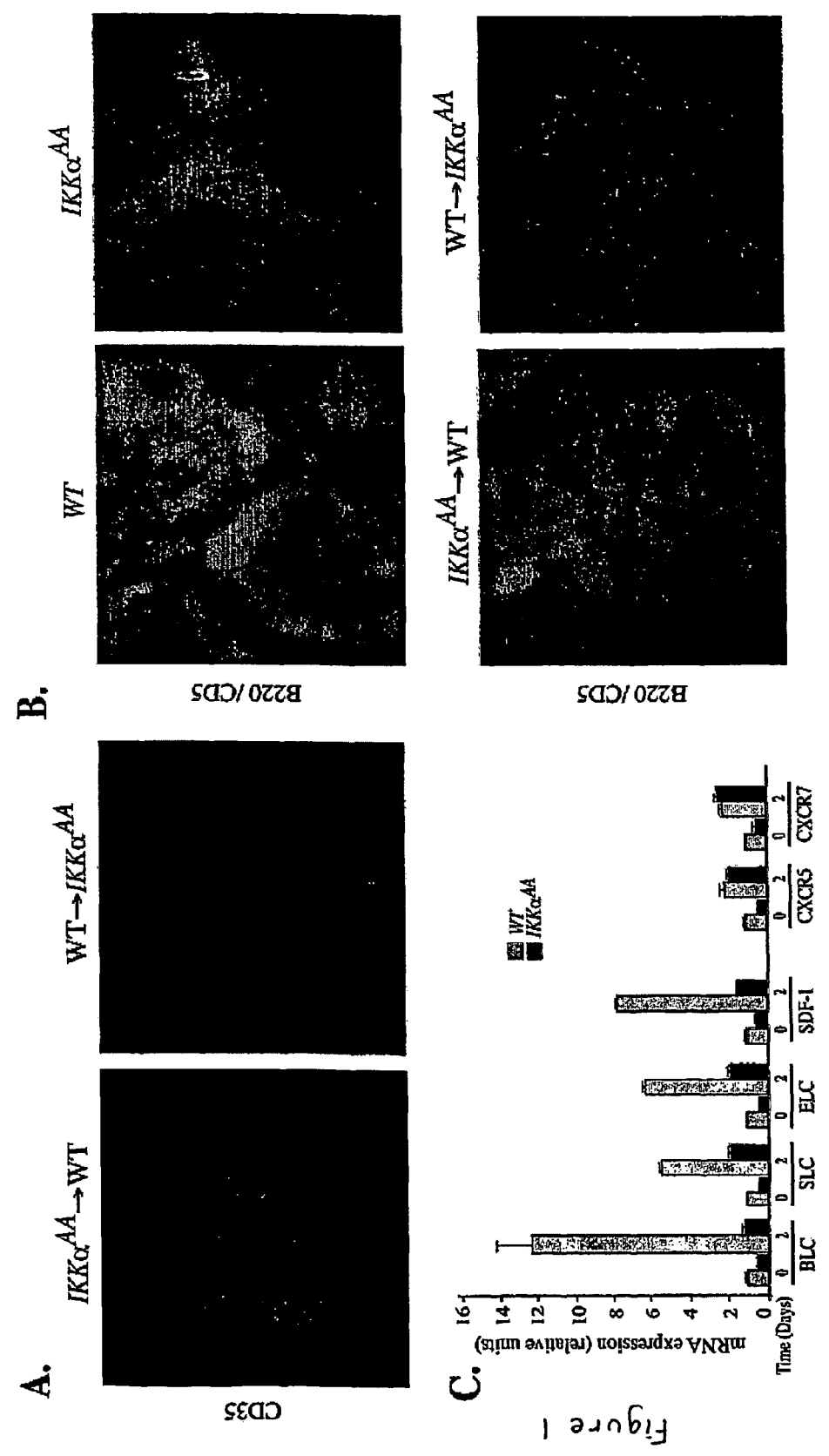

Lethally irradiated mice reconstituted with Ikkα$^{-/-}$ hematopoietic progenitors revealed a role for IKKα in late B-cell maturation, splenic organization and germinal center (GC) formation (U. Senftleben et al., *Science* 293, 1495-1499 (2001); T. Kaisho et al., *J. Exp. Med.* 193, 417-426 (2001)). However, embryonic lethality precludes the use of Ikkα$^{-/-}$ mice to identify functions for IKKα in other cell types. Homozygous knock-in mice expressing an IKKα variant that cannot be activated (Ikkα$^{AA/AA}$ mice) are viable, yet show defective lymphoid organogenesis and GC formation (U. Senftleben et al., *Science* 293, 1495-1499 (2001)). To identify the cells in which IKKα acts to control secondary lymphoid organogenesis, reciprocal bone marrow chimeras were generated between Ikkα$^{AA/AA}$ and WT mice. The chimeric mice were challenged with a T-cell dependent antigen, sheep red blood cells (SRBC), and sacrificed 7 days later. Using an antibody against FDC-M2 or CD35, we examined formation of mature follicular dendritic cells (FDC). FDC maturation was impaired in Ikkα$^{AA/AA}$ recipients reconstituted with WT bone marrow, whereas a mature FDC network formed in WT recipients reconstituted with Ikkα$^{AA/AA}$ bone marrow (FIG. 1A). These results suggest that IKKα acts in stromal cells of the spleen to induce their maturation into FDCs.

Another aspect of proper splenic development is segregation of B and T-lymphocytes to the follicles and the periarterial lymphatic sheath (PALS), respectively. WT chimeras reconstituted with Ikkα$^{AA/AA}$ bone marrow, but not Ikkα$^{AA/AA}$ mice reconstituted with WT bone marrow, exhibited normal B- and T-cell segregation (FIG. 1B). These results also point to a critical action of IKKα in stromal cells, which control splenic microarchitecture through production of organogenic chemokines that dictate cell migration and positioning (K. M. Ansel, J. G. Cyster, *Curr Opin Immunol* 13, 172-179 (2001)), other than the hematopoietic compartment as previously assumed (U. Senftleben et al., *Science* 293, 1495-1499 (2001); T. Kaisho et al., *J. Exp. Med.* 193, 417-426 (2001)). Critical chemokines for spleen development include ELC and SLC, ligands for the chemokine receptor CCR7, BLC, which binds CXCR5 (R. Forster et al., *Cell* 99, 23-33 (1999); K. M. Ansel et al., *Nature* 406, 309-314 (2000)) and SDF-1, which promotes trafficking of both immature and naïve lymphocytes to lymphoid tissues (C. H. Kim, H. E. Broxmeyer, *J Leukoc Biol* 65, 6-15 (1999)). Previous work revealed that induction of these chemokines in response to engagement of LTβR is defective in Ikkα$^{AA/AA}$ mice (E. Dejardin et al., *Immunity* 17, 525-535 (2002)). We extended these observations to SRBC immunized mice (FIG. 1C).

Example 3

IKKα is Required for LTβR-Induced RelB:p52 Nuclear Translocation and Chemokine Expression in Splenic Stromal Cells and Myeloid Dendritic Cells The defects described in Example 2 were very similar to those exhibited by mice lacking LTβR (Y. X. Fu, D. D. Chaplin, *Annu Rev Immunol* 17, 399-433 (1999)). The major cell type expressing LTβR in the spleen is the stromal cell. To examine the role of IKKα in LTβR signaling in splenic stromal cells, as well as in bone marrow derived dendritic cells (BMDC), which also express LTβR (J. L. Browning, L. E. French, *J Immunol* 168, 5079-5087 (2002)), we isolated and cultured these cells from WT and Ikkα$^{AA/AA}$ mice. Stimulation of WT stromal cells with agonistic anti-LTβR antibody (E. Dejardin et al., *Immunity* 17, 525-535 (2002)) resulted in 4-6-fold induction of BLC, SDF-1, TNFα and VCAM-1 mRNAs (FIG. 2A). Modest induction of ELC and SLC mRNAs was also observed. Both basal expression and induction of BLC, SDF-1, ELC and SLC mRNAs were defective in Ikkα$^{AA/AA}$ stromal cells, but induction of TNFα and VCAM-1 remained intact or became more efficient. By contrast, very little differences in expression of TNFα-inducible genes were found between WT and Ikkα$^{AA/AA}$ stromal cells (FIG. 2A).

TNFα induced both rapid and delayed nuclear translocation of RelA in WT and Ikkα$^{AA/AA}$ stroma cells (FIG. 2B). Induction of RelA nuclear translocation by anti-LTβR was slower than the response to TNFα and was also not affected by the Ikkα$^{AA/AA}$ mutation. Neither TNFα nor anti-LTβR had a significant effect on the subcellular distribution of p50, as this NF-κB subunit was constitutively nuclear. Both TNFα and anti-LTβR induced nuclear translocation of RelB in WT cells, but TNFα was capable of sending RelB to the nucleus of Ikkα$^{AA/AA}$ cells. As expected, anti-LTβR, but not TNFα, stimulated nuclear entry of p52 and this effect was seen in WT cells (FIG. 2B). In WT BMDCs, LTβR engagement led to induction of SLC, ELC and IκBα mRNAs (FIG. 2C). SLC and ELC, however, were not induced in BMDC from Ikkα$^{AA/AA}$ mice. Again, we found that at least one gene, this time CXCR5, was hyperinducible in mutant cells. As in stromal cells, anti-LTβR induced RelA nuclear translocation in both WT and Ikkα$^{AA/AA}$ BMDCs, but its ability to induce p52 and RelB nuclear entry was abolished in Ikkα$^{AA/AA}$ cells (FIG. 2D).

The results shown above and genetic analysis of NF-κB2 (G. Franzoso et al., *J. Exp. Med.* 187, 147-159 (1998)) and RelB-(D. S. Weih, Z. B. Yilmaz, F. Weih, *J Immunol* 167, 1909-1919 (2001)) deficient mice suggest that Blc, Sdf-1, Elc and Slc genes induction requires RelB:p52 nuclear translocation.

Example 4

Figure 3:
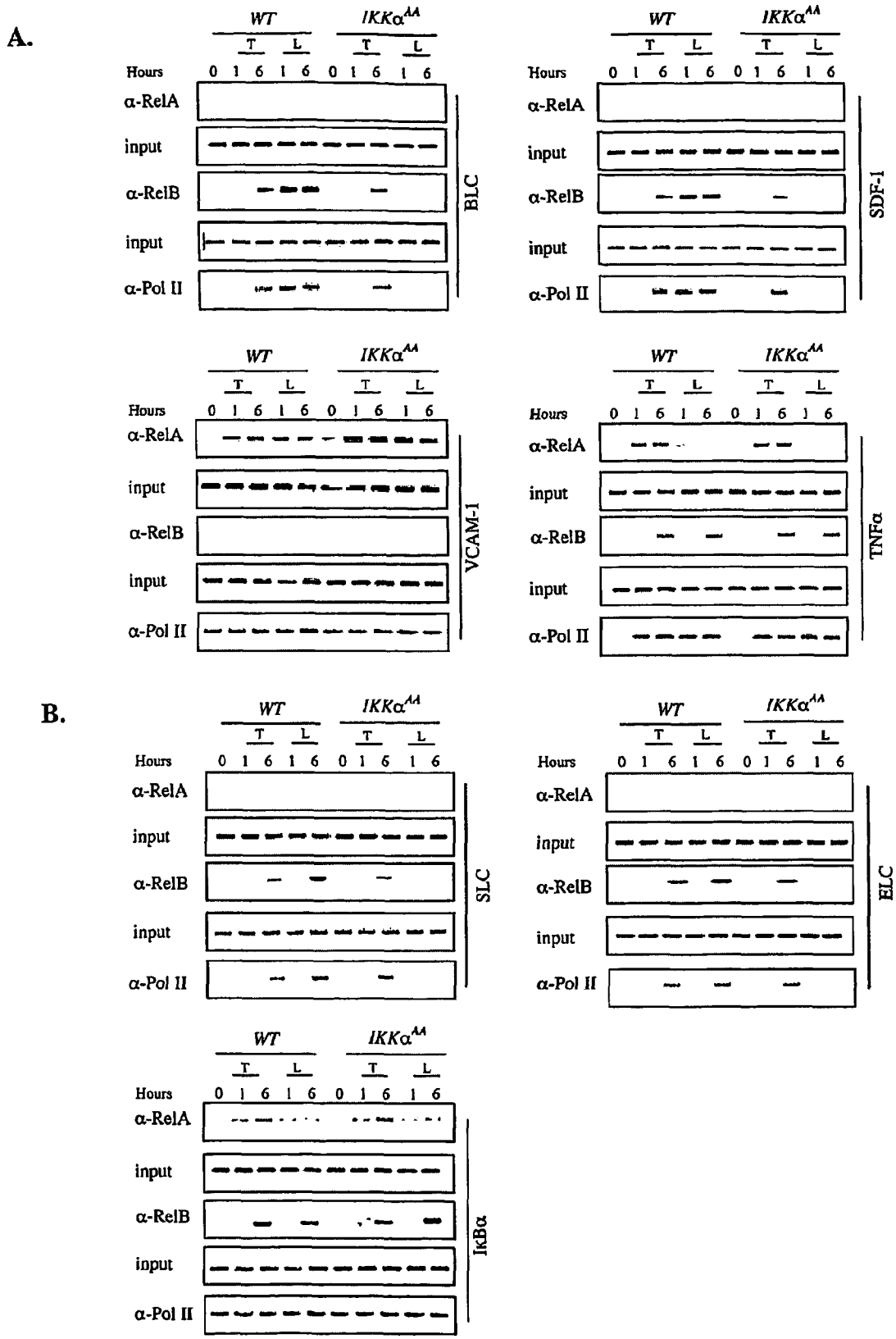
FIG. 3 shows that IKKα is required for recruitment of RelB to the Blc, Sdf-1, Elc and Slc promoters. Primary cultures of stromal cells (A) and bone marrow-derived dendritic cells (BMDC) (B) from WT and Ikkα$^{AA/AA}$ mice were left unstimulated or stimulated with TNFα (T) or anti-LTβR (L). At the indicated time points (hrs) the cells were collected and recruitment of RelA, RelB and the large subunit of RNA polymerase (Pol II) to the indicated promoter regions was examined by ChIP experiments.

IKKα is Required for Recruitment of RelB to the Blc, Sdf-1, Elc and Slc Promoters To address whether the Blc, Sdf-1, Elc and Slc genes are in fact direct targets for RelB-containing dimers and determine whether they are also recognized by RelA-containing dimers, we performed chromatin immunoprecipitation (ChIP) experiments (S. Saccani, G. Natoli, *Genes Dev* 16, 2219-2224 (2002)). In splenic stromal cells, anti-LTβR induced efficient recruitment of RelB, but not RelA, to the Blc and Sdf-1 promoters (FIG. 3A). This response was abolished in Ikkα$^{AA/AA}$ cells. Treatment with TNFα also induced RelB recruitment to these promoters, but this response was slower and weaker than the response to anti-LTβR and not affected by the Ikkα$^{AA/AA}$ mutation (FIG. 3A). As a control we analyzed the same immunoprecipitates for presence of the Tnfα and Vcam1 promoter regions. We found efficient precipitation of both promoter fragments by anti-RelA antibodies and weak or no signal with anti-RelB (FIG. 3A). Recruitment of either Rel protein to these promoters was not IKKα-dependent. We also examined recruitment of the large subunit of RNA polymerase II (Pol II). Importantly, recruitment of Pol II to the Blc and Sdf-1 promoters correlated with recruitment of RelB and was seen in anti-LTβR stimulated WT cells, while recruitment of Pol II to the Vcam1 and Tnfα promoters was IKKα-independent (FIG. 3A). In BMDC, treatment with anti-LTβR induced efficient recruitment of RelB, but not RelA, to the Elc and Slc promoters (FIG. 3B). No recruitment of RelA was observed. By contrast, both RelB and RelA were recruited to the IκBα promoter (whose activation was IKKα-dependent) in response to either TNFα or anti-LTβR, but neither response was IKKα-dependent (FIG. 3B). As observed for RelB, the LTβR-induced recruitment of Pol II to the Slc and Elc promoters was IKKα-dependent (FIG. 3B).

Example 5

The Blc and Elc Promoters Contain a Unique κB Site that is Selectively Recognized by RelB:p52 Dimers Selective recruitment of RelB-containing NF-κB dimers to the Blc, Sdf-1, Elc and Slc promoters could reflect, previously unknown, intrinsic differences in sequence selectivity between RelB- and RelA-containing dimers. To examine this possibility, we analyzed binding of NF-κB proteins to the Blc promoter. The results are shown in FIG. 4.

Figure 4:
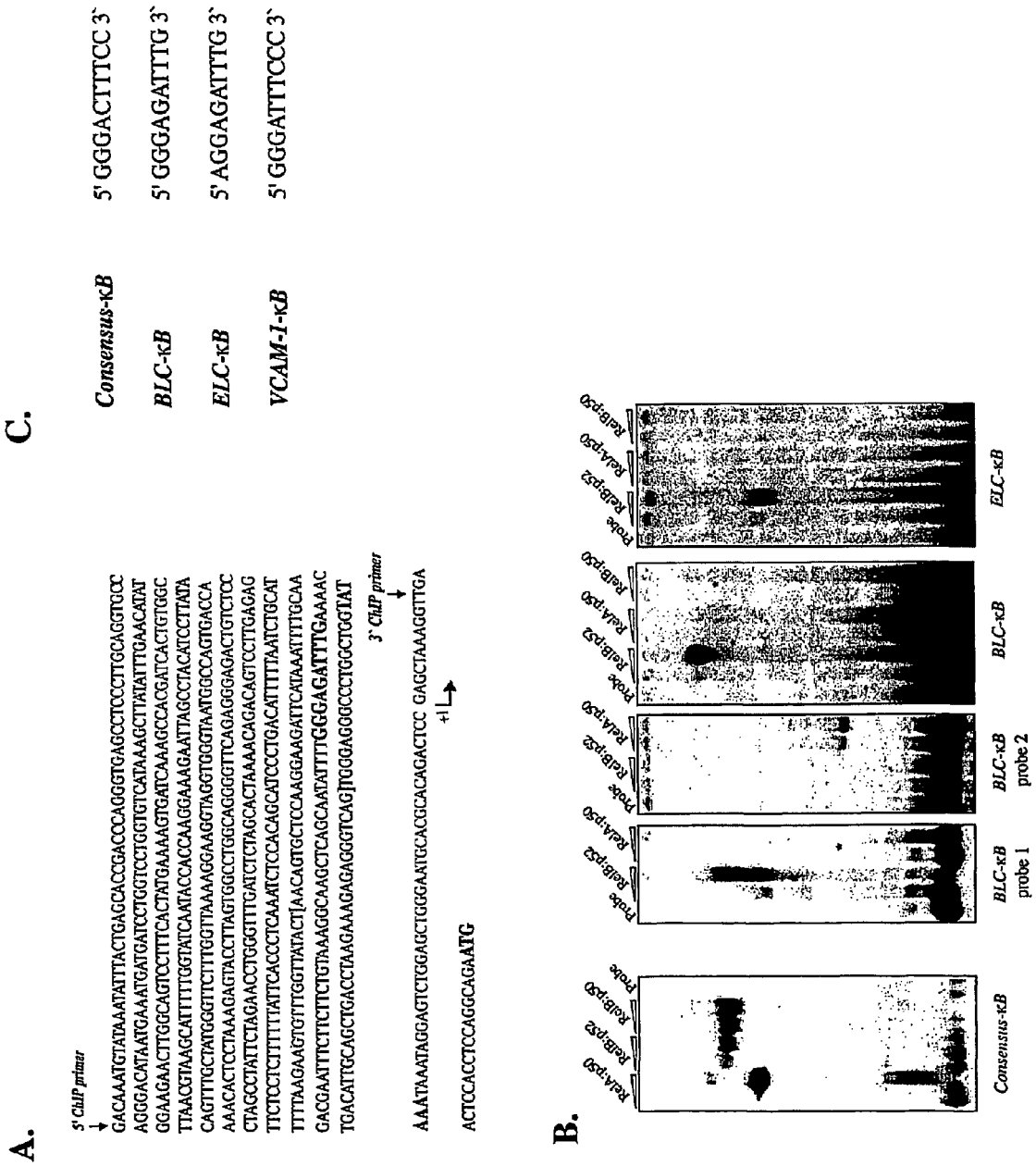
FIG. 4 shows that the Blc and Elc promoters contain a unique κB site that is selectively recognized by RelB:p52 dimers. Panel (A) shows the sequence of the 700 bp region covering the proximal Blc promoter, contained within the ChIP primer set. The RelB:p52-selective κB site and the TATA box are highlighted. The sequence contained within Probe 1 is indicated by the brackets. Panel (B) shows DNA binding analysis. The different probes were incubated with two different amounts (250 and 500 ng) of the indicated NF-κB dimers and DNA binding was analyzed by EMSA. Panel (C) shows the sequences of the different κB sites 5'-GGGACTTTCC-3' (SEQ ID NO:58), 5'-GGGAGATTTG-3' (SEQ ID NO:59), AGGAGATTTG-3' (SEQ ID NO:60), and 5'-GGGATTTCCC-3' (SEQ ID NO:61).

The proteins referred to in FIG. 4 are as follows: RelB RHD (SEQ ID NO:62, i.e., residues 1-400 of GenBank accession A42023 shown in FIG. 13), p52 RHD (SEQ ID NO:64, i.e., residues 1-340 of GenBank Accession NM 002502 shown in FIG. 8), RelB dimerization domain (DD) (SEQ ID NO:63, i.e., residues 278-378 of GenBank accession A42023 shown in FIG. 13), p50 RHD (residues 1-363), p50 RHD (residues 39-363), (residues 1-363), and RelA RHD (SEQ ID NO:65, i.e., residues 19-291 of GenBank accession M61909 shown in FIG. 20).

Several $^{32}$-labeled probes were derived from the 700 base pair (bp) region (−688 to +12) contained within the ChIP primer set (FIG. 4A). One of them, covering the region from −191 to −20, exhibited strong binding to recombinant RelB:p52 and weak binding to RelA:p50 dimers. Several other probes (from −770 to −460, −460 to −380 and −380 to −200, as well as −770 to −980) did not bind either dimer. To narrow down the sequence responsible for RelB:p52 binding we generated a shorter probe (Probe 1) covering the region from −191 to −64. This probe exhibited very strong binding to RelB:p52 and weak binding to RelA:p50 (FIG. 4B). On the other hand, RelA:p50 and RelB:p52 exhibited little differences in their ability to bind a consensus κB probe, whereas a 200 bp probe (Probe 2) derived from the far 5' upstream region (−1900 to −1700) of the blc-1 gene was preferentially recognized by RelA:p50 (FIG. 4B). Probe 1 (−191 to −64) contains one potential NF-κB binding site. We synthesized two overlapping smaller probes containing this site (FIG. 4C) and used them to examine binding of RelA:p50, RelB:p52, as well as RelB:p50. Both probes, which contained the sequence 5'-GGGAGATTTG-3' (SEQ ID NO:59), were efficiently recognized by RelB:p52 and weakly by RelA:p50 (FIG. 4B).

Binding of RelB:p50 to this probe was barely detectable. To identify whether another IKKα-dependent chemokine gene contains a similar sequence, we have used the Trafac server (A. G. Jegga et al., *Genome Res* 12, 1408-1417 (2002)), which identifies ortholog conserved transcription factor binding sites, to examine human and rodent Elc genes. The putative binding sites were first identified using the MatInspector (Professional Version 4.3, 2000) program that utilizes a database of eukaryotic transcription factor binding sites (A. G. Jegga et al., *Genome Res* 12, 1408-1417 (2002)). This procedure identified a very similar sequence to the Blc-κB site at positions −64 to −50 of the Elc genes (FIG. 4C). This site, termed the Elc-κB site, was also preferentially recognized by RelB:p52 dimers (FIG. 4B).

Example 6

Figure 5:
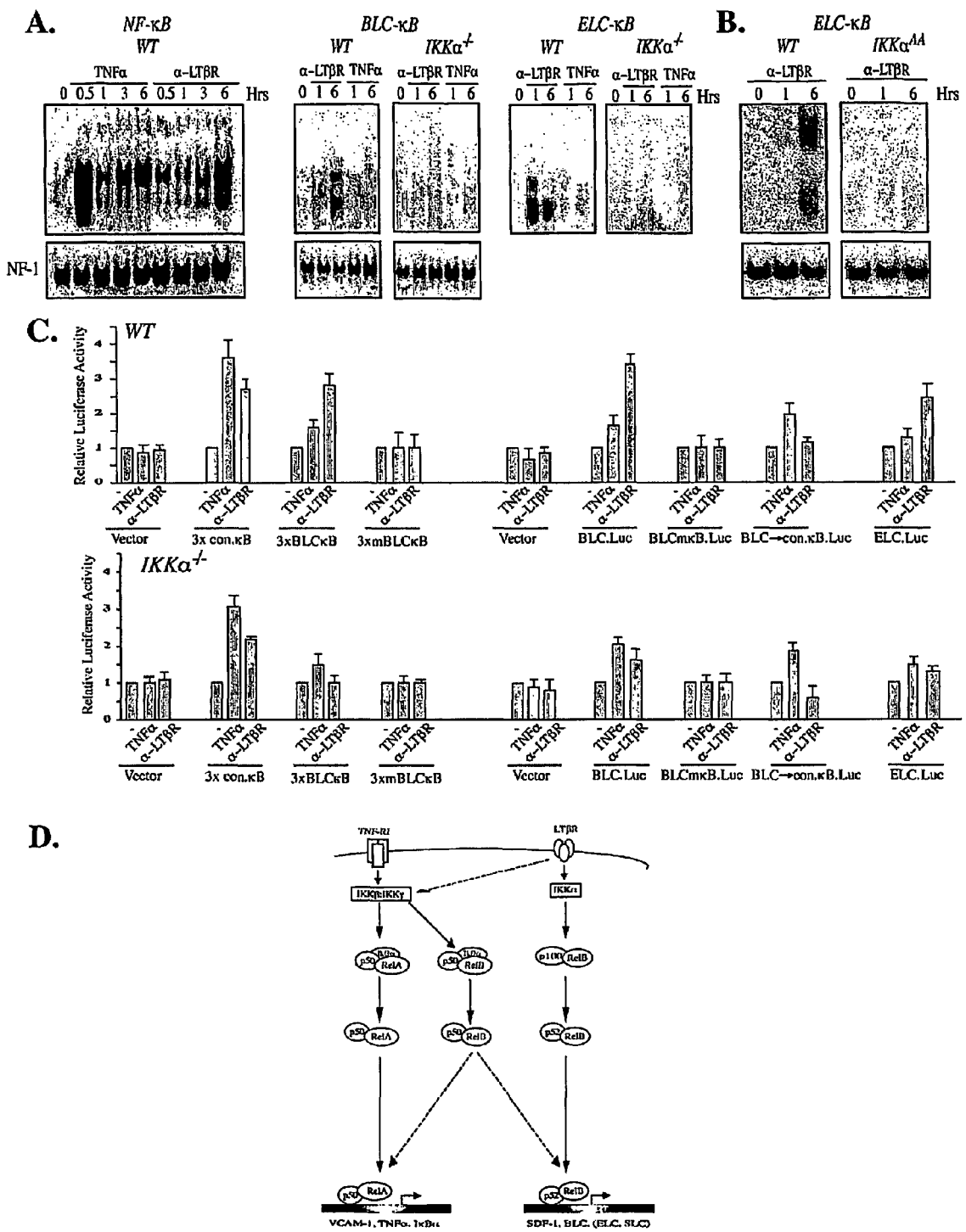
FIG. 5 shows selective, IKKα-dependent, activation of the Blc and Elc promoters by LTβR engagement and a model explaining these results. Panels (A-B) show that engagement of LTβR selectively induces Blc-κB and Elc-κB binding activities. WT and IKKα-defective MEFs (A) and bone marrow-derived dendritic cells (BMDC) (B) were left unstimulated or stimulated with either TNFα or anti-LTβR for the indicated times. Nuclear extracts were prepared and incubated with $^{32}$P-labeled probes corresponding to the consensus κB site (NF-κB) or the Blc-κB and Elc-κB sites. DNA binding activity was analyzed by EMSA. NF-1 DNA binding activity was measured as an internal control. Panel (C) shows functional analysis of the different κB sites in the Blc and Elc promoters. Triple repeats of the consensus κB (conκB), Blc-κB and a mutant Blc-κB (mBlc-κB) site were cloned upstream to a minimal SV40 promoter (pGL3-Promoter vector, Promega). In addition, the Blc (+12 to −688) and Elc (+530 to −320) promoter regions were cloned upstream to a luciferase reporter (pGL3-Basic vector, Promega). To determine the importance of the Blc-κB site, it was converted by site directed mutagenesis either to an inactive mutant version (mκB) or the consensus κB (conκB) site. The different plasmids were transfected into WT and Ikkα$^{−/−}$ MEFs. After 6 hrs with TNFα or anti-LTβR, luciferase activity was determined. The results are averages±SD of three independent experiments normalized to β-galactosidase activity produced by a cotransfected β-galactosidase expression vector.

Selective, IKKα-Dependent, Activation of the Blc and Elc Promoters by LTβR Engagement Stimulation of WT MEFs with either TNFα or α-LTβR-induced DNA binding activities recognized by the consensus κB site (FIG. 5A). Using the Blc-κB and Elc-κB sites as probes, we detected induced DNA binding activity in WT MEFs stimulated with anti-LTβR (FIG. 5A). This activity was not induced in Ikkα$^{-/-}$ MEFs. Similar results were obtained in BMDCs analyzed with the Elc-κB probe (FIG. 5B).

To examine the function of the newly discovered κB sites, we cloned three copies of either the consensus κB site, the Blc-κB site or an inactive version of the latter (mBlc-κB) upstream to a minimal SV40 promoter driving a luciferase reporter (Promega). Whereas the consensus κB site conferred inducibility by either TNFα or anti-LTβR, the Blc-κB site conferred an efficient response to anti-LTβR but a weak response to TNFα (FIG. 5C). The mutated Blc-κB site was inactive. While the consensus κB site was equally active in WT and Ikkα$^{-/-}$ MEFs, the Blc-κB site no longer conferred anti-LTβR responsiveness in Ikkα$^{-/-}$ MEFs (FIG. 5C). Using the intact Blc promoter fused to a luciferase reporter we found efficient induction by anti-LTβR in WT but not in Ikkα$^{-/-}$ MEFs. This response was dependent on integrity of the Blc-κB site and even its conversion to a consensus κB site attenuated the response to anti-LTβR (FIG. 5C). The Elc promoter also exhibited preferential activation by anti-LTβR that was IKKα-dependent.

Example 7

Materials And Methods

The following is a brief description of additional exemplary materials and methods that may be used in the invention's methods.
A. Primary Cell Cultures Stromal cell cultures were established from spleens of WT and Ikkα$^{AA/AA}$ mice as described (Skibinski et al. (1998) Eur J Immunol, 28, 3940-3948). Spleens were gently ground and released cells cultured in DMEM supplemented with heat-inactivated FCS (Invitrogen, Carlsbad, Calif.). After one week, non-adherent cells were removed, adherent cells were washed twice with PBS and cultured one more week in DMEM/FCS. Absence of contaminating myeloid and lymphoid cells was verified by flow cytometry (FACSCalibur, Becton Dickinson). Stromal cells are uniformly positive for ICAM-1. BMDCs were cultured as described (Wu et al. (2002) J Immunol, 168, 5096-5102).

B. Adoptive Transfers

Bone marrow cells (3-4×10$^6$ cells per mouse) were isolated from femurs of WT or Ikkα$^{AA/AA}$ mice and injected intravenously into lethally irradiated recipients. Mice were H-2 matched and, in the case of Ikkα$^{AA/AA}$, were from the F3-F5 backcross to C57Bl/6. Mice were provided antibiotics in drinking water and sacrificed 6-8 weeks post reconstitution. When indicated, mice were immunized i.p. with SRBC (Colorado Serum Company, Denver, Co) 7 days prior to sacrifice (Poljak et al. (1999) J Immunol, 163, 6581-6588).

C. Immunohistochemical Analysis

Cryosections (8-10 μM) of spleen were prepared, dried and fixed with acetone before immunohistochemical analysis (Poljak et al. (1999) J Immunol, 163, 6581-6588; Weih et al. (2001) J Immunol, 167, 1909-1919). Staining reagents were: FDC-M2 (ImmunoKontact, UK), ICAM-1 (Santa-Cruz Biologicals, Ca), B220, and CD35-bio (clone 8C12) (all from BD Pharmingen). Immunecomplexes were detected using species-specific secondary reagents. Sections were viewed by immunofluorescence microscopy (HM505E Microm Inc, Walldorf, Germany) and images captured with a digital camera (Nikon E800 Scope with Spot Diagnostics Digital Camera, A.G. Heinze Inc., Lake Forest, Ca).

D. Electrophoretic Mobility Shift Assay and Immunoblots

Nuclear and cytoplasmic extracts were prepared and analyzed for levels of NF-κB subunits and DNA binding activity (Bonizzi et al. (1999) et al. Mol Cell Biol, 19, 1950-1960; Senftleben et al. (2001) Science, 293, 1495-1499). Recombinant NF-κB subunits (not full length proteins) were produced in E. coli and purified as described (Chen et al. (1999) Protein Eng, 12, 423-428). All antibodies and immunoblotting procedures were described (Senftleben et al. (2001) Science, 293, 1495-1499).

E. Real Time PCR Analysis and Chromatin Immunoprecipitation Assay (ChIP)

Real Time-PCR was performed using a PE Biosystems 5700 thermocycler following the SyBr Green™ protocol. Briefly, 12 ng of total cDNA, 50 nM of each primer and 1× SyBr Green™ mix were used in a total volume of 25 μl. All values were standardized to that of cyclophilin mRNA. Primer sequences are available upon request. ChIP assays were as described (Saccani et al. (2002) Genes Dev, 16, 2219-2224). Polyclonal antibodies to p65 (C-20), RelB (C-19) and Pol II (N-19) were from Santa Cruz. The sequences of the promoter-specific primers (Blc +12 to −688, Sdf-1 +22 to −678, Vcam-1 +30 to −640, Iκbα +20 to −340, Tnfα +20 to −545) and a detailed experimental protocol are available upon request.

Example 8

Impaired FDC Maturation and Chemokine Production in Stromal Cell-Derived Requires IKKα

Figure 26:
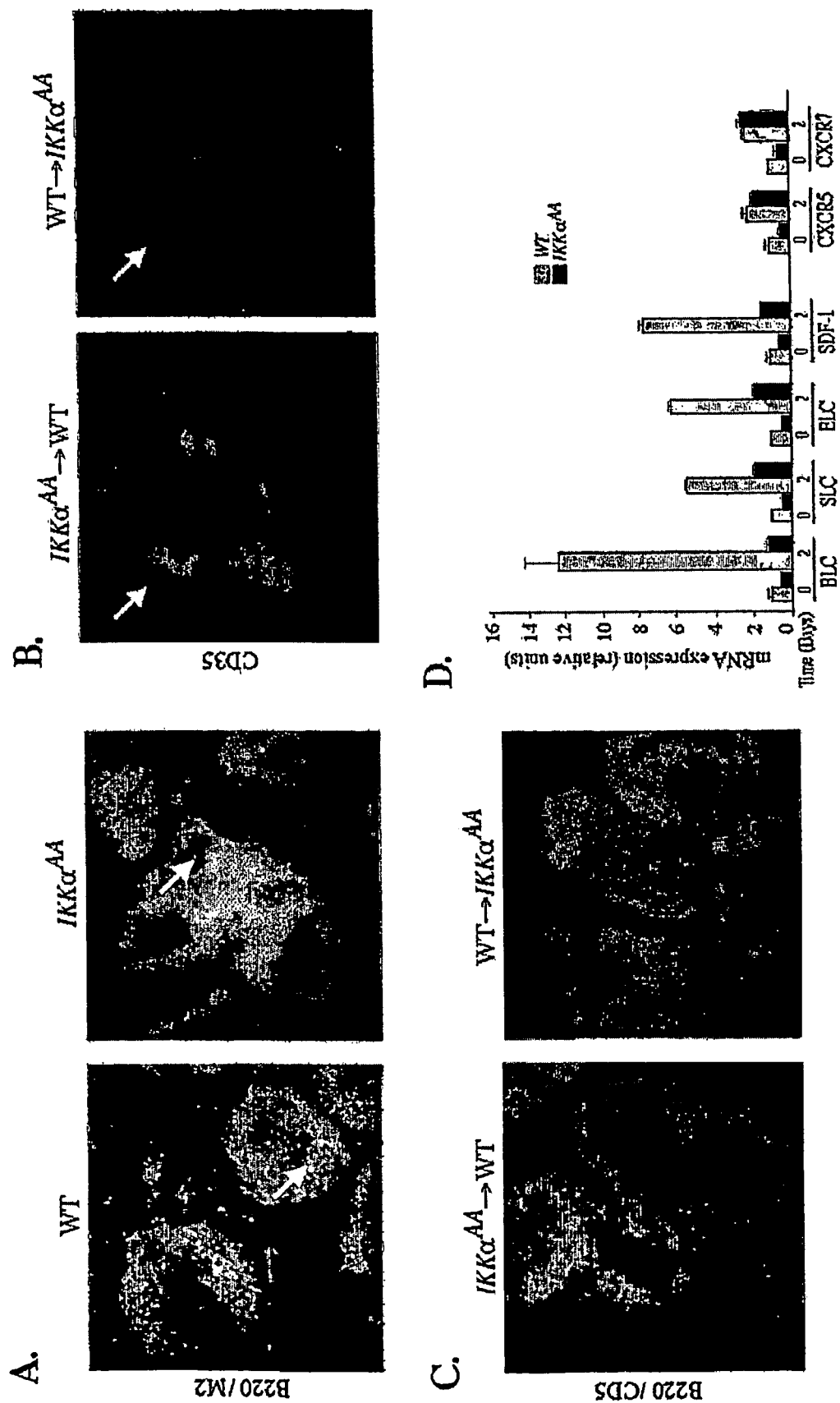
FIG. 26 shows that impaired FDC maturation and chemokine production in Stromal cell-derived requires IKKα. Panel (A) shows absence of mature FDC network in Ikkα$^{AA/AA}$ mice. Cryosections of spleen from WT (n=6) and Ikkα$^{AA/AA}$ (n=6) mice, isolated 7 days post-immunization with SRBC, were stained for FDCs (arrows) with FDC-M2 (orange) and anti-B220 (green). Panel (B) shows impaired FDC maturation is inherent to the Ikkα$^{AA/AA}$ stroma. Lethally irradiated WT (n=6) or/(n=6) mice were reconstituted with Ikkα$^{AA/AA}$ or WT bone marrow, respectively. Spleens were isolated 7 days after immunization with SRBC, cryosectioned and stained with anti-CD35. An FDC network is present in WT mice reconstituted with Ikkα$^{AA/AA}$ bone marrow, while primarily peri-follicular rings of CD35$^+$ immature FDCs are present in Ikkα$^{AA/AA}$ mice reconstituted with WT bone marrow. Panel (C) shows impaired B/T cell segregation in Ikkα$^{AA/AA}$ spleens. Lethally irradiated WT (n=6) or Ikkα$^{AA/AA}$ (n=6) mice reconstituted with Ikkα$^{AA/AA}$ or WT bone marrow cells were immunized and analyzed as above using anti-CD5 (to recognize T cells) and anti-B220 (to recognize B cells). Impaired B/T cell segregation is intrinsic to the Ikkα$^{AA/AA}$ stroma Panel (D) shows defective chemokine gene expression in Ikkα$^{AA/AA}$ spleens. Total splenocytes from naïve and SRBC-immunized (day 2) WT (n=6) and Ikkα$^{AA/AA}$ (n=6) mice were isolated. RNA was extracted and analyzed by RT PCR for expression of mRNAs encoding BLC, SLC, ELC and SDF-1 and two of their receptors (CXCR5, CCR7). The results are averages±SD of three independent experiments normalized to the level of cyclophilin mRNA.

Reconstitution of lethally irradiated mice with Ikkα$^{-/-}$ fetal liver hematopoietic progenitors revealed a role for IKKα in late B-cell maturation, splenic organization and germinal center (GC) formation (Kaisho et al. (2001) J. Exp. Med., 193, 417-426; Senftleben et al. (2001) Science, 293, 1495-1499). However, embryonic lethality precludes the use of Ikkα$^{-/-}$ mice to identify functions for IKKα in other cell types involved in spleen development and organization. Homozygous knock-in mice expressing an IKKα variant that cannot be activated (Ikkα$^{AA/AA}$ mice) are viable, yet show defects in lymphoid organogenesis and GC formation (Senftleben et al. (2001) Science, 293, 1495-1499). Using an antibody against FDC-M2, an FDC (follicular dendritic cell) marker, we found that Ikkα$^{AA/AA}$ mice lack mature FDCs (FIG. 26A). To identify the cells in which IKKα acts, reciprocal bone marrow chimeras were generated using Ikkα$^{AA/AA}$ and WT mice. Six weeks after adoptive transfer, mice were challenged with a T-cell dependent antigen, sheep red blood cells (SRBC), and sacrificed 7 days later. FDC maturation remained impaired in Ikkα$^{AA/AA}$ recipients reconstituted with WT bone marrow, whereas a mature FDC network formed in WT recipients reconstituted with Ikkα$^{AA/AA}$ bone marrow. Using an antibody against CD35, another FDC marker, we examined formation of mature FDCs, a cell type derived from mesenchymal stromal cells which are important for GC formation. FDC maturation was impaired in Ikkα$^{AA/AA}$ recipients reconstituted with WT bone marrow, whereas a mature FDC network formed in WT recipients reconstituted with Ikkα$^{AA/AA}$ bone marrow (FIG. 26B). These results suggest that Ikkα$^{AA/AA}$ acts in stromal cells of the spleen to induce maturation of FDCs, which are thought to be derived from mesenchymal stromal cells (Fu et al. (1999) Annu Rev Immunol, 17, 399-433).

Another aspect of spleen development is segregation of B- and T-lymphocytes to the follicles and the peri-arterial lymphatic sheath (PALS), respectively. WT chimeras reconstituted with Ikkα$^{AA/AA}$ bone marrow, but not Ikkα$^{AA/AA}$ mice reconstituted with WT bone marrow, exhibited normal B- and T-cell segregation detected by staining with anti-B220 and anti-CD5 antibodies, respectively (FIG. 26C). These results also point to a critical action of IKKα in stromal cells, which in addition to giving rise to FDCs, control splenic microarchitecture through production of organogenic chemokines that dictate cell migration and localization (Ansel et al. (2001) Curr Opin Immunol, 13, 172-179).

Critical organogenic chemokines for spleen development include: ELC and SLC, ligands for the chemokine receptor CCR7; BLC, which binds CXCR5 (Ansel et al. (2000) Nature, 406, 309-314; Forster et al. (1999) Cell, 99, 23-33) and SDF-1, which promotes trafficking of both immature and naïve lymphocytes to lymphoid tissues (Kim et al. (1999) J Leukoc Biol, 65, 6-15). Previous work revealed that induction of these chemokines in response to engagement of LTβR is defective in Ikkα$^{AA/AA}$ mice (Dejardin et al. (2002) Immunity, 17, 525-535). We extended these observations to SRBC immunized mice (FIG. 26D). Based on previous experiments, we examined the expression of the different genes 48 hrs post-immunization. While induction of the mRNAs for BLC, ELC, SLC and SDF-1 was readily detected in WT spleens, these genes were barely induced in the mutant.

Example 9

Figure 27:
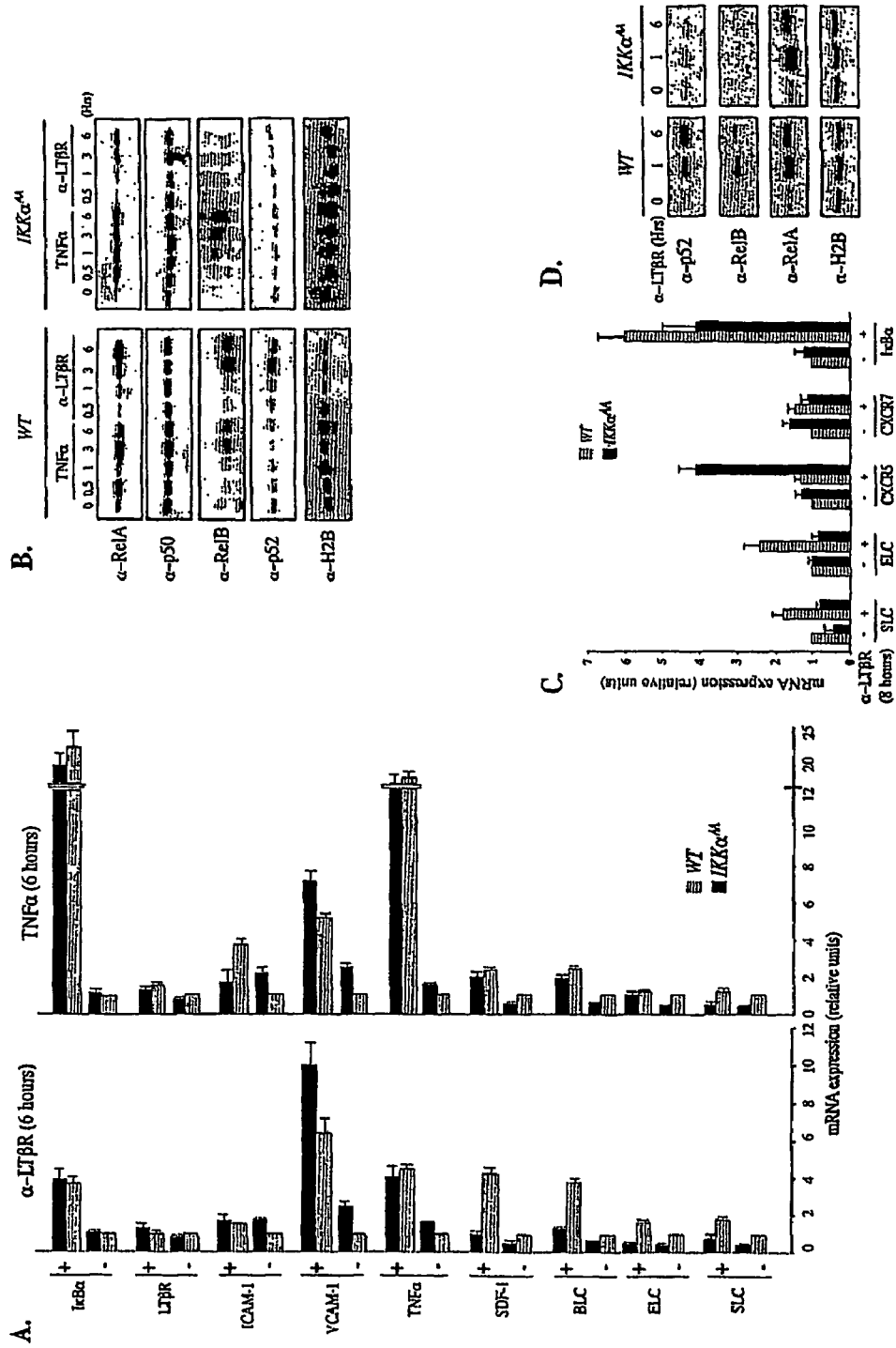
FIG. 27 shows that IKKα is required for LTβR-induced RelB:p52 nuclear translocation and chemokine expression in splenic stromal cells and myeloid dendritic cells. Panel (A) shows Ikkα$^{AA/AA}$ stromal cells and (C) bone marrow-derived dendritic cells (BMDC) exhibit specific defects in LTβR-induced gene expression. Total RNA was extracted from either WT or Ikkα$^{AA/AA}$ stromal cells or BMDC before and after stimulation with 2 μg/ml agonistic anti-LTβR antibody or 20 ng/ml TNFα. Gene expression was analyzed by Real Time-PCR. Results are averages±SD of three independent experiments normalized to the level of cyclophilin mRNA. Panels (B, D) shows nuclear translocation of NF-κB proteins. Stromal cells as in Panel (B) and BMDC as in Panel (D) were stimulated with either anti-LTβR antibody or TNFα as indicated. At the indicated time points (hrs), nuclear extracts were prepared and analyzed by immunoblotting for presence of the indicated NF-κB subunits. The levels of histone H2B were examined to control for loading and proper cell fractionation. Contamination with cytoplasmic proteins was monitored by blotting with anti-actin antibody (not shown).

IKKα is Required for LTβR-Induced RelB:p52 Nuclear Translocation and Chemokine Expression in Splenic Stromal Cells and Myeloid Dendritic Cells The defects shown above are very similar to those exhibited by mice lacking LTβR (Fu et al. (1999) Annu Rev Immunol, 17, 399-433). The majority of LT®R LTβR expression is restricted to stromal cells of the spleen, however BMDCs have also been shown to express LT®R LTβR (Browning et al. (2002) et al. J Immunol, 168, 5079-5087). We therefore isolated and cultured these cells both of these cell types from WT and Ikkα$^{AA/AA}$ mice. Stimulation of WT stromal cells with agonistic anti-LTβR antibody (Dejardin et al. (2002) Immunity, 17, 525-535) resulted in 4-6-fold induction of BLC, SDF-1, TNFα, VCAM-1 and IκBα mRNA (FIG. 27A). Modest induction of ELC and SLC mRNAs was also observed. Both basal expression and induction of BLC, SDF- 1, ELC and SLC mRNAs were defective in Ikkα$^{AA/AA}$ stromal cells. Similar defects in expression of these chemokines in RelB$^{-/-}$ and Nfkb2$^{-/-}$ mice have been described in RelB$^{-/-}$ and Nfkb2$^{-/-}$ mice (Poljak et al. (1999) J Immunol, 163, 6581-6588; Weih et al. (2001) J Immunol, 167, 1909-1919). Moreover, induction of TNFα, IκBα and VCAM-1 in Ikkα$^{AA/AA}$ stromal cells remained intact or was even elevated. The increased expression of VCAM-1 could be related to the defective nuclear entry of RelB in Ikkα$^{AA/AA}$ cells (see below), as RelB-deficiency was previously found to increase the expression of certain inflammatory genes (Xia et al. (1999) Mol Cell Biol, 19, 7688-7696). By contrast, very few differences in expression of TNFα-inducible genes were found between WT and Ikkα$^{AA/AA}$ stromal cells (FIG. 27A). Unlike anti-LTβR, TNFα was a poor activator of the organogenic chemokines, but was a potent activator of TNFα, IκBα and VCAM-1.

TNFα induced both rapid and delayed nuclear translocation of RelA in WT and Ikkα$^{AA/AA}$ stromal cells (FIG. 27B). This response was not considerably different in Ikkα$^{AA/AA}$ cells (FIG. 27B, right panel). Neither TNFα nor anti-LTβR had a significant effect on the subcellular distribution of p50, as this NF-κB subunit was constitutively nuclear (FIG. 27B). Both TNFα and anti-LTβR induced nuclear translocation of RelB in WT cells, but TNFα was capable of sending RelB to the nucleus of Ikkα$^{AA/AA}$ cells (FIG. 27B). In either case, the nuclear translocation of RelB is delayed relative to that of RelA. As expected, anti-LTβR, but not TNFα, stimulated nuclear entry of p52 and this effect was seen in WT cells (FIG. 27B). Similar results in regards to both gene expression and nuclear translocation of NF-κB subunits was observed in BMDCs. In WT BMDCs, LTβR engagement led to induction of SLC, ELC and IκBα mRNA (FIG. 27C).

However, SLC and ELC were not induced in BMDC from Ikkα$^{AA/AA}$ mice. Again, we found that at least one gene, in this case CXCR5, was elevated in mutant cells. Whereas engagement of LTβR resulted in nuclear entry of RelB and p52 in WT BMDCs, this response was defective in Ikkα$^{AA/AA}$ cells (FIG. 27D). Nuclear translocation of RelA was not affected in Ikkα$^{AA/AA}$ cells. These results and the previous genetic analysis of NF-κB2-(Poljak et al. (1999) J Immunol, 163, 6581-6588) and RelB-(Weih et al. (2001) J Immunol, 167, 1909-1919) deficient mice strongly suggest that Blc, Sdf-1, Elc and Slc gene induction requires RelB:p52 nuclear translocation. Curiously, the induction of RelB and p52 nuclear entry following LTβR engagement was considerably faster in BMDCs than in splenic stromal cells. This is likely to be related to the different origins of these cell types and/or the expression of different levels of LTβR molecules on their surface.

Example 10

IKKα is Required for Recruitment of RelB to the Blc, Sdf-1, Elc and Slc Promoters To address whether the IKKα-dependent genes are in fact direct targets for RelB-containing dimers and whether they are also recognized by RelA-containing dimers, we performed chromatin immunoprecipitation (ChIP) experiments (Saccani et al. (2002) Genes Dev, 16, 2219-2224). In splenic stromal cells, anti-LTβR induced efficient recruitment of RelB, but not RelA, to the Blc and Sdf-1 promoters (FIG. 28A), which encode the two organogenic chemokines that are most efficiently expressed by these cells (Cyster et al. (2003) Immunol Rev, 195, 5-14). As previously shown, recruitment of NF-κB subunits to promoter DNA may be detected at earlier time points than the ones revealed by immunoblot analysis of nuclear translocation, due to the increased sensitivity of the ChIP assay (Saccani et al. (2001) J Exp Med, 193, 1351-1359). Anti-LTβR-induced recruitment of RelB to target gene promoters was abolished in Ikkα$^{AA/AA}$ cells.

However, TNFα-induced RelB promoter recruitment, which was slower and weaker than the response elicited by anti-LTβR, was not affected by the Ikkα$^{AA/AA}$ mutation (FIG. 28A). The response to TNFα may depend on formation of RelB:p50 dimers. As a control we analyzed the same immunoprecipitates for the presence of the Tnfα and Vcam1 promoter regions. Efficient precipitation of both promoter fragments by anti-RelA antibodies was shown with a weak signal obtained with anti-RelB (FIG. 28A). Recruitment of either Rel protein to these promoters was not IKKα-dependent. Importantly, recruitment of Pol II to the Blc and Sdf-1 promoters correlated with recruitment of RelB and was seen in anti-LTβR stimulated WT cells (FIG. 28A).

As mentioned above, splenic stromal cells are the major source of production of BLC and SDF, while BMDCs are a major source of ELC and SLC (Cyster et al. (2003) Immunol Rev, 195, 5-14). Therefore, in BMDCs we examined recruitment of the different NF-κB subunits in response to LTβ signaling to the Elc and Slc promoters. Treatment with anti-LTβR induced efficient recruitment of RelB, but not RelA, to the Elc and Slc promoters (FIG. 28B). No [Little] recruitment of RelA was observed. By contrast, both RelB and RelA were recruited to the IκBα promoter in response to either TNFα or anti-LTβR, but neither response was IKKα-dependent (FIG. 28B). As observed for RelB, the LTβR-induced recruitment of Pol II to the Slc and Elc promoters was IKKα-dependent (FIG. 28B).

Example 11

The Blc and Elc Promoters Contain a Unique κB Site that is Selectively Recognized by RelB:p52 Dimers Selective recruitment of RelB-containing NF-κB dimers to the Blc, Sdf-1, Elc and Slc promoters could reflect, previously unknown, intrinsic differences in sequence selectivity between RelB- and RelA-containing dimers. To examine this possibility, we analyzed binding of NF-κB proteins to the Blc and Elc promoters. In this experiment we used truncated recombinant NF-κB proteins to generate NF-κB dimers of known composition. All of the proteins used in these experiments were fully characterized and even crystallized (Ghosh et al. (1995) Nature, 373, 303-310; Chen et al. (1999) Protein Eng, 12, 423-428; G. Ghosh, unpublished data). Several $^{32}$P-labeled probes were derived from the 700 base pair (bp) proximal region (−688 to +12) of the Blc promoter, contained within the ChIP primer set (FIG. 29A). One of the probes, spanning positions −191 to −20, exhibited strong binding to recombinant RelB:p52 and weak binding to RelA:p50 dimers. Several other probes (from −770 to −460, −460 to −380 and −380 to −150, as well as from −770 to −980) did not detectably bind either dimer. To narrow down the sequence responsible for RelB:p52 binding we generated a shorter probe (Probe 1) covering the region from −191 to −64. This probe exhibited very strong binding to recombinant RelB:p52 and weak binding to RelA:p50 (FIG. 29B). On the other hand, the RelA:p50 and RelB:p52 dimers exhibited little differences in their ability to bind a consensus κB probe, whereas a 200 bp probe (Probe 2) derived from the far 5' upstream region (−1900 to −1700) of the Blc gene was preferentially recognized by RelA:p50. Probe 1 (−191 to −64) contained one potential NF-κB binding site. We synthesized two overlapping smaller probes containing this site (FIG. 29C) and used them to examine binding of RelA:p50, RelB:p52, as well as RelB:p50. Both probes, which contained the sequence 5'-GGGAGATTTG-3' (SEQ ID NO:59), were efficiently recognized by RelB:p52 and weakly by RelA:p50 (FIG. 29B). Binding of RelB:p50 to these probes was barely detectable. In all cases, the detected protein-DNA complexes were specific as indicated by competition experiments.

To identify whether another IKKα-dependent chemokine genes contain a similar sequence, we used the Trafac server (Jegga et al. (2002) Genome Res, 12, 1408-1417), which identifies ortholog conserved transcription factor binding sites, to examine the human and rodent Elc genes. The putative binding sites were first identified using the MatInspector program (Professional Version 4.3, 2000) that utilizes a database of eukaryotic transcription factor binding sites (Jegga et al. (2002) Genome Res, 12, 1408-1417). This procedure identified a very similar sequence to the Blc-κB site at positions −64 to −50 of the Elc genes (FIG. 29C). This site, termed the Elc-κB site, was also preferentially recognized by RelB:p52 dimers (FIG. 29B).

Example 12

Selective, IKKα-Dependent, Activation of the Blc and Elc Promoters by LTβR Engagement and IKKα-Dependent Induction of Rxra, Irf3 and Baff mRNAs We next used MEFs, which unlike the related stromal cells are amenable to transfection (Bebien M., unpublished results), to examine the function of the RelB:p52 specific sites. Stimulation of WT MEFs with either TNFα or α-LTβR-induced DNA binding activities recognized by the consensus κB site (FIG. 30A). Using the Blc-κB and Elc-κB sites as probes, we detected induced DNA binding activity in WT MEFs stimulated with anti-LTβR (FIG. 30A). This activity was not induced in Ikkα$^{-/-}$ MEFs. Similar results were obtained in BMDCs analyzed with the Elc-κB probe (FIG. 30B). Next, we cloned three copies of either the consensus κB site, the Blc-κB site or an inactive version of the latter (mBlc-κB) upstream to a minimal SV40 promoter driving a luciferase reporter and transfected the constructs into WT and Ikkα$^{-/-}$ MEFs. The consensus κB site conferred inducibility by either TNFα or anti-LTβR, whereas the Blc-κB site conferred an efficient response to anti-LTβR but a weak response to TNFα and the mutated Blc-κB site was inactive (FIG. 30C). While the consensus κB site was equally active in WT and Ikkα$^{-/-}$ MEFs, the Blc-κB site did not confer anti-LTβR responsiveness in Ikkα$^{-/-}$ MEFs (FIG. 30C). Using the intact Blc promoter fused to a luciferase reporter we found efficient induction by anti-LTβR in WT but not in Ikkα$^{-/-}$ MEFs. This response was dependent on the integrity of the Blc-κB site and even its conversion to a consensus κB site attenuated the response to anti-LTβR (FIG. 30C). The Elc promoter also exhibited preferential activation by anti-LTβR that was IKKα-dependent.

To further examine the relevance of the RelB:p52 selective binding site, we conducted a pattern search with two strings, namely AGGAGATTTG (Elc-κB) (SEQ ID NO:60) and GGGAGATTTG (Blc-κB) (SEQ ID NO:59) using the Trafac server and the BlastZ algorithm. Closely similar (at least 8/10 identity) sites were detected within 5 kb upstream to the start sites of the Sdf-1 and Baff genes, whose expression is known to be Ikkα-dependent (Dejardin et al. (2002) Immunity, 17, 525-535) (FIGS. 26D, 27A, 30D). We also detected similar and evolutionary conserved sites with the same region of several other genes, whose IKKα-dependence was previously unknown (FIG. 30D). RT-PCR analysis revealed that two of these genes, Rxra and Irf3, coding for important transcription factors, were induced in stromal cells in response to anti-LTβR in a manner dependent on IKKα (FIG. 30E).

From the above, it is clear that the invention provides nucleotide sequences that mediate one or more functions of IKKα, kits and methods for using these sequences to identify therapeutic compounds that alter IKKα related pathology.

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiment, it should be understood that the invention as claimed should not be unduly limited to such specific embodiment. Indeed, various modifications of the described modes for carrying out the invention which are obvious to those skilled in the art and in fields related thereto are intended to be within the scope of the claims.

The invention claimed is:

1. A method for identifying one or more test compounds that alters binding of RelB Rel homology domain (RelB RHD) with RelBκB sequence, comprising:
   a) providing
      i) an isolated nucleotide sequence comprising 5'-NG-GAGANNTG-3' (SEQ ID NO:57); wherein N at position 1 is chosen from G and A, N at position 7 is chosen from T and C, and N at position 8 is chosen from T and C, and wherein said isolated sequence specifically binds with a polypeptide sequence comprising RelB Rel homology domain (RHD) as comprising SEQ ID NO:62,
      ii) a polypeptide comprising RelB RHD comprising SEQ ID NO:62, and
      iii) one or more test compounds;
   b) contacting said isolated nucleotide sequence with said polypeptide in the presence and absence of said one or more test compounds; and
   determining the level of specific binding of said nucleotide sequence with said polypeptide in the presence of said one or more test compounds compared to in the absence of said one or more test compounds, wherein detecting altered specific binding of said nucleotide sequence with said polypeptide in the presence of said one or more test compounds compared to in the absence of said one or more test compounds identifies said one or more test compounds as altering binding of RelB RHD with RelBκB sequence.

2. The method claim 1, wherein said polypeptide is recombinant.

3. The method of claim 2, wherein said polypeptide comprises RelB:p52.

4. The method of claim 2, wherein said polypeptide comprises RelB.

5. The method of claim 2, wherein said contacting is in vivo.

6. The method of claim 2, wherein said contacting is in vitro.

7. The method of claim 1, further comprising detecting unaltered binding of said nucleotide sequence to a protein comprising one or more of (a) RelA Rel homology domain (RelA RHD) comprising SEQ ID NO:65, (b) RelA, (c) p50, (d) RelA:p50, (e) p52, and (f) RelA:p52, in the presence and absence of said one or more test compounds, wherein said unaltered binding indicates specific binding of said nucleotide sequence with said polypeptide.

8. The method of claim 1, further comprising detecting unaltered binding of an isolated nucleotide sequence comprising the consensus-KB sequence 5'-GGGACTTTCC-3' (SEQ ID NO:58) to a polypeptide comprising one or more of RelB RHD comprising SEQ ID NO:62, and RelB in the presence of said one or more test compounds, wherein said unaltered binding indicates specific binding of said nucleotide sequence with said polypeptide.

* * * * *

SEQUENCE LISTING

```
<160> NUMBER OF SEQ ID NOS: 134

<210> SEQ ID NO 1
<211> LENGTH: 700
<212> TYPE: DNA
<213> ORGANISM: Mus musculus

<400> SEQUENCE: 1
ttcgtaccat ccacccaccc ccagtcgaga gaatagggt acagagggga ggtggcaaag      60
aaaattcacg atactgagta tctctgggag acctgtttgg tctctttgct cggtagcgca     120
gccctacgtt agaatgcatc ttcccgggaa tgactgtagt gagactttgg ctgggaatcc     180
aagttattct aactgtagat tggtccacgt tgccctaagc ctagcagtcc actgcggcac     240
agacaccctg gacatgaggt gggtcagctt aagttcctgg cacgaaagaa agggtactct     300
ggcaactttt ggatgcggcg aaacagactg tttcgtctct caggttctta tttcacggct     360
```

```
tgtgcctttg acagcccctt agtttctcta tctgcaggat gggagcatta agctctacga    420
cccagcctct ttacaattca ggtccaaaga gcccgcccaa gttggggact gggaagatca    480
aaggtctcag cacccagcgg agccgcggac actgagggcg ccaagaaggg ggtgggtagg    540
tagggaactg gaagggcggc tgctccgcag gggatgcgcg tcagagaccc cagccacact    600
ccaggcccgc cccttgatga gccccgcccc gccccgcctg gttttcgcct ctaaagcgcc    660
cagcgctcgc ctcccgctgc cgcactttca ctctcggtcc                         700

<210> SEQ ID NO 2
<211> LENGTH: 10
<212> TYPE: DNA
<213> ORGANISM: Mus musculus

<400> SEQUENCE: 2
gggagacctg                                                          10

<210> SEQ ID NO 3
<211> LENGTH: 933
<212> TYPE: PRT
<213> ORGANISM: Homo sapiens

<400> SEQUENCE: 3

Met Glu Ser Cys Tyr Asn Pro Gly Leu Asp Gly Ile Ile Glu Tyr Asp
1               5                   10                  15

Asp Phe Lys Leu Asn Ser Ser Ile Val Glu Pro Lys Glu Pro Ala Pro
            20                  25                  30

Glu Thr Ala Asp Gly Pro Tyr Leu Val Ile Val Glu Gln Pro Lys Gln
        35                  40                  45

Arg Gly Phe Arg Phe Arg Tyr Gly Cys Glu Gly Pro Ser His Gly Gly
    50                  55                  60

Leu Pro Gly Ala Ser Ser Glu Lys Gly Arg Lys Thr Tyr Pro Thr Val
65                  70                  75                  80

Lys Ile Cys Asn Tyr Glu Gly Pro Ala Lys Ile Glu Val Asp Leu Val
                85                  90                  95

Thr His Ser Asp Pro Pro Arg Ala His Ala His Ser Leu Val Gly Lys
            100                 105                 110

Gln Cys Ser Glu Leu Gly Ile Cys Ala Val Ser Val Gly Pro Lys Asp
        115                 120                 125

Met Thr Ala Gln Phe Asn Asn Leu Gly Val Leu His Val Thr Lys Lys
    130                 135                 140

Asn Met Met Gly Thr Met Ile Gln Lys Leu Gln Arg Gln Arg Leu Arg
145                 150                 155                 160

Ser Arg Pro Gln Gly Leu Thr Glu Ala Glu Gln Arg Glu Leu Glu Gln
                165                 170                 175

Glu Ala Lys Glu Leu Lys Lys Val Met Asp Leu Ser Ile Val Arg Leu
            180                 185                 190

Arg Phe Ser Ala Phe Leu Arg Ala Ser Asp Gly Ser Phe Ser Leu Pro
        195                 200                 205

Leu Lys Pro Val Thr Ser Gln Pro Ile His Asp Ser Lys Ser Pro Gly
    210                 215                 220

Ala Ser Asn Leu Lys Ile Ser Arg Met Asp Lys Thr Ala Gly Ser Val
225                 230                 235                 240

Arg Gly Gly Asp Glu Val Tyr Leu Leu Cys Asp Lys Val Gln Lys Asp
                245                 250                 255

Asp Ile Glu Val Arg Phe Tyr Glu Asp Asp Glu Asn Gly Trp Gln Ala
            260                 265                 270
```

```
Phe Gly Asp Phe Ser Pro Thr Asp Val His Lys Gln Tyr Ala Ile Val
            275                 280                 285
Phe Arg Thr Pro Pro Tyr His Lys Met Lys Ile Glu Arg Pro Val Thr
            290                 295                 300
Val Phe Leu Gln Leu Lys Arg Lys Arg Gly Gly Asp Val Ser Asp Ser
305                 310                 315                 320
Lys Gln Phe Thr Tyr Tyr Pro Leu Val Glu Asp Lys Glu Val Gln
            325                 330                 335
Arg Lys Arg Arg Lys Ala Leu Pro Thr Phe Ser Gln Pro Phe Gly Gly
            340                 345                 350
Gly Ser His Met Gly Gly Gly Ser Gly Gly Ala Ala Gly Gly Tyr Gly
            355                 360                 365
Gly Ala Gly Gly Gly Ser Leu Gly Phe Phe Pro Ser Ser Leu Ala
370                 375                 380
Tyr Ser Pro Tyr Gln Ser Gly Ala Gly Pro Met Arg Cys Tyr Pro Gly
385                 390                 395                 400
Gly Gly Gly Gly Ala Gln Met Ala Ala Thr Val Pro Ser Arg Asp Ser
            405                 410                 415
Gly Glu Glu Ala Ala Glu Pro Ser Ala Pro Ser Arg Thr Pro Gln Cys
            420                 425                 430
Glu Pro Gln Ala Pro Glu Met Leu Gln Arg Ala Arg Glu Tyr Asn Ala
            435                 440                 445
Arg Leu Phe Gly Leu Ala His Ala Ala Pro Ser Pro Thr Arg Leu Leu
450                 455                 460
Arg His Arg Gly Arg Arg Ala Leu Leu Ala Gly Gln Arg His Leu Leu
465                 470                 475                 480
Thr Ala Gln Asp Glu Asn Gly Asp Thr Pro Leu His Leu Ala Ile Ile
            485                 490                 495
His Gly Gln Thr Ser Val Ile Glu Gln Ile Val Tyr Val Ile His His
            500                 505                 510
Ala Gln Asp Leu Gly Val Val Asn Leu Thr Asn His Leu His Gln Thr
            515                 520                 525
Pro Leu His Leu Ala Val Ile Thr Gly Gln Thr Ser Val Val Ser Phe
530                 535                 540
Leu Leu Arg Val Gly Ala Asp Pro Ala Leu Leu Asp Arg His Gly Asp
545                 550                 555                 560
Ser Ala Met His Leu Ala Leu Arg Ala Gly Ala Gly Ala Pro Glu Leu
            565                 570                 575
Leu Arg Ala Leu Leu Gln Ser Gly Ala Pro Ala Val Pro Gln Leu Leu
            580                 585                 590
His Met Pro Asp Phe Glu Gly Leu Tyr Pro Val His Leu Ala Val Arg
            595                 600                 605
Ala Arg Ser Pro Glu Cys Leu Asp Leu Leu Val Asp Ser Gly Ala Glu
610                 615                 620
Val Glu Ala Thr Glu Arg Gln Gly Gly Arg Thr Ala Leu His Leu Ala
625                 630                 635                 640
Thr Glu Met Glu Glu Leu Gly Leu Val Thr His Leu Val Thr Lys Leu
            645                 650                 655
Arg Ala Asn Val Asn Ala Arg Thr Phe Ala Gly Asn Thr Pro Leu His
            660                 665                 670
Leu Ala Ala Gly Leu Gly Tyr Pro Thr Leu Thr Arg Leu Leu Leu Lys
            675                 680                 685
Ala Gly Ala Asp Ile His Ala Glu Asn Glu Glu Pro Leu Cys Pro Leu
```

```
                690             695             700
Pro Ser Pro Pro Thr Ser Asp Ser Asp Ser Asp Ser Glu Gly Pro Glu
705                 710                 715                 720

Lys Asp Thr Arg Ser Ser Phe Arg Gly His Thr Pro Leu Asp Leu Thr
                725                 730                 735

Cys Ser Thr Leu Val Lys Thr Leu Leu Leu Asn Ala Ala Gln Asn Thr
            740                 745                 750

Met Glu Pro Pro Leu Thr Pro Pro Ser Pro Ala Gly Pro Gly Leu Ser
        755                 760                 765

Leu Gly Asp Thr Ala Leu Gln Asn Leu Glu Gln Leu Leu Asp Gly Pro
    770                 775                 780

Glu Ala Gln Gly Ser Trp Ala Glu Leu Ala Glu Arg Leu Gly Leu Arg
785                 790                 795                 800

Ser Leu Val Asp Thr Tyr Arg Gln Thr Thr Ser Pro Ser Gly Ser Leu
                805                 810                 815

Leu Arg Ser Tyr Glu Leu Ala Gly Gly Asp Leu Ala Gly Leu Leu Glu
                820                 825                 830

Ala Leu Ser Asp Met Gly Leu Glu Glu Gly Val Arg Leu Leu Arg Gly
            835                 840                 845

Pro Glu Thr Arg Asp Lys Leu Pro Ser Thr Glu Val Lys Glu Asp Ser
850                 855                 860

Ala Tyr Gly Ser Gln Ser Val Glu Gln Glu Ala Glu Lys Leu Gly Pro
865                 870                 875                 880

Pro Pro Glu Pro Pro Gly Gly Leu Ser His Gly His Pro Gln Pro Gln
                885                 890                 895

Val Thr Asp Leu Leu Pro Ala Pro Ser Pro Leu Pro Gly Pro Pro Val
            900                 905                 910

Gln Arg Pro His Leu Phe Gln Ile Leu Phe Asn Thr Pro His Pro Pro
        915                 920                 925

Leu Ser Trp Asp Lys
    930

<210> SEQ ID NO 4
<211> LENGTH: 3001
<212> TYPE: DNA
<213> ORGANISM: Homo sapiens

<400> SEQUENCE: 4
actttcctgc ccctccccg gccaagccca actccggatc tcgctctcca ccggatctca      60
cccgccacac ccggacaggc ggctggagga ggcgggcgtc taaaattctg ggaagcagaa     120
cctggccgga gccactagac agagccgggc ctagcccaga gacatggaga gttgctacaa     180
cccaggtctg gatggtatta ttgaatatga tgatttcaaa ttgaactcct ccattgtgga     240
acccaaggag ccagccccag aaacagctga tggcccctac ctggtgatcg tggaacagcc     300
taagcagaga ggcttccgat tcgatatgg ctgtgaaggc ccctcccatg gaggactgcc     360
cggtgcctcc agtgagaagg gccgaaagac ctatccccact gtcaagatct gtaactacga     420
gggaccagcc aagatcgagg tggacctggt aacacacagt gacccacctc gtgctcatgc     480
ccacagtctg gtgggcaagc aatgctcgga gctgggatc tgcgccgttt ctgtggggcc     540
caaggacatg actgcccaat ttaacaacct gggtgtcctg catgtgacta agaagaacat     600
gatggggact atgatacaaa aacttcagag gcagcggctc cgctctaggc cccagggcct     660 tacgaggcc gagcagcggg agctggagca agaggccaaa gaactgaaga aggtgatgga     720
tctgagtata gtgcggctgc gcttctctgc cttccttaga gccagtgatg ctccttctc      780
```

```
cctgccctg aagccagtca cctcccagcc catccatgat agcaaatctc cgggggcatc      840
aaacctgaag atttctcgaa tggacaagac agcaggctct gtgcggggtg agatgaagt      900 ttatctgctt tgtgacaagg tgcagaaaga tgacattgag gttcggttct atgaggatga     960
tgagaatgga tggcaggcct tggggacttc tctcccaca gatgtgcata acagtatgc      1020 cattgtgttc cggacacccc cctatcacaa gatgaagatt gagcggcctg taacagtgtt    1080
tctgcaactg aaacgcaagc gaggagggga cgtgtctgat ccaaacagt tcacctatta    1140 ccctctggtg gaagacaagg aagaggtgca gcggaagcgg aggaaggcct tgcccaccttt   1200 ctcccagccc ttcggggggtg ctcccacat gggtggaggc tctggggggtg cagccggggg   1260 ctacggagga gctggaggag gtggcagcct cggtttcttc ccctcctccc tggcctacag    1320
cccctaccag tccggcgcgg gccccatgcg gtgctacccg ggaggcgggg gcggggcgca    1380
gatggccgcc acggtgccca gcagggactc cggggaggaa gccgcggagc cgagcgcccc    1440
ctccaggacc ccccagtgcg agccgcaggc cccggagatg ctgcagcgag ctcgagagta    1500
caacgcgcgc ctgttcggcc tggcgcacgc agccccgagc cctactcgac tactgcgtca    1560
ccgcggacgc cgcgcgctgc tggcgggaca cgcgccacctg ctgacggcgc aggacgagaa    1620
cggagacaca ccactgcacc tagccatcat ccacgggcag accagtgtca ttgagcagat    1680
agtctatgtc atccaccacg cccaggacct cggcgttgtc aacctcacca accacctgca    1740
ccagacgccc ctgcacctgg cggtgatcac ggggcagacg agtgtggtga gctttctgct    1800
gcgggtaggt gcagacccag ctctgctgga tcggcatgga gactcagcca tgcatctggc    1860
gctgcgggca ggcgctggtg ctcctgagct gctgcgtgca ctgcttcaga gtggagctcc    1920
tgctgtgccc cagctgttgc atatgcctga ctttgaggga ctgtatccag tacacctggc    1980
ggtccgagcc cgaagccctg agtgcctgga tctgctggtg gacagtgggg ctgaagtgga    2040
ggccacagag cggcagggg gacgaacagc cttgcatcta gccacagaga tggaggagct    2100
ggggttggtc acccatctgg tcaccaagct ccgggccaac gtgaacgctc gcacctttgc    2160
gggaaacaca cccctgcacc tggcagctgg actgggtac ccgaccctca cccgcctcct    2220
tctgaaggct ggtgctgaca tccatgctga aaacgaggag cccctgtgcc cactgccttc    2280
accccctacc tctgatagcg actcggactc tgaagggcct gagaaggaca cccgaagcag    2340 cttccgggggc cacacgcctc ttgacctcac ttgcagcacc ttggtgaaga ccttgctgct    2400
aaatgctgct cagaacacca tggagccacc cctgaccccg cccagcccag cagggccggg    2460
actgtcactt ggtgatacag ctctgcagaa cctggagcag ctgctagacg gccagaagc     2520 ccagggcagc tggcagagc tggcagagcg tctggggctg cgcagcctgg tagacacgta    2580
ccgacagaca acctcaccca gtggcagcct cctgcgcagc tacgagctgg ctggcgggga    2640
cctggcaggt ctactggagg ccctgtctga catgggccta aggagggag tgaggctgct    2700 gagggggtcca gaaacccgag acaagctgcc cagcacagag gtgaaggaag acagtgcgta    2760
cgggagccag tcagtggagc aggaggcaga gaagctgggc ccaccccctg agccaccagg   2820
agggctctcg cacgggcacc cccagcctca ggtgactgac ctgctgcctg ccccagccc     2880 ccttcccgga cccctgtac agcgtcccca cctatttcaa atcttattta cacccaca     2940 cccaccctc agttgggaca aataaaggat tctcatggga aggggaggac cccgaattcc   3000
t                                                                  3001
```

<210> SEQ ID NO 5
<211> LENGTH: 899

```
<212> TYPE: PRT
<213> ORGANISM: Mus musculus

<400> SEQUENCE: 5

Met Asp Asn Cys Tyr Asp Pro Gly Leu Asp Gly Ile Pro Glu Tyr Asp
1               5                   10                  15

Asp Phe Glu Phe Ser Pro Ser Ile Val Glu Pro Lys Asp Pro Ala Pro
            20                  25                  30

Glu Thr Ala Asp Gly Pro Tyr Leu Val Ile Val Glu Gln Pro Lys Gln
        35                  40                  45

Arg Gly Phe Arg Phe Arg Tyr Gly Cys Glu Gly Pro Ser His Gly Gly
    50                  55                  60

Leu Pro Gly Ala Ser Ser Glu Lys Gly Arg Lys Thr Tyr Pro Thr Val
65                  70                  75                  80

Lys Ile Cys Asn Tyr Glu Gly Pro Ala Lys Ile Glu Val Asp Leu Val
                85                  90                  95

Thr His Ser Asp Pro Pro Arg Ala His Ala His Ser Leu Val Gly Lys
            100                 105                 110

Gln Cys Ser Glu Leu Gly Val Cys Ala Val Ser Val Gly Pro Lys Asp
        115                 120                 125

Met Thr Ala Gln Phe Asn Asn Leu Gly Val Leu His Val Thr Lys Lys
    130                 135                 140

Asn Met Met Glu Ile Met Ile Gln Lys Leu Gln Arg Gln Arg Leu Arg
145                 150                 155                 160

Ser Lys Pro Gln Gly Leu Thr Glu Ala Glu Arg Arg Glu Leu Glu Gln
                165                 170                 175

Glu Ala Lys Glu Leu Lys Lys Val Met Asp Leu Ser Ile Val Arg Leu
            180                 185                 190

Arg Phe Ser Ala Phe Leu Arg Ala Ser Asp Gly Ser Phe Ser Leu Pro
        195                 200                 205

Leu Lys Pro Val Ile Ser Gln Pro Ile His Asp Ser Lys Ser Pro Gly
    210                 215                 220

Ala Ser Asn Leu Lys Ile Ser Arg Met Asp Lys Thr Ala Gly Ser Val
225                 230                 235                 240

Arg Gly Gly Asp Glu Val Tyr Leu Leu Cys Asp Lys Val Gln Lys Asp
                245                 250                 255

Asp Ile Glu Val Arg Phe Tyr Glu Asp Asp Glu Asn Gly Trp Gln Ala
            260                 265                 270

Phe Gly Asp Phe Ser Pro Thr Asp Val His Lys Gln Tyr Ala Ile Val
        275                 280                 285

Phe Arg Thr Pro Pro Tyr His Lys Met Lys Ile Glu Arg Pro Val Thr
    290                 295                 300

Val Phe Leu Gln Leu Lys Arg Lys Arg Gly Gly Asp Val Ser Asp Ser
305                 310                 315                 320

Lys Gln Phe Thr Tyr Tyr Pro Leu Val Glu Asp Lys Glu Glu Val Gln
                325                 330                 335

Arg Lys Arg Arg Lys Ala Leu Pro Thr Phe Ser Gln Pro Phe Gly Gly
            340                 345                 350

Gly Ser His Met Gly Gly Gly Ser Gly Gly Ser Ala Gly Gly Tyr Gly
        355                 360                 365

Gly Ala Gly Gly Gly Gly Ser Leu Gly Phe Phe Ser Ser Ser Leu Ala
    370                 375                 380

Tyr Asn Pro Tyr Gln Ser Gly Ala Ala Pro Met Gly Cys Tyr Pro Gly
385                 390                 395                 400
```

```
Gly Gly Gly Gly Ala Gln Met Ala Gly Ser Arg Arg Asp Thr Asp Ala
            405                 410                 415
Gly Glu Gly Ala Glu Glu Pro Arg Thr Pro Pro Glu Ala Pro Gln Gly
        420                 425                 430
Glu Pro Gln Ala Leu Asp Thr Leu Gln Arg Ala Arg Glu Tyr Asn Ala
            435                 440                 445
Arg Leu Phe Gly Leu Ala Gln Arg Ser Ala Arg Ala Leu Leu Asp Tyr
        450                 455                 460
Gly Val Thr Ala Asp Ala Arg Ala Leu Leu Ala Gly Gln Arg His Leu
465                 470                 475                 480
Leu Met Ala Gln Asp Glu Asn Gly Asp Thr Pro Leu His Leu Ala Ile
            485                 490                 495
Ile His Gly Gln Thr Gly Val Ile Glu Gln Ile Ala His Val Ile Tyr
        500                 505                 510
His Ala Gln Tyr Leu Gly Val Ile Asn Leu Thr Asn His Leu His Gln
        515                 520                 525
Thr Pro Leu His Leu Ala Val Ile Thr Gly Gln Thr Arg Val Val Ser
    530                 535                 540
Phe Leu Leu Gln Val Gly Ala Asp Pro Thr Leu Leu Asp Arg His Gly
545                 550                 555                 560
Asp Ser Ala Leu His Leu Ala Leu Arg Ala Gly Ala Ala Ala Pro Glu
            565                 570                 575
Leu Leu Gln Ala Leu Leu Arg Ser Gly Ala His Ala Val Pro Gln Ile
        580                 585                 590
Leu His Met Pro Asp Phe Glu Gly Leu Tyr Pro Val His Leu Ala Val
        595                 600                 605
His Ala Arg Ser Pro Glu Cys Leu Asp Leu Leu Val Asp Cys Gly Ala
    610                 615                 620
Glu Val Glu Ala Pro Glu Arg Gln Gly Gly Arg Thr Ala Leu His Leu
625                 630                 635                 640
Ala Thr Glu Met Glu Glu Leu Gly Leu Val Thr His Leu Val Thr Lys
            645                 650                 655
Leu His Ala Asn Val Asn Ala Arg Thr Phe Ala Gly Asn Thr Pro Leu
        660                 665                 670
His Leu Ala Ala Gly Leu Gly Ser Pro Thr Leu Thr Arg Leu Leu Leu
        675                 680                 685
Lys Ala Gly Ala Asp Ile His Ala Glu Asn Glu Glu Pro Leu Cys Pro
    690                 695                 700
Leu Pro Ser Pro Ser Thr Ser Gly Ser Asp Ser Asp Ser Glu Gly Pro
705                 710                 715                 720
Glu Arg Asp Thr Gln Arg Asn Phe Arg Gly His Thr Pro Leu Asp Leu
            725                 730                 735
Thr Cys Ser Thr Lys Val Lys Thr Leu Leu Leu Asn Ala Ala Gln Asn
        740                 745                 750
Thr Thr Glu Pro Pro Leu Ala Pro Pro Ser Pro Ala Gly Pro Gly Leu
        755                 760                 765
Ser Leu Gly Asp Ala Ala Leu Gln Asn Leu Glu Gln Leu Leu Asp Gly
    770                 775                 780
Pro Glu Ala Gln Gly Ser Trp Ala Glu Leu Ala Glu Arg Leu Gly Leu
785                 790                 795                 800
Arg Ser Leu Val Asp Thr Tyr Arg Lys Thr Pro Ser Pro Ser Gly Ser
            805                 810                 815
Leu Leu Arg Ser Tyr Lys Leu Ala Gly Gly Asp Leu Val Gly Leu Leu
        820                 825                 830
```

| Glu | Ala | Leu | Ser | Asp | Met | Gly | Leu | His | Glu | Gly | Val | Arg | Leu | Leu | Lys |
|---|---|---|---|---|---|---|---|---|---|---|---|---|---|---|---|
| | | | 835 | | | | | 840 | | | | | 845 | | |

| Gly | Pro | Glu | Thr | Arg | Asp | Lys | Leu | Pro | Ser | Thr | Glu | Val | Lys | Glu | Asp |
|---|---|---|---|---|---|---|---|---|---|---|---|---|---|---|---|
| | 850 | | | | | 855 | | | | | 860 | | | | |

| Ser | Ala | Tyr | Gly | Ser | Gln | Ser | Val | Glu | Gln | Glu | Ala | Glu | Lys | Leu | Cys |
|---|---|---|---|---|---|---|---|---|---|---|---|---|---|---|---|
| 865 | | | | | 870 | | | | | 875 | | | | | 880 |

| Pro | Pro | Pro | Glu | Pro | Pro | Gly | Gly | Leu | Cys | His | Gly | His | Pro | Gln | Pro |
|---|---|---|---|---|---|---|---|---|---|---|---|---|---|---|---|
| | | | | 885 | | | | | 890 | | | | | 895 | |

Gln Val His

<210> SEQ ID NO 6
<211> LENGTH: 2918
<212> TYPE: DNA
<213> ORGANISM: Mus musculus

<400> SEQUENCE: 6

```
ggcgggcgtc cgaaactctg gaaagctgaa ccggggcccg aagccgcaag acacagcagg      60
gcctagccca gagatatgga caattgctac gatccaggcc tggatggcat ccccgaatat     120
gatgattttg aattcagccc ctccatcgtg gagcctaagg atccagcccc tgagacagct     180
gatggcccct atctggtgat gtgtggaaca gcccaaacagc gaggcttcag atttcgatat    240
ggctgtgaag cccctcccca tggaggtttg ccaggtgcct ccagtgagaa gggccggaag    300
acctatccta ctgtcaagat ctgtaactat gagggaccgg ccaagattga ggtggacctg    360
gtgacacaca gtgacccacc tcgtgcgcat gcccacagtc tggtgggcaa gcagtgttca    420
gagttgggag tgtgcgctgt gtctgtagga cccaaggaca tgactgctca atttaataat    480
ctgggtgtcc tgcatgtaac caagaagaac atgatggaga ttatgatcca gaaacttcag    540
aggcagcgtc tccgctccaa gcctcagggc cttacagagg ctgagcggcg ggagctagag    600
caggaggcca aggagctgaa gaaagtcatg gatctgagca ttgtacggct gcgcttctca    660
gctttccttc gagctagcga tggctccttc tccttgcccc tgaagcctgt gatctcccag    720
cccatccatg acagcaagtc tccaggggcc tcgaacctga agatctcccg aatggacaag    780
acagcgggtt ccgtgcgcgg tggagacgaa gtttatttgc tctgtgataa ggtgcaaaaa    840
gacgacattg aggttcggtt ctatgaggat gatgagaatg gatggcaagc ctttggggac    900
ttctctccca gacgttca taaacagtat gccattgtgt tccggacacc gccctatcac    960
aagatgaaga tcgagaggcc tgtaacagtg ttcctgcagc tgaaacgcaa gcgtgggggc   1020
gatgtctcgg actccaaaca gttcacatat taccctctgg tggaagacaa ggaggaagtg   1080
cagaggaagc ggagaaaggc cttgcccacc ttctcccagc ccttcggggg cggatcccac   1140
atgggtggag ttctgggggg ctccgctggg ggttatggag gcgctggagg aggtggcagc   1200
ctcggctttt tctcctcctc cttggcctac aaccctacc aatccggtgc agccccaatg   1260
ggctgttatc cgggtgggg aggtggagcg cagatggccg ttctagacg ggacaccgat   1320
gctggcgagg gggcagagga gcccaggacg ccccggagg ctccccaggg cgaaccacag   1380
gcccttgaca cactgcagcg agctcgcgag tacaacgcgc gcctgttcgg tctggcgcag   1440
cgcagcgccc gagcgttgct ggactacggc gtcaccgcag acgcgcgtgc tctgctagcg   1500
ggacagcgcc acctgctgat ggcacaggac gagaacggag acacgccact gcacctggcc   1560
atcatccatg gcagactgg tgtcattgag cagatagccc acgtcattta tcacgctcag   1620
tacctcggcg tcatcaacct caccaaccac ctgcaccaga cgcctctgca cctggcggta   1680
atcactgggc agacaagggt ggtgagcttc ctgctgcagg tgggtgcaga ccccacgctg   1740
```

```
ctggatcggc acggagactc cgccctccac ttggctctcc gggcaggtgc tgcagcccca    1800
gagctgttgc aggcactgtt gcgcagcgga gcccatgctg tgccccaaat attgcacatg    1860
cctgattttg agggactata ccctgtacac ctggcagtcc atgcccgaag ccctgagtgc    1920
ctggatctgt tagttgactg tggagctgaa gtggaggccc agagaggca aggggggccga    1980 actgccctgc atctagccac agagatggag gagttggggc tggtcaccca tctagtcacc    2040
aagctccatg ctaatgtgaa tgcccggacc tttgctggaa acacacccct ccacctggca    2100
gctggactcg ggtccccaac tcttactcgc ctccttctaa aggctggtgc tgacatccat    2160
gcagagaatg aggagcctct gtgcccgctg ccctcaccct cgacctctgg gagcgactcc    2220
gactctgaag ggcctgagag ggatacccaa agaaacttcc gaggccatac ccctcttgac    2280
ctcacttgca gtaccaaggt gaagactctg ctgctaaatg ctgctcagaa caccacggag    2340
ccacccctgg ccccacccag ccctgcaggg ccagggctgt ccctggggga tgcagccctg    2400
cagaacctgg agcaactgct ggatggtccc gaagcccagg gcagctgggc agagctggca    2460
gagcgactgg ggttgagaag cctggtggac acatacagga gaccccgtc tcccagcggc    2520 agtctccttc gtagttacaa gctggctggt ggggacttgg tgggtctatt ggaggccttg    2580
tctgacatgg gtctccatga gggagtcagg ctgctgaaag gtcctgagac ccgcgacaag    2640
ctgcccagca cagaggtgaa agaagacagt gcctatggga gccagtcagt ggagcaggag    2700
gcagagaagc tgtgtccacc ccctgagcct ccaggagggc tctgccacgg cacccccag    2760 cctcaggtgc actgaatggc cccggtcaac ttccacccag atccctctgt acagcatccc    2820
tgtctaatcg aaatcttatt taaacctcaa gcccacatct cggtgggtca ataaagggg    2880 aagacccctc cccaacttac ggtaaaaaaa aaaaaaaa                            2918

<210> SEQ ID NO 7
<211> LENGTH: 187
<212> TYPE: DNA
<213> ORGANISM: Macaca mulatta

<400> SEQUENCE: 7
atattacaac tttttctact cttgatggac atttatattt tcaacttttg cctgttataa      60
ataatgctgc tatgaatatt attctacatg tcttttgaca gaactatgca ctaattttc      120 agagaatata cttaggaata gcattgctat catagggcag gcgaatattt aattttggca     180
gatattg                                                              187

<210> SEQ ID NO 8
<211> LENGTH: 558
<212> TYPE: PRT
<213> ORGANISM: Mus musculus

<400> SEQUENCE: 8

Met Pro Ser Arg Arg Ala Ala Arg Glu Ser Ala Pro Glu Leu Gly Ala
  1               5                  10                  15

Leu Gly Ser Ser Asp Leu Ser Ser Leu Ser Leu Thr Val Ser Arg Thr
             20                  25                  30

Thr Asp Glu Leu Glu Ile Ile Asp Glu Tyr Ile Lys Glu Asn Gly Phe
         35                  40                  45

Gly Leu Val Gly Thr Gln Leu Ser Glu Met Pro Arg Leu Val Pro Arg
     50                  55                  60

Gly Pro Ala Ser Leu Ser Ser Val Thr Leu Gly Pro Ala Ala Pro Pro
 65                  70                  75                  80
```

```
Pro Pro Ala Thr Pro Ser Trp Ser Cys Thr Leu Gly Arg Leu Val Ser
            85                  90                  95
Pro Gly Pro Cys Pro Arg Pro Tyr Leu Val Ile Thr Glu Gln Pro Lys
        100                 105                 110
Gln Arg Gly Met Arg Phe Arg Tyr Glu Cys Glu Gly Arg Ser Ala Gly
    115                 120                 125
Ser Ile Leu Gly Glu Ser Ser Thr Glu Ala Ser Lys Thr Gln Pro Ala
130                 135                 140
Ile Glu Leu Arg Asp Cys Gly Gly Leu Arg Glu Val Glu Val Thr Ala
145                 150                 155                 160
Cys Leu Val Trp Lys Asp Trp Pro His Arg Val His Pro His Ser Leu
                165                 170                 175
Val Gly Lys Asp Cys Thr Asp Gly Val Cys Arg Val Arg Leu Arg Pro
            180                 185                 190
His Val Ser Pro Arg His Ser Phe Asn Asn Leu Gly Ile Gln Cys Val
        195                 200                 205
Arg Lys Lys Glu Ile Glu Ala Ala Ile Glu Arg Lys Ile Gln Leu Gly
    210                 215                 220
Ile Asp Pro Tyr Asn Ala Gly Ser Leu Lys Asn His Gln Glu Val Asp
225                 230                 235                 240
Met Asn Val Val Arg Ile Cys Phe Gln Ala Ser Tyr Arg Asp Gln Gln
                245                 250                 255
Gly His Leu His Arg Met Asp Pro Ile Leu Ser Glu Pro Val Tyr Asp
            260                 265                 270
Lys Lys Ser Thr Asn Thr Ser Glu Leu Arg Ile Cys Arg Ile Asn Lys
        275                 280                 285
Glu Ser Gly Pro Cys Thr Gly Gly Glu Glu Leu Tyr Leu Leu Cys Asp
    290                 295                 300
Lys Val Gln Lys Glu Asp Ile Ser Val Val Phe Ser Thr Ala Ser Trp
305                 310                 315                 320
Glu Gly Arg Ala Asp Phe Ser Gln Ala Asp Val His Arg Gln Ile Ala
                325                 330                 335
Ile Val Phe Lys Thr Pro Pro Tyr Glu Asp Leu Glu Ile Ser Glu Pro
            340                 345                 350
Val Thr Val Asn Val Phe Leu Gln Arg Leu Thr Asp Gly Val Cys Ser
        355                 360                 365
Glu Pro Leu Pro Phe Thr Tyr Leu Pro Arg Asp His Asp Ser Tyr Gly
    370                 375                 380
Val Asp Lys Lys Arg Lys Arg Gly Leu Pro Asp Val Leu Gly Glu Leu
385                 390                 395                 400
Ser Ser Ser Asp Pro His Gly Ile Glu Ser Lys Arg Arg Lys Lys Lys
                405                 410                 415
Pro Val Phe Leu Asp His Phe Leu Pro Gly His Ser Ser Gly Leu Phe
            420                 425                 430
Leu Pro Pro Ser Ala Leu Gln Pro Ala Asp Ser Asp Phe Pro Ala
    435                 440                 445
Ser Ile Ser Leu Pro Gly Leu Glu Pro Pro Gly Gly Pro Asp Leu Leu
    450                 455                 460
Asp Asp Gly Phe Ala Tyr Asp Pro Ser Ala Pro Thr Leu Phe Thr Met
465                 470                 475                 480
Leu Asp Leu Leu Pro Pro Ala Pro Pro Leu Ala Ser Ala Val Val Gly
                485                 490                 495
Ser Gly Gly Ala Gly Ala Thr Val Val Glu Ser Ser Gly Pro Glu Pro
            500                 505                 510
```

-continued

```
Leu Ser Leu Asp Ser Phe Ala Ala Pro Gly Pro Gly Asp Val Gly Thr
            515                 520                 525

Ala Ser Leu Val Gly Ser Asn Met Phe Pro Asn Gln Tyr Arg Glu Ala
        530                 535                 540

Ala Phe Gly Gly Gly Leu Leu Ser Pro Gly Pro Glu Ala Thr
545                 550                 555
```

<210> SEQ ID NO 9
<211> LENGTH: 558
<212> TYPE: PRT
<213> ORGANISM: Mus musculus

<400> SEQUENCE: 9

```
Met Pro Ser Arg Arg Ala Ala Arg Glu Ser Ala Pro Glu Leu Gly Ala
1               5                   10                  15

Leu Gly Ser Ser Asp Leu Ser Ser Leu Ser Leu Thr Val Ser Arg Thr
            20                  25                  30

Thr Asp Glu Leu Glu Ile Ile Asp Glu Tyr Ile Lys Glu Asn Gly Phe
        35                  40                  45

Gly Leu Val Gly Thr Gln Leu Ser Glu Met Pro Arg Leu Val Pro Arg
    50                  55                  60

Gly Pro Ala Ser Leu Ser Ser Val Thr Leu Gly Pro Ala Ala Pro Pro
65                  70                  75                  80

Pro Pro Ala Thr Pro Ser Trp Ser Cys Thr Leu Gly Arg Leu Val Ser
                85                  90                  95

Pro Gly Pro Cys Pro Arg Pro Tyr Leu Val Ile Thr Glu Gln Pro Lys
            100                 105                 110

Gln Arg Gly Met Arg Phe Arg Tyr Glu Cys Glu Gly Arg Ser Ala Gly
        115                 120                 125

Ser Ile Leu Gly Glu Ser Ser Thr Glu Ala Ser Lys Thr Gln Pro Ala
    130                 135                 140

Ile Glu Leu Arg Asp Cys Gly Gly Leu Arg Glu Val Glu Val Thr Ala
145                 150                 155                 160

Cys Leu Val Trp Lys Asp Trp Pro His Arg Val His Pro His Ser Leu
                165                 170                 175

Val Gly Lys Asp Cys Thr Asp Gly Val Cys Arg Val Arg Leu Arg Pro
            180                 185                 190

His Val Ser Pro Arg His Ser Phe Asn Asn Leu Gly Ile Gln Cys Val
        195                 200                 205

Arg Lys Lys Glu Ile Glu Ala Ala Ile Glu Arg Lys Ile Gln Leu Gly
    210                 215                 220

Ile Asp Pro Tyr Asn Ala Gly Ser Leu Lys Asn His Gln Glu Val Asp
225                 230                 235                 240

Met Asn Val Val Arg Ile Cys Phe Gln Ala Ser Tyr Arg Asp Gln Gln
                245                 250                 255

Gly His Leu His Arg Met Asp Pro Ile Leu Ser Glu Pro Val Tyr Asp
            260                 265                 270

Lys Lys Ser Thr Asn Thr Ser Glu Leu Arg Ile Cys Arg Ile Asn Lys
        275                 280                 285

Glu Ser Gly Pro Cys Thr Gly Gly Glu Glu Leu Tyr Leu Leu Cys Asp
    290                 295                 300

Lys Val Gln Lys Glu Asp Ile Ser Val Val Phe Ser Thr Ala Ser Trp
305                 310                 315                 320

Glu Gly Arg Ala Asp Phe Ser Gln Ala Asp Val His Arg Gln Ile Ala
                325                 330                 335
```

```
Ile Val Phe Lys Thr Pro Pro Tyr Glu Asp Leu Glu Ile Ser Glu Pro
        340                 345                 350

Val Thr Val Asn Val Phe Leu Gln Arg Leu Thr Asp Gly Val Cys Ser
        355                 360                 365

Glu Pro Leu Pro Phe Thr Tyr Leu Pro Arg Asp His Asp Ser Tyr Gly
    370                 375                 380

Val Asp Lys Lys Arg Lys Arg Gly Leu Pro Asp Val Leu Gly Glu Leu
385                 390                 395                 400

Ser Ser Ser Asp Pro His Gly Ile Glu Ser Lys Arg Arg Lys Lys Lys
                405                 410                 415

Pro Val Phe Leu Asp His Phe Leu Pro Gly His Ser Ser Gly Leu Phe
                420                 425                 430

Leu Pro Pro Ser Ala Leu Gln Pro Ala Asp Ser Asp Phe Phe Pro Ala
                435                 440                 445

Ser Ile Ser Leu Pro Gly Leu Glu Pro Pro Gly Gly Pro Asp Leu Leu
450                 455                 460

Asp Asp Gly Phe Ala Tyr Asp Pro Ser Ala Pro Thr Leu Phe Thr Met
465                 470                 475                 480

Leu Asp Leu Leu Pro Pro Ala Pro Pro Leu Ala Ser Ala Val Val Gly
                485                 490                 495

Ser Gly Gly Ala Gly Ala Thr Val Val Glu Ser Ser Gly Pro Glu Pro
                500                 505                 510

Leu Ser Leu Asp Ser Phe Ala Ala Pro Gly Pro Gly Asp Val Gly Thr
                515                 520                 525

Ala Ser Leu Val Gly Ser Asn Met Phe Pro Asn Gln Tyr Arg Glu Ala
                530                 535                 540

Ala Phe Gly Gly Gly Leu Leu Ser Pro Gly Pro Glu Ala Thr
545                 550                 555

<210> SEQ ID NO 10
<211> LENGTH: 2055
<212> TYPE: DNA
<213> ORGANISM: Mus musculus

<400> SEQUENCE: 10
ggccttcggg ctgtcggtcc ctacggccgg gccatgccga gtcgccgcgc tgccagagag    60
tccgcgcccg agctaggggc cttgggttcc agtgacctct cttccctgtc actaacggtc   120
tccaggacca cagatgaatt ggaaatcatc gacgaataca ttaaggagaa cggctttggc   180
ctggtcggga cacagctgag tgagatgccg cgcctggtgc cccgcgggcc cgcctcactg   240
agcagcgtca cgctgggccc tgctgcacca ccgcctccgg ccacgccgtc ctggagctgc   300
acactgggca ggctggtgtc acccggcccg tgcccacggc cgtacctggt catcacagag   360
cagccaaagc agcgtggcat gcgcttccgc tacgagtgcg agggccgctc ggccggcagc   420
atcctcgggg agagcagcac cgaagccagc aagacccagc ccgccatcga gcttcgagac   480
tgtggcgggc tgcggaggt ggaggtgacg gcgtgcctgg tgtggaagga ctggccacac   540
cgggtacacc cacatagcct cgtggggaaa gactgcacgg acggcgtctg cagggtgcgg   600
ctgcggcctc acgtcagccc ccggcacagc tttaacaacc tgggcatcca gtgtgttagg   660
aagaaggaaa ttgaagctgc cattgagcgg aagatccagc tgggaattga ccctacaat   720 gctggctccc tgaagaacca tcaggaggtc gacatgaatg tcgtcaggat ctgcttccag   780
gcctcctatc gggaccagca gggacatctg caccgcatgg accccatcct ctctgagcct   840
gtctacgaca agaagtccac caacacatcg gagctgcgga tttgccgaat caacaaggag   900
```

```
agcgggccgt gcacaggtgg tgaggagctg tacttgctct gtgacaaggt gcaaaaagag    960
gacatatccg tggtgttcag cacagcttcc tgggaaggcc gtgccgactt ctctcaagct   1020
gatgtgcacc ggcagatcgc cattgtgttc aaaacgccac cctacgagga cctggagatc   1080
tcagagcccg tgactgtcaa tgtgttcttg cagcggctca cggatggggt gtgcagcgag   1140
ccgctgccct tcacgtacct gcctcgggat catgacagct acggtgtgga caagaagcga   1200
aagcggggac tgcctgatgt ccttggagag ttgagcagct ctgatccaca tggaatcgag   1260
agcaaacgaa ggaaaaagaa accagtgttc ttggaccact tcctgcctgg ccacagctca   1320
ggcctgttcc tcccaccatc ggctctgcag ccggcagact ctgatttctt ccctgcttcc   1380
atatcccttc ctgggctgga gcctcctggt ggacccgatc tcctggacga tggctttgcc   1440
tatgatcctt ctgcccccac gctcttcact atgttggacc tgctgccccc agcaccacca   1500
cttgccagtg ctgtggtggg tagcgggggt gcagggccca cgttgtgga gtcttctggc   1560 ccagagcccc tatcactgga ctcttttgca gcgccgggcc ccggggatgt tggtactgct   1620
agccttgtgg gcagcaacat gtttcccaac cagtaccgag aggcagcttt cggggggtggc   1680 ctcctatctc cagggcctga agccacgtag cctctgaggt aacagaggag cactgggtg    1740 aggtatgtgg tatagcactc cattccgaag ccaaccttga tcagtcttcc agcttcctca   1800
tcctgaatcg acatctgca gcgctggtgg aagatgggg agcactccgg ttctctttga    1860
gcccatttta cagaatgctg agtccgaaga ggaaaagggg ctcctgcaga tggacccctt   1920
ctcaggacag attctcagag attgtacata ggggaggagg gagcaggtcc ccagccttct   1980
cccctaatcc tgaagaaggc agtggattgt tcagttttcc caataaaaat tagtttttta   2040 aaaaaagga attcc                                                    2055

<210> SEQ ID NO 11
<211> LENGTH: 497
<212> TYPE: PRT
<213> ORGANISM: Xenopus laevis

<400> SEQUENCE: 11

Met Arg Glu Gln Gly Arg Glu Gly Ser Ser Phe Leu Ser Gln Gln Leu
1               5                   10                  15

Gly Pro Thr Ile Glu Asp Val Met Asp Leu Ile Asn Ser Asp Arg Asp
            20                  25                  30

Val Ile Ser Ser Pro Ser Val Phe Val Cys Glu Asp Ala Pro Ser Ser
        35                  40                  45

Ile Leu Ser Thr Val Thr Val Ala His Tyr Val Pro His Glu Gln Cys
    50                  55                  60

Pro Ser Thr Ser Trp Ala Pro Gln Arg Glu Gly Pro Asn Pro Glu Leu
65                  70                  75                  80

Asn Ile Thr Glu Gln Pro Lys Gln Arg Gly Met Arg Phe Arg Tyr Gln
                85                  90                  95

Cys Glu Gly Arg Ser Thr Gly Ser Ile Leu Gly Glu Lys Ser Thr Glu
            100                 105                 110

His Asn Lys Thr Leu Pro Glu Ile Glu Ile Ile Asn Cys Asp Gly Leu
        115                 120                 125

Glu Glu Ile His Val Ile Cys Leu Val Trp Arg Asp Pro His
    130                 135                 140

Arg Val His Pro His Gly Leu Val Gly Lys Asp Cys His Asn Gly Ile
145                 150                 155                 160

Cys Glu Val Thr Leu Asn Pro Gln Asn Gly Val Ala Lys His Ser Phe
```

```
                        165                 170                 175
Ser Asn Leu Gly Ile Gln Cys Val Arg Lys Arg Glu Ile Asp Ser Ala
        180                 185                 190

Val Asn Glu Arg Leu Lys Leu Asn Ile Asp Pro Tyr Lys Ala Gly Lys
        195                 200                 205

Trp Arg Leu His Glu Val Asp Leu Asn Val Val Arg Leu Cys Phe
        210                 215                 220

Gln Ala Ser Cys Thr Gly Pro Gly Phe Lys Tyr Asp Ile Pro Val
225                 230                 235                 240

Leu Ser Asp Pro Ile Tyr Asp Lys Lys Ser Thr Asn Thr Ser Glu Leu
                245                 250                 255

Lys Ile Ser Arg Met Asn Lys Glu Tyr Gly Arg Cys Glu Gly Gly Glu
            260                 265                 270

Glu Val Tyr Ile Leu Cys Asp Lys Val Gln Lys Glu Asp Ile Leu Val
            275                 280                 285

Ile Phe Gly Glu Asp Lys Trp Glu Ala Arg Ala Asp Phe Ser Gln Ala
        290                 295                 300

Asp Val His Arg Gln Ile Ala Ile Val Leu Lys Thr Pro Pro Tyr His
305                 310                 315                 320

Asp Leu His Ile Thr Glu Pro Ala Cys Val Arg Val Phe Leu Gln Arg
                325                 330                 335

Ile Thr Asp Gly Ile Arg Ser Glu Gly Met Pro Phe Val Tyr Met Pro
            340                 345                 350

Arg Val Lys Asp Pro Asn Gly Val His Ser Lys Arg Lys His Arg Asp
            355                 360                 365

Cys Ser Gln Leu Gly Asp Ile Gly Asp Pro Asp Pro His Gly Ile Glu
        370                 375                 380

Met Lys Arg Arg Lys Val Arg Pro Ser Tyr Ala Asp His Leu Ile Pro
385                 390                 395                 400

Pro Tyr Pro Asp Ile Asn Leu Pro Leu Met Asp Ser Phe Asn His Asn
                405                 410                 415

Glu Gly Tyr His Asp Leu Pro Leu Met Asn Pro Asp Glu Asp Ala Phe
            420                 425                 430

His Phe Leu Thr Glu Asp Pro His Phe Ser Asp Leu Leu Thr His Asp
        435                 440                 445

Pro Tyr Phe Leu Asp Gly Tyr Ser Asn Gln Phe Leu Pro Asp Gln Val
        450                 455                 460

Asn Gly Val Thr Ala His Leu Val Gly Ser Ser Leu Ala Leu Thr Asp
465                 470                 475                 480

Glu Glu Gln Pro Leu Pro Asp Cys Ala Phe Asn Asp Ser Gly Cys Arg
                485                 490                 495

Arg

<210> SEQ ID NO 12
<211> LENGTH: 2288
<212> TYPE: DNA
<213> ORGANISM: Xenopus laevis

<400> SEQUENCE: 12
ggttcgtccg tggttagggg ggtgtgtata agcgctgcca agccactcgc atgataaggg      60
ttcacttaca aatgtaatat ttctcagctt ttaattacgc ctttggataa agaaacaca     120 atgagagaac aggggaggga aggtcttct tttttgtctc agcaacttgg accaacaatt     180
gaagatgtca tggatcttat taattctgac cgggatgtaa tttcttcgcc ttccgtgttt     240
```

| | |
|---|---|
| gtttgcgagg acgcccttc tagtatcctc agtactgtaa ctgtcgcaca ttatgtgccc | 300 |
| catgagcaat gcccatccac atcctgggct cctcagcgag aaggtccaaa tccagaatta | 360 |
| aacatcactg agcaaccaaa acagagaggg atgcgcttcc gttaccagtg tgagggaga | 420 |
| tcgactggaa gtatacttgg ggagaaaagc acagagcata ataagaccct tccagagatt | 480 |
| gagatcatca actgtgatgg gcttgaagaa attcatgtca ttgtgtgtct cgtctggaga | 540 |
| gatcctcccc atcgcgtgca cccccatggc cttgtaggta aagactgcca taatggcatc | 600 |
| tgtgaggtca ccctgaatcc tcagaatgga gtagcaaagc acagtttcag taatcttggc | 660 |
| attcagtgtg tgcggaaaag ggaaatcgac tcggcggtaa atgaacggct gaaattaaat | 720 |
| atcgatcctt ataaagctgg gaaatggcgt ctccatgaag aagtagattt gaacgtggtc | 780 |
| agactctgct tccaggcctc ctgtactggg ccggggttta aatatgacat tccccctgtg | 840 |
| ctttctgacc cgatctatga caagaaatct acaaatacat cagaactgaa gatttctcgc | 900 |
| atgaacaaag aatatggacg atgtgaaggg gcgaggagg tctatatcct ctgtgataag | 960 |
| gttcagaaag aggatatcct ggtaatattt ggagaagata agtgggaggc tcgtgctgat | 1020 |
| ttctcacagg cagatgtgca cagacagata gcgattgtgc taaagacacc accatatcat | 1080 |
| gatctgcata tcacagaacc agcttgtgtg cgtgtgtttc tgcagaggat tacagatggc | 1140 |
| atacgcagtg aagggatgcc atttgtctac atgccacgag ttaaagatcc caatggtgtg | 1200 |
| cactctaaga ggaaacatcg ggactgttca caactcggtg ataggaga tcctgatcca | 1260 |
| catgggattg aaatgaagag aagaaaagta agacctagtt atgcagatca tttaatccct | 1320 |
| ccttacccag atataaattt acccctcatg gattccttca accataatga aggttaccac | 1380 |
| gaccttcctc tgatgaaccc tgatgaagat gcatttcact ttctcactga ggacccacat | 1440 |
| ttttcagatc tcctgacaca cgacccttac tttctggatg gttattcgaa tcaatttctg | 1500 |
| ccagaccagg tgaatggagt cacagctcat cttgtgggtt ccagccttgc tttaaccgac | 1560 |
| gaagaacaac ctttaccaga ctgtgctttt aatgacagtg gttgccggag ataaccgtat | 1620 |
| attcagagat ccaatatttt gactctgttt tcagcacttg aactacaaag cccacttcag | 1680 |
| ttacagtttg tatatacata gatacatgta tatatatgtg taagagagct tatagttctg | 1740 |
| ggaaatataa ggaatttctg ttgttagagg gaggataaaa cacagtgatc taaagatttc | 1800 |
| taccatgaag tcttaatatt ccatagctga caaaatggtc cctactgaag aggtccatgc | 1860 |
| ctccgcaata tggaataaag ttcacaaaca gaaagacact gaagaaacca ctatatattt | 1920 |
| ctaattctaa aaaatagata ccactttttg tatgaacttg taagctcaat aatgaccaa | 1980 |
| catttattct aggctgtaga aaagaataaa gaggacctt taatggggag aggaattag | 2040 |
| gaagcagtac cattggcttg tcagtaacta ggatcacaat tgcatcctcc agtaaagaca | 2100 |
| gaactctgga cttcagtggc acttgctctg tatgtacaga gatatgtatt taataaaggt | 2160 |
| agtttggtct gtttatgtga aaatatggta taggacagag gggacatagt ttttgcacta | 2220 |
| gtatatgatg acagaataga agattggtgg ttaaaaggat ttattactta atatacatt | 2280 |
| gaaacact | 2288 |

<210> SEQ ID NO 13
<211> LENGTH: 971
<212> TYPE: PRT
<213> ORGANISM: Mus musculus

<400> SEQUENCE: 13

Met Ala Asp Asp Asp Pro Tyr Gly Thr Gly Gln Met Phe His Leu Asn
1               5                   10                  15

Thr Ala Leu Thr His Ser Ile Phe Asn Ala Glu Leu Tyr Ser Pro Glu
            20                  25                  30

Ile Pro Leu Ser Thr Asp Gly Pro Tyr Leu Gln Ile Leu Glu Gln Pro
            35                  40                  45

Lys Gln Arg Gly Phe Arg Phe Arg Tyr Val Cys Glu Gly Pro Ser His
50                  55                  60

Gly Gly Leu Pro Gly Ala Ser Ser Glu Lys Asn Lys Lys Ser Tyr Pro
65                  70                  75                  80

Gln Val Lys Ile Cys Asn Tyr Val Gly Pro Ala Lys Val Ile Val Gln
                85                  90                  95

Leu Val Thr Asn Gly Lys Asn Ile His Leu His Ala His Ser Leu Val
            100                 105                 110

Gly Lys His Cys Glu Asp Gly Val Cys Thr Val Thr Ala Gly Pro Lys
            115                 120                 125

Asp Met Val Val Gly Phe Ala Asn Leu Gly Ile Leu His Val Thr Lys
130                 135                 140

Lys Lys Val Phe Glu Thr Leu Glu Ala Arg Met Thr Glu Ala Cys Ile
145                 150                 155                 160

Arg Gly Tyr Asn Pro Gly Leu Leu Val His Ser Asp Leu Ala Tyr Leu
                165                 170                 175

Gln Ala Glu Gly Gly Gly Asp Arg Gln Leu Thr Asp Arg Glu Lys Glu
            180                 185                 190

Ile Ile Arg Gln Ala Ala Val Gln Gln Thr Lys Glu Met Asp Leu Ser
            195                 200                 205

Val Val Arg Leu Met Phe Thr Ala Phe Leu Pro Asp Ser Thr Gly Ser
210                 215                 220

Phe Thr Arg Arg Leu Glu Pro Val Val Ser Asp Ala Ile Tyr Asp Ser
225                 230                 235                 240

Lys Ala Pro Asn Ala Ser Asn Leu Lys Ile Val Arg Met Asp Arg Thr
                245                 250                 255

Ala Gly Cys Val Thr Gly Gly Glu Glu Ile Tyr Leu Leu Cys Asp Lys
            260                 265                 270

Val Gln Lys Asp Asp Ile Gln Ile Arg Phe Tyr Glu Glu Glu Glu Asn
            275                 280                 285

Gly Gly Val Trp Glu Gly Phe Gly Asp Phe Ser Pro Thr Asp Val His
            290                 295                 300

Arg Gln Phe Ala Ile Val Phe Lys Thr Pro Lys Tyr Lys Asp Val Asn
305                 310                 315                 320

Ile Thr Lys Pro Ala Ser Val Phe Val Gln Leu Arg Arg Lys Ser Asp
                325                 330                 335

Leu Glu Thr Ser Glu Pro Lys Pro Phe Leu Tyr Tyr Pro Glu Ile Lys
            340                 345                 350

Asp Lys Glu Glu Val Gln Arg Lys Arg Gln Lys Leu Met Pro Asn Phe
            355                 360                 365

Ser Asp Ser Phe Gly Gly Gly Ser Gly Ala Gly Ala Gly Gly Gly Gly
            370                 375                 380

Met Phe Gly Ser Gly Gly Gly Gly Ser Thr Gly Ser Pro Gly Pro
385                 390                 395                 400

Gly Tyr Gly Tyr Ser Asn Tyr Gly Phe Pro Pro Tyr Gly Gly Ile Thr
                405                 410                 415

Phe His Pro Gly Val Thr Lys Ser Asn Ala Gly Val Thr His Gly Thr
            420                 425                 430

Ile Asn Thr Lys Phe Lys Asn Gly Pro Lys Asp Cys Ala Lys Ser Asp

```
                435                440                445
Asp Glu Glu Ser Leu Thr Leu Pro Glu Lys Thr Glu Gly Glu Gly
    450                455                460

Pro Ser Leu Pro Met Ala Cys Thr Lys Thr Glu Pro Ile Ala Leu Ala
465                470                475                480

Ser Thr Met Glu Asp Lys Glu Gln Asp Met Gly Phe Gln Asp Asn Leu
                485                490                495

Phe Leu Glu Lys Ala Leu Gln Leu Ala Arg Arg His Ala Asn Ala Leu
                500                505                510

Phe Asp Tyr Ala Val Thr Gly Asp Val Lys Met Leu Leu Ala Val Gln
            515                520                525

Arg His Leu Thr Ala Val Gln Asp Glu Asn Gly Asp Ser Val Leu His
    530                535                540

Leu Ala Ile Ile His Leu His Ala Gln Leu Val Arg Asp Leu Leu Glu
545                550                555                560

Val Thr Ser Gly Leu Ile Ser Asp Asp Ile Ile Asn Met Arg Asn Asp
                565                570                575

Leu Tyr Gln Thr Pro Leu His Leu Ala Val Ile Thr Lys Gln Glu Asp
                580                585                590

Val Val Glu Asp Leu Leu Arg Val Gly Ala Asp Leu Ser Leu Leu Asp
            595                600                605

Arg Trp Gly Asn Ser Val Leu His Leu Ala Ala Lys Glu Gly His Asp
    610                615                620

Arg Ile Leu Ser Ile Leu Leu Lys Ser Arg Lys Ala Ala Pro Leu Ile
625                630                635                640

Asp His Pro Asn Gly Glu Gly Leu Asn Ala Ile His Ile Ala Val Met
                645                650                655

Ser Asn Ser Leu Pro Cys Leu Leu Leu Leu Val Ala Ala Gly Ala Glu
                660                665                670

Val Asn Ala Gln Glu Gln Lys Ser Gly Arg Thr Pro Leu His Leu Ala
            675                680                685

Val Glu Tyr Asp Asn Ile Ser Leu Ala Gly Cys Leu Leu Leu Glu Gly
    690                695                700

Asp Ala His Val Asp Ser Thr Thr Tyr Asp Gly Thr Thr Pro Leu His
705                710                715                720

Ile Ala Ala Gly Arg Gly Ser Thr Arg Leu Ala Ala Leu Leu Lys Ala
                725                730                735

Ala Gly Ala Asp Pro Leu Val Glu Asn Phe Glu Pro Leu Tyr Asp Leu
                740                745                750

Asp Asp Ser Trp Glu Lys Ala Gly Glu Asp Glu Gly Val Val Pro Gly
            755                760                765

Thr Thr Pro Leu Asp Met Ala Ala Asn Trp Gln Val Phe Asp Ile Leu
    770                775                780

Asn Gly Lys Pro Tyr Glu Pro Val Phe Thr Ser Asp Asp Ile Leu Pro
785                790                795                800

Gln Gly Asp Met Lys Gln Leu Thr Glu Asp Thr Arg Leu Gln Leu Cys
                805                810                815

Lys Leu Leu Glu Ile Pro Asp Pro Asp Lys Asn Trp Ala Thr Leu Ala
                820                825                830

Gln Lys Leu Gly Leu Gly Ile Leu Asn Asn Ala Phe Arg Leu Ser Pro
            835                840                845

Ala Pro Ser Lys Thr Leu Met Asp Asn Tyr Glu Val Ser Gly Gly Thr
    850                855                860
```

| | | | | | | | | | | | |
|---|---|---|---|---|---|---|---|---|---|---|---|
| Ile | Lys | Glu | Leu | Met | Glu | Ala | Leu | Gln | Gln | Met | Gly | Tyr | Thr | Glu | Ala |
| 865 | | | | 870 | | | | | 875 | | | | | 880 | |

Ile Lys Glu Leu Met Glu Ala Leu Gln Gln Met Gly Tyr Thr Glu Ala
865                 870                 875                 880

Ile Glu Val Ile Gln Ala Ala Phe Arg Thr Pro Ala Thr Thr Ala Ser
                885                 890                 895

Ser Pro Val Thr Thr Ala Gln Val His Cys Leu Pro Leu Ser Ser Ser
                900                 905                 910

Ser Thr Arg Gln His Ile Asp Glu Leu Arg Asp Ser Asp Ser Val Cys
        915                 920                 925

Asp Ser Gly Val Glu Thr Ser Phe Arg Lys Leu Ser Phe Thr Glu Ser
        930                 935                 940

Leu Thr Gly Asp Ser Pro Leu Leu Ser Leu Asn Lys Met Pro His Gly
945                 950                 955                 960

Tyr Gly Gln Glu Gly Pro Ile Glu Gly Lys Ile
                965                 970

<210> SEQ ID NO 14
<211> LENGTH: 3892
<212> TYPE: DNA
<213> ORGANISM: Mus musculus
<220> FEATURE:
<221> NAME/KEY: misc_feature
<222> LOCATION: (3755)..(3755)
<223> OTHER INFORMATION: n is a, c, g, or t

<400> SEQUENCE: 14

```
agcggccgcc gcgggcgcgc tctagcagcg caggccggag ctcagggccc cgcgcgcccg      60
gcccgccccg cgcttctccg cccgcgccgc agccatggcg cgccgctgag ccgcccgccc     120
gcccgcccgc gccccgaccc ggctcggctc ccgccggtcc gcgccgctcc gcagcggagc     180
ccgcaggcga ggagaggccg cgcgcatctc cagggtaccc tcagaggcca aagagggtg      240
tcagagccct tgtaactgga gtttgacggt cgtgagctgc gcatcttcac catggcagac     300
gatgatccct acggaactgg gcaaatgttt catttgaaca ctgctttgac tcactcaata     360
tttaatgcag aattatattc accagaaata ccactgtcaa cagatggccc ataccttcaa     420
atattagagc aaccaaaaca gaggggattt cgattccgct atgtgtgtga aggcccatca     480
cacggagggc ttccgggagc tctagtgag aagaacaaga atcctaccc acaggtcaaa      540
atttgcaact atgtggggcc tgcaaaggtt atcgttcagt tggtcacaaa tggaaaaaac     600
atccacctgc acgcccacag cctggtgggc aagcactgtg aggacggggt atgcaccgta     660
acagcaggac ccaaggacat ggtggttggc tttgcaaacc tgggaatact tcatgtgact     720
aagaaaaagg tatttgaaac actggaagca cggatgacag aggcgtgtat tagggctat     780
aatcctggac ttctggtgca ttctgacctt gcctatctac aagcagaagg cggaggagac     840
cggcaactca cagacagaga gaaggagatc atccgccagg cagccgtgca gcagaccaag     900
gagatggacc tgagcgtggt gcgcctcatg ttcacagcct cctccctga cagcactggc     960
agcttcactc ggagactgga gcctgtggtg tcagacgcca tctatgatag caaagccccg    1020
aatgcatcca acctgaaaat cgtgagaat gacagaacag caggatgtgt gacgggaggg    1080
gaggagattt accttctctg tgacaaggtt cagaaagatg acatccagat tcggttttat    1140
gaagaggaag aaaatggcgg agtttgggaa ggatttgggg acttttcccc cacggatgtt    1200
catagacagt ttgccattgt cttcaaaacg ccaaagtata aggatgtcaa cattacaaag    1260
ccagcttccg tgtttgttca gcttcggagg aaatcagacc tggaaactag tgaaccgaaa    1320
cccctttctct actaccctga aatcaaagac aaagaggaag tgcaaggaa acgccagaag    1380
cttatgccga acttctcgga cagcttcggc ggcggcagtg gagcgggagc cggtggtgga    1440
```

```
ggcatgttcg gtagtggcgg tggcggaggg agtaccggaa gccctggccc agggtatggc    1500
tactcgaact acggatttcc tccctacggt gggattacat tccatcccgg agtcacgaaa    1560
tccaacgcag gggtcaccca tggcaccata aacaccaaat ttaaaaatgg ccctaaagat    1620
tgtgccaaga gtgatgacga ggagagtctg actctccctg agaaggaaac tgaaggtgaa    1680
gggcccagcc tgcccatggc ctgcaccaag acggaaccca tcgccttggc atccaccatg    1740
gaagacaagg agcaggacat gggatttcag gataacctct ttctcgagaa ggctctgcag    1800
ctcgccaggc gacacgccaa cgcccttttc gactacgcag tgacggggga tgtgaagatg    1860
ttgctggccg tgcaacgcca tctcaccgcc gtgcaggatg agaatgggga cagtgtctta    1920
cacttagcca tcatccacct ccacgctcag ctcgtgaggg atctgctgga agtcacatct    1980
ggtttgatct ctgatgacat catcaacatg agaaatgacc tgtatcagac acctctgcac    2040
ttggccgtga tcaccaagca ggaagatgta gtagaggatt tgctgagggt tggggctgac    2100
ctgagccttc tggaccgctg gggcaactct gtcctgcacc tagctgccaa agaaggacac    2160
gacagaatcc tcagcatcct gctcaagagc agaaaagcag cgcccttat cgaccacccc    2220 aatggggaag gtctaaatgc catccacata gctgtgatga gcaatagcct gccatgtctg    2280
ctgctgctgg tggctgccgg ggcagaagtc aatgctcagg agcagaagtc tgggcgcacg    2340
ccgctgcacc tggccgtgga gtacgacaac atctccttgg ctggctgcct gcttctggag    2400
ggtgatgccc acgtggacag taccacctat gatgggacta cacctctgca tatagcggcc    2460
ggaagagggt ccaccagact ggcagctctt ctcaaagcag caggagcaga cccctggtg    2520 gagaactttg agcctctcta tgacctggac gactcttggg agaaggctgg agaagatgag    2580
ggagtggtgc caggtaccac accctgac atggctgcca actggcaggt atttgacata    2640
ctaaatggga aaccgtatga gcctgtgttc acatctgatg atatactacc acaaggggac    2700
atgaagcagc tgacagaaga cacgaggcta caactctgca aactgctgga aattcctgat    2760
ccagacaaaa actgggccac tctggcacag aagttgggtc tggggatatt gaacaatgcc    2820
ttccggctga gtcctgctcc ttctaaaact ctcatggaca actatgaggt ctctgggggt    2880
accatcaaag agctgatgga ggccctgcaa cagatgggct acacagaggc cattgaagtg    2940
atccaggcag ccttccgcac cccggcaacc acagcctcca gccccgtgac cactgctcag    3000
gtccactgtc tgcctctctc gtcttcctcc acgaggcagc acatagatga actccgggat    3060
agtgacagcg tctgtgacag tggtgtggag acatccttcc gcaaactcag ctttacagag    3120
tctcttactg gagacagccc actgctatct ctgaacaaaa tgccccacgg ttatgggcag    3180
gaaggaccta ttgaaggcaa aatttagcct gctggccgtt cccccacact gtgtaaacca    3240
aagccctgac agtccattgc atcgtcccaa aggaggaagg caaagcgaat ccaaaggtgc    3300
tggagaatcg ccggcctgca gggtcactcg atttcattca aggccttccg aatttggcgt    3360
ccttcttggt tctgaaatga aatgtagttg ccacgcacag acggtgtcta gcaatcatgg    3420
cgctcgctcg ctcagctgca ctctatggct caggtgcagt gtcttgagct ttctctgctg    3480
ctactggatc acatttgctt tgtgttgtta ctgctgtccc tccgctgggt tctgctgtc    3540 attaaaaggt gtcgctgtcc ccacccggtg tcctttctag ccatctactg taagttgtgc    3600
attcaaatta agattaagga aaacatatt tttaaatgag taccttgatg cgcaataaaa    3660
aaaaagacat ttctttttttt aatgtggttt atctgtgatt taaaaataaa aaacacatga    3720
acttatcaat atttaaaaca tgctacaatc agtgntgaaa atagtatttt ccccgtttta    3780 tgcatttac atttgtaaat atgttttcta atcaatactt taaaagaaga atgttgaatt    3840
```
tataaaatgc tatttacttt tttatttata ataaagtaca gcacatgtga ct          3892

<210> SEQ ID NO 15
<211> LENGTH: 549
<212> TYPE: PRT
<213> ORGANISM: Mus musculus

<400> SEQUENCE: 15

Met Asp Asp Leu Phe Pro Leu Ile Phe Pro Ser Glu Pro Ala Gln Ala
1               5                   10                  15

Ser Gly Pro Tyr Val Glu Ile Ile Glu Gln Pro Lys Gln Arg Gly Met
            20                  25                  30

Arg Phe Arg Tyr Lys Cys Glu Gly Arg Ser Ala Gly Ser Ile Pro Gly
        35                  40                  45

Glu Arg Ser Thr Asp Thr Thr Lys Thr His Pro Thr Ile Lys Ile Asn
    50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

Asp Gly Tyr Tyr Glu Ala Asp Leu Cys Pro Asp Arg Ser Ile His Ser
            100                 105                 110

Phe Gln Asn Leu Gly Ile Gln Cys Val Lys Lys Arg Asp Leu Glu Gln
        115                 120                 125

Ala Ile Ser Gln Arg Ile Gln Thr Asn Asn Asn Pro Phe His Val Pro
    130                 135                 140

Ile Glu Glu Gln Arg Gly Asp Tyr Asp Leu Asn Ala Val Arg Leu Cys
145                 150                 155                 160

Phe Gln Val Thr Val Arg Asp Pro Ala Gly Arg Pro Leu Leu Leu Thr
                165                 170                 175

Pro Val Leu Ser His Pro Ile Phe Asp Asn Arg Ala Pro Asn Thr Ala
            180                 185                 190

Glu Leu Lys Ile Cys Arg Val Asn Arg Asn Ser Gly Ser Cys Leu Gly
        195                 200                 205

Gly Asp Glu Ile Phe Leu Leu Cys Asp Lys Val Gln Lys Glu Asp Ile
    210                 215                 220

Glu Val Tyr Phe Thr Gly Pro Gly Trp Glu Ala Arg Gly Ser Phe Ser
225                 230                 235                 240

Gln Ala Asp Val His Arg Gln Val Ala Ile Val Phe Arg Thr Pro Pro
                245                 250                 255

Tyr Ala Asp Pro Ser Leu Gln Ala Pro Val Arg Val Ser Met Gln Leu
            260                 265                 270

Arg Arg Pro Ser Asp Arg Glu Leu Ser Glu Pro Met Glu Phe Gln Tyr
        275                 280                 285

Leu Pro Asp Thr Asp Asp Arg His Arg Ile Glu Glu Lys Arg Lys Arg
    290                 295                 300

Thr Tyr Glu Thr Phe Lys Ser Ile Met Lys Lys Ser Pro Phe Asn Gly
305                 310                 315                 320

Pro Thr Glu Pro Arg Pro Pro Thr Arg Arg Ile Ala Val Pro Thr Arg
                325                 330                 335

Asn Ser Thr Ser Val Pro Lys Pro Ala Pro Gln Pro Tyr Thr Phe Pro
            340                 345                 350

Ala Ser Leu Ser Thr Ile Asn Phe Asp Glu Phe Ser Pro Met Leu Leu
        355                 360                 365

-continued

```
Pro Ser Gly Gln Ile Ser Asn Gln Ala Leu Ala Leu Ala Pro Ser Ser
    370                 375                 380

Ala Pro Val Leu Ala Gln Thr Met Val Pro Ser Ala Met Val Pro
385                 390                 395                 400

Leu Ala Gln Pro Pro Ala Pro Ala Pro Val Leu Thr Pro Gly Pro Pro
                405                 410                 415

Gln Ser Leu Ser Ala Pro Val Pro Lys Ser Thr Gln Ala Gly Glu Gly
                420                 425                 430

Thr Leu Ser Glu Ala Leu Leu His Leu Gln Phe Asp Ala Asp Glu Asp
            435                 440                 445

Leu Gly Ala Leu Leu Gly Asn Ser Thr Asp Pro Gly Val Phe Thr Asp
    450                 455                 460

Leu Ala Ser Val Asp Asn Ser Glu Phe Gln Gln Leu Leu Asn Gln Gly
465                 470                 475                 480

Val Ser Met Ser His Ser Thr Ala Glu Pro Met Leu Met Glu Tyr Pro
                485                 490                 495

Glu Ala Ile Thr Arg Leu Val Thr Gly Ser Gln Arg Pro Pro Asp Pro
                500                 505                 510

Ala Pro Thr Pro Leu Gly Thr Ser Gly Leu Pro Asn Gly Leu Ser Gly
            515                 520                 525

Asp Glu Asp Phe Ser Ser Ile Ala Asp Met Asp Phe Ser Ala Leu Leu
    530                 535                 540

Ser Gln Ile Ser Ser
545

<210> SEQ ID NO 16
<211> LENGTH: 2424
<212> TYPE: DNA
<213> ORGANISM: Mus musculus

<400> SEQUENCE: 16
tttactttag cgcgccgtgg gctcagctgc gaccccggcc ccgcccccgg gaccctgacc      60
atggacgatc tgtttcccct catctttccc tcagagccag cccaggcttc tgggccttat     120
gtggagatca tcgaacagcc gaagcaacgg ggcatgcgat tccgctataa atgcgagggg     180
cgctcagcgg gcagtattcc tggcgagaga agcacagata ccaccaagac acaccccacc     240
atcaagatca atggctacac aggaccagga acagttcgaa tctccctggt caccaaggat     300
ccacctcacc ggcctcatcc acatgaactt gtggggaagg actgccggga tggctactat     360
gaggctgacc tctgcccaga ccgcagtatc catagcttcc agaacctggg gatccagtgt     420
gtgaagaagc gagacctgga gcaagccatt agccagcgaa tccagaccaa caataacccc     480
tttcacgttc ctatagagga gcagcgcggg gactatgact tgaatgcagt gcgcctctgc     540
ttccaggtga cagtgcggga cccagcaggc aggcccctcc tcctgacccc tgtcctctca     600
catccgattt tgataaccg ggcccccaac actgccgagc tcaagatctg ccgagtaaac     660
cggaactctg ggagctgcct cggtggggat gagatcttct tgctgtgcga caaggtgcag     720
aaagaagaca ttgaggtgta tttcacggga ccaggctggg aggcacgagg ctcctttttct    780 caagctgatg tgcatcggca agtggccatt gtgttccgga ctcctccgta cgccgacccc     840
agcctccagg ctcctgttcg agtctccatg cagctacggc ggccttctga tcgcgagctc     900
agtgagccca tggagttcca gtacttgcca gacacagatg atcgccaccg gattgaagag     960
aagcgcaaaa ggacctatga gaccttcaag agtatcatga agaagagtcc tttcaatgga    1020
ccaactgaac cccggcctcc aacccggcgt attgctgtgc ctacccgaaa ctcaacttct    1080
```

-continued

```
gtccccaagc cagccccgca gccctacacc ttcccagcat ccctcagcac catcaacttt    1140
gatgagtttt cccccatgct gttaccatca gggcagatct caaaccaggc cctggcctta    1200
gcaccgtcct ctgccccagt ccttgcccag accatggtcc cttcctcagc catggtacct    1260
ctggctcagc ccccagctcc tgccccagtt ctaaccccgg gtcctcccca gtccctgtct    1320
gcacctgttc caaagagcac ccaggctggg gaaggcacgc tgtcggaagc cctgctgcac    1380
ctgcagtttg atgctgatga agacttgggg gccttgcttg caacagcac agacccagga    1440
gtgttcacag acctggcatc tgtggacaac tcagagtttc agcagctcct gaaccagggt    1500
gtgtccatgt ctcactccac agctgagccc atgctgatgg agtaccctga agctataact    1560
cgcctggtga cagggtccca gaggcccccct gacccagctc ccacacccct ggggacctcg    1620
gggcttccca atggtctctc cggagatgaa gacttctcct ccattgcgga catggacttc    1680
tctgctcttt tgagtcagat cagctcctaa ggtgctgaca gcgaccctgc tcagagcacc    1740
aggtttcagg gcactgaagc cttcccgaag tgcgtacaca ttctggggag tgtgctccag    1800
ctgccccga cttgtttggg tgatctctct ggggcggcac gttttactct ttatctcgct    1860
ttcggaggtg ctttcgcagg agcattaacc tcctggagac ggagctggga ggactcggtg    1920
catccctgtg ttgatagctc ctgcttcggt agggaactct gagatcctgc ttccatctcc    1980
agcttctagc actctcctag agagggacag actggagcca tgccttaggc catatagcct    2040
tactatcaag tgtcttcctc cacgcggatt cctgtacacc ttgatccaaa gcagtgctcc    2100
caagagcagc tcctacgtgg tgctgcccga caccagcaca tgaggggccg ctcttctgtc    2160
ctgtggagct cctgccctgc cagctctcca tgctgagctg tggccaaggg gaacaggtgg    2220
gatgttgctg ccgccttca gaatcagggg gagtttagtc tgagacatcc ctgctccccc    2280
ttttttttcaa gtgccttaat agcagggcaa actgtagagt caggagggca ggctagatgc    2340
tcagccacaa gacagccttt actgaaaaag ctattggact cttgctcttt ctagctctga    2400
actaataaat gtcttatcac gctg                                             2424
```

<210> SEQ ID NO 17
<211> LENGTH: 745
<212> TYPE: PRT
<213> ORGANISM: Homo sapiens

<400> SEQUENCE: 17

```
Met Glu Arg Pro Pro Gly Leu Arg Pro Gly Ala Gly Gly Pro Trp Glu
1               5                   10                  15

Met Arg Glu Arg Leu Gly Thr Gly Gly Phe Gly Asn Val Cys Leu Tyr
                20                  25                  30

Gln His Arg Glu Leu Asp Leu Lys Ile Ala Ile Lys Ser Cys Arg Leu
            35                  40                  45

Glu Leu Ser Thr Lys Asn Arg Glu Arg Trp Cys His Glu Ile Gln Ile
        50                  55                  60

Met Lys Lys Leu Asn His Ala Asn Val Val Lys Ala Cys Asp Val Pro
65                  70                  75                  80

Glu Glu Leu Asn Ile Leu Ile His Asp Val Pro Leu Leu Ala Met Glu
                85                  90                  95

Tyr Cys Ser Gly Gly Asp Leu Arg Lys Leu Leu Asn Lys Pro Glu Asn
                100                 105                 110

Cys Cys Gly Leu Lys Glu Ser Gln Ile Leu Ser Leu Leu Ser Asp Ile
            115                 120                 125

Gly Ser Gly Ile Arg Tyr Leu His Glu Asn Lys Ile Ile His Arg Asp
        130                 135                 140
```

```
Leu Lys Pro Glu Asn Ile Val Leu Gln Asp Val Gly Lys Ile Ile
145                 150                 155                 160

His Lys Ile Ile Asp Leu Gly Tyr Ala Lys Asp Val Asp Gln Gly Ser
                165                 170                 175

Leu Cys Thr Ser Phe Val Gly Thr Leu Gln Tyr Leu Ala Pro Glu Leu
            180                 185                 190

Phe Glu Asn Lys Pro Tyr Thr Ala Thr Val Asp Tyr Trp Ser Phe Gly
            195                 200                 205

Thr Met Val Phe Glu Cys Ile Ala Gly Tyr Arg Pro Phe Leu His His
    210                 215                 220

Leu Gln Pro Phe Thr Trp His Glu Lys Ile Lys Lys Asp Pro Lys
225                 230                 235                 240

Cys Ile Phe Ala Cys Glu Glu Met Ser Gly Glu Val Arg Phe Ser Ser
            245                 250                 255

His Leu Pro Gln Pro Asn Ser Leu Cys Ser Leu Ile Val Glu Pro Met
            260                 265                 270

Glu Asn Trp Leu Gln Leu Met Leu Asn Trp Asp Pro Gln Gln Arg Gly
            275                 280                 285

Gly Pro Val Asp Leu Thr Leu Lys Gln Pro Arg Cys Phe Val Leu Met
290                 295                 300

Asp His Ile Leu Asn Leu Lys Ile Val His Ile Leu Asn Met Thr Ser
305                 310                 315                 320

Ala Lys Ile Ile Ser Phe Leu Leu Pro Pro Asp Glu Ser Leu His Ser
            325                 330                 335

Leu Gln Ser Arg Ile Glu Arg Glu Thr Gly Ile Asn Thr Gly Ser Gln
            340                 345                 350

Glu Leu Leu Ser Glu Thr Gly Ile Ser Leu Asp Pro Arg Lys Pro Ala
            355                 360                 365

Ser Gln Cys Val Leu Asp Gly Val Arg Gly Cys Asp Ser Tyr Met Val
    370                 375                 380

Tyr Leu Phe Asp Lys Ser Lys Thr Val Tyr Glu Gly Pro Phe Ala Ser
385                 390                 395                 400

Arg Ser Leu Ser Asp Cys Val Asn Tyr Ile Val Gln Asp Ser Lys Ile
                405                 410                 415

Gln Leu Pro Ile Ile Gln Leu Arg Lys Val Trp Ala Glu Ala Val His
            420                 425                 430

Tyr Val Ser Gly Leu Lys Glu Asp Tyr Ser Arg Leu Phe Gln Gly Gln
    435                 440                 445

Arg Ala Ala Met Leu Ser Leu Leu Arg Tyr Asn Ala Asn Leu Thr Lys
    450                 455                 460

Met Lys Asn Thr Leu Ile Ser Ala Ser Gln Gln Leu Lys Ala Lys Leu
465                 470                 475                 480

Glu Phe Phe His Lys Ser Ile Gln Leu Asp Leu Glu Arg Tyr Ser Glu
                485                 490                 495

Gln Met Thr Tyr Gly Ile Ser Ser Glu Lys Met Leu Lys Ala Trp Lys
            500                 505                 510

Glu Met Glu Glu Lys Ala Ile His Tyr Ala Glu Val Gly Val Ile Gly
    515                 520                 525

Tyr Leu Glu Asp Gln Ile Met Ser Leu His Ala Glu Ile Met Gly Leu
    530                 535                 540

Gln Lys Ser Pro Tyr Gly Arg Arg Gln Gly Asp Leu Met Glu Ser Leu
545                 550                 555                 560

Glu Gln Arg Ala Ile Asp Leu Tyr Lys Gln Leu Lys His Arg Pro Ser
```

```
                                565                 570                 575
Asp His Ser Tyr Ser Asp Ser Thr Glu Met Val Lys Ile Ile Val His
            580                 585                 590

Thr Val Gln Ser Gln Asp Arg Val Leu Lys Glu Leu Phe Gly His Leu
            595                 600                 605

Ser Lys Leu Leu Gly Cys Lys Gln Lys Ile Ile Asp Leu Leu Pro Lys
            610                 615                 620

Val Glu Val Ala Leu Ser Asn Ile Lys Glu Ala Asp Asn Thr Val Met
625                 630                 635                 640

Phe Met Gln Gly Lys Arg Gln Lys Glu Ile Trp His Leu Leu Lys Ile
                645                 650                 655

Ala Cys Thr Gln Ser Ser Ala Arg Ser Leu Val Gly Ser Ser Leu Glu
            660                 665                 670

Gly Ala Val Thr Pro Gln Thr Ser Ala Trp Leu Pro Pro Thr Ser Ala
            675                 680                 685

Glu His Asp His Ser Leu Ser Cys Val Val Thr Pro Gln Asp Gly Glu
            690                 695                 700

Thr Ser Ala Gln Met Ile Glu Glu Asn Leu Asn Cys Leu Gly His Leu
705                 710                 715                 720

Ser Thr Ile Ile His Glu Ala Asn Glu Gln Gly Asn Ser Met Met
                725                 730                 735

Asn Leu Asp Trp Ser Trp Leu Thr Glu
            740                 745

<210> SEQ ID NO 18
<211> LENGTH: 2273
<212> TYPE: DNA
<213> ORGANISM: Homo sapiens

<400> SEQUENCE: 18
tcgacggaac ctgaggccgc ttgccctccc gccccatgga gcggcccccg gggctgcggc        60
cgggcgcggg cgggccctgg gagatgcggg agcggctggg caccggcggc ttcgggaacg       120
tctgtctgta ccagcatcgg gaacttgatc tcaaaatagc aattaagtct tgtcgcctag       180
agctaagtac caaaaacaga gaacgatggt gccatgaaat ccagattatg aagaagttga       240
accatgccaa tgttgtaaag gcctgtgatg ttcctgaaga attgaatatt ttgattcatg       300
atgtgcctct tctagcaatg gaatactgtt ctggaggaga tctccgaaag ctgctcaaca       360
aaccagaaaa ttgttgtgga cttaaagaaa gccagatact ttctttacta agtgatatag       420
ggtctgggat tcgatatttg catgaaaaca aaattataca tcgagatcta aaacctgaaa       480
acatagttct tcaggatgtt ggtggaaaga taatacataa ataattgat ctgggatatg       540 ccaaagatgt tgatcaagga agtctgtgta catctttgt gggaacactg cagtatctgg       600
ccccagagct ctttgagaat aagccttaca cagccactgt tgattattgg agctttggga       660
ccatggtatt tgaatgtatt gctggatata ggcctttttt gcatcatctg cagccattta       720
cctggcatga agagattaag aagaaggatc aaagtgtat atttgcatgt gaagagatgt       780
caggagaagt tcggtttagt agccatttac ctcaaccaaa tagcctttgt agtttaatag       840
tagaacccat ggaaaactgg ctacagttga tgttgaattg ggaccctcag cagagaggag       900
gacctgttga ccttactttg aagcagccaa gatgttttgt attaatggat cacatttga       960 atttgaagat agtacacatc ctaaatgat cttctgcaaa gataatttct tttctgttac      1020
cacctgatga aagtcttcat tcactacagt tcgtattga gcgtgaaact ggaataaata      1080
ctggttctca agaacttctt tcagagacag gaatttctct ggatcctcgg aaaccagcct      1140
```

```
ctcaatgtgt tctagatgga gttagaggct gtgatagcta tatggtttat ttgtttgata    1200
aaagtaaaac tgtatatgaa gggccatttg cttccagaag tttatctgat tgtgtaaatt    1260
atattgtaca ggacagcaaa atacagcttc caattataca gctgcgtaaa gtgtgggctg    1320
aagcagtgca ctatgtgtct ggactaaaag aagactatag caggctcttt cagggacaaa    1380
gggcagcaat gttaagtctt cttagatata atgctaactt aacaaaaatg aagaacactt    1440
tgatctcagc atcacaacaa ctgaaagcta aattggagtt ttttcacaaa agcattcagc    1500
ttgacttgga gagatacagc gagcagatga cgtatgggat atcttcagaa aaaatgctaa    1560
aagcatggaa agaaatggaa gaaaaggcca tccactatgc tgaggttggt gtcattggat    1620
acctggagga tcagattatg tctttgcatg ctgaaatcat ggggctacag aagagcccct    1680
atggaagacg tcagggagac ttgatggaat ctctggaaca gcgtgccatt gatctatata    1740
agcagttaaa acacagacct tcagatcact cctacagtga cagcacagag atggtgaaaa    1800
tcattgtgca cactgtgcag agtcaggacc gtgtgctcaa ggagctgttt ggtcatttga    1860
gcaagttgtt gggctgtaag cagaagatta ttgatctact ccctaaggtg gaagtggccc    1920
tcagtaatat caaagaagct gacaatactg tcatgttcat gcagggaaaa aggcagaaag    1980
aaatatggca tctccttaaa attgcctgta cacagagttc tgcccgctct cttgtaggat    2040
ccagtctaga aggtgcagta acccctcaga catcagcatg gctgccccg acttcagcag    2100 aacatgatca ttctctgtca tgtgtggtaa ctcctcaaga tggggagact tcagcacaaa    2160
tgatagaaga aaatttgaac tgccttggcc atttaagcac tattattcat gaggcaaatg    2220
aggaacaggg caatagtatg atgaatcttg attggagttg gttaacagaa tga            2273
```

<210> SEQ ID NO 19
<211> LENGTH: 745
<212> TYPE: PRT
<213> ORGANISM: Mus musculus

<400> SEQUENCE: 19

```
Met Glu Arg Pro Pro Gly Leu Arg Pro Gly Ala Gly Gly Pro Trp Glu
1               5                   10                  15

Met Arg Glu Arg Leu Gly Thr Gly Gly Phe Gly Asn Val Ser Leu Tyr
            20                  25                  30

Gln His Arg Glu Leu Asp Leu Lys Ile Ala Ile Lys Ser Cys Arg Leu
        35                  40                  45

Glu Leu Ser Ser Lys Asn Arg Glu Arg Trp Cys His Glu Ile Gln Ile
    50                  55                  60

Met Lys Lys Leu Asp His Ala Asn Val Val Lys Ala Cys Asp Val Pro
65                  70                  75                  80

Glu Glu Leu Asn Phe Leu Ile Asn Asp Val Pro Leu Leu Ala Met Glu
                85                  90                  95

Tyr Cys Ser Gly Gly Asp Leu Arg Lys Leu Leu Asn Lys Pro Glu Asn
            100                 105                 110

Cys Cys Gly Leu Lys Glu Ser Gln Ile Leu Ser Leu Leu Ser Asp Ile
        115                 120                 125

Gly Ser Gly Ile Arg Tyr Leu His Glu Asn Lys Ile Ile His Arg Asp
    130                 135                 140

Leu Lys Pro Glu Asn Ile Val Leu Gln Asp Val Gly Gly Lys Thr Ile
145                 150                 155                 160

His Lys Ile Ile Asp Leu Gly Tyr Ala Lys Asp Val Asp Gln Gly Ser
                165                 170                 175
```

```
Leu Cys Thr Ser Phe Val Gly Thr Leu Gln Tyr Leu Ala Pro Glu Leu
            180                 185                 190

Phe Glu Asn Lys Pro Tyr Thr Ala Thr Val Asp Tyr Trp Ser Phe Gly
            195                 200                 205

Thr Met Val Phe Glu Cys Ile Ala Gly Tyr Arg Pro Phe Leu His His
            210                 215                 220

Leu Gln Pro Phe Thr Trp His Glu Lys Ile Lys Lys Asp Pro Lys
225                 230                 235                 240

Cys Ile Phe Ala Cys Glu Glu Met Thr Gly Glu Val Arg Phe Ser Ser
                245                 250                 255

His Leu Pro Gln Pro Asn Ser Leu Cys Ser Leu Ile Val Glu Pro Met
            260                 265                 270

Glu Ser Trp Leu Gln Leu Met Leu Asn Trp Asp Pro Gln Gln Arg Gly
            275                 280                 285

Gly Pro Ile Asp Leu Thr Leu Lys Gln Pro Arg Cys Phe Ala Leu Met
            290                 295                 300

Asp His Ile Leu Asn Leu Lys Ile Val His Ile Leu Asn Met Thr Ser
305                 310                 315                 320

Ala Lys Ile Ile Ser Phe Leu Leu Pro Cys Asp Glu Ser Leu His Ser
                325                 330                 335

Leu Gln Ser Arg Ile Glu Arg Glu Thr Gly Ile Asn Thr Gly Ser Gln
            340                 345                 350

Glu Leu Leu Ser Glu Thr Gly Ile Ser Leu Asp Pro Arg Lys Pro Ala
            355                 360                 365

Ser Gln Cys Val Leu Asp Gly Val Arg Gly Cys Asp Ser Tyr Met Val
            370                 375                 380

Tyr Leu Phe Asp Lys Ser Lys Thr Val Tyr Glu Gly Pro Phe Ala Ser
385                 390                 395                 400

Arg Ser Leu Ser Asp Cys Val Asn Tyr Ile Val Gln Asp Ser Lys Ile
                405                 410                 415

Gln Leu Pro Ile Ile Gln Leu Arg Lys Val Trp Ala Glu Ala Val His
            420                 425                 430

Tyr Val Ser Gly Leu Lys Glu Asp Tyr Ser Arg Leu Phe Gln Gly Gln
            435                 440                 445

Arg Ala Ala Met Leu Ser Leu Leu Arg Tyr Asn Ala Asn Leu Thr Lys
450                 455                 460

Met Lys Asn Thr Leu Ile Ser Ala Ser Gln Gln Leu Lys Ala Lys Leu
465                 470                 475                 480

Glu Phe Phe Arg Lys Ser Ile Gln Leu Asp Leu Glu Arg Tyr Ser Glu
                485                 490                 495

Gln Met Thr Tyr Gly Ile Ser Ser Glu Lys Met Leu Lys Ala Trp Lys
            500                 505                 510

Glu Met Glu Glu Lys Ala Ile His Tyr Ser Glu Val Gly Val Ile Gly
            515                 520                 525

Tyr Leu Glu Asp Gln Ile Met Ser Leu His Thr Glu Ile Met Glu Leu
            530                 535                 540

Gln Lys Ser Pro Tyr Gly Arg Arg Gln Gly Asp Leu Met Glu Ser Leu
545                 550                 555                 560

Glu Gln Arg Ala Ile Asp Leu Tyr Lys Gln Leu Lys His Arg Pro Pro
                565                 570                 575

Asp His Leu Tyr Ser Asp Ser Thr Glu Met Val Lys Ile Ile Val His
            580                 585                 590

Thr Val Gln Ser Gln Asp Arg Val Leu Lys Glu Leu Phe Gly His Leu
            595                 600                 605
```

```
Ser Lys Leu Leu Gly Cys Lys Gln Lys Ile Ile Asp Leu Leu Pro Lys
    610                 615                 620

Val Glu Val Ala Leu Ser Asn Ile Lys Glu Ala Asp Asn Thr Val Met
625                 630                 635                 640

Phe Met Gln Gly Lys Arg Gln Lys Glu Ile Trp His Leu Leu Lys Ile
                645                 650                 655

Ala Cys Thr Gln Ser Ser Ala Arg Ser Leu Val Gly Ser Ser Leu Glu
            660                 665                 670

Gly Thr Val Thr Pro Pro Val Ser Ala Trp Leu Pro Pro Thr Leu Ala
        675                 680                 685

Asp Arg Glu His Pro Leu Thr Cys Val Val Thr Pro Gln Asp Gly Glu
    690                 695                 700

Thr Leu Ala Gln Met Ile Glu Glu Asn Leu Asn Cys Leu Gly His Leu
705                 710                 715                 720

Ser Thr Ile Ile Arg Glu Ala Asn Glu Asp Gln Ser Ser Ser Leu Met
                725                 730                 735

Ser Leu Asp Trp Ser Trp Leu Ala Glu
            740                 745

<210> SEQ ID NO 20
<211> LENGTH: 3466
<212> TYPE: DNA
<213> ORGANISM: Mus musculus

<400> SEQUENCE: 20
gggaccggcc ttagaccggc ggcgttgcct gaggcggctg cgcgctcccgc cccatggagc      60
ggccccccggg gctgcggccg ggcgcgggcg gcccctggga gatgcgggaa cggcttggca     120
ccggcggttt cgggaacgtc agtctgtacc agcaccggga acttgatctc aaaatagcaa     180
ttaagtcttg tcgtttagag ctaagttcca aaaacagaga gcgatggtgc atgaaaatcc     240
agatcatgaa aaagttggac catgcgaatg ttgtaaaggc ctgtgatgtc cctgaggaat     300
tgaacttttt aattaacgat gtgcctcttc tggcaatgga gtactgttct ggaggggacc     360
tccggaagct actcaacaaa ccagaaaatt gttgtggact aaagaaagc cagatacttt     420
ctttactgag tgacatagga tctgggatcc gatatctgca tgaaaacaaa attatacatc     480
gagatctaaa acctgaaaat atagttcttc aagatgttgg tgggaagaca atacataaaa     540
taattgattt gggttatgcc aaagatgttg atcaaggaag tctctgtaca tcttttgtgg     600
gaacattgca gtatttggcc ccagagctct ttgaaaataa gccgtacaca gccactgtgg     660
attattggag ctttgggacc atggtgtttg aatgtattgc tggatatagg ccttttttgc     720
atcatctgca gccatttacc tggcatgaga agattaagaa gaaagatcca aagtgtatat     780
ttgcatgtga agagatgact ggagaagttc ggtttagtag ccatttacct cagccaaaca     840
gcctttgtag tttaatagta gagccaatgg aaagctggct ccaattgatg ctgaattggg     900
acccacagca gagaggggga cctattgatc ttactttgaa gcagccaaga tgttttgcat     960
taatggatca cattctcaat ttaaagatag tgcacatcct aaatatgact ctgcaaaaa    1020
tcatttcttt tctgttacca tgtgatgaaa gtcttcattc actacagtct cgaattgagc    1080
gtgaaacagg aataaataca ggttctcagg agcttctgtc agagacaggg atttctctgg    1140
atcctcggaa accagcctct cagtgtgttc tagatggagt tagaggctgt gatagctaca    1200
tggtttattt gtttgataaa agtaagactg tatatgaagg accatttgca tccagaagtt    1260
tatctgattg tgtaaattat attgtacaag acagcaaat acaactgcca attatacagc    1320
```

-continued

```
tgcggaaagt atgggctgaa gcagtgcact acgtatctgg gctaaaggaa gactacagca    1380
ggctcttcca gggacaaaga gcagcaatgt taagtcttct tagatataat gctaacttga    1440
caaaaatgaa gaatactttg atctcagcat cacagcaact caaagctaaa ttggagtttt    1500
ttcgaaaaag cattcagctt gacttggaga gatatagtga gcagatgact tatgggatat    1560
cttcagaaaa aatgttaaaa gcatggaaag aaatggaaga aaaggccatt cactattctg    1620
aggttggtgt cattggttat cttgaggatc aaattatgtc tttgcacact gaatcatgg     1680 agctgcagaa gagcccctac ggacgacgcc agggagactt gatggagtct ctggagcagc    1740
gtgccattga tctctataag cagctaaagc acagacctcc tgatcacttg tacagcgaca    1800
gcacagagat ggtgaagatc atcgtgcaca ccgtgcagag tcaggaccgt gttctcaagg    1860
agctgtttgg tcacctgagc aagttgttgg gctgcaagca gaagattatt gatctactcc    1920
ccaaggtgga agtggccctc agtaacatca agaagctgga caatactgtc atgtttatgc    1980
agggaaagag gcagaaagaa atttggcacc tccttaaaat tgcctgtaca cagagttctg    2040
cccgctctct tgtaggatcc agtctagaag gcacagtaac ccctccagta tcagcatggc    2100 tgcccccctac attagcagac cgtgaacatc ctctgacatg tgtggtaact cctcaagatg    2160
gagagacgtt agcacaaatg atagaagaaa atctgaactg tcttggccat ttaagtacta    2220
ttattcgtga agcaaatgag gaccagagca gtagtttgat gagtcttgat tggagttggt    2280
tagcagaatg actcgacact cgttcactgt cctggagcct acgaagctgt tttgtcattt    2340
actccaaagt catctttact tgctgaagcc attcctcact taccagtccg tgaggagatg    2400
gctgtgatcg gaaactacga gtgactttac aagcacagta gcttggtgtt ttgtttgttt    2460
ctaataatta tgatctctga acagataaaa ttttatagca aattagtgaa attaattatt    2520 cttttttaaca ccgcaactaa tgagggagat cattagtgac ctgcttatct tataaaattg    2580
gaaaaatact actactagtt tagctgatga aaaagataat cttctaaagg cctaaatttt    2640
cggcataagg cccaacatgg tattagtata caggaatgaa aaattcaccc agtgttcatt    2700
tgaagtaaag ttttatctat gggttttctg tggaagagac tgctgacaag taaaattgct    2760
cttcctgaag actaagccca gcctccttgt gttgctctca gcaagtgttc ttcatggcat    2820
cacatggagt cagatgaatc ccatctttaa tcacacattt aatagagtcc ttttcctgtg    2880
taaggggttg gacttttgtg cctttgatat cagctgacca taatgaattg tgttgtgtgc    2940
tatatgtata tgtatttaag gtgtacattt aataatatca agagaagat gcctgttaat     3000 ttataatgta tttgaaagtt gtattgtttt tgcatttgta aaaatgggtt acttgtttaa    3060
acaatctttt atgtcttgtc atacaaattc caagggtct gcattccttt atctgtaatt      3120
acagtctcag aatccaagtt ctgaaaacaa ggtatctatt ctgatctgac actggatctg    3180
cttatcccat ttagtgtgaa tattcattga tttatgtgtt tgattattgg gatgtgctgc    3240
cacaggctct cttgaaggtt gatgtagtgt ggcgtatgca ctgaattacc tttctaaaat    3300
ctgaacagtt ctcattctga aacatctaga cttaagggtt tcagataaaa gactgcggtt    3360
ctctgcctta tgttaaataa cttagaagat gttattttgt ttgaaaaaat gtgaaatgct    3420
tttatattct agtttttcac tttgcatatt aaatgatttt aaaatt                   3466
```

```
<210> SEQ ID NO 21
<211> LENGTH: 21
<212> TYPE: DNA
<213> ORGANISM: Artificial sequence
<220> FEATURE:
<223> OTHER INFORMATION: synthetic
```

```
<400> SEQUENCE: 21
ccagaacaac ctgcagcaga c                                              21

<210> SEQ ID NO 22
<211> LENGTH: 21
<212> TYPE: DNA
<213> ORGANISM: Artificial sequence
<220> FEATURE:
<223> OTHER INFORMATION: synthetic

<400> SEQUENCE: 22
gctcaggatc acagccagct t                                              21

<210> SEQ ID NO 23
<211> LENGTH: 20
<212> TYPE: DNA
<213> ORGANISM: Artificial sequence
<220> FEATURE:
<223> OTHER INFORMATION: synthetic

<400> SEQUENCE: 23
catctgagcg attccagtca                                                20

<210> SEQ ID NO 24
<211> LENGTH: 20
<212> TYPE: DNA
<213> ORGANISM: Artificial sequence
<220> FEATURE:
<223> OTHER INFORMATION: synthetic

<400> SEQUENCE: 24
actgtgtgcg caagaatctg                                                20

<210> SEQ ID NO 25
<211> LENGTH: 20
<212> TYPE: DNA
<213> ORGANISM: Artificial sequence
<220> FEATURE:
<223> OTHER INFORMATION: synthetic

<400> SEQUENCE: 25
gagtgtctcc cagggaatga                                                20

<210> SEQ ID NO 26
<211> LENGTH: 20
<212> TYPE: DNA
<213> ORGANISM: Artificial sequence
<220> FEATURE:
<223> OTHER INFORMATION: synthetic

<400> SEQUENCE: 26
cttgggacct gagtgaccct                                                20

<210> SEQ ID NO 27
<211> LENGTH: 21
<212> TYPE: DNA
<213> ORGANISM: Artificial sequence
<220> FEATURE:
<223> OTHER INFORMATION: synthetic

<400> SEQUENCE: 27
ccatttggca cgaggattca c                                              21

<210> SEQ ID NO 28
<211> LENGTH: 20
<212> TYPE: DNA
```

```
<213> ORGANISM: Artificial sequence
<220> FEATURE:
<223> OTHER INFORMATION: synthetic

<400> SEQUENCE: 28
atgaggctca gcacagcaac                                               20

<210> SEQ ID NO 29
<211> LENGTH: 22
<212> TYPE: DNA
<213> ORGANISM: Artificial sequence
<220> FEATURE:
<223> OTHER INFORMATION: synthetic

<400> SEQUENCE: 29
gagagacaag aaccaaaagc ac                                            22

<210> SEQ ID NO 30
<211> LENGTH: 22
<212> TYPE: DNA
<213> ORGANISM: Artificial sequence
<220> FEATURE:
<223> OTHER INFORMATION: synthetic

<400> SEQUENCE: 30
gggaagaatt aggaggaaaa gg                                            22

<210> SEQ ID NO 31
<211> LENGTH: 20
<212> TYPE: DNA
<213> ORGANISM: Artificial sequence
<220> FEATURE:
<223> OTHER INFORMATION: synthetic

<400> SEQUENCE: 31
actacccact aaccctggac                                               20

<210> SEQ ID NO 32
<211> LENGTH: 22
<212> TYPE: DNA
<213> ORGANISM: Artificial sequence
<220> FEATURE:
<223> OTHER INFORMATION: synthetic

<400> SEQUENCE: 32
aggtgatgtg gatggagagg ag                                            22

<210> SEQ ID NO 33
<211> LENGTH: 21
<212> TYPE: DNA
<213> ORGANISM: Artificial sequence
<220> FEATURE:
<223> OTHER INFORMATION: synthetic

<400> SEQUENCE: 33
agctccagga gaaggcaact c                                             21

<210> SEQ ID NO 34
<211> LENGTH: 20
<212> TYPE: DNA
<213> ORGANISM: Artificial sequence
<220> FEATURE:
<223> OTHER INFORMATION: synthetic

<400> SEQUENCE: 34
acggcacgct tatttctgct                                               20
```

<210> SEQ ID NO 35
<211> LENGTH: 20
<212> TYPE: DNA
<213> ORGANISM: Artificial sequence
<220> FEATURE:
<223> OTHER INFORMATION: synthetic

<400> SEQUENCE: 35
cagcaagcag aactcactgc                                          20

<210> SEQ ID NO 36
<211> LENGTH: 20
<212> TYPE: DNA
<213> ORGANISM: Artificial sequence
<220> FEATURE:
<223> OTHER INFORMATION: synthetic

<400> SEQUENCE: 36
aagagaagcc atgtcggaga                                          20

<210> SEQ ID NO 37
<211> LENGTH: 20
<212> TYPE: DNA
<213> ORGANISM: Artificial sequence
<220> FEATURE:
<223> OTHER INFORMATION: synthetic

<400> SEQUENCE: 37
tacaccagat ccaggggttc                                          20

<210> SEQ ID NO 38
<211> LENGTH: 20
<212> TYPE: DNA
<213> ORGANISM: Artificial sequence
<220> FEATURE:
<223> OTHER INFORMATION: synthetic

<400> SEQUENCE: 38
gagctcaggg ttgaggtcag                                          20

<210> SEQ ID NO 39
<211> LENGTH: 20
<212> TYPE: DNA
<213> ORGANISM: Artificial sequence
<220> FEATURE:
<223> OTHER INFORMATION: synthetic

<400> SEQUENCE: 39
cgggacactt ccagaacact                                          20

<210> SEQ ID NO 40
<211> LENGTH: 20
<212> TYPE: DNA
<213> ORGANISM: Artificial sequence
<220> FEATURE:
<223> OTHER INFORMATION: synthetic

<400> SEQUENCE: 40
ccctggatct cacatctggt                                          20

<210> SEQ ID NO 41
<211> LENGTH: 19
<212> TYPE: DNA
<213> ORGANISM: Artificial sequence
<220> FEATURE:
<223> OTHER INFORMATION: synthetic

<400> SEQUENCE: 41
acagaaagca tgatccgcg					19

<210> SEQ ID NO 42
<211> LENGTH: 17
<212> TYPE: DNA
<213> ORGANISM: Artificial sequence
<220> FEATURE:
<223> OTHER INFORMATION: synthetic

<400> SEQUENCE: 42
gccccccatc ttttggg					17

<210> SEQ ID NO 43
<211> LENGTH: 20
<212> TYPE: DNA
<213> ORGANISM: Artificial sequence
<220> FEATURE:
<223> OTHER INFORMATION: synthetic

<400> SEQUENCE: 43
gacagcccac taaacgcgaa					20

<210> SEQ ID NO 44
<211> LENGTH: 20
<212> TYPE: DNA
<213> ORGANISM: Artificial sequence
<220> FEATURE:
<223> OTHER INFORMATION: synthetic

<400> SEQUENCE: 44
cagaacggac ttggacccct					20

<210> SEQ ID NO 45
<211> LENGTH: 19
<212> TYPE: DNA
<213> ORGANISM: Artificial sequence
<220> FEATURE:
<223> OTHER INFORMATION: synthetic

<400> SEQUENCE: 45
gatcacattc acggtgctg					19

<210> SEQ ID NO 46
<211> LENGTH: 20
<212> TYPE: DNA
<213> ORGANISM: Artificial sequence
<220> FEATURE:
<223> OTHER INFORMATION: synthetic

<400> SEQUENCE: 46
gagaaattgg ctccgtggtc					20

<210> SEQ ID NO 47
<211> LENGTH: 24
<212> TYPE: DNA
<213> ORGANISM: Artificial sequence
<220> FEATURE:
<223> OTHER INFORMATION: synthetic

<400> SEQUENCE: 47
gacaaatgta taaatattta ctga					24

<210> SEQ ID NO 48
<211> LENGTH: 23
<212> TYPE: DNA

```
<213> ORGANISM: Artificial sequence
<220> FEATURE:
<223> OTHER INFORMATION: synthetic

<400> SEQUENCE: 48
aacctttagc tcggagtctg cat                                           23

<210> SEQ ID NO 49
<211> LENGTH: 24
<212> TYPE: DNA
<213> ORGANISM: Artificial sequence
<220> FEATURE:
<223> OTHER INFORMATION: synthetic

<400> SEQUENCE: 49
ttcgtaccat ccacccaccc ccag                                          24

<210> SEQ ID NO 50
<211> LENGTH: 24
<212> TYPE: DNA
<213> ORGANISM: Artificial sequence
<220> FEATURE:
<223> OTHER INFORMATION: synthetic

<400> SEQUENCE: 50
accgagagtg aaagtgcggc agcg                                          24

<210> SEQ ID NO 51
<211> LENGTH: 21
<212> TYPE: DNA
<213> ORGANISM: Artificial sequence
<220> FEATURE:
<223> OTHER INFORMATION: synthetic

<400> SEQUENCE: 51
ggcatttaag acacttaatt g                                             21

<210> SEQ ID NO 52
<211> LENGTH: 21
<212> TYPE: DNA
<213> ORGANISM: Artificial sequence
<220> FEATURE:
<223> OTHER INFORMATION: synthetic

<400> SEQUENCE: 52
ataaatctct ggcttttcct g                                             21

<210> SEQ ID NO 53
<211> LENGTH: 20
<212> TYPE: DNA
<213> ORGANISM: Artificial sequence
<220> FEATURE:
<223> OTHER INFORMATION: synthetic

<400> SEQUENCE: 53
cgctaagagg aacagcctag                                               20

<210> SEQ ID NO 54
<211> LENGTH: 18
<212> TYPE: DNA
<213> ORGANISM: Artificial sequence
<220> FEATURE:
<223> OTHER INFORMATION: synthetic

<400> SEQUENCE: 54
cagctggctg aaacatgg                                                 18
```

```
<210> SEQ ID NO 55
<211> LENGTH: 21
<212> TYPE: DNA
<213> ORGANISM: Artificial sequence
<220> FEATURE:
<223> OTHER INFORMATION: synthetic

<400> SEQUENCE: 55
gctgctctgc cttcagccag c                                              21

<210> SEQ ID NO 56
<211> LENGTH: 20
<212> TYPE: DNA
<213> ORGANISM: Artificial sequence
<220> FEATURE:
<223> OTHER INFORMATION: synthetic

<400> SEQUENCE: 56
tccacgctga gggagcttct                                                20

<210> SEQ ID NO 57
<211> LENGTH: 10
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: n = a, c, g, or t
<220> FEATURE:
<221> NAME/KEY: misc_feature
<222> LOCATION: (7)..(7)
<223> OTHER INFORMATION: n = a, c, g, or t
<220> FEATURE:
<221> NAME/KEY: misc_feature
<222> LOCATION: (8)..(8)
<223> OTHER INFORMATION: n = a, c, g, or t

<400> SEQUENCE: 57 nggaganntg                                                           10

<210> SEQ ID NO 58
<211> LENGTH: 10
<212> TYPE: DNA
<213> ORGANISM: Artificial Sequence
<220> FEATURE:
<223> OTHER INFORMATION: Synthetic

<400> SEQUENCE: 58
gggactttcc                                                           10

<210> SEQ ID NO 59
<211> LENGTH: 10
<212> TYPE: DNA
<213> ORGANISM: Artificial Sequence
<220> FEATURE:
<223> OTHER INFORMATION: Synthetic

<400> SEQUENCE: 59
gggagatttg                                                           10

<210> SEQ ID NO 60
<211> LENGTH: 10
<212> TYPE: DNA
<213> ORGANISM: Artificial Sequence
<220> FEATURE:
<223> OTHER INFORMATION: Synthetic
```

```
<400> SEQUENCE: 60
aggagatttg                                                          10

<210> SEQ ID NO 61
<211> LENGTH: 10
<212> TYPE: DNA
<213> ORGANISM: Artificial Sequence
<220> FEATURE:
<223> OTHER INFORMATION: Synthetic

<400> SEQUENCE: 61
gggatttccc                                                          10

<210> SEQ ID NO 62
<211> LENGTH: 400
<212> TYPE: PRT
<213> ORGANISM: Mus musculus

<400> SEQUENCE: 62
```

Met Pro Ser Arg Arg Ala Ala Arg Glu Ser Ala Pro Glu Leu Gly Ala
 1               5                  10                  15

Leu Gly Ser Ser Asp Leu Ser Ser Leu Ser Leu Thr Val Ser Arg Thr
                20                  25                  30

Thr Asp Glu Leu Glu Ile Ile Asp Glu Tyr Ile Lys Glu Asn Gly Phe
            35                  40                  45

Gly Leu Val Gly Thr Gln Leu Ser Glu Met Pro Arg Leu Val Pro Arg
        50                  55                  60

Gly Pro Ala Ser Leu Ser Ser Val Thr Leu Gly Pro Ala Ala Pro Pro
 65                 70                  75                  80

Pro Pro Ala Thr Pro Ser Trp Ser Cys Thr Leu Gly Arg Leu Val Ser
                85                  90                  95

Pro Gly Pro Cys Pro Arg Pro Tyr Leu Val Ile Thr Glu Gln Pro Lys
            100                 105                 110

Gln Arg Gly Met Arg Phe Arg Tyr Glu Cys Glu Gly Arg Ser Ala Gly
        115                 120                 125

Ser Ile Leu Gly Glu Ser Ser Thr Glu Ala Ser Lys Thr Gln Pro Ala
    130                 135                 140

Ile Glu Leu Arg Asp Cys Gly Gly Leu Arg Glu Val Glu Val Thr Ala
145                 150                 155                 160

Cys Leu Val Trp Lys Asp Trp Pro His Arg Val His Pro His Ser Leu
                165                 170                 175

Val Gly Lys Asp Cys Thr Asp Gly Val Cys Arg Val Arg Leu Arg Pro
            180                 185                 190

His Val Ser Pro Arg His Ser Phe Asn Asn Leu Gly Ile Gln Cys Val
        195                 200                 205

Arg Lys Lys Glu Ile Glu Ala Ala Ile Glu Arg Lys Ile Gln Leu Gly
    210                 215                 220

Ile Asp Pro Tyr Asn Ala Gly Ser Leu Lys Asn His Gln Glu Val Asp
225                 230                 235                 240

Met Asn Val Val Arg Ile Cys Phe Gln Ala Ser Tyr Arg Asp Gln Gln
                245                 250                 255

Gly His Leu His Arg Met Asp Pro Ile Leu Ser Glu Pro Val Tyr Asp
            260                 265                 270

Lys Lys Ser Thr Asn Thr Ser Glu Leu Arg Ile Cys Arg Ile Asn Lys
        275                 280                 285

Glu Ser Gly Pro Cys Thr Gly Gly Glu Glu Leu Tyr Leu Leu Cys Asp
    290                 295                 300

```
Lys Val Gln Lys Glu Asp Ile Ser Val Val Phe Ser Thr Ala Ser Trp
305                 310                 315                 320

Glu Gly Arg Ala Asp Phe Ser Gln Ala Asp Val His Arg Gln Ile Ala
                325                 330                 335

Ile Val Phe Lys Thr Pro Pro Tyr Glu Asp Leu Glu Ile Ser Glu Pro
                340                 345                 350

Val Thr Val Asn Val Phe Leu Gln Arg Leu Thr Asp Gly Val Cys Ser
                355                 360                 365

Glu Pro Leu Pro Phe Thr Tyr Leu Pro Arg Asp His Asp Ser Tyr Gly
                370                 375                 380

Val Asp Lys Lys Arg Lys Arg Gly Leu Pro Asp Val Leu Gly Glu Leu
385                 390                 395                 400

<210> SEQ ID NO 63
<211> LENGTH: 100
<212> TYPE: PRT
<213> ORGANISM: Mus musculus

<400> SEQUENCE: 63

Ser Glu Leu Arg Ile Cys Arg Ile Asn Lys Glu Ser Gly Pro Cys Thr
1               5                   10                  15

Gly Gly Glu Glu Leu Tyr Leu Leu Cys Asp Lys Val Gln Lys Glu Asp
                20                  25                  30

Ile Ser Val Val Phe Ser Thr Ala Ser Trp Glu Gly Arg Ala Asp Phe
                35                  40                  45

Ser Gln Ala Asp Val His Arg Gln Ile Ala Ile Val Phe Lys Thr Pro
                50                  55                  60

Pro Tyr Glu Asp Leu Glu Ile Ser Glu Pro Val Thr Val Asn Val Phe
65              70                  75                  80

Leu Gln Arg Leu Thr Asp Gly Val Cys Ser Glu Pro Leu Pro Phe Thr
                85                  90                  95

Tyr Leu Pro Arg
            100

<210> SEQ ID NO 64
<211> LENGTH: 340
<212> TYPE: PRT
<213> ORGANISM: Homo sapiens

<400> SEQUENCE: 64

Met Glu Ser Cys Tyr Asn Pro Gly Leu Asp Gly Ile Ile Glu Tyr Asp
1               5                   10                  15

Asp Phe Lys Leu Asn Ser Ser Ile Val Glu Pro Lys Glu Pro Ala Pro
                20                  25                  30

Glu Thr Ala Asp Gly Pro Tyr Leu Val Ile Val Glu Gln Pro Lys Gln
                35                  40                  45

Arg Gly Phe Arg Phe Arg Tyr Gly Cys Glu Gly Pro Ser His Gly Gly
                50                  55                  60

Leu Pro Gly Ala Ser Ser Glu Lys Gly Arg Lys Thr Tyr Pro Thr Val
65              70                  75                  80

Lys Ile Cys Asn Tyr Glu Gly Pro Ala Lys Ile Glu Val Asp Leu Val
                85                  90                  95

Thr His Ser Asp Pro Pro Arg Ala His Ala His Ser Leu Val Gly Lys
                100                 105                 110

Gln Cys Ser Glu Leu Gly Ile Cys Ala Val Ser Val Gly Pro Lys Asp
                115                 120                 125
```

```
Met Thr Ala Gln Phe Asn Asn Leu Gly Val Leu His Val Thr Lys Lys
        130                 135                 140

Asn Met Met Gly Thr Met Ile Gln Lys Leu Gln Arg Gln Arg Leu Arg
145                 150                 155                 160

Ser Arg Pro Gln Gly Leu Thr Glu Ala Glu Gln Arg Glu Leu Glu Gln
                165                 170                 175

Glu Ala Lys Glu Leu Lys Lys Val Met Asp Leu Ser Ile Val Arg Leu
            180                 185                 190

Arg Phe Ser Ala Phe Leu Arg Ala Ser Asp Gly Ser Phe Ser Leu Pro
        195                 200                 205

Leu Lys Pro Val Thr Ser Gln Pro Ile His Asp Ser Lys Ser Pro Gly
210                 215                 220

Ala Ser Asn Leu Lys Ile Ser Arg Met Asp Lys Thr Ala Gly Ser Val
225                 230                 235                 240

Arg Gly Gly Asp Glu Val Tyr Leu Leu Cys Asp Lys Val Gln Lys Asp
                245                 250                 255

Asp Ile Glu Val Arg Phe Tyr Glu Asp Glu Asn Gly Trp Gln Ala
            260                 265                 270

Phe Gly Asp Phe Ser Pro Thr Asp Val His Lys Gln Tyr Ala Ile Val
        275                 280                 285

Phe Arg Thr Pro Pro Tyr His Lys Met Lys Ile Glu Arg Pro Val Thr
290                 295                 300

Val Phe Leu Gln Leu Lys Arg Lys Arg Gly Gly Asp Val Ser Asp Ser
305                 310                 315                 320

Lys Gln Phe Thr Tyr Tyr Pro Leu Val Glu Asp Lys Glu Glu Val Gln
                325                 330                 335

Arg Lys Arg Arg
            340

<210> SEQ ID NO 65
<211> LENGTH: 273
<212> TYPE: PRT
<213> ORGANISM: Mus musculus

<400> SEQUENCE: 65

Pro Tyr Val Glu Ile Ile Glu Gln Pro Lys Gln Arg Gly Met Arg Phe
1               5                   10                  15

Arg Tyr Lys Cys Glu Gly Arg Ser Ala Gly Ser Ile Pro Gly Glu Arg
                20                  25                  30

Ser Thr Asp Thr Thr Lys Thr His Pro Thr Ile Lys Ile Asn Gly Tyr
            35                  40                  45

Thr Gly Pro Gly Thr Val Arg Ile Ser Leu Val Thr Lys Asp Pro Pro
        50                  55                  60

His Arg Pro His Pro His Glu Leu Val Gly Lys Asp Cys Arg Asp Gly
65                  70                  75                  80

Tyr Tyr Glu Ala Asp Leu Cys Pro Asp Arg Ser Ile His Ser Phe Gln
                85                  90                  95

Asn Leu Gly Ile Gln Cys Val Lys Lys Arg Asp Leu Glu Gln Ala Ile
            100                 105                 110

Ser Gln Arg Ile Gln Thr Asn Asn Asn Pro Phe His Val Pro Ile Glu
        115                 120                 125

Glu Gln Arg Gly Asp Tyr Asp Leu Asn Ala Val Arg Leu Cys Phe Gln
    130                 135                 140

Val Thr Val Arg Asp Pro Ala Gly Arg Pro Leu Leu Leu Thr Pro Val
145                 150                 155                 160
```

```
Leu Ser His Pro Ile Phe Asp Asn Arg Ala Pro Asn Thr Ala Glu Leu
            165                 170                 175

Lys Ile Cys Arg Val Asn Arg Asn Ser Gly Ser Cys Leu Gly Gly Asp
        180                 185                 190

Glu Ile Phe Leu Leu Cys Asp Lys Val Gln Lys Glu Asp Ile Glu Val
    195                 200                 205

Tyr Phe Thr Gly Pro Gly Trp Glu Ala Arg Gly Ser Phe Ser Gln Ala
    210                 215                 220

Asp Val His Arg Gln Val Ala Ile Val Phe Arg Thr Pro Pro Tyr Ala
225                 230                 235                 240

Asp Pro Ser Leu Gln Ala Pro Val Arg Val Ser Met Gln Leu Arg Arg
            245                 250                 255

Pro Ser Asp Arg Glu Leu Ser Glu Pro Met Glu Phe Gln Tyr Leu Pro
            260                 265                 270

Asp

<210> SEQ ID NO 66
<211> LENGTH: 5
<212> TYPE: DNA
<213> ORGANISM: Artificial Sequence
<220> FEATURE:
<223> OTHER INFORMATION: Synthetic

<400> SEQUENCE: 66 gggag                                                            5

<210> SEQ ID NO 67
<211> LENGTH: 4
<212> TYPE: DNA
<213> ORGANISM: Artificial Sequence
<220> FEATURE:
<223> OTHER INFORMATION: Synthetic

<400> SEQUENCE: 67 tttg                                                             4

<210> SEQ ID NO 68
<211> LENGTH: 6
<212> TYPE: DNA
<213> ORGANISM: Artificial Sequence
<220> FEATURE:
<223> OTHER INFORMATION: Synthetic

<400> SEQUENCE: 68 gtgaag                                                           6

<210> SEQ ID NO 69
<211> LENGTH: 40
<212> TYPE: DNA
<213> ORGANISM: Artificial Sequence
<220> FEATURE:
<223> OTHER INFORMATION: Bacteriophage

<400> SEQUENCE: 69
taatacgact cactataggg attaaccctc actaaaggga                      40

<210> SEQ ID NO 70
<211> LENGTH: 40
<212> TYPE: DNA
<213> ORGANISM: Artificial Sequence
<220> FEATURE:
<223> OTHER INFORMATION: Bacteriophage

<400> SEQUENCE: 70
```

```
attaccctc actaaaggga taatacgact cactataggg                    40

<210> SEQ ID NO 71
<211> LENGTH: 39
<212> TYPE: DNA
<213> ORGANISM: Artificial Sequence
<220> FEATURE:
<223> OTHER INFORMATION: Bacteriophage

<400> SEQUENCE: 71
taatacgact cactataggg tatttaggtg acactatag                    39

<210> SEQ ID NO 72
<211> LENGTH: 39
<212> TYPE: DNA
<213> ORGANISM: Artificial Sequence
<220> FEATURE:
<223> OTHER INFORMATION: Bacteriophage

<400> SEQUENCE: 72
tatttaggtg acactatagt aatacgactc actataggg                    39

<210> SEQ ID NO 73
<211> LENGTH: 39
<212> TYPE: DNA
<213> ORGANISM: Artificial Sequence
<220> FEATURE:
<223> OTHER INFORMATION: Bacteriophage

<400> SEQUENCE: 73
tatttaggtg acactataga ttaccctca ctaaaggga                     39

<210> SEQ ID NO 74
<211> LENGTH: 39
<212> TYPE: DNA
<213> ORGANISM: Artificial Sequence
<220> FEATURE:
<223> OTHER INFORMATION: Bacteriophage

<400> SEQUENCE: 74 attaccctc actaaaggga tatttaggtg acactatag                     39

<210> SEQ ID NO 75
<211> LENGTH: 20
<212> TYPE: DNA
<213> ORGANISM: Artificial Sequence
<220> FEATURE:
<223> OTHER INFORMATION: Bacteriophage

<400> SEQUENCE: 75
taatacgact cactataggg                                         20

<210> SEQ ID NO 76
<211> LENGTH: 17
<212> TYPE: DNA
<213> ORGANISM: Artificial Sequence
<220> FEATURE:
<223> OTHER INFORMATION: Bacteriophage

<400> SEQUENCE: 76
taatacgact cactata                                            17

<210> SEQ ID NO 77
<211> LENGTH: 16
<212> TYPE: DNA
<213> ORGANISM: Artificial Sequence
```

```
<220> FEATURE:
<223> OTHER INFORMATION: Bacteriophage

<400> SEQUENCE: 77
taatacgact cactat                                                    16

<210> SEQ ID NO 78
<211> LENGTH: 16
<212> TYPE: DNA
<213> ORGANISM: Artificial Sequence
<220> FEATURE:
<223> OTHER INFORMATION: Bacteriophage

<400> SEQUENCE: 78
aatacgactc actata                                                    16

<210> SEQ ID NO 79
<211> LENGTH: 16
<212> TYPE: DNA
<213> ORGANISM: Artificial Sequence
<220> FEATURE:
<223> OTHER INFORMATION: Bacteriophage

<400> SEQUENCE: 79
atacgactca ctatag                                                    16

<210> SEQ ID NO 80
<211> LENGTH: 14
<212> TYPE: DNA
<213> ORGANISM: Artificial Sequence
<220> FEATURE:
<223> OTHER INFORMATION: Bacteriophage

<400> SEQUENCE: 80
acgactcact atag                                                      14

<210> SEQ ID NO 81
<211> LENGTH: 14
<212> TYPE: DNA
<213> ORGANISM: Artificial Sequence
<220> FEATURE:
<223> OTHER INFORMATION: Bacteriophage

<400> SEQUENCE: 81
atacgactca ctat                                                      14

<210> SEQ ID NO 82
<211> LENGTH: 14
<212> TYPE: DNA
<213> ORGANISM: Artificial Sequence
<220> FEATURE:
<223> OTHER INFORMATION: Bacteriophage

<400> SEQUENCE: 82
tacgactcac tata                                                      14

<210> SEQ ID NO 83
<211> LENGTH: 10
<212> TYPE: DNA
<213> ORGANISM: Artificial Sequence
<220> FEATURE:
<223> OTHER INFORMATION: Bacteriophage

<400> SEQUENCE: 83
cgactcacta                                                           10
```

```
<210> SEQ ID NO 84
<211> LENGTH: 10
<212> TYPE: DNA
<213> ORGANISM: Artificial Sequence
<220> FEATURE:
<223> OTHER INFORMATION: Bacteriophage

<400> SEQUENCE: 84
tacgactcac                                                          10

<210> SEQ ID NO 85
<211> LENGTH: 10
<212> TYPE: DNA
<213> ORGANISM: Artificial Sequence
<220> FEATURE:
<223> OTHER INFORMATION: Bacteriophage

<400> SEQUENCE: 85
atacgactca                                                          10

<210> SEQ ID NO 86
<211> LENGTH: 6
<212> TYPE: DNA
<213> ORGANISM: Artificial Sequence
<220> FEATURE:
<223> OTHER INFORMATION: Bacteriophage

<400> SEQUENCE: 86 ataggg                                                               6

<210> SEQ ID NO 87
<211> LENGTH: 6
<212> TYPE: DNA
<213> ORGANISM: Artificial Sequence
<220> FEATURE:
<223> OTHER INFORMATION: Bacteriophage

<400> SEQUENCE: 87 taatac                                                               6

<210> SEQ ID NO 88
<211> LENGTH: 6
<212> TYPE: DNA
<213> ORGANISM: Artificial Sequence
<220> FEATURE:
<223> OTHER INFORMATION: Bacteriophage

<400> SEQUENCE: 88 acgact                                                               6

<210> SEQ ID NO 89
<211> LENGTH: 20
<212> TYPE: DNA
<213> ORGANISM: Artificial Sequence
<220> FEATURE:
<223> OTHER INFORMATION: Bacteriophage

<400> SEQUENCE: 89
attaaccctc actaaaggga                                               20

<210> SEQ ID NO 90
<211> LENGTH: 18
<212> TYPE: DNA
<213> ORGANISM: Artificial Sequence
<220> FEATURE:
<223> OTHER INFORMATION: Bacteriophage

<400> SEQUENCE: 90
```

```
ttaaccctca ctaaaggg                                                     18

<210> SEQ ID NO 91
<211> LENGTH: 18
<212> TYPE: DNA
<213> ORGANISM: Artificial Sequence
<220> FEATURE:
<223> OTHER INFORMATION: Bacteriophage

<400> SEQUENCE: 91
taaccctcac taaaggga                                                     18

<210> SEQ ID NO 92
<211> LENGTH: 18
<212> TYPE: DNA
<213> ORGANISM: Artificial Sequence
<220> FEATURE:
<223> OTHER INFORMATION: Bacteriophage

<400> SEQUENCE: 92
attaaccctc actaaagg                                                     18

<210> SEQ ID NO 93
<211> LENGTH: 16
<212> TYPE: DNA
<213> ORGANISM: Artificial Sequence
<220> FEATURE:
<223> OTHER INFORMATION: Bacteriophage

<400> SEQUENCE: 93
accctcacta aaggga                                                       16

<210> SEQ ID NO 94
<211> LENGTH: 16
<212> TYPE: DNA
<213> ORGANISM: Artificial Sequence
<220> FEATURE:
<223> OTHER INFORMATION: Bacteriophage

<400> SEQUENCE: 94
taaccctcac taaagg                                                       16

<210> SEQ ID NO 95
<211> LENGTH: 16
<212> TYPE: DNA
<213> ORGANISM: Artificial Sequence
<220> FEATURE:
<223> OTHER INFORMATION: Bacteriophage

<400> SEQUENCE: 95
ttaaccctca ctaaag                                                       16

<210> SEQ ID NO 96
<211> LENGTH: 14
<212> TYPE: DNA
<213> ORGANISM: Artificial Sequence
<220> FEATURE:
<223> OTHER INFORMATION: Bacteriophage

<400> SEQUENCE: 96
cctcactaaa ggga                                                         14

<210> SEQ ID NO 97
<211> LENGTH: 14
<212> TYPE: DNA
<213> ORGANISM: Artificial Sequence
```

```
<220> FEATURE:
<223> OTHER INFORMATION: Bacteriophage

<400> SEQUENCE: 97
attaaccctc acta                                                      14

<210> SEQ ID NO 98
<211> LENGTH: 14
<212> TYPE: DNA
<213> ORGANISM: Artificial Sequence
<220> FEATURE:
<223> OTHER INFORMATION: Bacteriophage

<400> SEQUENCE: 98
aaccctcact aaag                                                      14

<210> SEQ ID NO 99
<211> LENGTH: 10
<212> TYPE: DNA
<213> ORGANISM: Artificial Sequence
<220> FEATURE:
<223> OTHER INFORMATION: Bacteriophage

<400> SEQUENCE: 99
accctcacta                                                           10

<210> SEQ ID NO 100
<211> LENGTH: 10
<212> TYPE: DNA
<213> ORGANISM: Artificial Sequence
<220> FEATURE:
<223> OTHER INFORMATION: Bacteriophage

<400> SEQUENCE: 100
cctcactaaa                                                           10

<210> SEQ ID NO 101
<211> LENGTH: 10
<212> TYPE: DNA
<213> ORGANISM: Artificial Sequence
<220> FEATURE:
<223> OTHER INFORMATION: Bacteriophage

<400> SEQUENCE: 101
attaaccctc                                                           10

<210> SEQ ID NO 102
<211> LENGTH: 6
<212> TYPE: DNA
<213> ORGANISM: Artificial Sequence
<220> FEATURE:
<223> OTHER INFORMATION: Bacteriophage

<400> SEQUENCE: 102 attaac                                                                6

<210> SEQ ID NO 103
<211> LENGTH: 6
<212> TYPE: DNA
<213> ORGANISM: Artificial Sequence
<220> FEATURE:
<223> OTHER INFORMATION: Bacteriophage

<400> SEQUENCE: 103 aaggga                                                                6
```

```
<210> SEQ ID NO 104
<211> LENGTH: 6
<212> TYPE: DNA
<213> ORGANISM: Artificial Sequence
<220> FEATURE:
<223> OTHER INFORMATION: Bacteriophage

<400> SEQUENCE: 104 cactaa                                                                      6

<210> SEQ ID NO 105
<211> LENGTH: 19
<212> TYPE: DNA
<213> ORGANISM: Artificial Sequence
<220> FEATURE:
<223> OTHER INFORMATION: Bacteriophage

<400> SEQUENCE: 105
tatttaggtg acactatag                                                       19

<210> SEQ ID NO 106
<211> LENGTH: 16
<212> TYPE: DNA
<213> ORGANISM: Artificial Sequence
<220> FEATURE:
<223> OTHER INFORMATION: Bacteriophage

<400> SEQUENCE: 106
ttaggtgaca ctatag                                                          16

<210> SEQ ID NO 107
<211> LENGTH: 16
<212> TYPE: DNA
<213> ORGANISM: Artificial Sequence
<220> FEATURE:
<223> OTHER INFORMATION: Bacteriophage

<400> SEQUENCE: 107
tttaggtgac actata                                                          16

<210> SEQ ID NO 108
<211> LENGTH: 16
<212> TYPE: DNA
<213> ORGANISM: Artificial Sequence
<220> FEATURE:
<223> OTHER INFORMATION: Bacteriophage

<400> SEQUENCE: 108
tatttaggtg acacta                                                          16

<210> SEQ ID NO 109
<211> LENGTH: 14
<212> TYPE: DNA
<213> ORGANISM: Artificial Sequence
<220> FEATURE:
<223> OTHER INFORMATION: Bacteriophage

<400> SEQUENCE: 109
atttaggtga cact                                                            14

<210> SEQ ID NO 110
<211> LENGTH: 14
<212> TYPE: DNA
<213> ORGANISM: Artificial Sequence
<220> FEATURE:
<223> OTHER INFORMATION: Bacteriophage

<400> SEQUENCE: 110
```

```
tatttaggtg acac                                                        14

<210> SEQ ID NO 111
<211> LENGTH: 14
<212> TYPE: DNA
<213> ORGANISM: Artificial Sequence
<220> FEATURE:
<223> OTHER INFORMATION: Bacteriophage

<400> SEQUENCE: 111
tttaggtgac acta                                                        14

<210> SEQ ID NO 112
<211> LENGTH: 10
<212> TYPE: DNA
<213> ORGANISM: Artificial Sequence
<220> FEATURE:
<223> OTHER INFORMATION: Bacteriophage

<400> SEQUENCE: 112
ttaggtgaca                                                             10

<210> SEQ ID NO 113
<211> LENGTH: 10
<212> TYPE: DNA
<213> ORGANISM: Artificial Sequence
<220> FEATURE:
<223> OTHER INFORMATION: Bacteriophage

<400> SEQUENCE: 113
taggtgacac                                                             10

<210> SEQ ID NO 114
<211> LENGTH: 10
<212> TYPE: DNA
<213> ORGANISM: Artificial Sequence
<220> FEATURE:
<223> OTHER INFORMATION: Bacteriophage

<400> SEQUENCE: 114
atttaggtga                                                             10

<210> SEQ ID NO 115
<211> LENGTH: 6
<212> TYPE: DNA
<213> ORGANISM: Artificial Sequence
<220> FEATURE:
<223> OTHER INFORMATION: Bacteriophage

<400> SEQUENCE: 115 ctatag                                                                  6

<210> SEQ ID NO 116
<211> LENGTH: 6
<212> TYPE: DNA
<213> ORGANISM: Artificial Sequence
<220> FEATURE:
<223> OTHER INFORMATION: Bacteriophage

<400> SEQUENCE: 116 tattta                                                                  6

<210> SEQ ID NO 117
<211> LENGTH: 6
<212> TYPE: DNA
<213> ORGANISM: Artificial Sequence
```

```
<220> FEATURE:
<223> OTHER INFORMATION: Bacteriophage

<400> SEQUENCE: 117 gacact                                                                    6

<210> SEQ ID NO 118
<211> LENGTH: 10
<212> TYPE: DNA
<213> ORGANISM: Artificial Sequence
<220> FEATURE:
<223> OTHER INFORMATION: Bacteriophage
<220> FEATURE:
<221> NAME/KEY: misc_feature
<222> LOCATION: (3)..(4)
<223> OTHER INFORMATION: n = a, c, g, or t
<220> FEATURE:
<221> NAME/KEY: misc_feature
<222> LOCATION: (10)..(10)
<223> OTHER INFORMATION: n = a, c, g, or t

<400> SEQUENCE: 118 gtnnagaggn                                                               10

<210> SEQ ID NO 119
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: y = c or t
<220> FEATURE:
<221> NAME/KEY: misc_feature
<222> LOCATION: (7)..(8)
<223> OTHER INFORMATION: n = a, c, g, or t
<220> FEATURE:
<221> NAME/KEY: misc_feature
<222> LOCATION: (11)..(11)
<223> OTHER INFORMATION: y = c or t

<400> SEQUENCE: 119
gggggynncc y                                                             11

<210> SEQ ID NO 120
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: r = a or g
<220> FEATURE:
<221> NAME/KEY: misc_feature
<222> LOCATION: (5)..(5)
<223> OTHER INFORMATION: n = a, c, g, or t
<220> FEATURE:
<221> NAME/KEY: misc_feature
<222> LOCATION: (6)..(6)
<223> OTHER INFORMATION: w = a or t

<400> SEQUENCE: 120 gggrnwttcc                                                               10

<210> SEQ ID NO 121
<211> LENGTH: 5
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (4)..(4)
<223> OTHER INFORMATION: r = a or g
<220> FEATURE:
<221> NAME/KEY: misc_feature
<222> LOCATION: (5)..(5)
<223> OTHER INFORMATION: n = a, c, g, or t

<400> SEQUENCE: 121 gggrn                                                                    5

<210> SEQ ID NO 122
<211> LENGTH: 4
<212> TYPE: DNA
<213> ORGANISM: Artificial Sequence
<220> FEATURE:
<223> OTHER INFORMATION: Synthetic

<400> SEQUENCE: 122 ttcc                                                                     4

<210> SEQ ID NO 123
<211> LENGTH: 971
<212> TYPE: PRT
<213> ORGANISM: Mus musculus

<400> SEQUENCE: 123
```

Met Ala Asp Asp Pro Tyr Gly Thr Gly Gln Met Phe His Leu Asn
1               5                   10                  15

Thr Ala Leu Thr His Ser Ile Phe Asn Ala Glu Leu Tyr Ser Pro Glu
            20                  25                  30

Ile Pro Leu Ser Thr Asp Gly Pro Tyr Leu Gln Ile Leu Glu Gln Pro
        35                  40                  45

Lys Gln Arg Gly Phe Arg Phe Arg Tyr Val Cys Glu Gly Pro Ser His
    50                  55                  60

Gly Gly Leu Pro Gly Ala Ser Ser Glu Lys Asn Lys Lys Ser Tyr Pro
65                  70                  75                  80

Gln Val Lys Ile Cys Asn Tyr Val Gly Pro Ala Lys Val Ile Val Gln
                85                  90                  95

Leu Val Thr Asn Gly Lys Asn Ile His Leu His Ala His Ser Leu Val
            100                 105                 110

Gly Lys His Cys Glu Asp Gly Val Cys Thr Val Thr Ala Gly Pro Lys
        115                 120                 125

Asp Met Val Val Gly Phe Ala Asn Leu Gly Ile Leu His Val Thr Lys
    130                 135                 140

Lys Lys Val Phe Glu Thr Leu Glu Ala Arg Met Thr Glu Ala Cys Ile
145                 150                 155                 160

Arg Gly Tyr Asn Pro Gly Leu Leu Val His Ser Asp Leu Ala Tyr Leu
                165                 170                 175

Gln Ala Glu Gly Gly Gly Asp Arg Gln Leu Thr Asp Arg Glu Lys Glu
            180                 185                 190

Ile Ile Arg Gln Ala Ala Val Gln Gln Thr Lys Glu Met Asp Leu Ser
        195                 200                 205

Val Val Arg Leu Met Phe Thr Ala Phe Leu Pro Asp Ser Thr Gly Ser
    210                 215                 220

Phe Thr Arg Arg Leu Glu Pro Val Val Ser Asp Ala Ile Tyr Asp Ser
225                 230                 235                 240

-continued

```
Lys Ala Pro Asn Ala Ser Asn Leu Lys Ile Val Arg Met Asp Arg Thr
                245                 250                 255
Ala Gly Cys Val Thr Gly Gly Glu Ile Tyr Leu Leu Cys Asp Lys
            260                 265                 270
Val Gln Lys Asp Asp Ile Gln Ile Arg Phe Tyr Glu Glu Glu Asn
        275                 280                 285
Gly Gly Val Trp Glu Gly Phe Gly Asp Phe Ser Pro Thr Asp Val His
    290                 295                 300
Arg Gln Phe Ala Ile Val Phe Lys Thr Pro Lys Tyr Lys Asp Val Asn
305                 310                 315                 320
Ile Thr Lys Pro Ala Ser Val Phe Val Gln Leu Arg Arg Lys Ser Asp
                325                 330                 335
Leu Glu Thr Ser Glu Pro Lys Pro Phe Leu Tyr Tyr Pro Glu Ile Lys
            340                 345                 350
Asp Lys Glu Glu Val Gln Arg Lys Arg Gln Lys Leu Met Pro Asn Phe
        355                 360                 365
Ser Asp Ser Phe Gly Gly Ser Gly Ala Gly Ala Gly Gly Gly Gly
    370                 375                 380
Met Phe Gly Ser Gly Gly Gly Gly Ser Thr Gly Ser Pro Gly Pro
385                 390                 395                 400
Gly Tyr Gly Tyr Ser Asn Tyr Gly Phe Pro Pro Tyr Gly Gly Ile Thr
                405                 410                 415
Phe His Pro Gly Val Thr Lys Ser Asn Ala Gly Val Thr His Gly Thr
            420                 425                 430
Ile Asn Thr Lys Phe Lys Asn Gly Pro Lys Asp Cys Ala Lys Ser Asp
        435                 440                 445
Asp Glu Glu Ser Leu Thr Leu Pro Glu Lys Glu Thr Glu Gly Glu Gly
    450                 455                 460
Pro Ser Leu Pro Met Ala Cys Thr Lys Thr Glu Pro Ile Ala Leu Ala
465                 470                 475                 480
Ser Thr Met Glu Asp Lys Glu Gln Asp Met Gly Phe Gln Asp Asn Leu
                485                 490                 495
Phe Leu Glu Lys Ala Leu Gln Leu Ala Arg Arg His Ala Asn Ala Leu
            500                 505                 510
Phe Asp Tyr Ala Val Thr Gly Asp Val Lys Met Leu Leu Ala Val Gln
        515                 520                 525
Arg His Leu Thr Ala Val Gln Asp Glu Asn Gly Asp Ser Val Leu His
    530                 535                 540
Leu Ala Ile Ile His Leu His Ala Gln Leu Val Arg Asp Leu Leu Glu
545                 550                 555                 560
Val Thr Ser Gly Leu Ile Ser Asp Asp Ile Ile Asn Met Arg Asn Asp
                565                 570                 575
Leu Tyr Gln Thr Pro Leu His Leu Ala Val Ile Thr Lys Gln Glu Asp
            580                 585                 590
Val Val Glu Asp Leu Leu Arg Val Gly Ala Asp Leu Ser Leu Leu Asp
        595                 600                 605
Arg Trp Gly Asn Ser Val Leu His Leu Ala Ala Lys Glu Gly His Asp
    610                 615                 620
Arg Ile Leu Ser Ile Leu Leu Lys Ser Arg Lys Ala Ala Pro Leu Ile
625                 630                 635                 640
Asp His Pro Asn Gly Glu Gly Leu Asn Ala Ile His Ile Ala Val Met
                645                 650                 655
Ser Asn Ser Leu Pro Cys Leu Leu Leu Leu Val Ala Ala Gly Ala Glu
            660                 665                 670
```

Val Asn Ala Gln Glu Gln Lys Ser Gly Arg Thr Pro Leu His Leu Ala
        675                 680                 685

Val Glu Tyr Asp Asn Ile Ser Leu Ala Gly Cys Leu Leu Leu Glu Gly
        690                 695                 700

Asp Ala His Val Asp Ser Thr Thr Tyr Asp Gly Thr Thr Pro Leu His
705                 710                 715                 720

Ile Ala Ala Gly Arg Gly Ser Thr Arg Leu Ala Ala Leu Leu Lys Ala
                725                 730                 735

Ala Gly Ala Asp Pro Leu Val Glu Asn Phe Glu Pro Leu Tyr Asp Leu
                740                 745                 750

Asp Asp Ser Trp Glu Lys Ala Gly Glu Asp Glu Gly Val Val Pro Gly
        755                 760                 765

Thr Thr Pro Leu Asp Met Ala Ala Asn Trp Gln Val Phe Asp Ile Leu
        770                 775                 780

Asn Gly Lys Pro Tyr Glu Pro Val Phe Thr Ser Asp Asp Ile Leu Pro
785                 790                 795                 800

Gln Gly Asp Met Lys Gln Leu Thr Glu Asp Thr Arg Leu Gln Leu Cys
                805                 810                 815

Lys Leu Leu Glu Ile Pro Asp Pro Asp Lys Asn Trp Ala Thr Leu Ala
                820                 825                 830

Gln Lys Leu Gly Leu Gly Ile Leu Asn Asn Ala Phe Arg Leu Ser Pro
        835                 840                 845

Ala Pro Ser Lys Thr Leu Met Asp Asn Tyr Glu Val Ser Gly Gly Thr
850                 855                 860

Ile Lys Glu Leu Met Glu Ala Leu Gln Gln Met Gly Tyr Thr Glu Ala
865                 870                 875                 880

Ile Glu Val Ile Gln Ala Ala Phe Arg Thr Pro Ala Thr Thr Ala Ser
                885                 890                 895

Ser Pro Val Thr Thr Ala Gln Val His Cys Leu Pro Leu Ser Ser Ser
                900                 905                 910

Ser Thr Arg Gln His Ile Asp Glu Leu Arg Asp Ser Asp Ser Val Cys
        915                 920                 925

Asp Ser Gly Val Glu Thr Ser Phe Arg Lys Leu Ser Phe Thr Glu Ser
930                 935                 940

Leu Thr Gly Asp Ser Pro Leu Leu Ser Leu Asn Lys Met Pro His Gly
945                 950                 955                 960

Tyr Gly Gln Glu Gly Pro Ile Glu Gly Lys Ile
                965                 970

<210> SEQ ID NO 124
<211> LENGTH: 645
<212> TYPE: DNA
<213> ORGANISM: Mus musculus

<400> SEQUENCE: 124
gacaaatgta taaatattta ctgagcaccg acccagggtg agcctccctt gcaggtgcca      60
gggacataat gaaatgatga tcctggtcct ggtgtcataa agcttatatt tgaacatatg     120
gaagaacttg gcagtccttt cactatgaaa agtgatcaaa gccacgatca ctgtggctta     180
acgtaagcat ttttggtatc aataccacca aggaaagaat tagcctacat ccttatacag     240
tttgctatgg gttctttggt taaaaggaag gtaggtgggt aatggccagt gaccaaaaca     300
ctcctaaaga gtaccttagt ggcctggcag gggttcagag ggagactgtc tccctagcct     360
attctagaac ctgggtttga tctctagcac taaaacagac agtccttgag agttctcctc     420

```
tttttttattc  accctcaaat  ctccacagca  tccctgacat  ttttaatctg  cattttttaag    480 aagtgtttgg  ttatactaac  agtgctccaa  ggaagattca  taaattttgc  aagacgaatt    540
tcttcttctg  taaaggcaag  ctcagcaata  ttttgggaga  tttgaaaact  gacattgcag    600
ctgacctaag  aaagagaggg  tcagtgggag  ggccctggct  ggtat                     645
```

<210> SEQ ID NO 125
<211> LENGTH: 78
<212> TYPE: DNA
<213> ORGANISM: Mus musculus

<400> SEQUENCE: 125

```
aaataaatag  gagtctggag  ctgggaatgc  acgcacagac  tccgagctaa  aggttgaact     60
ccacctccag  gcagaatg                                                      78
```

<210> SEQ ID NO 126
<211> LENGTH: 10
<212> TYPE: DNA
<213> ORGANISM: Mus musculus

<400> SEQUENCE: 126

```
aggagacttg                                                                10
```

<210> SEQ ID NO 127
<211> LENGTH: 10
<212> TYPE: DNA
<213> ORGANISM: Mus musculus

<400> SEQUENCE: 127

```
gtgagatttg                                                                10
```

<210> SEQ ID NO 128
<211> LENGTH: 10
<212> TYPE: DNA
<213> ORGANISM: Mus musculus

<400> SEQUENCE: 128

```
aggaaattta                                                                10
```

<210> SEQ ID NO 129
<211> LENGTH: 10
<212> TYPE: DNA
<213> ORGANISM: Mus musculus

<400> SEQUENCE: 129

```
gggagatgta                                                                10
```

<210> SEQ ID NO 130
<211> LENGTH: 707
<212> TYPE: PRT
<213> ORGANISM: Homo sapiens

<400> SEQUENCE: 130

```
Met Ser Arg Asp Arg Phe Arg Ser Arg Gly Gly Gly Gly Gly Phe
  1               5                  10                  15

His Arg Arg Gly Gly Gly Gly Arg Gly Gly Leu His Asp Phe Arg
                 20                  25                  30

Ser Pro Pro Pro Gly Met Gly Leu Asn Gln Asn Arg Gly Pro Met Gly
                 35                  40                  45

Pro Gly Pro Gly Gln Ser Gly Pro Lys Pro Ile Pro Pro Pro
         50                  55                  60
```

-continued

```
Pro His Gln Gln Gln Gln Pro Pro Gln Gln Pro Pro Gln
 65                  70                  75                  80

Gln Pro Pro Pro His Gln Pro Pro His Pro Gln Pro His Gln Gln
                 85                  90                  95

Gln Gln Pro Pro Pro Pro Gln Asp Ser Ser Lys Pro Val Val Ala
            100                 105                 110

Gln Gly Pro Gly Pro Ala Pro Val Gly Ser Ala Pro Pro Ala Ser
            115                 120                 125

Ser Ser Ala Pro Pro Ala Thr Pro Pro Thr Ser Gly Ala Pro Pro Gly
130                 135                 140

Ser Gly Pro Gly Pro Thr Pro Thr Pro Pro Ala Val Thr Ser Ala
145                 150                 155                 160

Pro Pro Gly Ala Pro Pro Thr Pro Ser Ser Gly Val Pro Thr
                165                 170                 175

Thr Pro Pro Gln Ala Gly Gly Pro Pro Pro Ala Ala Val Pro
            180                 185                 190

Gly Pro Gly Pro Gly Lys Gln Gly Pro Gly Gly Pro Lys
            195                 200                 205

Gly Gly Lys Met Pro Gly Gly Pro Lys Pro Gly Gly Pro Gly Leu
210                 215                 220

Ser Thr Pro Gly Gly His Pro Lys Pro Pro His Arg Gly Gly Glu
225                 230                 235                 240

Pro Arg Gly Gly Arg Gln His His Pro Pro Tyr His Gln Gln His His
                245                 250                 255

Gln Gly Pro Pro Pro Gly Gly Pro Gly Gly Arg Ser Glu Glu Lys Ile
            260                 265                 270

Ser Asp Ser Glu Gly Phe Lys Ala Asn Leu Ser Leu Leu Arg Arg Pro
275                 280                 285

Gly Glu Lys Thr Tyr Thr Gln Arg Cys Arg Leu Phe Val Gly Asn Leu
290                 295                 300

Pro Ala Asp Ile Thr Glu Asp Glu Phe Lys Arg Leu Phe Ala Lys Tyr
305                 310                 315                 320

Gly Glu Pro Gly Glu Val Phe Ile Asn Lys Gly Lys Gly Phe Gly Phe
                325                 330                 335

Ile Lys Leu Glu Ser Arg Ala Leu Ala Glu Ile Ala Lys Ala Glu Leu
                340                 345                 350

Asp Asp Thr Pro Met Arg Gly Arg Gln Leu Arg Val Arg Phe Ala Thr
            355                 360                 365

His Ala Ala Ala Leu Ser Val Arg Asn Leu Ser Pro Tyr Val Ser Asn
370                 375                 380

Glu Leu Leu Glu Glu Ala Phe Ser Gln Phe Gly Pro Ile Glu Arg Ala
385                 390                 395                 400

Val Val Ile Val Asp Asp Arg Gly Arg Ser Thr Gly Lys Gly Ile Val
                405                 410                 415

Glu Phe Ala Ser Lys Pro Ala Ala Arg Lys Ala Phe Glu Arg Cys Ser
                420                 425                 430

Glu Gly Val Phe Leu Leu Thr Thr Thr Pro Arg Pro Val Ile Val Glu
            435                 440                 445

Pro Leu Glu Gln Leu Asp Asp Glu Asp Gly Leu Pro Glu Lys Leu Ala
450                 455                 460

Gln Lys Asn Pro Met Tyr Gln Lys Glu Arg Glu Thr Pro Pro Arg Phe
465                 470                 475                 480

Ala Gln His Gly Thr Phe Glu Tyr Glu Tyr Ser Gln Arg Trp Lys Ser
                485                 490                 495
```

```
Leu Asp Glu Met Glu Lys Gln Gln Arg Glu Gln Val Glu Lys Asn Met
                500                 505                 510
Lys Asp Ala Lys Asp Lys Leu Glu Ser Glu Met Glu Asp Ala Tyr His
            515                 520                 525
Glu His Gln Ala Asn Leu Leu Arg Gln Asp Leu Met Arg Arg Gln Glu
        530                 535                 540
Glu Leu Arg Arg Met Glu Glu Leu His Asn Gln Glu Met Gln Lys Arg
545                 550                 555                 560
Lys Glu Met Gln Leu Arg Gln Glu Glu Arg Arg Arg Glu Glu
                565                 570                 575
Glu Met Met Ile Arg Gln Arg Glu Met Glu Gln Met Arg Arg Gln
                580                 585                 590
Arg Glu Glu Ser Tyr Ser Arg Met Gly Tyr Met Asp Pro Arg Glu Arg
            595                 600                 605
Asp Met Arg Met Gly Gly Gly Ala Met Asn Met Gly Asp Pro Tyr
    610                 615                 620
Gly Ser Gly Gly Gln Lys Phe Pro Pro Leu Gly Gly Gly Gly Ile
625                 630                 635                 640
Gly Tyr Glu Ala Asn Pro Gly Val Pro Pro Ala Thr Met Ser Gly Ser
                645                 650                 655
Met Met Gly Ser Asp Met Arg Thr Glu Arg Phe Gly Gln Gly Gly Ala
                660                 665                 670
Gly Pro Val Gly Gly Gln Gly Pro Arg Gly Met Gly Pro Gly Thr Pro
            675                 680                 685
Ala Gly Tyr Gly Arg Gly Arg Glu Glu Tyr Glu Gly Pro Asn Lys Lys
        690                 695                 700
Pro Arg Phe
705

<210> SEQ ID NO 131
<211> LENGTH: 2622
<212> TYPE: DNA
<213> ORGANISM: Homo sapiens

<400> SEQUENCE: 131
tctgtgtcat ccgccatttt gtgagaagca aggtggcctc cacgtttcct gagcgtcttc      60
ttcgcttttg cctcgaccgc cccttgacca cagacatgtc tcgggatcgg ttccggagtc     120
gtggcggtgg cggtggtggc ttccacaggc gtggaggagg cggcggccgc ggcggcctcc     180
acgacttccg ttctccgccg cccggcatgg gcctcaatca gaatcgcggc cccatgggtc     240
ctggcccggg ccagagcggc cctaagcctc cgatcccgcc accgcctcca caccaacagc     300
agcaacagcc accaccgcag cagccaccgc cgcagcagcc gccaccgcat cagccgccgc     360
cgcatccaca gccgcatcag cagcagcagc cgccgccacc gccgcaggac tcttccaagc     420
ccgtcgttgc tcagggaccc ggccccgctc ccggagtagg cagcacacca ccagcctcca     480
gctcggcccc gcccgccact ccaccaacct cggggggccc gccagggtcc gggccaggcc     540
cgactccgac cccgccgcct gcagtcacct cggcccctcc cggggcgccg ccacccaccc     600
cgccaagcag cggggtccct accacacctc ctcaggccgg aggcccgccg cctccgcccg     660
cggcagtccc gggcccgggt ccaggcccta agcagggcc aggtccgggt ggtcccaaag     720
gcggcaaaat gcctggcggg ccgaagccag gtggcggccc gggcctaagt acgcctggcg     780
gccaccccaa gccgccgcgt cgaggcggcg gggagcccg cggggccgc cagcaccacc     840 cgccctacca ccagcagcat caccagggc cccgcccgg cgggcccggc ggccgcagcg     900
```

```
aggagaagat ctcggactcg gaggggttta aagccaattt gtctctcttg aggaggcctg    960
gagagaaaac ttacacacag cgatgtcggt tgtttgttgg aatctacct gctgatatca   1020 cggaggatga attcaaaaga ctatttgcta aatatggaga accaggagaa gtttttatca   1080
acaaaggcaa aggattcgga tttattaagc ttgaatctag agctttggct gaaattgcca   1140
aagccgaact ggatgataca cccatgagag gtagacagct tcgagttcgc tttgccacac   1200
atgctgctgc cctttctgtt cgtaatcttt caccttatgt ttccaatgaa ctgttggaag   1260
aagcctttag ccaatttggt cctattgaaa gggctgttgt aatagtggat gatcgtggaa   1320
gatctacagg gaaaggcatt gttgaatttg cttctaagcc agcagcaaga aaggcatttg   1380
aacgatgcag tgaaggtgtt ttcttactga cgacaactcc tcgtccagtc attgtggaac   1440
cacttgaaca actagatgat gaagatggtc ttcctgaaaa acttgcccag aagaatccaa   1500
tgtatcaaaa ggagagagaa accccctactc gttttgccca gcatggcacg tttgagtacg   1560
aatattctca gcgatggaag tctttggatg aaatggaaaa cagcaaagg gaacaagttg   1620 aaaaaaacat gaaagatgca aaagacaaat tggaaagtga atggaagat gcctatcatg   1680 aacatcaggc aaatcttttg cgccaagatc tgatgagacg acaggaagaa ttaagacgca   1740
tggaagaact tcacaatcaa gaaatgcaga acgtaaaga aatgcaattg aggcaagagg   1800
aggaacgacg tagaagagag gaagagatga tgattcgtca acgtgagatg gaagaccaaa   1860
tgaggcgcca aagagaggaa agttacagcc gaatgggcta catggatcca cgggaaagag   1920
acatgcgaat gggtggcgga ggagcaatga acatgggaga tccctatggt tcaggaggcc   1980
agaaatttcc acctctagga ggtggtggtg gcataggtta tgaagctaat cctggcgttc   2040
caccagcaac catgagtggt tccatgatgg gaagtgacat gcgtactgag cgctttgggc   2100
agggaggtgc ggggcctgtg ggtggacagg gtcctagagg aatggggcct ggaactccag   2160
caggatatgg tagagggaga gaagagtacg aaggcccaaa caaaaaaccc cgatttagaa   2220
tgtgatattt aggctttcat tccagtttgt tttgtttttt tgtttagata ccaatctttt   2280
aaattcttgc attttagtaa gaaagctatc ttttttatgga tgttagcagt ttattgacct   2340
aatatttgta aatggtctgt ttgggcaggt aaaattatgt aatgcagtgt ttggaacagg   2400 agaattttt tttcctttt atttctttat tttttcttt ttactgtata atgtccctca   2460
agtttatggc agtgtacctt gtgccactga atttccaaag tgtaccaatt ttttttttt   2520 tactgtgctt caaataaata gaaaatagt tataaaaaaa aaaaaaaaaa aaaaaaaaa   2580 aaaaaaaaaa aaaaaaaaaa aaaaaaaaaa aaaaaaaa aa                        2622
```

<210> SEQ ID NO 132
<211> LENGTH: 699
<212> TYPE: PRT
<213> ORGANISM: Mus musculus

<400> SEQUENCE: 132

```
Met Ser Arg Asp Arg Phe Arg Ser Arg Gly Gly Gly Gly Gly Gly Phe
1               5                   10                  15

His Arg Arg Gly Gly Gly Gly Gly Arg Gly Gly Leu His Asp Phe Arg
            20                  25                  30

Ser Pro Pro Pro Gly Met Gly Leu Asn Gln Asn Arg Gly Pro Met Gly
        35                  40                  45

Pro Gly Pro Gly Gly Pro Lys Pro Leu Pro Pro Pro Pro His
    50                  55                  60

Gln Gln Gln Gln Gln Pro Pro Pro Gln Gln Pro Pro Pro Gln Gln Pro
```

```
65                  70                  75                  80
Pro Pro His Gln Gln Pro Pro His Gln Pro Pro His Gln Gln Pro
                85                  90                  95
Pro Pro Pro Gln Glu Ser Lys Pro Val Pro Gln Gly Pro Gly
            100                 105                 110
Ser Ala Pro Gly Val Ser Ser Ala Pro Pro Ala Val Ser Ala Pro
            115                 120                 125
Pro Ala Asn Pro Pro Thr Thr Gly Ala Pro Pro Gly Pro Thr
130                 135                 140
Pro Thr Pro Pro Pro Ala Val Pro Ser Thr Ala Pro Gly Pro Pro
145                 150                 155                 160
Pro Ser Thr Pro Ser Ser Gly Val Ser Thr Thr Pro Gln Thr Gly
            165                 170                 175
Gly Pro Pro Pro Pro Ala Gly Gly Ala Gly Pro Gly Pro Lys Pro
            180                 185                 190
Gly Pro Gly Pro Gly Pro Lys Gly Gly Lys Met Pro Gly Gly Pro
            195                 200                 205
Lys Pro Gly Gly Pro Gly Met Gly Ala Pro Gly Gly His Pro Lys
            210                 215                 220
Pro Pro His Arg Gly Gly Glu Pro Arg Gly Gly Arg Gln His His
225                 230                 235                 240
Ala Pro Tyr His Gln Gln His Gln Gly Pro Pro Gly Gly Pro
            245                 250                 255
Gly Pro Arg Thr Glu Glu Lys Ile Ser Asp Ser Glu Gly Phe Lys Ala
            260                 265                 270
Asn Leu Ser Leu Leu Arg Arg Pro Gly Glu Lys Thr Tyr Thr Gln Arg
            275                 280                 285
Cys Arg Leu Phe Val Gly Asn Leu Pro Ala Asp Ile Thr Glu Asp Glu
290                 295                 300
Phe Lys Arg Leu Phe Ala Lys Tyr Gly Glu Pro Gly Glu Val Phe Ile
305                 310                 315                 320
Asn Lys Gly Lys Gly Phe Gly Phe Ile Lys Leu Glu Ser Arg Ala Leu
            325                 330                 335
Ala Glu Ile Ala Lys Ala Glu Leu Asp Asp Thr Pro Met Arg Gly Arg
            340                 345                 350
Gln Leu Arg Val Arg Phe Ala Thr His Ala Ala Ala Leu Ser Val Arg
            355                 360                 365
Asn Leu Ser Pro Tyr Val Ser Asn Glu Leu Leu Glu Glu Ala Phe Ser
            370                 375                 380
Gln Phe Gly Pro Ile Glu Arg Ala Val Val Ile Val Asp Asp Arg Gly
385                 390                 395                 400
Arg Ser Thr Gly Lys Gly Ile Val Glu Phe Ala Ser Lys Pro Ala Ala
            405                 410                 415
Arg Lys Ala Phe Glu Arg Cys Ser Glu Gly Val Phe Leu Leu Thr Thr
            420                 425                 430
Thr Pro Arg Pro Val Ile Val Glu Pro Leu Glu Gln Leu Asp Asp Glu
            435                 440                 445
Asp Gly Leu Pro Glu Lys Leu Ala Gln Lys Asn Pro Met Tyr Gln Lys
            450                 455                 460
Glu Arg Glu Thr Pro Pro Arg Phe Ala Gln His Gly Thr Phe Glu Tyr
465                 470                 475                 480
Glu Tyr Ser Gln Arg Trp Lys Ser Leu Asp Glu Met Glu Lys Gln Gln
            485                 490                 495
```

```
Arg Glu Gln Val Glu Lys Asn Met Lys Asp Ala Lys Asp Lys Leu Glu
            500                 505                 510
Ser Glu Met Glu Asp Ala Tyr His Glu His Gln Ala Asn Leu Leu Arg
            515                 520                 525
Gln Asp Leu Met Arg Arg Gln Glu Glu Leu Arg Arg Met Glu Glu Leu
530                 535                 540
His Ser Gln Glu Met Gln Lys Arg Lys Glu Met Gln Leu Arg Gln Glu
545                 550                 555                 560
Glu Glu Arg Arg Arg Arg Glu Glu Met Met Ile Arg Gln Arg Glu
                565                 570                 575
Met Glu Glu Gln Met Arg Arg Gln Arg Glu Glu Ser Tyr Ser Arg Met
            580                 585                 590
Gly Tyr Met Asp Pro Arg Glu Arg Asp Met Arg Met Gly Gly Gly Gly
            595                 600                 605
Thr Met Asn Met Gly Asp Pro Tyr Gly Ser Gly Gly Gln Lys Phe Pro
            610                 615                 620
Pro Leu Gly Gly Gly Gly Ile Gly Tyr Glu Ala Asn Pro Gly Val
625                 630                 635                 640
Pro Pro Ala Thr Met Ser Gly Ser Met Met Gly Ser Asp Met Arg Thr
                645                 650                 655
Glu Arg Phe Gly Gln Gly Gly Ala Gly Pro Val Gly Gly Gln Gly Pro
            660                 665                 670
Arg Gly Met Gly Pro Gly Thr Pro Ala Gly Tyr Gly Arg Gly Arg Glu
            675                 680                 685
Glu Tyr Glu Gly Pro Asn Lys Lys Pro Arg Phe
            690                 695

<210> SEQ ID NO 133
<211> LENGTH: 2464
<212> TYPE: DNA
<213> ORGANISM: Mus musculus

<400> SEQUENCE: 133
cttctgcctc gaccgcccct tgactacagc tatgtctcgg gatcggttcc ggagtcgcgg      60
tggcggcggt ggaggctttc accggcgtgg aggaggtggc ggccgcggcg gccttcacga     120
cttccgctct ccgccgccgg gcatgggcct caaccagaac cgcggcccca tgggcccggg     180
ccctggcggc ccgaagccgc cgctcccgcc tccacctcct caccagcagc agcagcagcc     240
gccgccgcag cagcctccgc cgcagcagcc gccgccgcac cagcagccgc cgccgcacca     300 gccgcccat caacagcccc cgcctccgcc gcaggaatcc aagcccgtcg tcccccaagg     360
ccccggctcg gcgccggggg tgagcagtgc cgctccgccg gcggtctcgg ctccgcccgc     420 caacccccg accaccggcg cccctccggg ccctggtcca accccgactc cgccgcccgc     480
cgtcccctcc accgccccg gaccgcctcc cccatcgacg ccgagcagcg gagtctcgac     540 caccctcca cagaccggcg gccctccgcc accgcccgcc gggggcgccg gccggggcc     600 taagccgggg ccaggccctg gcggtccaaa aggcggcaag atgcccggtg ggcctaagcc     660
tggaggtggc ccgggcatgg gcgctcctgg tggccacccg aagccaccac accgaggtgg     720
cggcgagccc cgtggggcc ggcagcatca tgcgccctac caccagcagc accaccaggg     780 gcccctcc ggcggaccgg gaccgcgcac ggaggagaag atctccgact cggagggatt     840
taaagccaac ttgtctctct tgcggaggcc tggagaaaaa acttacacac agcgctgtcg     900
gttgtttgtg gggaatctac ctgctgatat cacagaggat gaattcaaaa gactgtttgc     960
taaatacgga gaacccggag aagttttat caacaaaggc aaagggttcg ggttcattaa    1020
```

```
gcttgaatct agagccttgg ctgaaatcgc caaagctgag cttgatgata ctcccatgag   1080
aggtagacag cttcgggttc gatttgccac acacgctgca gccctgtctg ttcgaaatct   1140
ctctccttat gtttccaacg aacttttgga agaggccttt agccagtttg gtcctattga   1200
aagggctgtt gtaattgtgg atgatcgcgg aagatctaca gggaaaggca ttgttgagtt   1260
tgcttccaag ccagcagcaa gaaaagcatt tgaaagatgc agtgaaggtg ttttcctact   1320
gacaacgact cctcgcccag tcattgtgga accacttgaa cagttagatg acgaagatgg   1380
tcttcctgaa aagctggccc agaagaatcc aatgtatcaa aaggagagag aaacaccacc   1440
tcgttttgct cagcatggca catttgagta tgaatattct caacgatgga agtccttgga   1500
tgaaatggaa aaacagcaaa gggaacaagt tgaaaaaaac atgaaggatg ctaaagacaa   1560
attggaaagt gaaatggaag atgcttacca tgaacaccaa gcaaatcttt tgcgccaaga   1620
tctgatgaga cgccaggaag aattaaggcg catggaggaa cttcacagtc aagaaatgca   1680
gaaacgtaaa gaaatgcagt tgaggcaaga ggaggaacgg cgtagacgag aggaagagat   1740
gatgattcgc caacgtgaga tggaagaaca aatgagacgc caacgagaag aaagttacag   1800
caggatgggc tacatggatc caagagaaag agacatgaga atgggtggtg gtggaacaat   1860
gaacatggga gatccctatg gttcaggagg ccagaaattt ccaccactag gtggtggtgg   1920
tggcataggt tatgaagcta atcctggagt tccaccagca accatgagtg gttccatgat   1980
gggaagcgac atgcgtactg agcgctttgg gcagggaggt gcgggtcctg tgggtggaca   2040
gggtcctaga ggaatggggc ctggaactcc agcaggatat ggtagaggga gagaagagta   2100
tgaagggcca aataaaaaac cccgatttta gatatttagg ctttcattct agtttggttt   2160
tgtcttttct tgtttagata ccacttaaat tcttggcatt ttagtaagca agctacccttt   2220
ttatggatgt tagcagtttta ttgacctgat atttgtaaat ggcctgtttg ggcaggtaaa   2280
attatgtaac gcagtgttca aaacaggaga aaaattttt tcatttactt ttttttttaa   2340
ctgtataatg tttctcaagt taatggcagt gtaccttgtg ccaccgaatt tccaaagtgt   2400
accattttttt ttttactgtg cttcaaataa atagaaaaaa tagttataaa aaaaaaaaa   2460
aaaa                                                                2464
```

<210> SEQ ID NO 134
<211> LENGTH: 707
<212> TYPE: PRT
<213> ORGANISM: Homo sapiens

<400> SEQUENCE: 134

```
Met Ser Arg Asp Arg Phe Arg Ser Arg Gly Gly Gly Gly Gly Gly Phe
1               5                   10                  15

His Arg Arg Gly Gly Gly Gly Arg Gly Gly Leu His Asp Phe Arg
                20                  25                  30

Ser Pro Pro Pro Gly Met Gly Leu Asn Gln Asn Arg Gly Pro Met Gly
            35                  40                  45

Pro Gly Pro Gly Gln Ser Gly Pro Lys Pro Ile Pro Pro Pro
        50                  55                  60

Pro His Gln Gln Gln Gln Pro Pro Gln Gln Pro Pro Gln
65                  70                  75                  80

Gln Pro Pro Pro His Gln Pro Pro His Pro Gln His Gln Gln
                85                  90                  95

Gln Gln Pro Pro Pro Pro Gln Asp Ser Ser Lys Pro Val Val Ala
            100                 105                 110
```

```
Gln Gly Pro Gly Pro Ala Pro Val Gly Ser Ala Pro Ala Ser
        115                 120                 125

Ser Ser Ala Pro Pro Ala Thr Pro Pro Thr Ser Gly Ala Pro Pro Gly
    130                 135                 140

Ser Gly Pro Gly Pro Thr Pro Thr Pro Pro Ala Val Thr Ser Ala
145                 150                 155                 160

Pro Pro Gly Ala Pro Pro Thr Pro Ser Ser Gly Val Pro Thr
            165                 170                 175

Thr Pro Pro Gln Ala Gly Gly Pro Pro Pro Ala Ala Val Pro
            180                 185                 190

Gly Pro Gly Pro Gly Pro Lys Gln Gly Pro Gly Pro Gly Pro Lys
        195                 200                 205

Gly Gly Lys Met Pro Gly Gly Pro Lys Pro Gly Gly Pro Gly Leu
        210                 215                 220

Ser Thr Pro Gly Gly His Pro Lys Pro Pro His Arg Gly Gly Glu
225                 230                 235                 240

Pro Arg Gly Gly Arg Gln His His Pro Pro Tyr His Gln Gln His His
            245                 250                 255

Gln Gly Pro Pro Pro Gly Gly Pro Gly Gly Arg Ser Glu Glu Lys Ile
        260                 265                 270

Ser Asp Ser Glu Gly Phe Lys Ala Asn Leu Ser Leu Leu Arg Arg Pro
    275                 280                 285

Gly Glu Lys Thr Tyr Thr Gln Arg Cys Arg Leu Phe Val Gly Asn Leu
    290                 295                 300

Pro Ala Asp Ile Thr Glu Asp Glu Phe Lys Arg Leu Phe Ala Lys Tyr
305                 310                 315                 320

Gly Glu Pro Gly Glu Val Phe Ile Asn Lys Gly Lys Gly Phe Gly Phe
            325                 330                 335

Ile Lys Leu Glu Ser Arg Ala Leu Ala Glu Ile Ala Lys Ala Glu Leu
            340                 345                 350

Asp Asp Thr Pro Met Arg Gly Arg Gln Leu Arg Val Arg Phe Ala Thr
        355                 360                 365

His Ala Ala Ala Leu Ser Val Arg Asn Leu Ser Pro Tyr Val Ser Asn
    370                 375                 380

Glu Leu Leu Glu Glu Ala Phe Ser Gln Phe Gly Pro Ile Glu Arg Ala
385                 390                 395                 400

Val Val Ile Val Asp Asp Arg Gly Arg Ser Thr Gly Lys Gly Ile Val
            405                 410                 415

Glu Phe Ala Ser Lys Pro Ala Ala Arg Lys Ala Phe Glu Arg Cys Ser
            420                 425                 430

Glu Gly Val Phe Leu Leu Thr Thr Thr Pro Arg Pro Val Ile Val Glu
        435                 440                 445

Pro Leu Glu Gln Leu Asp Asp Glu Asp Gly Leu Pro Glu Lys Leu Ala
450                 455                 460

Gln Lys Asn Pro Met Tyr Gln Lys Glu Arg Glu Thr Pro Pro Arg Phe
465                 470                 475                 480

Ala Gln His Gly Thr Phe Glu Tyr Glu Tyr Ser Gln Arg Trp Lys Ser
            485                 490                 495

Leu Asp Glu Met Glu Lys Gln Gln Arg Glu Gln Val Glu Lys Asn Met
            500                 505                 510

Lys Asp Ala Lys Asp Lys Leu Glu Ser Glu Met Glu Asp Ala Tyr His
        515                 520                 525

Glu His Gln Ala Asn Leu Leu Arg Gln Asp Leu Met Arg Arg Gln Glu
530                 535                 540
```

-continued

```
Glu Leu Arg Arg Met Glu Leu His Asn Gln Glu Met Gln Lys Arg
545                 550                 555                 560

Lys Glu Met Gln Leu Arg Gln Glu Glu Glu Arg Arg Arg Glu Glu
                565                 570                 575

Glu Met Met Ile Arg Gln Arg Glu Met Glu Glu Gln Met Arg Arg Gln
            580                 585                 590

Arg Glu Glu Ser Tyr Ser Arg Met Gly Tyr Met Asp Pro Arg Glu Arg
        595                 600                 605

Asp Met Arg Met Gly Gly Gly Ala Met Asn Met Gly Asp Pro Tyr
        610             615                 620

Gly Ser Gly Gly Gln Lys Phe Pro Pro Leu Gly Gly Gly Gly Ile
625                 630                 635                 640

Gly Tyr Glu Ala Asn Pro Gly Val Pro Pro Ala Thr Met Ser Gly Ser
                645                 650                 655

Met Met Gly Ser Asp Met Arg Thr Glu Arg Phe Gly Gln Gly Gly Ala
            660                 665                 670

Gly Pro Val Gly Gly Gln Gly Pro Arg Gly Met Gly Pro Gly Thr Pro
        675                 680                 685

Ala Gly Tyr Gly Arg Gly Arg Glu Glu Tyr Glu Gly Pro Asn Lys Lys
        690                 695                 700

Pro Arg Phe
705
```